(12) United States Patent
Choi

(10) Patent No.: US 10,351,519 B2
(45) Date of Patent: Jul. 16, 2019

(54) SULFAMATE DERIVATIVE COMPOUNDS, PROCESSES FOR PREPARING THEM AND THEIR USES

(71) Applicant: BIO-PHARM SOLUTIONS CO., LTD., Gyeonggi-do (KR)

(72) Inventor: Yong Moon Choi, Seoul (KR)

(73) Assignee: BIO-PHARM SOLUTIONS CO., LTD. (KR)

( * ) Notice: Subject to any disclaimer, the term of this patent is extended or adjusted under 35 U.S.C. 154(b) by 126 days.

(21) Appl. No.: 15/516,133

(22) PCT Filed: Feb. 28, 2017

(86) PCT No.: PCT/KR2017/002235
§ 371 (c)(1),
(2) Date: Mar. 31, 2017

(87) PCT Pub. No.: WO2017/150903
PCT Pub. Date: Sep. 8, 2017

(65) Prior Publication Data
US 2018/0230090 A1    Aug. 16, 2018

Related U.S. Application Data

(60) Provisional application No. 62/300,985, filed on Feb. 29, 2016.

(51) Int. Cl.
| | | |
|---|---|---|
| *A61P 25/08* | (2006.01) | |
| *A61P 25/18* | (2006.01) | |
| *C07C 307/02* | (2006.01) | |
| *C07D 213/46* | (2006.01) | |
| *C07D 213/61* | (2006.01) | |
| *C07D 277/24* | (2006.01) | |
| *C07D 277/32* | (2006.01) | |
| *C07D 333/16* | (2006.01) | |

(52) U.S. Cl.
CPC ............ *C07C 307/02* (2013.01); *A61P 25/08* (2018.01); *A61P 25/18* (2018.01); *C07D 213/46* (2013.01); *C07D 213/61* (2013.01); *C07D 277/24* (2013.01); *C07D 277/32* (2013.01); *C07D 333/16* (2013.01); *C07C 2601/02* (2017.05)

(58) Field of Classification Search
CPC combination set(s) only.
See application file for complete search history.

(56) References Cited

U.S. PATENT DOCUMENTS

| | | | |
|---|---|---|---|
| 4,824,475 A | 4/1989 | Markley et al. | |
| 9,029,589 B2* | 5/2015 | Choi | C07C 33/26 560/32 |
| 9,034,848 B2* | 5/2015 | Choi | C07C 33/26 514/63 |
| 9,504,668 B2* | 11/2016 | Choi | C07C 271/12 |
| 9,682,059 B2* | 6/2017 | Choi | C07C 271/12 |
| 9,872,847 B2* | 1/2018 | Choi | C07C 271/12 |
| 9,956,197 B2* | 5/2018 | Choi | C07C 271/12 |
| 2001/0034365 A1 | 10/2001 | Choi et al. | |
| 2007/0117798 A1 | 5/2007 | Kimura et al. | |
| 2014/0275243 A1* | 9/2014 | Choi | C07C 271/12 514/487 |

FOREIGN PATENT DOCUMENTS

WO    WO 2014/142520    9/2014

OTHER PUBLICATIONS

Rinner et al. "New Application of Burgess Reagent in its Reaction with Epoxides" Synlett 2003, 9, 1247-1252. (Year: 2003).*
Leisch et al. "Chiral Version of the Burgess Reagent" Synlett 2006, 3, 445-449. (Year: 2006).*
Amarante et al., "Hyphenating the Curtius Rearrangement with Morita-Baylis-Hillman Adducts: Synthesis of Biologically Active Acyloins and Vicinal Aminoalcohols," J. Braz. Chem. Soc., 2011, vol. 22(8), pp. 1568-1584.
International Search Report for International (PCT) Patent Application No. PCT/KR2017/002235, dated Jun. 13, 2017, 6 pages.

\* cited by examiner

*Primary Examiner* — Amanda L Aguirre
(74) *Attorney, Agent, or Firm* — Sheridan Ross P.C.

(57) ABSTRACT

The present invention relates to a pharmaceutical composition for treating or preventing CNS disorders containing a sulfamate derivative compound and/or pharmaceutically acceptable salt thereof as an active ingredient. Furthermore, the present invention relates to a method for treatment or prevention CNS disorders comprising administering a sulfamate derivative compound in a pharmaceutically effective amount to a subject in need of treatment or prevention of CNS disorders.

16 Claims, 1 Drawing Sheet

[Fig. 1]
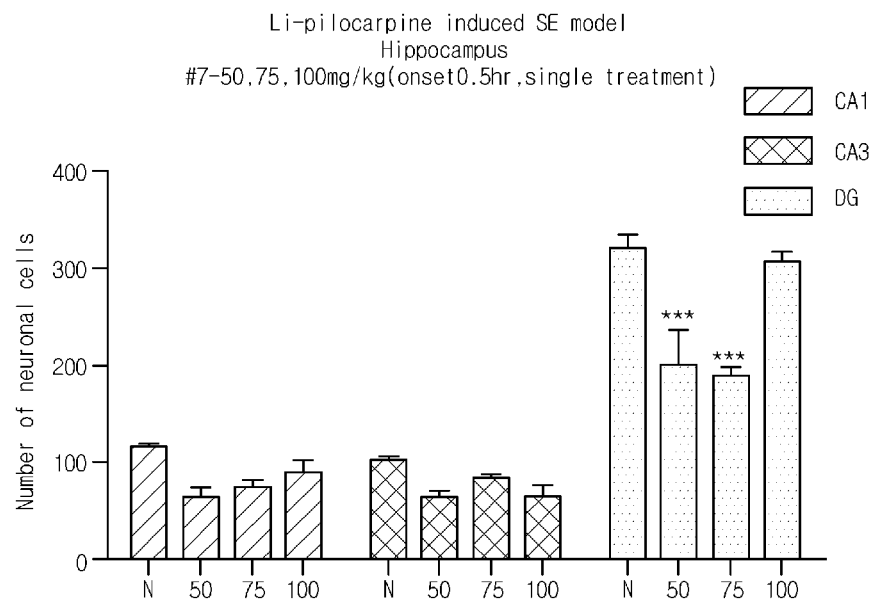
[Fig. 2]
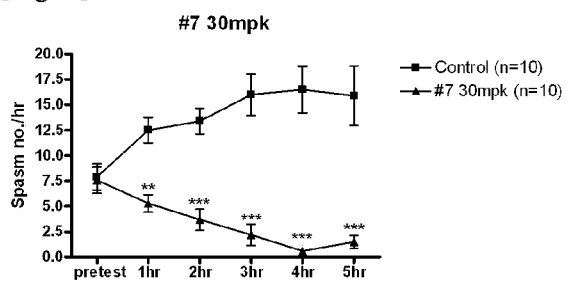

SULFAMATE DERIVATIVE COMPOUNDS, PROCESSES FOR PREPARING THEM AND THEIR USES

CROSS REFERENCE TO RELATED APPLICATIONS

This application is a national stage application under 35 U.S.C. 371 and claims the benefit of PCT Application No. PCT/KR2017/002235 having an international filing date of Feb. 28, 2017, which designated the United States, which PCT application claimed the benefit of U.S. Provisional Application No. 62/300,985 filed Feb. 29, 2016, the disclosures of each of which are incorporated herein by reference.

TECHNICAL FIELD

The present invention relates to a sulfamate derivative compound for treating or preventing CNS disorders and/or pain and/or pharmaceutically acceptable salt thereof as an active ingredient. Furthermore, the present invention relates to a method for treatment or prevention of CNS disorders and/or pain comprising administering a sulfamate derivative compound in a pharmaceutically effective amount to a subject in need of treatment or prevention of CNS disorders like epilepsy and/or pain.

BACKGROUND ART

Central nervous system (hereinafter referred to as "CNS") disorders nowadays concern large sections of the population. In particular on account of the increase in elderly people, the numbers of patients are increasing continuously.

CNS disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses; and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neu-rotransmitters and neu-rotransmitter receptors). Several CNS disorders can be attributed to a deficiency of choline, dopamine, norepinephrine and/or serotonin. Relatively common CNS disorders include or go along with pain, epilepsy or epilepsy-related syndrome, pediatric epilepsy or pediatric epilepsy-related syndrome, memory pre-senile dementia (early-onset Alzheimer's disease), senile dementia (dementia of the Alzheimer's type), micro-infarct dementia, AIDS-related dementia, Creutzfeld-Jakob disease, Pick's disease, Parkinsonism including Parkinson's disease, Lewy body dementia, progressive supranuclear palsy, Huntington's chorea, tardive dyskinesia, hy-perkinesia, mania, attention deficit disorder, anxiety, dyslexia, schizophrenia, de-pression, obsessive-compulsive disorders, and Tourette's syndrome.

Particularly, epilepsy is the most common CNS disorder, affecting about 1% of the population worldwide. Epilepsy describes a condition in which a person has recurrent seizures due to a chronic, underlying process. Epilepsy refers to a clinical phenomenon rather than a single disease entity, since there are many forms and causes of epilepsy. Using a definition of epilepsy as two or more unprovoked seizures, the incidence of epilepsy is estimated at 5 to 10 people per 1000. An essential step in the diagnosis and treatment of a patient with a seizure is to determine the type of seizure that has occurred. The main characteristic that distinguishes the different categories of seizure is whether the seizure activity is partial or generalized or unclassified.

For the general population there are approximately 20-70 new cases per 100,000 diagnosed each year with a 3-5% lifetime probability of developing the disease. The older established antiepileptic drugs (AEDs) phenytoin, carbamazepine, clonazepam, ethosuximide, valproic acid and barbiturates are widely prescribed but suffer from a range of side effects. Furthermore, there is a significant group of patients (20-30%) that are resistant to the currently available therapeutic agents. Since 1989 several new drugs have been launched, including felbamate, gabapentin, lamotrigine, oxcar-bazepine, tiagabine, topiramate, vigabartrin, zonisamide and levetiracetam. While many of new AEDs show improved efficacies and side-effect profiles, about 30% of patients with epilepsy remain untreated. There is clearly a need for improved medication.

Pain is one of the most common reasons for a patient to seek medical care and in consequence, pain results in a tremendous number of lost work days per year.

Pain is an unpleasant feeling often caused by intense or damaging stimuli, such as stubbing a toe, burning a finger, putting alcohol on a cut, and bumping the funny bone. The International Association for the Study of Pain's widely used definition states: "Pain is an unpleasant sensory and emotional experience associated with actual or potential tissue damage, or described in terms of such damage". Pain motivates the in-dividual to withdraw from damaging situations, to protect a damaged body part while it heals, and to avoid similar experiences in the future. Most pain resolves promptly once the painful stimulus is removed and the body has healed, but sometimes pain persists despite removal of the stimulus and apparent healing of the body; and sometimes pain arises in the absence of any detectable stimulus, damage or disease.

Pain is the most common reason for physician consultation. It is a major symptom in many medical conditions, and can significantly interfere with a person's quality of life and general functioning. Psychological factors such as social support, hypnotic suggestion, excitement, or distraction can significantly modulate pain's intensity or unpleasantness.

In 1994, responding to the need for a more useful system for describing chronic pain, the International Association for the Study of Pain (.IASP) classified pain according to specific characteristics: (1) region of the body involved (e.g., abdomen, lower limbs), (2) system whose dysfunction may be causing the pain (e.g., nervous, gastrointestinal), (3) duration and pattern of occurrence, (4) intensity and time since onset, and (5) etiology.

This system has been criticized by Clifford J. Woo If and others as inadequate for guiding research and treatment. According to Woolf, there are three classes of pain: nociceptive pain (see hereunder), inflammatory pain which is associated with tissue damage and the infiltration of immune cells, and pathological pain which is a disease state caused by damage to the nervous system or by its abnormal function (dysfunctional pain, irritable bowel syndrome, tension type headache, etc.).

In nociceptive pain, the stimulation of the sensory nerve endings called nociceptors causes the sensation of pain. Such pain often occurs after injury or surgery. The pain signals are transmitted by the nociceptors to the brain. Often the pain is localised, constant and has an aching or throbbing quality. Once the damage to the tissue heals the pain usually resolves. Treatment with opioids may resolve nociceptive pain. Psychogenic pain is a pain disorder that is associated with psychological factors. Some types of mental or emotional problems can cause pain. They can also increase or prolong pain. Stomach pain is one of the most common types of psychogenic pain. People with this pain disorder actually have real pain. The diagnosis is made when all physical causes of pain are ruled out.

Neuropathic pain is caused by abnormalities in the nerves, spinal cord or brain and is a chronic type of non-malignant pain with an estimated prevalence of over 1% of the population. Optimizing pain relief in these patients is crucial in helping a patient regain control of his or her life. The most common cause of neuropathic pain is injury or dysfunction of nerves. Injury or dysfunction of peripheral nerves or nerves descending from the spinal cord results in disinhibition of nerve impulses at the spinal cord which in consequence results in pain. Neuropathic pain can also be centrally mediated, rather than peripheral, in conditions such as spinal cord injury and multiple sclerosis.

Neuropathic pain can therefore be divided into two further classes; peripheral neuropathic pain and central neuropathic pain depending on whether the peripheral or central nervous system is affected.

Inadequate treatment of pain is widespread throughout surgical wards, intensive care units, accident and emergency departments, in general practice, in the management of all forms of chronic pain and in end of life care. This neglect is extended to all ages, from neonates to the frail elderly. African and Hispanic Americans are more likely than others to suffer needlessly in the hands of a physician; and women's pain is more likely to be undertreated than men's. Therefore, it is needed to develop therapeutic measures for treating or alleviating pain.

DISCLOSURE OF INVENTION

Technical Problem

The present inventor has done intensive studies to develop a novel drug with excellent activity and low toxicity which may be an effective treatment for CNS disorders and/or pain. As a result, the present inventors have discovered that the sulfamate derivatives represented by the below Chemical formula I provide highly enhanced anti-epileptic activity with significantly decreased side effects.

The present inventor has done intensive studies to develop a novel drug with excellent activity and low toxicity which may be an effective treatment for CNS disorders and/or pain. As a result, the present inventors have discovered that the sulfamate derivatives represented by the below Chemical formula I provide highly enhanced anti-epileptic activity with significantly decreased side effects.

Accordingly, it is an object of this invention is to provide a novel compound represented by the following formula 1 or pharmaceutically acceptable salt thereof.

Another object of this invention is to provide a novel pharmaceutical composition for treating or preventing CNS disorders and/or pain containing a sulfamate derivative compound and/or pharmaceutically acceptable salt thereof as an active ingredient.

Another object of this invention is to provide a method for treatment or prevention of CNS disorders and/or pain comprising administering a sulfamate derivative compound in a pharmaceutically effective amount to a subject in need of treatment or prevention of CNS disorders and/or pain.

Solution to Problem

As used herein, the below terms have the following meanings unless specified otherwise:

Definitions

It is noted here that as used in this specification and the appended claims, the singular forms "a," "an," and "the" include plural reference unless the context clearly dictates otherwise.

"Alkyl," by itself or as part of another substituent, means, unless specified otherwise, a straight or branched chain, fully saturated aliphatic hydrocarbon radical having the number of carbon atoms designated. For example, "$C_1$-$C_{10}$ alkyl" refers to a hydrocarbon radical straight or branched, containing from 1 to 10 carbon atoms that is derived by the removal of one hydrogen atom from a single carbon atom of a parent alkane. In the context of the invention, unless specified otherwise, the term "alkyl" means "$C_1$-$C_{10}$ alkyl", preferably "$C_1$-$C_5$ alkyl."

"Alkenyl" by itself or as part of another substituent refers to a straight or branched chain, which may be mono- or polyunsaturated, having the number of carbon atoms designated. For example, "$C_2$-$C_8$ alkenyl" means an alkenyl radical having 2, 3, 4, 5, 6, 7 or 8 atoms that is derived by the removal of one hydrogen atom from a single carbon atom of a parent alkane. In the context of the invention, unless specified otherwise, the term "alkenyl" means "$C_2$-$C_{10}$ alkenyl," preferably "$C_2$-$C_5$ alkenyl."

"Alkynyl", by itself or as part of another substituent, means a straight or branched chain hydrocarbon radical, which may be mono- or polyunsaturated, having the number of carbon atoms designated. For example, "$C_2$-$C_8$ alkynyl" means an alkynyl radical having from 2 to 8 carbon atoms that is derived by the removal of one hydrogen atom from a single carbon atom of a parent alkane. In the context of the invention, unless specified otherwise, the term "alkynyl" means "$C_2$-$C_{10}$ alkynyl," preferably "$C_2$-$C_5$ alkynyl."

"Cycloalkyl" by itself or as part of another substituent, represent, unless otherwise stated, cyclic versions of "alkyl", "alkenyl" and "alkynyl" in which all ring atoms are carbon. "Cycloalkyl" or "carbocycle" refers to a mono- or polycyclic group. When used in connection with cycloalkyl substituents, the term "polycyclic" refers herein to fused and non-fused alkyl cyclic structures. "Cycloalkyl" or "carbocycle" may form a bridged ring or a spiro ring. The cycloalkyl group may have one or more double or triple bond(s). The term "cycloalkenyl" refers to a cycloalkyl group that has at least one site of alkenyl unsaturation between the ring vertices. The term "cycloalkynyl" refers to a cycloalkyl group that has at least one site of alkynyl unsaturation between the ring vertices. When "cycloalkyl" is used in combination with "alkyl", as in $C_{3-8}$ cycloalkyl$C_{3-8}$alkylene-, the cycloalkyl portion is meant to have the stated number of carbon atoms (e.g., from three to eight carbon atoms), while the alkylene portion has from one to eight carbon atoms. Typical cycloalkyl substituents have from 3 to 8 ring atoms. Examples of cycloalkyl include cyclopentyl, cyclohexyl, 1-cyclohexenyl, 3-cyclohexenyl, cycloheptyl, and the like.

"Heterocycle", "heterocyclyl" or "heterocyclic" refers to a saturated or unsaturated non-aromatic cyclic group containing at least one heteroatom. As used herein, the term "heteroatom" is meant to include oxygen (O), nitrogen (N), sulfur (S) and silicon (Si). Each heterocycle can be attached at any available ring carbon or heteroatom. Each heterocycle may have one or more rings. Each heterocycle typically contains independently selected 1, 2, 3, 4 or 5 heteroatoms. Preferably, these groups contain 1, 2, 3, 4, 5, 6, 7, 8, 9 or 10 carbon atoms, 0, 1, 2, 3, 4 or 5 nitrogen atoms, 0, 1 or 2 sulfur atoms and 0, 1 or 2 oxygen atoms. More preferably, these groups contain 1, 2 or 3 nitrogen atoms, 0-1 sulfur atoms and 0-1 oxygen atoms. Non-limiting examples of heterocycle groups include morpholin-3-one, piperazine-2-one, piperazin-1-oxide, pyridine-2-one, piperidine, morpholine, piperazine, isoxazoline, pyrazoline, imi-dazoline, pyrazol-5-one, pyrrolidine-2,5-dione, imidazolidine-2,4-dione, pyrrolidine, tetrahydrofuran, tetrahydroquinolinyl, decahydroquinolinyl, tetrahydrobenzoox-azepinyl dihydrodibenzooxepin and the like.

"Aryl" by itself or as part of another substituent refers to a polyunsaturated, aromatic, hydrocarbon group containing from 6 to 14 carbon atoms, which can be a single ring or multiple rings (up to three rings) which are fused together or linked covalently. Thus the phrase includes, but is not limited to, groups such as phenyl, biphenyl, anthracenyl, naphthyl by way of example. Non-limiting examples of unsubstituted aryl groups include phenyl, 1-naphthyl, 2-naphthyl and 4-biphenyl. In the context of the invention, unless specified otherwise, the term "aryl" means "$C_6$-$C_{12}$ aryl," preferably "$C_6$-$C_{10}$ aryl."

"Arylalkyl" or "aralkyl" refers to a monovalent alkyl group substituted with aryl. An example of arylalkyl includes, but is not limited to, benzyl. In certain embodiments, both alkyl and aryl may be optionally substituted with one or more substituents as described herein elsewhere. Example of arylalkyl is benzyl.

"Heteroaryl" refers to a cyclic or polycyclic aromatic radical that contains from one to five heteroatoms selected from N, O, and S, wherein the nitrogen and sulfur atoms are optionally oxidized, and the nitrogen atom(s) are optionally quaternized. In the context of the invention, unless specified otherwise, the term "heteroaryl" means "$C_1$-$C_{10}$ heteroaryl," preferably "$C_1$-$C_8$ heteroaryl." Non-limiting examples of heteroaryl groups include 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl and 4-pyrimidyl. If not specifically stated, substituents for each of the above noted aryl and heteroaryl ring systems are selected from the group of acceptable substituents described herein.

"Alkoxy" refers to —$OR^d$ wherein $R^d$ is alkyl as defined herein. Representative examples of alkoxy groups include methoxy, ethoxy, t-butoxy, trifluoromethoxy, and the like. In the context of the invention, unless specified otherwise, the term "alkoxy" means "$C_1$-$C_{10}$ alkoxy," preferably "$C_1$-$C_5$ alkoxy."

"Alkoxyalkyl" refers to a monovalent alkyl group substituted with alkoxy. For example, "$C_1$-$C_5$alkoxy$C_1$-$C_5$alkyl" means an alkyl radical having from 1 to 5 carbon atoms that is derived by the substitution of one hydrogen atom with $C_1$-$C_5$alkoxy. An example of alkoxyalkyl includes, but is not limited to, methoxymethyl, ethoxymethyl, ethoxyethyl and 2-methoxyethyl. Particularly preferred is methoxymethyl.

"Aryloxyalkyl" or "arylalkyloxyalkyl" refers to a monovalent alkyl group substituted with aryloxy or arylalkyloxy. For example, "$C_6$-$C_{10}$arylalkyloxy$C_1$-$C_5$alkyl" means an alkyl radical having from 1 to 5 carbon atoms that is derived by the substitution of one hydrogen atom with $C_6$-$C_{10}$ arylalkyloxy. An example of arylalkyloxyalkyl includes, but is not limited to benzyloxymethyl.

"Alkoxyalkoxyalkyl" refers to a divalent alkyl group substituted with alkoxy groups. For example, "$C_1$-$C_5$alkoxy ($C_1$-$C_5$alkoxy)$C_1$-$C_5$alkyl" means an alkyl radical having from 1 to 5 carbon atoms that is derived by the substitutions of two hydrogen atom with $C_1$-$C_5$ alkoxy groups respectively. An example of alkoxyalkoxyalky includes, but is not limited to methoxyethoxymethyl.

"Acyl" refers to the group —C(=O)$R^c$ wherein $R^c$ is alkyl, alkenyl, alkynyl, cycloalkyl, cycloalkenyl, aryl, heteroaryl or heterocyclyl. Acyl includes the "acetyl" group —C(=O)CH$_3$. "Acylamino-" refers to the group —$NR^aC$(=O)$R^c$ wherein $R^c$ is alkyl, alkenyl, alkynyl, cycloalkyl, cycloalkenyl, aryl, heteroaryl or heterocyclyl.

"Amino" refers to a monovalent radical —$NR^aR^b$ or divalent radical —$NR^a$—. The term "alkylamino" refers to the group —$NR^aR^b$ wherein $R^a$ is alkyl and $R^b$ is H or alkyl.

"Alkylamino-" refers to the group —$NR^aR^c$ wherein $R^c$ is alkyl, alkenyl or alkynyl.

"Alkylsulfanyl", "alkylthio", or "thioalkoxy" refers to the group S—$R^d$, wherein $R^d$ is alkyl.

"Carbonyl" refers to the divalent group —C(=O)—. "Carboxy" or "carboxyl" refers to the group —CO$_2$H. "Carboxyl ester" or "carboxy ester" refers to the groups —C(=O)O$R^c$ wherein $R^c$ is alkyl, alkenyl, alkynyl, cycloalkyl, cycloalkenyl, aryl, heteroaryl or heterocyclyl.

"Alkoxycarbonyl" refers to —C(=O)O$R^d$ wherein $R^d$ is alkyl.

Each of the terms herein (e.g., "alkyl," "heteroalkyl," "aryl" and "heteroaryl") is meant to include both "unsubstituted" and optionally "substituted" forms of the indicated radical, unless otherwise indicated. Typically each radical is substituted with 0, 1, 2 3 4 or 5 substituents, unless otherwise indicated. Examples of substituents for each type of radical are provided below.

"Substituted" refers to a group as defined herein in which one or more bonds to a carbon(s) or hydrogen(s) are replaced by a bond to non-hydrogen and non-carbon atom "substituents" such as, but not limited to, a halogen atom such as F, Cl, Br, and I; an oxygen atom in groups such as hydroxyl groups, alkoxy groups, aryloxy, and acyloxy groups; a sulfur atom in groups such as thiol groups, alkyl and aryl sulfide groups, sulfone groups, sulfonyl groups, and sulfoxide groups; a nitrogen atom in groups such as amino, alkylamines, dialkylamines, arylamines, alkylarylamines, diarylamines, alkoxyamino, hydroxyamino, acylamino, sulfonylamino, N-oxides, imides, and enamines; and other heteroatoms in various other groups. "Substituents" also include groups in which one or more bonds to a carbon(s) or hydrogen(s) atom is replaced by a higher-order bond (e.g., a double- or triple-bond) to a heteroatom such as oxygen in oxo, acyl, amido, alkoxycarbonyl, aminocarbonyl, carboxyl, and ester groups; nitrogen in groups such as imines, oximes, hydrazones, and nitriles. "Substituents" further include groups in which one or more bonds to a carbon(s) or hydrogen(s) atoms is replaced by a bond to a cycloalkyl, heterocyclyl, aryl, and heteroaryl groups. Representative "substituents" include, among others, groups in which one or more bonds to a carbon or hydrogen atom is/are replaced by one or more bonds to fluoro, chloro, or bromo group. Another representative "substituent" is the trifluoromethyl group and other groups that contain the trifluoromethyl group. Other representative "substituents" include those in which one or more bonds to a carbon or hydrogen atom is replaced by a bond to an oxygen atom such that the substituted alkyl group contains a hydroxyl, alkoxy, or aryloxy group. Other representative "substituents" include alkyl groups that have an amine, or a substituted or unsubstituted alkylamine, dialkylamine, arylamine, (alkyl)(aryl) amine, diarylamine, heterocyclylamine, diheterocyclylamine, (alkyl)(heterocyclyl)amine, or (aryl)(heterocyclyl) amine group. Still other representative "substituents" include those in which one or more bonds to a carbon(s) or hydrogen(s) atoms is replaced by a bond to an alkyl, cycloalkyl, aryl, heteroaryl, or heterocyclyl group. The herein-defined groups may include prefixes and/or suffixes that are commonly used in the art to create additional well-recognized substituent groups.

In one aspect of this invention, there is provided a compound represented by the following formula 1 or pharmaceutically acceptable salt thereof:

[Chemical formula I]

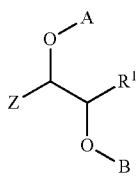

Wherein,
Z is selected from

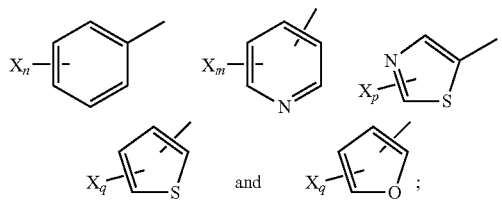

X is selected from the group consisting of halogen, hydroxyl, $C_1$-$C_5$ alkoxy, $C_1$-$C_5$ alkyl, $C_2$-$C_5$ alkenyl, $C_2$-$C_5$ alkynyl, $C_6$-$C_{10}$ aryl, $C_1$-$C_5$ alkoxycarbonyl, carboxyl, $C_2$-$C_5$ acyl, $C_1$-$C_5$ alkylthio, cyano, nitro, amine and $C_1$-$C_5$ alkylamine; n is an integer from 1 to 5; m is an integer from 1 to 4; p is an integer from 1 to 2; q is an integer from 1 to 3; $R^1$ is selected from the group consisting of hydrogen, $C_1$-$C_5$ alkoxy, $C_1$-$C_5$ alkyl, $C_2$-$C_5$ alkenyl, $C_2$-$C_5$ alkynyl and $C_6$-$C_{10}$ aryl; A and B are each independently selected from the group consisting of hydrogen, $C_1$-$C_{10}$ alkyl, $C_1$-$C_5$alkoxy$C_1$-$C_5$alkyl, $C_6$-$C_{10}$ ary-lalkyloxy$C_1$-$C_5$alkyl, $C_1$-$C_5$alkoxy($C_1$-$C_5$alkoxy)$C_1$-$C_5$alkyl, $C_3$-$C_5$ heterocyclyl, $C_1$-$C_5$ alkylthio$C_1$-$C_5$alkyl and

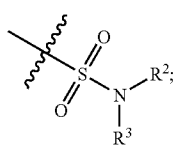

and $R^2$ and $R^3$ are each independently selected from the group consisting of hydrogen, $C_1$-$C_5$ alkyl, $C_3$-$C_8$ cycloalkyl, $C_6$-$C_{10}$ aryl and $C_1$-$C_5$ alkoxycarbonyl.

In one particular embodiment of the present invention, in Chemical formula I, Z is

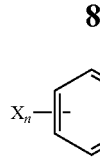

and X and n is the same as defined above.

In one particular embodiment of the present invention, in Chemical formula I, X is F, Br, Cl or I.

In one particular embodiment of the present invention, in Chemical formula I, A and B are each independently selected from the group consisting of hydrogen, $C_1$-$C_{10}$ alkyl, $C_1$-$C_5$alkoxy$C_1$-$C_5$alkyl, $C_6$-$C_{10}$ aryloxy$C_1$-$C_5$alkyl, $C_1$-$C_5$alkoxy($C_1$-$C_5$alkoxy)$C_1$-$C_5$ alkyl, $C_3$-$C_5$ heterocyclyl, $C_1$-$C_5$alkylthio$C_1$-$C_5$alkyl and

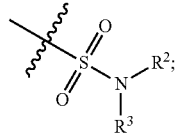

and $R^2$ and $R^3$ are the same as defined above.

In a preferred embodiment of the present invention, in Chemical formula I, at least one of A and B is at least one of A and B is

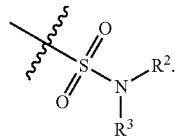

In one particular embodiment of the present invention, in Chemical formula I, A and B are each independently selected from the group consisting of hydrogen, $C_1$-$C_{10}$ alkyl, methoxymethyl (MOM), methoxyethoxymethyl (MEM), ethoxyethyl (EE), tetrahydropyranyl (THP) methylthiomethyl (MTM) and benzyloxymethyl (BOM) and

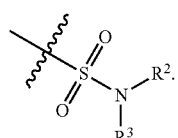

In a preferred embodiment of the present invention, in Chemical formula I,
Z is

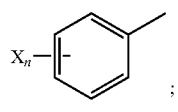

X is F, Br, Cl or I; n is an integer from 1 to 5; $R^1$ is selected from the group consisting of hydrogen, methoxy, ethoxy, propoxy, butoxy, methyl, ethyl, propyl, isopropyl, sec-butyl and t-butyl; A and B are each independently selected from the group consisting of hydrogen, methyl, ethyl, propyl, isopropyl, sec-butyl, t-butyl, methoxymethyl (MOM), methoxyethoxymethyl (MEM), ethoxyethyl (EE), tetrahydropyranyl (THP) methylthiomethyl (MTM), benzyloxymethyl (BOM) and

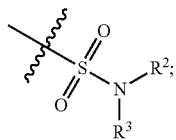

and R² and R³ are each independently selected from the group consisting of halogen, hydrogen, methyl, ethyl, propyl, isopropyl, sec-butyl or t-butyl, cyclopropyl, cyclohexyl, bicycloheptyl, phenyl and benzyl.

In one embodiment of the present invention, the compound of Chemical formula I may be selected from the group consisting of:

(1) (1S, 2S)-1-(2-chlorophenyl)-10-hydroxypropan-2-yl sulfamate
(2) (1R, 2R)-1-(2-chlorophenyl)-1-hydroxypropan-2-yl sulfamate
(3) (1S, 2S)-1-(2,4-dichlorophenyl)-1-hydroxypropan-2-yl sulfamate
(4) (1R, 2R)-1-(2,4-dichlorophenyl)-1-hydroxypropan-2-yl sulfamate
(5) (1S, 2S)-1-(3,4-dichlorophenyl)-1-hydroxypropan-2-yl sulfamate
(6) (1R, 2R)-1-(3,4-dichlorophenyl)-1-hydroxypropan-2-yl sulfamate
(7) (1S, 2S)-1-(2, 6-dichlorophenyl)-1-hydroxypropan-2-yl sulfamate
(8) (1R, 2R)-1-(2, 6-dichlorophenyl)-1-hydroxypropan-2-yl sulfamate
(9) (1S, 2S)-1-(2,3-dichlorophenyl)-1-hydroxypropan-2-yl sulfamate
(10) (1R, 2R)-1-(2,3-dichlorophenyl)-1-hydroxypropan-2-yl sulfamate
(11) (1S, 2S)-1-(2-chlorophenyl)-1-hydroxybutan-2-yl sulfamate
(12) (1R, 2R)-1-(2-chlorophenyl)-1-hydroxybutan-2-yl sulfamate
(13) (1S, 2S)-1-(2-chlorophenyl)-1-hydroxy-3-methylbutan-2-yl sulfamate
(14) (1R, 2R)-1-(2-chlorophenyl)-1-hydroxy-3-methylbutan-2-yl sulfamate
(15) (1S, 2S)-1-(2-chlorophenyl)-1-hydroxypentan-2-yl sulfamate
(16) (1R, 2R)-1-(2-chlorophenyl)-1-hydroxypentan-2-yl sulfamate
(17) (1S, 2S)-1-(2-fluorophenyl)-1-hydroxypropan-2-yl sulfamate
(18) (1R, 2R)-1-(2-fluorophenyl)-1-hydroxypropan-2-yl sulfamate
(19) (1S, 2S)-1-(2-iodophenyl)-1-hydroxypropan-2-yl sulfamate
(20) (1R, 2R)-1-(2-iodophenyl)-1-hydroxypropan-2-yl sulfamate
(21) (1S, 2S)-1-(2,6-difluorophenyl)-1-hydroxypropan-2-yl sulfamate
(22) (1S, 2S)-1-(2,5-dichlorophenyl)-1-hydroxypropan-2-yl sulfamate
(23) (1R, 2R)-1-(2,5-dichlorophenyl)-1-hydroxypropan-2-yl sulfamate
(24) (1S, 2S)-1-(2-chloro-6-fluorophenyl)-1-hydroxypropan-2-yl sulfamate
(25) (1S, 2S)-1-hydrpxy-1-(3-hydroxyphenyl)propan-2-yl sulfamate
(26) (1S, 2R)-1-(2,6-dichlorophenyl)-1-hydroxypropan-2-yl sulfamate
(27) (1R, 2S)-1-(2,6-dichlorophenyl)-1-hydroxypropan-2-yl sulfamate
(28) (1S, 2S)-1-(2-iodophenyl)-1-hydroxybutan-2-yl sulfamate
(29) (1S, 2S)-1-(2,6-dichlorophenyl)-1-hydroxybutan-2-yl sulfamate
(30) (1R, 2R)-1-(2,6-dichlorophenyl)-1-hydroxybutan-2-yl sulfamate
(31) (1S, 2S)-1-(2,6-dichlorophenyl)-1-hydroxy-3-methylbutan-2-yl sulfamate
(32) (1R, 2R)-1-(2,6-dichlorophenyl)-1-hydroxy-3-methylbutan-2-yl sulfamate
(33) (1S, 2S)-1-(2,6-dichlorophenyl)-1-hydroxyhexan-2-yl sulfamate
(34) (1R, 2R)-1-(2,6-dichlorophenyl)-1-hydroxyhexan-2-yl sulfamate
(35) (1S, 2S)-1-(2-chlorophenyl)-1-hydroxypropan-2-yl methylsulfamate
(36) (1R, 2R)-1-(2-chlorophenyl)-1-hydroxypropan-2-yl methylsulfamate
(37) (1S, 2S)-1-(2-chlorophenyl)-1-hydroxypropan-2-yl isopropylsulfamate
(38) (1R, 2R)-1-(2-chlorophenyl)-1-hydroxypropan-2-yl isopropylsulfamate
(39) (1S, 2S)-1-(2,6-dichlorophenyl)-1-hydroxypropan-2-yl isopropylsulfamate
(40) (1S, 2S)-1-(2-chlorophenyl)-1-hydroxypropan-2-yl cyclopropylsulfamate
(41) (1R, 2R)-1-(2-chlorophenyl)-1-hydroxypropan-2-yl cyclopropylsulfamate
(42) (1S, 2S)-1-(2,6-dichlorophenyl)-1-methoxypropan-2-yl sulfamate
(43) (1R, 2R)-1-(2,6-dichlorophenyl)-1-methoxypropan-2-yl sulfamate
(44) (1S, 2S)-1-(2,6-dichlorophenyl)-1-methoxybutan-2-yl sulfamate
(45) (1R, 2R)-1-(2,6-dichlorophenyl)-1-methoxybutan-2-yl sulfamate
(46) (1S, 2S)-1-(2,6-dichlorophenyl)-1-methoxy-3-methylbutan-2-yl sulfamate
(47) (1R, 2R)-1-(2,6-dichlorophenyl)-1-methoxy-3-methylbutan-2-yl sulfamate
(48) (1S, 2S)-1-(2,6-dichlorophenyl)-1-methoxyhexan-2-yl sulfamate
(49) (1R, 2R)-1-(2,6-dichlorophenyl)-1-methoxyhexan-2-yl sulfamate
(50) (1S, 2S)-1-(2,6-dichlorophenyl)-1-methoxypropan-2-yl isopropylsulfamate
(51) (1S, 2S)-1-(2,4-dichlorophenyl)-1-(methoxymethoxy)propan-2-yl sulfamate
(52) (1R, 2R)-1-(2,4-dichlorophenyl)-1-(methoxymethoxy)propan-2-yl sulfamate
(53) (1S, 2S)-1-(2,3-dichlorophenyl)-1-(methoxymethoxy)propan-2-yl sulfamate
(54) (1R, 2R)-1-(2,3-dichlorophenyl)-1-(methoxymethoxy)propan-2-yl sulfamate
(55) (1S, 2S)-1-(3,4-dichlorophenyl)-1-(methoxymethoxy)propan-2-yl sulfamate
(56) (1R, 2R)-1-(3,4-dichlorophenyl)-1-(methoxymethoxy)propan-2-yl sulfamate
(57) (1S, 2S)-1-(2,6-dichlorophenyl)-1-(methoxymethoxy)propan-2-yl sulfamate

(58) (1R, 2R)-1-(2,6-dichlorophenyl)-1-(methoxymethoxy)propan-2-yl sulfamate
(59) (1S, 2S)-1-(2,5-dichlorophenyl)-1-(methoxymethoxy)propan-2-yl sulfamate
(60) (1R, 2R)-1-(2,5-dichlorophenyl)-1-(methoxymethoxy)propan-2-yl sulfamate
(61) (1S, 2S)-1-(2-chloro-6-fluorophenyl)-1-(methoxymethoxy)propan-2-yl sulfamate
(62) (1S, 2S)-1-(2,6-dichlorophenyl)-1-(methoxymethoxy)propan-2-yl sulfamate
(63) (1S, 2S)-1-(2,6-dichlorophenyl)-1-(methoxymethoxy)butan-2-yl sulfamate
(64) (1R, 2R)-1-(2,6-dichlorophenyl)-1-(methoxymethoxy)butan-2-yl sulfamate
(65) (1S, 2S)-1-(2,6-dichlorophenyl)-1-(methoxymethoxy)-3-methylbutan-2-yl sulfamate
(66) (1R, 2R)-1-(2,6-dichlorophenyl)-1-(methoxymethoxy)-3-methylbutan-2-yl sulfamate
(67) (1S, 2S)-1-(2,6-dichlorophenyl)-1-(methoxymethoxy)hexan-2-yl sulfamate
(68) (1R, 2R)-1-(2,6-dichlorophenyl)-1-(methoxymethoxy)hexan-2-yl sulfamate
(69) (1S, 2S)-1-(2-chlorophenyl)-1-(methoxymethoxy)propan-2-yl sulfamate
(70) (1R, 2R)-1-(2-chlorophenyl)-1-(methoxymethoxy)propan-2-yl sulfamate
(71) (1R, 2R)-1-(2-chlorophenyl)-1-(methoxymethoxy)butan-2-yl sulfamate
(72) (1S, 2S)-1-(2-fluorophenyl)-1-(methoxymethoxy)propan-2-yl sulfamate
(73) (1R, 2R)-1-(2-fluorophenyl)-1-(methoxymethoxy)propan-2-yl sulfamate
(74) (1S, 2S)-1-(2-iodophenyl)-1-(methoxymethoxy)propan-2-yl sulfamate
(75) (1R, 2R) 1-(2-iodophenyl)-1-(methoxymethoxy)propan-2-yl sulfamate
(76) (1S, 2S)-1-(2-chlorophenyl)-1-(methoxymethoxy)propan-2-yl methylsulfamate
(77) (1R, 2R)-1-(2-chlorophenyl)-1-(methoxymethoxy)propan-2-yl methylsulfamate
(78) (1S, 2S)-1-(2-chlorophenyl)-1-(methoxymethoxy)propan-2-yl cyclopropylsulfamate
(79) (1R, 2R)-1-(2-chlorophenyl)-1-(methoxymethoxy)propan-2-yl cyclopropylsulfamate
(80) (1S,2S)-1-(2,6-dichlorophenyl)-1-(methoxymethoxy)propan-2-yl isopropylsulfamate
(81) (1S,2S)-1-(2-chlorophenyl)-1-(methoxymethoxy)propan-2-yl isopropylsulfamate
(82) (1R, 2R)-1-(2-chlorophenyl)-1-(methoxymethoxy)propan-2-yl isopropylsulfamate
(83) (1R, 2R)-1-(2,6-dichlorophenyl)-2-hydroxypropyl sulfamate
(84) (1S, 2S)-1-(2-chlorophenyl)propane-1,2-diyl bis(sulfamate)
(85) (1R, 2R)-1-(2-chlorophenyl)propane-1,2-diyl bis(sulfamate)
(86) (1S, 2S)-1-(2-chlorophenyl)butane-1,2-diyl bis(sulfamate)
(87) (1R, 2R)-1-(2-chlorophenyl)butane-1,2-diyl bis(sulfamate)
(88) (1S, 2S)-1-(2-chlorophenyl)-3-methylbutane-1,2-diyl bis(sulfamate)
(89) (1R, 2R)-1-(2-chlorophenyl)-3-methylbutane-1,2-diyl bis(sulfamate)
(90) (1S, 2S)-1-(2-chlorophenyl)pentane-1,2-diyl bis(sulfamate)
(91) (1R, 2R)-1-(2-chlorophenyl)pentane-1,2-diyl bis(sulfamate)
(92) (1S,2S)-1-(2-iodophenyl)-1-methoxypropan-2-yl sulfamate
(93) (1S, 2S)-1-(2,6-dichlorophenyl)-2-hydroxypropyl sulfamate
(94) (1R,2R)-1-(2,6-dichlorophenyl)-1-methoxypropan-2-yl cyclopropylsulfamate
(95) (1R,2R)-1-(2,6-dichlorophenyl)-1-methoxypropan-2-yl methylsulfamate
(96) (1R,2R)-1-(2,6-dichlorophenyl)-1-hydroxypropan-2-yl methylsulfamate
(97) (1S,2S)-1-(2-chlorophenyl)-1-methoxypropan-2-yl sulfamate
(98) (1R,2R)-1-hydroxy-1-(pyridin-2-yl)propan-2-yl sulfamate
(99) (1R,2R)-1-(3,5-dichloropyridin-4-yl)-1-(methoxymethoxy)propan-2-yl sulfamate
(100) (1R,2R)-1-(3,5-dichloropyridin-4-yl)-1-hydroxypropan-2-yl sulfamate
(101) (1R,2R)-1-(3,5-dichloropyridin-4-yl)-1-methoxypropan-2-yl sulfamate
(102) (1R,2S)-1-(2,4-dichlorothiazol-5-yl)-1-hydroxypropan-2-yl sulfamate
(103) (1R,2S)-1-(2,4-dichlorothiazol-5-yl)-1-(methoxymethoxy)propan-2-yl sulfamate
(104) (1R,2S)-1-hydroxy-1-(4-methylthiazol-5-yl)propan-2-yl sulfamate
(105) (1S,2R)-1-(2,4-dichlorothiazol-5-yl)-1-hydroxypropan-2-yl sulfamate
(106) (1S,2R)-1-methoxy-1-(thiophen-2-yl)propan-2-yl sulfamate In another embodiment of the present invention, there is provided a method of preventing or treating disease comprising administering a therapeutically effective amount of the compound having the formula 1 or a pharmaceutically acceptable salt thereof as an active ingredient, to a subject in need of treatment, wherein the disease is CNS disorder.

In one particular embodiment of the present invention, the compound having the formula 1 is in the form of racemate, enantiomer, diastereomer, a mixture of enantiomer, or a mixture of diastereomer.

In one particular embodiment of the present invention, the CNS disorders may include epilepsy or epilepsy-related syndrome, pediatric epilepsy or pediatric epilepsy-related syndrome, memory loss related disease, psychiatric disorder, movement disorder, neurodegenerative disease, Autism spectrum disease, prion disease, stroke, epileptogenesis, cerebral ischemia, myotonia, neonatal cerebral hemorrhage, amy-otrophic lateral sclerosis and so on.

In one particular embodiment of the present invention, the pain is one or more selected from nociceptive pain, psychogenic pain, inflammatory pain, pathological pain, neuropathic pain, cancer pain, postoperative pain, trigeminal neuralgia pain, idiopathic pain, diabetic neuropathic pain, and migraine.

In one particular embodiment of the present invention, the epilepsy is an intractable epilepsy.

In one particular embodiment of the present invention, wherein the intractable epilepsy is selected from the group consisting of the group consisting of localization-related epilepsy, generalized epilepsy and syndromes thereof.

In one particular embodiment of the present invention, the localization-related epilepsy is cortical epilepsy or temporal lobe epilepsy.

In one particular embodiment of the present invention, the cortical epilepsy is a frontal lobe epilepsy, parietal lobe epilepsy, or occipital lobe epilepsy.

In one particular embodiment of the present invention, the epilepsy-related syndrome is an epileptic seizure.

In one particular embodiment of the present invention, the epileptic seizure is an intractable localization-related epilepsy, an intractable secondary generalized seizure, an intractable complex partial seizure or an intractable status epilepticus.

In one particular embodiment of the present invention, the memory loss related disease is Alzheimer's disease.

In one particular embodiment of the present invention, the movement disorder may include CBGD (Corticobasal Ganglionic Degeneration) Diskinesia, Dystonia, Tremors, Essential tremor, Parkinsonian tremor, Hereditary spastic paraplegia, Multiple system atrophy, Myoclonus, Parkinson's disease, Progressive supranuclear palsy, Restless legs syndrome, Rett syndrome, Spasticity, Sydenham's chorea, other choreas, Athetosis, Ballism Sterotypy, Tardive dyskinesia/dystonia, Tics, Tourette's syndrome, OPCA (Olivopontocerebellar atrophy), Hemibalisus, Hemi-facial spasm, Wilson's disease, Stiff man syndrome, Akinetic mutism, Psychomotor retardation, Painful legs moving toes syndrome, A gait disorder, Drug induced movement disorder.

In one particular embodiment of the present invention, the pediatric epilepsy or pediatric epilepsy-related syndrome is selected from the group consisting of Benign Myoclonic Epilepsy (BME), Severe Myoclonic Epilepsy of Infancy Borderland (SMEB), Severe Infantile Multifocal Epilepsy (SIMFE), and Intractable Childhood Epilepsy with Generalized Tonic Clonic Seizures (ICE-GTC), Dravet syndrome (Ds), Severe Myoclonic Epilepsy of Infancy (SMEI), Benign neonatal convulsions, Benign neonatal familial convulsions, Miscellaneous neonatal seizures, Febrile seizures, Early infantile epileptic encephalopathy, Early myoclonic encephalopathy, Infantile spasm, West syndromes, Severe myoclonic epilepsy of infancy, Benign myoclonic epilepsy of infancy, Benign partial epilepsy of infancy, Benign infantile familial convulsion, Symptomatic/cryptogenic partial epilepsies, Epilepsy with myoclonic absences, Lennox-Gastaut syndrome, Epilepsy with myoclonic-astatic seizures (Doose syndrome), Acquired epileptic aphasia (Landaw-Kleffner syndrome), Epilepsy with continuous spike-wave during low-wave sleep, Epilepsy with gastric seizures and hy-pothalamic hamartoma, Symptomatic/cryptogenic partial epilepsies and Childhood absence epilepsy.

In one particular embodiment of the present invention, the psychiatric disorder may include depressive disorder, bipolar disorder, anxiety disorder, mania, cocaine abuse, and so on.

In one particular embodiment of the present invention, the neurodegenerative disease may include Huntington's disease, Pick's disease, Diffuse Lewy body disease, Drug intoxication or withdrawal, Steel-Richardson syndrome, Shy-Drager syndrome, Cortical basal degeneration, Subacute sclerosing panencephalitis, Synucleinopathies, Primary progressive aphasia, Striatonigral degeneration, Machado-Joseph disease, Spinocerebellar ataxia, Olivopontocerebellar degenerations, Macular degeneration, Bulbar and Pseudobulbar palsy, Spinal and Spinobulbar muscular atrophy, Systemic lupus erythematosus, Primary lateral sclerosis, Familial spastic paraplegia, Werdnig-Hoffmann disease, Kugelberg-Welander disease, Tay-Sach's disease, Sandhoff disease, Familial spastic disease, Wohlfart-Kugelberg-Welander disease, Spastic paraparesis, Progressive multifocal leuko-encephalopathy, Familial dysautonomia and so on.

In one particular embodiment of the present invention, the stroke may include ischemic stroke or a hemorrhagic stroke and so on.

In one particular embodiment of the present invention, the Autism spectrum disease may include Autism, Asperger syndrome, PDD-NOS (Pervasive Developmental Disorder) and so on.

In one particular embodiment of the present invention, the prion disease may include Creutzfeldt-Jakob disease, Gerstmann-Straussler-Scheinker disease, Kuru disease, Fatal familial insomnia and so on.

In other embodiment of the present invention, a pharmaceutical composition comprising a therapeutically effective amount of the compound having the formula 1 or a pharmaceutically acceptable salt thereof as an active ingredient.

Advantageous Effects of Invention

The present invention provides a compound for treating or preventing CNS disorders and/or pain containing a sulfamate derivative compound and/or pharmaceutically acceptable salt thereof as an active ingredient.

Furthermore, the present invention provides a method for treatment or prevention of CNS disorders and/or pain comprising administering a sulfamate derivative compound in a pharmaceutically effective amount to a subject in need of treatment or prevention of CNS disorders like epilepsy and/or pain.

BRIEF DESCRIPTION OF DRAWINGS

FIG. 1 illustrates the number of cells in the region of interest (dorsal hippocampus—CA1, CA3, DG) in the Neuroprotection SE Model test.

FIG. 2 illustrates an effect of suppressing spasm in a rat model of symptomatic infantile spasms.

MODE FOR THE INVENTION

The sulfamate derivative compound of the present invention having the formula 1 may be prepared by the following reaction schemes

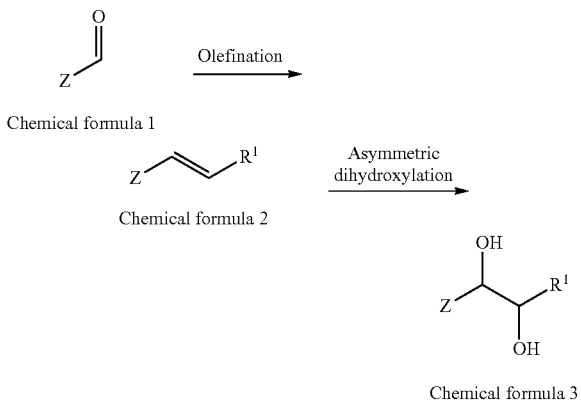

Trans-Olefin compound (Chemical formula 1) is synthesized by using Olefination reagent in various Aldehyde compounds (Chemical formula 1). Diol compound (Chemical formula 3) may be synthesized herein by asymmetric dihydroxylation. $R^1$ is hydrogen, $C_1$-$C_5$ alkoxy, $C_1$-$C_5$ alkyl, $C_2$-$C_5$ alkenyl, $C_2$-$C_5$ alkynyl and $C_6$-$C_{10}$ aryl and preferably $C_1$-$C_{10}$ alkyl.

[Reaction scheme 2] Synthesis of Intermediate & sulfonamide compound

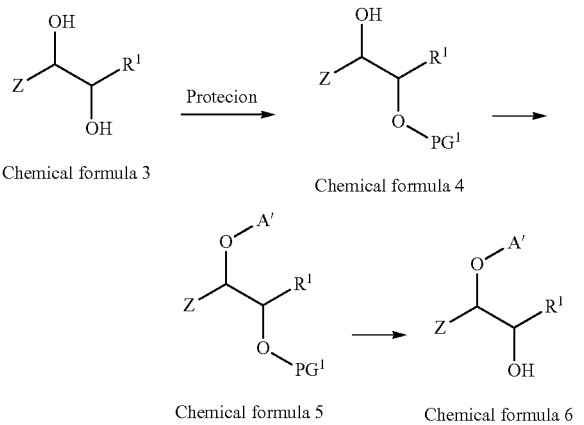

The regioselective protection group adopted Chemical formula 4 in one side of OH may be synthesized by using the steric hindrance of diol compound (Chemical formula 3). The examples of the protecting groups used herein are Bn (benxyl), Trityl(Triphenylmethyl), Acetyl, Benzoyl, Piv (Pivaloyl), MOM (Methoxymethyl), TMS (Trimethyl silyl), TES (Triethyl silyl), TIPS (Triisopropyl silyl), TBDMS (tert-butyldimethyl silyl), TBDPS (tert-butyldiphenyl silyl), and preferably TBDMS (tert-butyldimethyl silyl), TBDPS (tert-butyldiphenyl silyl). A' adopted in-termediate Chemical formula 5 in the other side of OH may be obtained by using various coupling reactions for Chemical formula 4, and A' adopted Chemical formula 6 may be synthesized by deprotecting group reaction. Herein, A may indicate hydrogen, $C_1$-$C_{10}$ alkyl, $C_1$-$C_5$alkoxy$C_1$-$C_5$alkyl, $C_6$-$C_{10}$arylalkyloxy$C_1$-$C_4$alkyl, $C_1$-$C_5$alkoxy($C_1$-$C_5$ alkoxy) $C_1$-$C_5$alkyl, $C_3$-$C_5$ heterocyclyl, $C_1$-$C_5$alkylthio$C_1$-$C_5$alkyl or

[Reaction scheme 3] Synthesis of sulfonamide compound

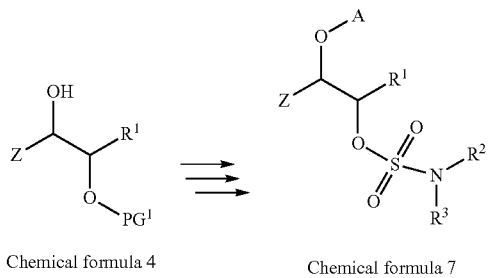

such as $S(=O)_2NH_2$ and so on.

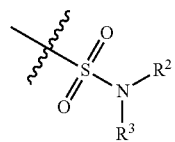

Chemical formula 7 may be synthesized by processing deprotecting group reaction through getting rid of the protecting group (PG1) after adopting A in the other side of OH on compound (Chemical formula 4) in which protecting group is regioselectively substituent in one side of OH of diol compound, and the introductory reaction of Sul-fornamied.

[Reaction scheme 4] Synthesis of sulfonamide compound

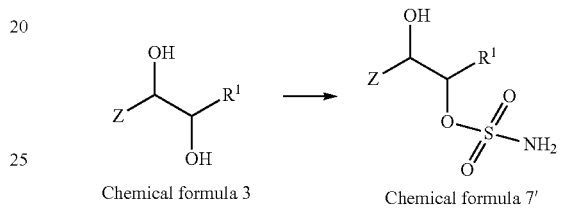

Sulfornamide compound (Chemical formula 7) may be synthesized by getting rid of Boc after reacting Cl—$SO_2$—NHBoc in the one side of OH using steric hindrance of diol compound (Chemical formula 3).

PREPARATION EXAMPLE 1

(E)-1-chloro-2-(prop-1-en-1-yl)Benzene

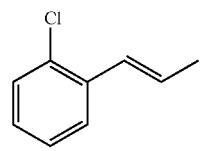

To a stirred solution of 2-chlorobenzaldehyde (48.0 mL, 420 mmol) and 3-pentanone (49.7 mL, 470 mmol) in hexane (600 mL) was heated to reflux then dropwise added $BF_3$·$OEt_2$ (53.6 mL, 420 mmol) at 65° C. then stirred under reflux conditions. When the reaction was completed, water was added thereto. After layer separation, the obtained organic layer was washed twice with 1M sodium hydroxide solution (1M NaOH), and then the separated organic layer was washed with water. The separated organic layer was dehydrated with anhydrous magnesium sulfate ($MgSO_4$) and concentrated. The concentrated residue was purified by a silica gel column chromatography to produce the title compound (38.0 g, yield 58%).

$^1$H NMR (400 MHz, $CDCl_3$) δ 1.94 (d, J=4.8 Hz, 3H), 6.24-6.30 (m, 1H), 6.78 (d, J=14.0 Hz, 1H), 7.11-7.51 (m, 4H).

PREPARATION EXAMPLE 2

(E)-2,4-dichloro-1-(prop-1-en-1-yl)benzene

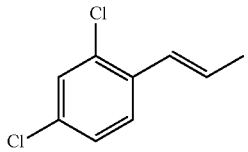

The substantially same method as described in preparation example 1 was conducted, except that 2,4-dichlorobenzaldehyde was used instead of 2-chlorobenzaldehyde, to obtain the title compound (2.4 g, yield 57%).

$^1$H NMR (400 MHz, CDCl$_3$) δ 1.95 (dd, J=6.8, 1.6 Hz, 3H), 6.24-6.30 (m, 1H), 6.72 (d, J=15.6 Hz, 1H), 7.18-7.44 (m, 3H).

PREPARATION EXAMPLE 3

(E)-1,2-dichloro-4-(prop-1-en-1-yl)benzene

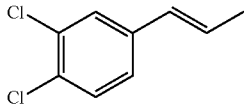

The substantially same method as described in preparation example 1 was conducted, except that 3,4-dichlorobenzaldehyde was used instead of 2-chlorobenzaldehyde, to obtain the title compound (1.2 g, yield 57%).

$^1$H NMR (400 MHz, CDCl$_3$) δ 1.86-1.89 (m, 3H), 6.19-6.34 (m, 2H), 7.10-7.15 (m, 1H), 7.33-7.40 (m, 2H).

PREPARATION EXAMPLE 4

5-(ethylsulfonyl)-1-phenyl-1H-tetrazole

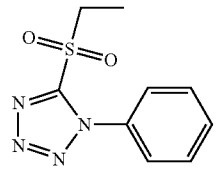

To a stirred solution of 5-mercapto-1-phenyl-1H-tetrazole (300.0 g, 1.68 mol) in EtOH (2.4 L) was added KOH (99.17 g, 1.77 mol) and bromoethane (131.9 mL, 1.77 mol) then heated to reflux. When the reaction was complete, the resulting mixture was cooled to room temperature, removed the solvent, diluted with EtOAc, washed with water and brine, dried over Na$_2$SO$_4$, filtered, and concentrated under reduced pressure to to produce the title compound (347.2 g, 100%). To a stirred solution of an above crude product (100.0 g, 484.80 mmol) in acetonitrile (1.4 L) was added urea-hydrogen peroxide (273.63 g, 2.91 mol) and phthalic anhydride (215.43 g, 1.45 mol) at room temperature then stirred for 12 h. When the reaction was complete, the resulting mixture was filtered. The filtrate was diluted EtOAc, washed with sat. NaHCO$_3$ and water, dried over Na$_2$SO$_4$, filtered, and concentrated under reduced pressure. The crude product was precipitated with EtOAc:Hex (=1:5 v/v) to produce the title compound (101.0 g, yield 87%).

$^1$H NMR (400 MHz, CDCl$_3$) δ 1.52 (t, J=7.4 Hz, 3H), 3.75 (q, J=7.4 Hz, 2H), 7.55-7.64 (m, 3H), 7.65-7.71 (m, 2H).

PREPARATION EXAMPLE 5

(E)-1,3-dichloro-2-(prop-1-en-1-yl)benzene

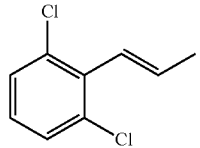

To a stirred solution of 2,6-dichlorobenzaldehyde (100.0 g, 571.40 mmol) and 5-(ethylsulfonyl)-1-phenyl-1H-tetrazole (Preparation example 4, 204.22 g, 857.09 mmol) in THF (800 mL) was dropwise added t-BuOK solution (1.0 M in THF, 799.95 mL) over a period of 1 h at −15--10° C. (maintained below −10° C.). When the reaction was complete, the resulting mixture was quenched with water, diluted with hexane, washed with brine, dried over Na$_2$SO$_4$, filtered, and concentrated under reduced pressure. The crude product was purified by silica gel column chromatography to produce the title compound (60.9 g, yield 57%).

$^1$H NMR (400 MHz, CDCl$_3$) δ 1.98 (dd, J=6.4, 1.6 Hz, 3H), 6.22-6.31 (m, 1H), 6.40 (dd, J=16.0, 1.6 Hz, 1H), 7.07 (t, J=8.0 Hz, 1H), 7.31 (d, J=8.0 Hz, 2 H).

PREPARATION EXAMPLE 6

(E)-1,2-dichloro-3-(prop-1-en-1-yl)benzene

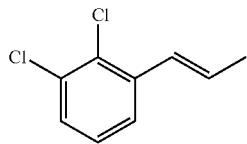

The substantially same method as described in preparation example 1 was conducted, except that 2,3-dichlorobenzaldehyde was used instead of 2-chlorobenzaldehyde, to obtain the title compound (1.2 g, yield 40%).

$^1$H NMR (400 MHz, CDCl$_3$) δ 1.94 (d, J=4.8 Hz, 3H), 6.24-6.30 (m, 1H), 6.78 (d, J=14.0 Hz, 1H), 7.11-7.51 (m, 3H).

PREPARATION EXAMPLE 7

(E)-1-(but-1-en-1-yl)-2-chlorobenzene

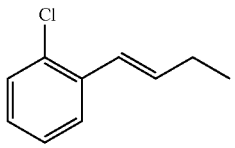

The substantially same method as described in preparation example 1 was conducted, except that 4-heptanone was used instead of 3-pentanone, to obtain the title compound (2.9 g, yield 83%).

$^1$H NMR (400 MHz, CDCl$_3$) δ 1.14 (d, J=7.6 Hz, 3H), 2.29-2.33 (m, 2H), 6.28 (dt, J=16.0, 6.4 Hz, 1H), 6.78 (d, J=15.6 Hz, 1H), 7.13-7.54 (m, 4H).

PREPARATION EXAMPLE 8

(E)-1-chloro-2-(3-methylbut-1-en-1-yl)benzene

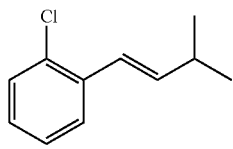

The substantially same method as described in preparation example 1 was conducted, except that 2,6-dimethylheptan-4-one was used instead of 3-pentanone, to obtain the title compound (8.0 g, yield 50%).

$^1$H NMR (400 MHz, CDCl$_3$) δ 1.14 (d, J=6.8 Hz, 6H), 2.25-2.57 (m, 1H), 6.20 (dd, J=16.0, 7.2 Hz, 1H), 7.64 (d, J=16.0 Hz, 1H), 7.12-7.54 (m, 4H).

PREPARATION EXAMPLE 9

(E)-1-chloro-2-(pent-1-en-1-yl)benzene

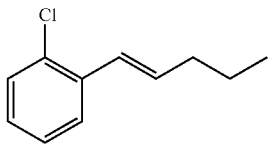

The substantially same method as described in preparation example 1 was conducted, except that 5-nonanone was used instead of 3-pentanone, to obtain the title compound (3.2 g, yield 50%).

$^1$H NMR (400 MHz, CDCl$_3$) δ 0.89 (t, J=7.0 Hz, 3H), 1.59-2.01 (m, 4H), 6.47 (dt, J=16.9, 6.9 Hz, 1H), 6.55 (d, J=16.9 Hz, 1H), 7.03-7.21 (m, 2H), 7.32-7.44 (m, 2H).

PREPARATION EXAMPLE 10

1-(2-fluorophenyl)-trans-1-propene

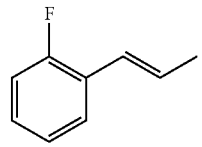

The substantially same method as described in preparation example 1 was conducted, except that 2-fluorobenzaldehyde was used instead of 2-chlorobenzaldehyde, to obtain the title compound (6.67 g, yield 61%).

$^1$H NMR (400 MHz, CDCl$_3$) δ 1.94 (d, J=6.8 Hz, 3H), 6.30-6.38 (m, 1H), 6.57 (d, J=16.0 Hz, 1H), 7.00-7.41 (m, 4H).

PREPARATION EXAMPLE 11

1-(2-iodophenyl)-trans-1-propene

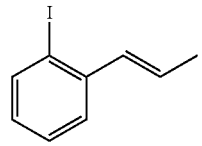

The substantially same method as described in preparation example 1 was conducted, except that 2-iodobenzaldehyde was used instead of 2-chlorobenzaldehyde, to obtain the title compound (3.4 g, yield 65%).

$^1$H NMR (400 MHz, CDCl$_3$) δ 1.95 (dd, J=6.8 Hz, 1.6, 3H), 6.09-6.18 (m, 1H), 6.60 (dd, J=15.7, 1.8 Hz, 1H), 6.89-7.84 (m, 4H).

PREPARATION EXAMPLE 12

1-(2,6-difluorophenyl)-trans-1-propene

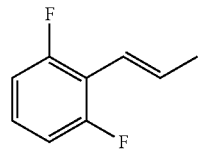

The substantially same method as described in preparation example 1 was conducted, except that 2,6-difluorobenzaldehyde was used instead of 2-chlorobenzaldehyde, to obtain the title compound (3.4 g, yield 52%).

$^1$H NMR (400 MHz, CDCl$_3$) δ 1.95 (dd, J=6.8, 1.6 Hz, 3H), 6.24 (m, 1H), 6.72 (d, J=15.6 Hz, 1H), 7.18-7.44 (m, 3H).

PREPARATION EXAMPLE 13

1-(2,5-dichlorophenyl)-trans-1-propene

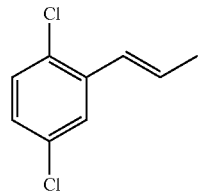

The substantially same method as described in preparation example 1 was conducted, except that 2,5-dichlorobenzaldehyde was used instead of 2-chlorobenzaldehyde, to obtain the title compound (3.1 g, yield 52%).

$^1$H NMR (400 MHz, CDCl$_3$) δ 1.95 (dd, J=6.8, 1.6 Hz, 3H), 6.24-6.26 (m, 1H), 6.72 (d, J=15.6 Hz, 1H), 7.09-7.25 (m, 3H).

PREPARATION EXAMPLE 14

(E)-1-chloro-3-fluoro-2-(prop-1-en-1-yl)benzene

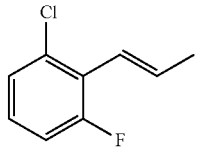

The substantially same method as described in preparation example 1 was conducted, except that 2-chloro-6-fluorobenzaldehyde was used instead of 2-chlorobenzaldehyde, to obtain the title compound (0.8 g, yield 42%).

$^1$H NMR (400 MHz, CDCl$_3$) δ 1.98 (dd, J=6.4, 1.6 Hz, 3H), 5.88-5.93 (m, 1H), 6.21-6.33 (m, 1H), 7.07 (t, J=8.0 Hz, 1H), 7.31 (d, J=8.0 Hz, 2 H).

PREPARATION EXAMPLE 15

3-(benzyloxy)benzaldehyde

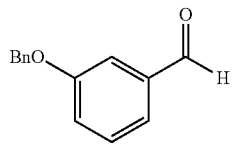

To a stirred solution of 3-hydroxybenzaldehyde (10.0 g, 81.88 mmol) in acetonitrile (130 mL) was added potassium carbonate (13.6 g, 98.26 mmol) and benzyl bromide (14.7 mL, 85.98 mmol) then heated to reflux. When the reaction was completed, the resulting mixture was cooled to room temperature, filtered through Celite and then concentrated under reduced pressure, to obtain the title compound (15.6 g, yield 90%).

$^1$H NMR (400 MHz, CDCl$_3$) δ 5.33 (s, 2H), 7.27-7.30 (m, 2H), 7.35-7.54 (m, 7H), 10.03 (s, 1H).

PREPARATION EXAMPLE 16

(E)-1-(benzyloxy)-3-(prop-1-en-1-yl)benzene

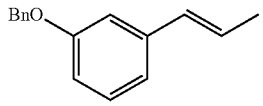 [SMILES: C/C=C/c1cccc(OCc2ccccc2)c1]

The substantially same method as described in preparation example 5 was conducted, except that 3-(benzyloxy)benzaldehyde was used instead of 2,6-dichlorobenzaldehyde, to obtain the title compound (1.22 g, yield 40%).

$^1$H NMR (400 MHz, CDCl$_3$) δ 1.90 (dd, J=6.4, 1.6 Hz, 3H), 5.10 (s, 2H), 6.21-6.30 (m, 1H), 6.39 (dd, J=15.6, 1.6 Hz, 1H), 6.83-7.03 (m, 3H), 7.20-7.54 (m, 6H).

PREPARATION EXAMPLE 17

1-(2-iodophenyl)-trans-1-butene

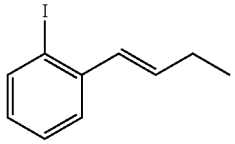

The substantially same method as described in preparation example 1 was conducted, except that 2-iodobenzaldehyde and 4-heptanone were used instead of 2-chlorobenzaldehyde and 3-pentanone, to obtain the title compound (8.5 g, yield 75%).

$^1$H NMR (400 MHz, CDCl$_3$) δ 1.46 (t, J=7.6 Hz, 3H), 2.26-2.34 (m, 2H), 6.17 (dt, J=15.6, 6.6 Hz, 1H), 6.57 (d, J=15.6 Hz, 1H), 6.89-7.85 (m, 4H).

PREPARATION EXAMPLE 18

(E)-2-(but-1-en-1-yl)-1,3-dichlorobenzene

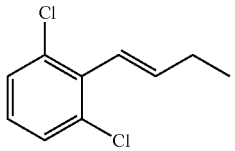

The substantially same method as described in preparation example 1 was conducted, except that 2,6-dichlorobenzaldehyde and 4-heptanone were used instead of 2-chlorobenzaldehyde and 3-pentanone, to obtain the title compound (12.25 g, yield 36%).

$^1$H NMR (400 MHz, CDCl$_3$) δ 1.16 (t, J=8.4 Hz, 3H), 2.28-2.36 (m, 2H), 6.24-6.38 (m, 2H), 7.07 (t, J=8.0 Hz, 1H), 7.31 (d, J=8.0 Hz, 2H).

PREPARATION EXAMPLE 19

1-(2,6-dichlorophenyl)-3-methyl-trans-1-butene

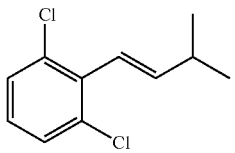

The substantially same method as described in preparation example 1 was conducted, except that 2,6-dichlorobenzaldehyde and 2,6-dimethyl-heptan-4-one were used instead of 2-chlorobenzaldehyde and 3-pentanone, to obtain the title compound (0.23 g, yield 40%).

$^1$H NMR (400 MHz, CDCl$_3$) δ 1.15 (d, J=6.8 Hz, 6H), 2.53-2.58 (m, 1H), 6.19 (dd, J=16.4, 6.8 Hz, 1H), 6.31 (d, J=16.4 Hz, 1H), 7.05-7.32 (m, 3H).

PREPARATION EXAMPLE 20

1-(2,6-dichlorophenyl)-trans-1-hexene

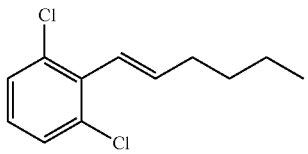

The substantially same method as described in preparation example 1 was conducted, except that 2,6-dichlorobenzaldehyde and 6-undecanone were used instead of 2-chlorobenzaldehyde and 3-pentanone, to obtain the title compound (0.2 g, yield 40%).
$^1$H NMR (400 MHz, CDCl$_3$) δ 0.99 (t, J=7.2 Hz, 3H), 1.14-1.59 (m, 4H), 2.30-2.36 (m, 2H), 6.24 (dt, J=16.0 6.6 Hz, 1H), 6.38 (d, J=16.4 Hz, 1H), 7.05-7.33 (m, 3H).

PREPARATION EXAMPLE 21

(1S,2S)-1-(2-chlorophenyl)propane-1,2-diol

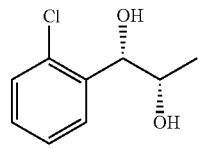

A 2000 mL round-bottomed flask, equipped with a magnetic stirrer, was filled with 440 mL of tert-butyl alcohol, 440 mL of water, K$_3$Fe(CN)$_6$ (226.76 g, 687.98 mmol), K$_2$CO$_3$ (95.09 g, 687.98 mmol), (DHQ)$_2$-PHAL (1.79 g, 2.29 mmol), K$_2$OsO$_2$(OH)$_4$ (0.17 g, 0.46 mmol), and methanesulfonamide (21.81 g, 229.33 mmol). The mixture was stirred for 1 h at 0° C. 1-(2-chlorophenyl)-trans-1-propene (Preparation example 1, 35.0 g, 229.33 mmol) was added at once and the mixture was stirred vigorously for 14 h. When the reaction was completed, the resulting mixture was added solid Na$_2$SO$_3$ (289.05 g, 2293.3 mmol), water, and EtOAc then stirred for 1 h at room temperature. The organic layer was washed with 2N KOH and water, dried over Na$_2$SO$_4$, filtered, and concentrated under reduced pressure. The crude product was purified by silica gel column chromatography to produce the title compound (29.86 g, yield 70%).
$^1$H NMR (400 MHz, CDCl$_3$) δ 1.20 (d, J=6.4 Hz, 3H), 2.48 (d, J=4.0 Hz, 1H), 2.92 (d, J=4.4 Hz, 1H), 3.93-3.97 (m, 1H), 4.97 (t, J=4.8 Hz, 1H), 7.22-7.51 (m, 4H).

PREPARATION EXAMPLE 22

(1R,2R)-1-(2-chlorophenyl)propane-1,2-diol

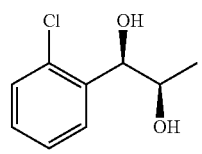

The substantially same method as described in preparation example 21 was conducted, except that (DHQD)$_2$-PHAL was used instead of (DHQ)$_2$-PHAL, to obtain the title compound (2.96 g, yield 72%).
$^1$H NMR (400 MHz, CDCl$_3$) δ 1.20 (d, J=6.4 Hz, 3H), 2.48 (d, J=4.0 Hz, 1H), 2.92 (d, J=4.4 Hz, 1H), 3.93-3.97 (m, 1H), 4.97 (t, J=4.8 Hz, 1H), 7.22-7.51 (m, 4H).

PREPARATION EXAMPLE 23

1-(2,4-dichlorophenyl)-(S,S)-1,2-propanediol

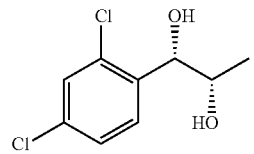

The substantially same method as described in preparation example 21 was conducted, except that (E)-2,4-dichloro-1-(prop-1-en-1-yl)benzene (Preparation example 2) was used instead of 1-(2-chlorophenyl)-trans-1-propene (Preparation example 1), to obtain the title compound (0.33 g, yield 60%).
$^1$H NMR (400 MHz, CDCl$_3$) δ 1.22 (d, J=6.4 Hz, 3H), 2.10 (d, J=4.4 Hz, 1H), 2.71 (d, J=4.8 Hz, 1H), 3.90-3.95 (m, 1H), 4.94 (t, J=5.0 Hz, 1H), 7.31 (dd, J=2.0, 8.0 Hz, 1H), 7.40 (d, J=2.0 Hz, 1H), 7.49 (d, J=8.4 Hz, 1H).

PREPARATION EXAMPLE 24

1-(2,4-dichlorophenyl)-(R,R)-1,2-propanediol

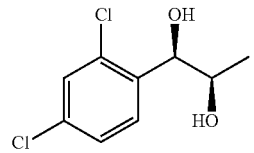

The substantially same method as described in preparation example 21 was conducted, except that (E)-2,4-dichloro-1-(prop-1-en-1-yl)benzene (Preparation example 2) and (DHQD)$_2$-PHAL were used instead of 1-(2-chlorophenyl)-trans-1-propene (Preparation example 1) and (DHQ)$_2$-PHAL, to obtain the title compound (0.45 g, yield 60%).
$^1$H NMR (400 MHz, CDCl$_3$) δ 1.22 (d, J=6.4 Hz, 3H), 2.10 (d, J=4.4 Hz, 1H), 2.71 (d, J=4.8 Hz, 1H), 3.90-3.95 (m, 1H), 4.94 (t, J=5.0 Hz, 1H), 7.31 (dd, J=2.0, 8.0 Hz, 1H), 7.40 (d, J=2.0 Hz, 1H), 7.49 (d, J=8.4 Hz, 1H).

PREPARATION EXAMPLE 25

(1S,2S)-1-(3,4-dichlorophenyl)propane-1,2-diol

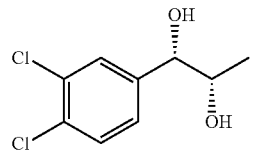

The substantially same method as described in preparation example 21 was conducted, except that (E)-1,2-dichloro-4-(prop-1-en-1-yl)benzene (Preparation example 3) was used instead of 1-(2-chlorophenyl)-trans-1-propene (Preparation example 1), to obtain the title compound (6.50 g, yield 74%).

$^1$H NMR (400 MHz, CDCl$_3$) δ 1.13 (d, J=6.4 Hz, 3H), 2.31 (br s, 1H), 2.76 (br s, 1H), 3.81-3.86 (m, 1H), 4.38-4.40 (m, 1H), 7.21 (dd, J=8.4, 2.0 Hz, 1H), 7.44-7.50 (m, 2H).

PREPARATION EXAMPLE 26

(1R,2R)-1-(3,4-dichlorophenyl)propane-1,2-diol

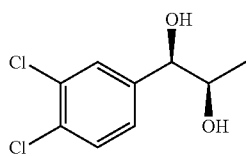

The substantially same method as described in preparation example 21 was conducted, except that (E)-1,2-dichloro-4-(prop-1-en-1-yl)benzene (Preparation example 3) and (DHQD)$_2$-PHAL were used instead of 1-(2-chlorophenyl)-trans-1-propene (Preparation example 1) and (DHQ)$_2$-PHAL, to obtain the title compound (7.35 g, yield 75%).

$^1$H NMR (400 MHz, CDCl$_3$) δ 1.13 (d, J=6.4 Hz, 3H), 2.29 (br s, 1H), 2.77 (br s, 1H), 3.81-3.86 (m, 1H), 4.38-4.40 (m, 1H), 7.21 (dd, J=8.4, 2.0 Hz, 1H), 7.44-7.50 (m, 2H).

PREPARATION EXAMPLE 27

(1S,2S)-1-(2,6-dichlorophenyl)propane-1,2-diol

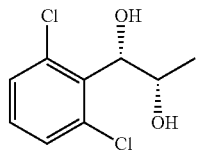

The substantially same method as described in preparation example 21 was conducted, except that (E)-1,3-dichloro-2-(prop-1-en-1-yl)benzene (Preparation example 5) was used instead of 1-(2-chlorophenyl)-trans-1-propene (Preparation example 1), to obtain the title compound (34.4 g, yield 70%).

$^1$H NMR (400 MHz, CDCl$_3$) δ 1.10 (d, J=6.4 Hz, 3H), 2.94 (s, 1H), 3.30 (s, 1H), 4.47-4.54 (m, 1H), 5.24 (d, J=8.0 Hz, 1H), 7.20 (t, J=8.0 Hz, 1H), 7.34 (d, J=8.0 Hz, 2H).

PREPARATION EXAMPLE 28

(1R,2R)-1-(2,6-dichlorophenyl)propane-1,2-diol

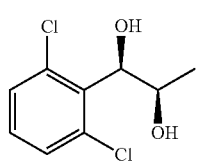

The substantially same method as described in preparation example 21 was conducted, except that (E)-1,3-dichloro-2-(prop-1-en-1-yl)benzene (Preparation example 5) and (DHQD)$_2$-PHAL were used instead of 1-(2-chlorophenyl)-trans-1-propene (Preparation example 1) and (DHQ)$_2$-PHAL, to obtain the title compound (23.54 g, yield 70%).

$^1$H NMR (400 MHz, CDCl$_3$) δ 1.10 (d, J=6.4 Hz, 3H), 2.87 (s, 1H), 3.25 (s, 1H), 4.47-4.54 (m, 1H), 5.24 (d, J=8.0 Hz, 1H), 7.20 (t, J=8.0 Hz, 1H), 7.34 (d, J=8.0 Hz, 2H).

PREPARATION EXAMPLE 29

1-(2,3-dichlorophenyl)-(S,S)-1,2-propanediol

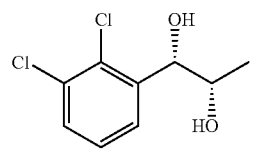

The substantially same method as described in preparation example 21 was conducted, except that (E)-1,2-dichloro-3-(prop-1-en-1-yl)benzene (Preparation example 6) was used instead of 1-(2-chlorophenyl)-trans-1-propene (Preparation example 1), to obtain the title compound (0.9 g, yield 60%).

$^1$H NMR (400 MHz, CDCl$_3$) δ 1.10 (d, J=6.4 Hz, 3H), 2.72 (d, J=2.4 Hz, 1H), 3.10 (d, J=8.4 Hz, 1H), 4.47-4.54 (m, 1H), 5.24 (t, J=8.8 Hz, 1H), 7.18-7.20 (m, 3H).

PREPARATION EXAMPLE 30

1-(2,3-dichlorophenyl)-(R,R)-1,2-propanediol

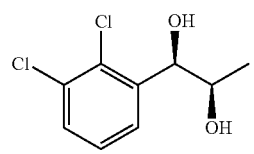

The substantially same method as described in preparation example 21 was conducted, except that (E)-1,2-dichloro-3-(prop-1-en-1-yl)benzene (Preparation example 6) and (DHQD)$_2$-PHAL were used instead of 1-(2-chlorophenyl)-trans-1-propene (Preparation example 1) and (DHQ)$_2$-PHAL, to obtain the title compound (0.84 g, yield 59%).

$^1$H NMR (400 MHz, CDCl$_3$) δ 1.10 (d, J=6.4 Hz, 3H), 2.72 (d, J=2.4 Hz, 1H), 3.10 (d, J=8.4 Hz, 1H), 4.47-4.54 (m, 1H), 5.24 (t, J=8.8 Hz, 1H), 7.18-7.20 (m, 3H).

PREPARATION EXAMPLE 31

1-(2-chlorophenyl)-(S,S)-1,2-butanediol

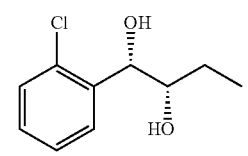

The substantially same method as described in preparation example 21 was conducted, except that (E)-1-(but-1-en-1-yl)-2-chlorobenzene (Preparation example 7) was used instead of 1-(2-chlorophenyl)-trans-1-propene (Preparation example 1), to obtain the title compound (0.36 g, yield 90%).

$^1$H NMR (400 MHz, CDCl$_3$) δ 1.01 (t, J=7.4 Hz, 3H), 1.52-1.65 (m, 2H), 2.01 (d, J=4.4 Hz, 1H), 2.74 (d, J=5.2 Hz, 1H), 3.69-3.75 (m, 1H), 5.05 (t, J=5.0 Hz, 1H), 7.23-7.54 (m, 4H).

PREPARATION EXAMPLE 32

1-(2-chlorophenyl)-(R,R)-1,2-butanediol

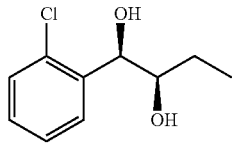

The substantially same method as described in preparation example 21 was conducted, except that (E)-1-(but-1-en-1-yl)-2-chlorobenzene (Preparation example 7) and (DHQD)$_2$-PHAL were used instead of 1-(2-chlorophenyl)-trans-1-propene (Preparation example 1) and (DHQ)$_2$-PHAL, to obtain the title compound (0.84 g, yield 90%).

$^1$H NMR (400 MHz, CDCl$_3$) δ 1.01 (t, J=7.4 Hz, 3H), 1.52-1.65 (m, 2H), 2.01 (d, J=4.4 Hz, 1H), 2.74 (d, J=5.2 Hz, 1H), 3.69-3.75 (m, 1H), 5.05 (t, J=5.0 Hz, 1H), 7.23-7.54 (m, 4H).

PREPARATION EXAMPLE 33

1-(2-chlorophenyl)-3-methyl-(S,S)-1,2-butanediol

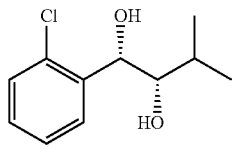

The substantially same method as described in preparation example 21 was conducted, except that (E)-1-chloro-2-(3-methylbut-1-en-1-yl)benzene (Preparation example 8) was used instead of 1-(2-chlorophenyl)-trans-1-propene (Preparation example 1), to obtain the title compound (0.96 g, yield 60%).

$^1$H NMR (400 MHz, CDCl$_3$) δ 1.07 (t, J=7.2 Hz, 6H), 1.83-1.89 (m, 1H), 1.92 (d, J=5.6 Hz, 1H), 2.69 (d, J=6.4 Hz, 1H), 3.53-3.56 (m, 1H), 5.22-5.25 (m, 1H), 7.23-7.55 (m, 4H).

PREPARATION EXAMPLE 34

1-(2-chlorophenyl)-3-methyl-(R,R)-1,2-butanediol

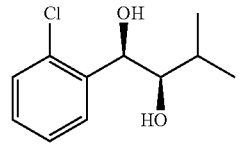

The substantially same method as described in preparation example 21 was conducted, except that (E)-1-chloro-2-(3-methylbut-1-en-1-yl)benzene (Preparation example 8) and (DHQD)$_2$-PHAL were used instead of 1-(2-chlorophenyl)-trans-1-propene (Preparation example 1) and (DHQ)$_2$-PHAL, to obtain the title compound (4.2 g, yield 60%).

$^1$H NMR (400 MHz, CDCl$_3$) δ 1.07 (t, J=7.2 Hz, 6H), 1.83-1.89 (m, 1H), 1.92 (d, J=5.6 Hz, 1H), 2.69 (d, J=6.4 Hz, 1H), 3.53-3.56 (m, 1H), 5.22-5.25 (m, 1H), 7.23-7.55 (m, 4H).

PREPARATION EXAMPLE 35

(1S,2S)-1-(2-chlorophenyl)pentane-1,2-diol

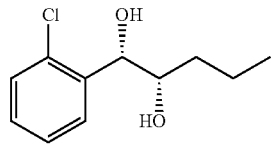

The substantially same method as described in preparation example 21 was conducted, except that (E)-1-chloro-2-(pent-1-en-1-yl)benzene (Preparation example 9) was used instead of 1-(2-chlorophenyl)-trans-1-propene (Preparation example 1), to obtain the title compound (2.1 g, yield 65%).

$^1$H NMR (400 MHz, CDCl$_3$) δ 0.82 (t, J=3.6 Hz, 3H), 1.20-1.32 (m, 2H), 1.34-1.49 (m, 2H), 3.47-3.50 (m, 1H), 4.47 (d, J=6.4 Hz, 1H), 4.76 (d, J=2.8 Hz, 1H), 5.33 (s, 1H), 7.23-7.27 (m, 1H), 7.30-7.39 (m, 2H), 7.55 (d, J=1.6 Hz, 2H).

PREPARATION EXAMPLE 36

(1R,2R)-1-(2-chlorophenyl)pentane-1,2-diol

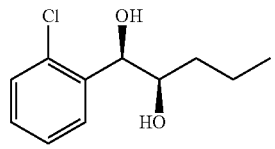

The substantially same method as described in preparation example 21 was conducted, except that (E)-1-chloro-2-(pent-1-en-1-yl)benzene (Preparation example 9) and (DHQD)$_2$-PHAL were used instead of 1-(2-chlorophenyl)- trans-1-propene (Preparation example 1) and (DHQ)₂-PHAL, to obtain the title compound (1.8 g, yield 64%).

¹H NMR (400 MHz, CDCl₃) δ 0.82 (t, J=3.6 Hz, 3H), 1.20-1.32 (m, 2H), 1.34-1.49 (m, 2H), 3.47-3.50 (m, 1H), 4.47 (d, J=6.4 Hz, 1H), 4.76 (d, J=2.8 Hz, 1H), 5.33 (s, 1H), 7.23-7.27 (m, 1H), 7.30-7.39 (m, 2H), 7.55 (d, J=1.6 Hz, 2H).

PREPARATION EXAMPLE 37

1-(2-fluorophenyl)-(S,S)-1,2-propanediol

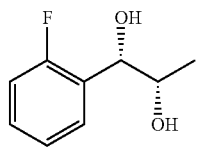

The substantially same method as described in preparation example 21 was conducted, except that 1-(2-fluorophenyl)-trans-1-propene (Preparation example 10) was used instead of 1-(2-chlorophenyl)-trans-1-propene (Preparation example 1), to obtain the title compound (6.46 g, yield 78%).

¹H NMR (400 MHz, CDCl₃) δ 1.15 (d, J=6.4 Hz, 3H), 2.43 (d, J=3.6 Hz, 1H), 2.69 (d, J=4.8 Hz, 1H), 3.90-3.98 (m, 1H), 4.78 (dd, J=7.2, 4.4 Hz, 1H), 7.04-7.50 (m, 4H).

PREPARATION EXAMPLE 38

1-(2-fluorophenyl)-(R,R)-1,2-propanediol

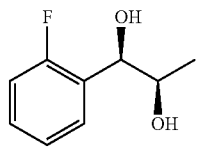

The substantially same method as described in preparation example 21 was conducted, except that 1-(2-fluorophenyl)-trans-1-propene (Preparation example 10) and (DHQD)₂-PHAL were used instead of 1-(2-chlorophenyl)-trans-1-propene (Preparation example 1) and (DHQ)₂-PHAL, to obtain the title compound (3.29 g, yield 79%).

¹H NMR (400 MHz, CDCl₃) δ 1.15 (d, J=6.4 Hz, 3H), 2.43 (d, J=3.6 Hz, 1H), 2.69 (d, J=4.8 Hz, 1H), 3.90-3.98 (m, 1H), 4.78 (dd, J=7.2, 4.4 Hz, 1H), 7.04-7.50 (m, 4H).

PREPARATION EXAMPLE 39

1-(2-iodophenyl)-(S,S)-1,2-propanediol

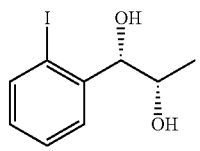

The substantially same method as described in preparation example 21 was conducted, except that 1-(2-iodophenyl)-trans-1-propene (Preparation example 11) was used instead of 1-(2-chlorophenyl)-trans-1-propene (Preparation example 1), to obtain the title compound (3.4 g, yield 88%).

¹H NMR (400 MHz, CDCl₃) δ 1.27 (d, J=6.4 Hz, 3H), 2.26 (br s, 1H), 2.74 (br s, 1H), 3.99 (t, J=6.0 Hz, 1H), 4.81 (d, J=4.0 Hz, 1H), 7.01-7.87 (m, 4H).

PREPARATION EXAMPLE 40

1-(2-iodophenyl)-(R,R)-1,2-propanediol

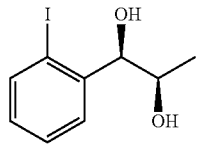

The substantially same method as described in preparation example 21 was conducted, except that 1-(2-iodophenyl)-trans-1-propene (Preparation example 11) and (DHQD)₂-PHAL were used instead of 1-(2-chlorophenyl)-trans-1-propene (Preparation example 1) and (DHQ)₂-PHAL, to obtain the title compound (7.40 g, yield 84%).

¹H NMR (400 MHz, CDCl₃) δ 1.26 (d, J=6.4 Hz, 3H), 2.35 (br s, 1H), 2.85 (d, J=4.0 Hz, 1H), 3.98 (t, J=6.2 Hz, 1H), 4.80 (dd, J=5.0, 4.4 Hz, 1H), 7.00-7.87 (m, 4H).

PREPARATION EXAMPLE 41

1-(2,6-difluorophenyl)-(S,S)-1,2-propanediol

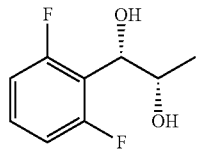

The substantially same method as described in preparation example 21 was conducted, except that 1-(2,6-difluorophenyl)-trans-1-propene (Preparation example 12) was used instead of 1-(2-chlorophenyl)-trans-1-propene (Preparation example 1), to obtain the title compound (1.5 g, yield 60%).

¹H NMR (400 MHz, CDCl₃) δ 1.10 (d, J=6.4 Hz, 3H), 2.72 (d, J=2.4 Hz, 1H), 3.10 (d, J=8.4 Hz, 1H), 4.47-4.54 (m, 1H), 5.24 (t, J=8.8 Hz, 1H), 7.18-7.36 (m, 3H).

PREPARATION EXAMPLE 42

1-(2,5-dichlorophenyl)-(S,S)-1,2-propanediol

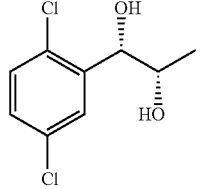

The substantially same method as described in preparation example 21 was conducted, except that 1-(2,5-dichlorophenyl)-trans-1-propene (Preparation example 13) was used instead of 1-(2-chlorophenyl)-trans-1-propene (Preparation example 1), to obtain the title compound (1.9 g, yield 60%).

¹H NMR (400 MHz, CDCl₃) δ 1.10 (d, J=6.4 Hz, 3H), 2.72 (d, J=2.4 Hz, 1H), 3.10 (d, J=8.4 Hz, 1H), 4.47-4.54 (m, 1H), 5.24 (t, J=8.8 Hz, 1H), 7.14-7.26 (m, 3H).

PREPARATION EXAMPLE 43

1-(2,5-dichlorophenyl)-(R,R)-1,2-propanediol

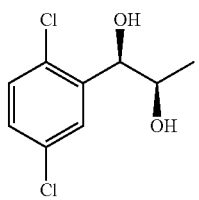

The substantially same method as described in preparation example 21 was conducted, except that 1-(2,5-dichlorophenyl)-trans-1-propene (Preparation example 13) and (DHQD)₂-PHAL were used instead of 1-(2-chlorophenyl)-trans-1-propene (Preparation example 1) and (DHQ)₂-PHAL, to obtain the title compound compound (2.29 g, yield 60%).

¹H NMR (400 MHz, CDCl₃) δ 1.15 (d, J=6.4 Hz, 3H), 3.66 (d, J=9.2 Hz, 1H), 4.73 (br s, 2H), 5.43 (t, J=9.0 Hz, 1H), 5.62-5.69 (m, 1H), 7.18-7.22 (m, 3H).

PREPARATION EXAMPLE 44

(1S,2S)-1-(2-chloro-6-fluorophenyl)propane-1,2-diol

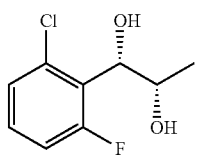

The substantially same method as described in preparation example 21 was conducted, except that (E)-1-chloro-3-fluoro-2-(prop-1-en-1-yl)benzene (Preparation example 14) was used instead of 1-(2-chlorophenyl)-trans-1-propene (Preparation example 1), to obtain the title compound (1.9 g, yield 60%).

¹H NMR (400 MHz, CDCl₃) δ 1.12 (d, J=6.4 Hz, 3H), 2.77 (br s, 1H), 2.94 (br s, 1H), 4.26-4.29 (m, 1H), 5.01 (t, J=7.8 Hz, 1H), 7.01-7.06 (m, 1H), 7.21-7.29 (m, 2H).

PREPARATION EXAMPLE 45

(1S,2S)-1-(3-(benzyloxy)phenyl)propane-1,2-diol

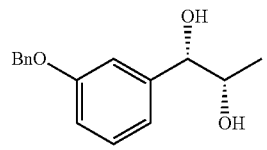 [SMILES: C[C@H](O)[C@@H](O)c1cccc(OCc2ccccc2)c1]

The substantially same method as described in preparation example 21 was conducted, except that (E)-1-(benzyloxy)-3-(prop-1-en-1-yl)benzene (Preparation example 16) was used instead of 1-(2-chlorophenyl)-trans-1-propene (Preparation example 1), to obtain the title compound (1.9 g, yield 60%).

¹H NMR (400 MHz, CDCl₃) δ 1.09 (d, J=6.4 Hz, 3H), 2.43 (s, 1H), 2.60 (s, 1H), 3.86-3.89 (m, 1H), 4.37 (d, J=6.4 Hz, 1H), 5.10 (s, 2H), 6.93-7.02 (m, 3H), 7.27-7.47 (m, 6H).

PREPARATION EXAMPLE 46

(1S,2S)-2-((tert-butyldimethylsilyl)oxy)-1-(2,6-dichlorophenyl)propan-1-ol

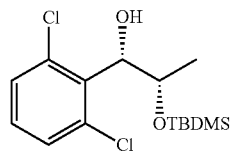 [SMILES: C[C@H](O[Si](C)(C)C(C)(C)C)[C@@H](O)c1c(Cl)cccc1Cl]

To a stirred solution of (1S,2S)-1-(2,6-dichlorophenyl)propane-1,2-diol (Preparation example 27, 8.0 g, 36.19 mmol) in CH₂Cl₂ (80 mL) was added imidazole (2.96 g, 43.42 mmol) at 0° C. then allowed to stir for 30 min. The mixture was added TBDMS-Cl (5.45 g, 36.19 mmol) at 0° C. When the reaction was completed, the resulting mixture was diluted with CH₂Cl₂, washed with water and brine, dried over Na₂SO₄, filtered, and concentrated under reduced pressure. The crude product was purified by silica gel column chromatography to produce the title compound (10.02 g, yield 83%).

¹H NMR (400 MHz, CDCl₃) δ 0.08 (d, J=8.4 Hz, 6H), 0.93 (s, 9H), 1.10 (d, J=6.0 Hz, 3H), 3.05 (d, J=5.2 Hz, 1H), 4.44-4.50 (m, 1H), 5.15-5.20 (m, 1H), 7.11-7.15 (m, 1H), 7.29 (d, J=8.0 Hz, 2H).

PREPARATION EXAMPLE 47

(5S,6S)-5-(2,6-dichlorophenyl)-6,8,8,9,9-pentamethyl-2,4,7-trioxa-8-siladecane

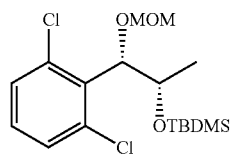

To a stirred solution of (1S,2S)-2-((tert-butyldimethylsilyl)oxy)-1-(2,6-dichlorophenyl)propan-1-ol (Preparation example 46, 8.0 g, 23.86 mmol) in CH₂Cl₂ (80 mL) was slowly N,N-diisopropylethylamine (20.9 mL, 119.28 mmol) and MOM-Cl (9.4 mL, 119.28 mmol) at 0° C. The mixture was warm to room temperature then stirred for 5 h. The resulting mixture was diluted with CH₂Cl₂, washed with H₂O, dried over anhydrous Na₂SO₄, filtered and concentrated under reduced pressure. The crude product was purified by a silica gel column to produce the title compound (8.7 g, yield 96%).

¹H NMR (400 MHz, CDCl₃) δ 0.15 (s, 6H), 0.95 (s, 9H), 1.00 (d, J=6.4 Hz, 3H), 3.17 (s, 3H), 4.58 (d, J=6.4 Hz, 1H), 4.68-4.73 (m, 1H), 4.74 (d, J=6.4 Hz, 1H), 5.14 (d, J=8.4 Hz, 1H), 7.14 (t, J=8.0 Hz, 1H), 7.31 (t, J=8.0 Hz, 2H).

PREPARATION EXAMPLE 48

(1S,2S)-1-(2,6-dichlorophenyl)-1-(methoxymethoxy)propan-2-ol

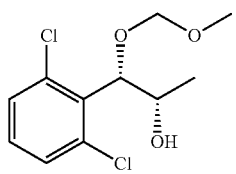

To a stirred solution of (5S,6S)-5-(2,6-dichlorophenyl)-6,8,8,9,9-pentamethyl-2,4,7-trioxa-8-siladecane (Preparation example 47, 8.7 g, 22.93 mmol) in THF (87 mL) was dropwise added TBAF (1 M solution, 25.2 mL, 25.22 mmol) at room temperature. When the reaction was completed, the resulting mixture was diluted with EtOAc, washed with sat. NaHCO₃ and brine, dried over Na₂SO₄, filtered, and concentrated under reduced pressure. The crude product was purified by silica gel column chromatography to produce the title compound (5.0 g, yield 82%).

¹H NMR (400 MHz, CDCl₃) δ 1.06 (d, J=6.4 Hz, 3H), 3.02 (s, 1H), 3.35 (s, 3H), 4.63 (d, J=6.8 Hz, 1H), 4.64-4.70 (m, 1H), 4.72 (d, J=6.8 Hz, 1H), 7.19 (t, J=8.0 Hz, 1H), 7.29-7.38 (m, 2H).

PREPARATION EXAMPLE 49

(S)-1-(2,6-dichlorophenyl)-1-(methoxymethoxy)propan-2-one

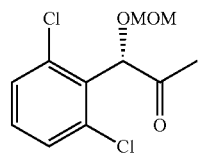

To a stirred solution of (1S,2S)-1-(2,6-dichlorophenyl)-1-(methoxymethoxy)propan-2-ol (Preparation example 48, 5.0 g, 18.86 mmol) in CH₂Cl₂ (50 mL) was added PCC (4.07 g, 18.86 mmol) at room temperature. When the reaction was completed, the resulting mixture was filtered through Celite, rinsed with CH₂Cl₂, and concentrated under reduced pressure. The crude product was purified by a silica gel column to produce the title compound (3.51 g, yield 71%).

¹H NMR (400 MHz, CDCl₃) δ 2.29 (s, 3H), 3.35 (s, 3H), 4.64 (d, J=6.8 Hz, 1H), 4.74 (d, J=6.8 Hz, 1H), 5.77 (s, 1H), 7.22 (dd, J=8.8, 7.6 Hz, 1H), 7.33 (d, J=8.4 Hz, 2H).

PREPARATION EXAMPLE 50

(1S,2R)-1-(2,6-dichlorophenyl)propane-1,2-diol

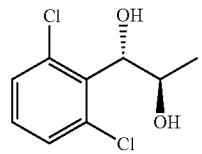

To a stirred solution of 1(S)-1-(2,6-dichlorophenyl)-1-(methoxymethoxy)propan-2-one (Preparation example 49, 3.3 g, 12.54 mmol) in toluene (33 mL) was added sodium bis(2-methoxyethoxy)aluminumhydride solution (3.6 M solution, 3.5 mL, 12.54 mmol) at −40° C. When the reaction was completed, the resulting mixture was diluted with EtOAc, washed with water and brine, dried over Na₂SO₄, filtered, and concentrated under reduced pressure.

To a stirred solution of an above crude product in MeOH (33 mL) was dropwise added 8N HCl (7.8 mL, 62.71 mmol) at room temperature. When the reaction was completed, the resulting mixture was diluted with EtOAc, washed with sat. NaHCO₃ and brine, dried over Na₂SO₄, filtered, and concentrated under reduced pressure. The crude product was purified by silica gel column chromatography to produce the title compound (2.33 g, yield 84%).

¹H NMR (400 MHz, CDCl₃) δ 1.43 (d, J=6.0 Hz, 3H), 3.04 (d, J=10.0 Hz, 1H), 4.35-4.43 (m, 1H), 5.24 (dd, J=10.0, 8.4 Hz, 1H), 7.18 (dd, J=8.4, 7.2 Hz, 1H), 7.34 (d, J=8.0 Hz, 2H).

PREPARATION EXAMPLE 51

(1R,2R)-2-((tert-butyldimethylsilyl)oxy)-1-(2,6-dichlorophenyl)propan-1-ol

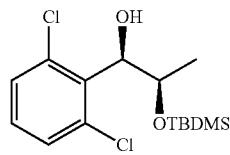 [SMILES: C[C@@H](O[Si](C)(C)C(C)(C)C)[C@H](O)c1c(Cl)cccc1Cl]

The substantially same method as described in preparation example 46 was conducted, except that (1R,2R)-1-(2,6-dichlorophenyl)propane-1,2-diol (Preparation example 28), was used instead of (1S,2S)-1-(2,6-dichlorophenyl)propane-1,2-diol (Preparation example 27), to obtain the title compound (13.69 g, yield 84%).

¹H NMR (400 MHz, CDCl₃) δ 0.08 (d, J=8.4 Hz, 6H), 0.93 (s, 9H), 1.10 (d, J=6.0 Hz, 3H), 3.05 (d, J=5.2 Hz, 1H), 4.44-4.50 (m, 1H), 5.15-5.20 (m, 1H), 7.11-7.15 (m, 1H), 7.29 (d, J=8.0 Hz, 2H).

PREPARATION EXAMPLE 52

(5R,6R)-5-(2,6-dichlorophenyl)-6,8,8,9,9-pentamethyl-2,4,7-trioxa-8-siladecane

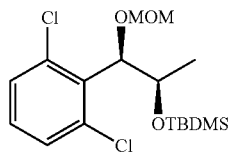

The substantially same method as described in preparation example 47 was conducted, except that (1R,2R)-2-((tert-butyldimethylsilyl)oxy)-1-(2,6-dichlorophenyl)propan-1-ol (Preparation example 51), was used instead of (1S,2S)-2-((tert-butyldimethylsilyl)oxy)-1-(2,6-dichlorophenyl)propan-1-ol (Preparation example 46), to obtain the title compound (14.98 g, yield 97%).

$^1$H NMR (400 MHz, CDCl$_3$) δ 0.13 (s, 6H), 0.92 (s, 9H), 0.94 (d, J=6.4 Hz, 3H), 3.15 (s, 3H), 4.55 (d, J=6.4 Hz, 1H), 4.66-4.71 (m, 1H), 4.73 (d, J=6.4 Hz, 1H), 5.13 (d, J=8.4 Hz, 1H), 7.11 (t, J=8.0 Hz, 1H), 7.29 (t, J=8.0 Hz, 2H).

PREPARATION EXAMPLE 53

(1R,2R)-1-(2,6-dichlorophenyl)-1-(methoxymethoxy)propan-2-ol

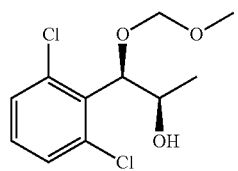 [SMILES: COCO[C@H](c1c(Cl)cccc1Cl)[C@@H](C)O]

The substantially same method as described in preparation example 48 was conducted, except that (5R,6R)-5-(2,6-dichlorophenyl)-6,8,8,9,9-pentamethyl-2,4,7-trioxa-8-siladecane (Preparation example 52), was used instead of (5S,6S)-5-(2,6-dichlorophenyl)-6,8,8,9,9-pentamethyl-2,4,7-trioxa-8-siladecane (Preparation example 47), to obtain the title compound (9.09 g, yield 87%).

$^1$H NMR (400 MHz, CDCl$_3$) δ 1.06 (d, J=6.4 Hz, 3H), 3.02 (s, 1H), 3.35 (s, 3H), 4.63 (d, J=6.8 Hz, 1H), 4.64-4.70 (m, 1H), 4.72 (d, J=6.8 Hz, 1H), 7.19 (t, J=8.0 Hz, 1H), 7.29-7.38 (m, 2H)

PREPARATION EXAMPLE 54

(R)-1-(2,6-dichlorophenyl)-1-(methoxymethoxy)propan-2-one

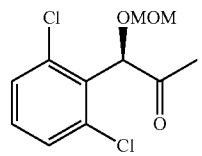

The substantially same method as described in preparation example 49 was conducted, except that (1R,2R)-1-(2,6-dichlorophenyl)-1-(methoxymethoxy)propan-2-ol (Preparation example 53), was used instead of (1S,2S)-1-(2,6-dichlorophenyl)-1-(methoxymethoxy)propan-2-ol (Preparation example 48), to obtain the title compound (2.1 g, yield 84%).

$^1$H NMR (400 MHz, CDCl$_3$) δ 2.30 (s, 3H), 3.37 (s, 3H), 4.65 (d, J=6.8 Hz, 1H), 4.76 (d, J=6.8 Hz, 1H), 5.78 (s, 1H), 7.23 (dd, J=8.4, 7.6 Hz, 1H), 7.35 (d, J=8.4 Hz, 2H).

PREPARATION EXAMPLE 55

(1R,2S)-1-(2,6-dichlorophenyl)propane-1,2-diol

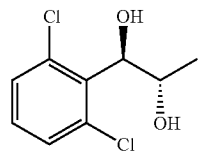

The substantially same method as described in preparation example 50 was conducted, except that (R)-1-(2,6-dichlorophenyl)-1-(methoxymethoxy)propan-2-one (Preparation example 54), was used instead of (S)-1-(2,6-dichlorophenyl)-1-(methoxymethoxy)propan-2-one (Preparation example 49), to obtain the title compound (4.59 g, yield 90%).

$^1$H NMR (400 MHz, CDCl$_3$) δ 1.43 (d, J=6.4 Hz, 3H), 3.05 (d, J=10.0 Hz, 1H), 4.35-4.43 (m, 1H), 5.24 (dd, J=10.0, 8.0 Hz, 1H), 7.18 (dd, J=8.4, 7.6 Hz, 1H), 7.34 (d, J=8.0 Hz, 2H).

PREPARATION EXAMPLE 56

1-(2-iodophenyl)-(S,S)-1,2-butanediol

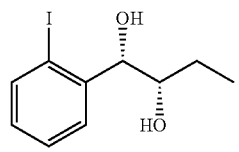

The substantially same method as described in preparation example 21 was conducted was conducted, except that 1-(2-iodophenyl)-trans-1-butene (Preparation example 17) was used instead of 1-(2-chlorophenyl)-trans-1-propene (Preparation example 1), to obtain the title compound (9.5 g, yield 84%).

$^1$H NMR (400 MHz, CDCl$_3$) δ 1.04 (t, J=7.6 Hz, 3H), 1.60-1.71 (m, 2H), 2.07 (br s, 1H), 2.74 (br s, 1H), 3.71-3.76 (m, 1H), 4.87 (d, J=4.8 Hz, 1H), 7.01-7.87 (m, 4H).

PREPARATION EXAMPLE 57

(1S,2S)-1-(2,6-dichlorophenyl)butane-1,2-diol

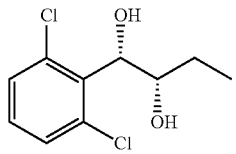

The substantially same method as described in preparation example 21 was conducted, except that (E)-2-(but-1-en-1-yl)-1,3-dichlorobenzene (Preparation example 18) was used instead of 1-(2-chlorophenyl)-trans-1-propene (Preparation example 1), to obtain the title compound (3.4 g, yield 66%).
$^1$H NMR (400 MHz, CDCl$_3$) δ 0.88 (t, J=7.4 Hz, 3H), 1.15-1.25 (m, 1H), 1.34-1.51 (m, 1H), 2.56 (d, J=2.4 Hz, 1H), 3.06 (d, J=8.4 Hz, 1H), 4.11-4.16 (m, 1H), 5.17 (t, J=8.4 Hz, 1H), 7.08-7.12 (m, 1H), 7.24-7.26 (m, 2H).

PREPARATION EXAMPLE 58

(1R,2R)-1-(2,6-dichlorophenyl)butane-1,2-diol

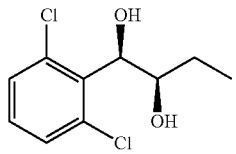

The substantially same method as described in preparation example 21 was conducted, except that (E)-2-(but-1-en-1-yl)-1,3-dichlorobenzene (Preparation example 18) and (DHQD)$_2$-PHAL were used instead of 1-(2-chlorophenyl)-trans-1-propene (Preparation example 1) and (DHQ)$_2$-PHAL, to obtain the title compound (6.9 g, yield 66%).
$^1$H NMR (400 MHz, CDCl$_3$) δ 0.88 (t, J=7.4 Hz, 3H), 1.15-1.25 (m, 1H), 1.34-1.51 (m, 1H), 2.56 (d, J=2.4 Hz, 1H), 3.06 (d, J=8.4 Hz, 1H), 4.11-4.16 (m, 1H), 5.17 (t, J=8.4 Hz, 1H), 7.08-7.12 (m, 1H), 7.24-7.26 (m, 2H).

PREPARATION EXAMPLE 59

(1S,2S)-1-(2,6-dichlorophenyl)-3-methylbutane-1,2-diol

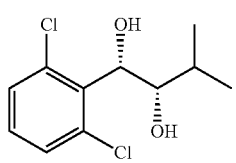

The substantially same method as described in preparation example 21 was conducted, except that 1-(2,6-dichlorophenyl)-3-methyl-trans-1-butene (Preparation example 19) was used instead of 1-(2-chlorophenyl)-trans-1-propene (Preparation example 1), to obtain the title compound (3.2 g, yield 56%).
$^1$H NMR (400 MHz, CDCl$_3$) δ 1.00 (d, J=6.8 Hz, 6H), 1.58-1.66 (m, 1H), 2.37 (d, J=3.6 Hz, 1H), 3.14 (d, J=8.4 Hz, 1H), 4.11-4.16 (m, 1H), 5.37 (t, J=8.0 Hz, 1H), 7.19 (dd, J=8.4, 7.2 Hz, 1H), 7.34 (d, J=8.0 Hz, 2H).

PREPARATION EXAMPLE 60

(1R,2R)-1-(2,6-dichlorophenyl)-3-methylbutane-1,2-diol

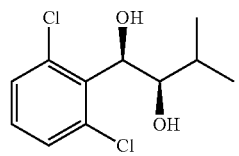

The substantially same method as described in preparation example 21 was conducted, except that 1-(2,6-dichlorophenyl)-3-methyl-trans-1-butene (Preparation example 19) and (DHQD)$_2$-PHAL were used instead of 1-(2-chlorophenyl)-trans-1-propene (Preparation example 1) and (DHQ)$_2$-PHAL, to obtain the title compound (5.29 g, yield 51%).
$^1$H NMR (400 MHz, CDCl$_3$) δ 1.00 (d, J=6.8 Hz, 6H), 1.58-1.66 (m, 1H), 2.37 (d, J=3.6 Hz, 1H), 3.14 (d, J=8.4 Hz, 1H), 4.11-4.16 (m, 1H), 5.37 (t, J=8.0 Hz, 1H), 7.19 (dd, J=8.4, 7.2 Hz, 1H), 7.34 (d, J=8.0 Hz, 2H).

PREPARATION EXAMPLE 61

(1S,2S)-1-(2,6-dichlorophenyl)hexane-1,2-diol

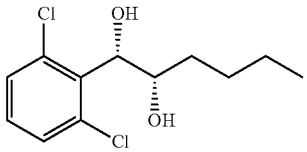 [SMILES: CCCC[C@H](O)[C@@H](O)c1c(Cl)cccc1Cl]

The substantially same method as described in preparation example 21 was conducted, except that 1-(2,6-dichlorophenyl)-trans-1-hexene (Preparation example 20) was used instead of 1-(2-chlorophenyl)-trans-1-propene (Preparation example 1), to obtain the title compound (5.4 g, yield 65%).
$^1$H NMR (400 MHz, CDCl$_3$) δ 0.88 (t, J=7.4 Hz, 3H), 1.15-1.25 (m, 1H), 1.34-1.51 (m, 1H), 2.56 (d, J=2.4 Hz, 1H), 3.06 (d, J=8.4 Hz, 1H), 4.11-4.16 (m, 1H), 5.17 (t, J=8.4 Hz, 1H), 7.08-7.12 (m, 1H), 7.24-7.26 (m, 2H).

PREPARATION EXAMPLE 62

(1R,2R)-1-(2,6-dichlorophenyl)hexane-1,2-diol

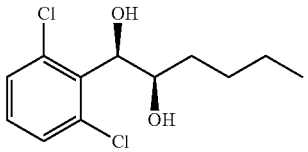 [SMILES: CCCC[C@@H](O)[C@H](O)c1c(Cl)cccc1Cl]

The substantially same method as described in preparation example 21 was conducted, except that 1-(2,6-dichlorophenyl)-trans-1-hexene (Preparation example 20) and (DHQD)$_2$-PHAL were used instead of 1-(2-chlorophenyl)-trans-1-propene (Preparation example 1) and (DHQ)$_2$-PHAL, to obtain the title compound (6.9 g, yield 66%).

$^1$H NMR (400 MHz, CDCl$_3$) δ 0.88 (t, J=7.4 Hz, 3H), 1.15-1.25 (m, 1H), 1.34-1.51 (m, 1H), 2.56 (d, J=2.4 Hz, 1H), 3.06 (d, J=8.4 Hz, 1H), 4.11-4.16 (m, 1H), 5.17 (t, J=8.4 Hz, 1H), 7.08-7.12 (m, 1H), 7.24-7.26 (m, 2H).

PREPARATION EXAMPLE 63 tert-butyl chlorosulfonylcarbamate

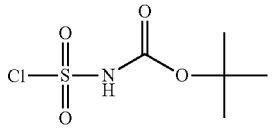

To a stirred solution of chlorosulfonyl isocyanate (24.6 mL, 282.63 mmol) in hexane (400 mL) was dropwise added tert-butanol (26.9 mL, 282.63 mmol) at 0° C. After 1 h, the resulting mixture was filtered and washed with hexane, to obtain the title compound (55.39 g, yield 91%)

$^1$H NMR (400 MHz, CDCl$_3$) δ 1.56 (s, 9H), 8.50 (s, 1H).

PREPARATION EXAMPLE 64

(1S,2S)-1-(2,4-dichlorophenyl)-1-hydroxypropan-2-yl carbamate

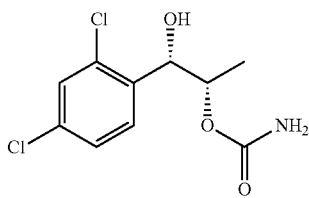 [SMILES: C[C@H](OC(N)=O)[C@@H](O)c1ccc(Cl)cc1Cl]

To a stirred solution of 1-(2,4-dichlorophenyl)-(S,S)-1,2-propanediol (Preparation example 23, 10.0 g, 45.23 mmol) in CH$_2$Cl$_2$ (100 mL) was added Et$_3$N (31.5 mL, 226.16 mmol) at 0° C. under N$_2$ then allowed to stir for 30 min. The mixture was added TMS-Cl (17.2 mL, 135.69 mmol) at 0° C. When the reaction was completed, the resulting mixture was quenched with water, diluted with CH$_2$Cl$_2$, washed with brine, dried over Na$_2$SO$_4$, filtered, and concentrated to give as a crude product.

To a stirred solution of an above crude product in toluene (100 mL) was slowly added chlorosulfonyl isocyanate (9.8 mL, 113.08 mmol) at 0° C. The reaction mixture was stirred for 5 h. The resulting mixture was quenched with cold water and then stirred by additional cold water for 1 h. After separation of organic layer, the aqueous layer was adjusted with pH 2-3 with sat. NaHCO$_3$ and extracted with EtOAc. The combined organic layer washed with sat. NaHCO$_3$ and water, dried over Na$_2$SO$_4$, filtered, and concentrated under reduced pressure. The crude product was purified by silica gel column chromatography to produce the title compound (8.0 g, yield 67%).

$^1$H NMR (400 MHz, CDCl$_3$) δ 1.22 (d, J=6.4 Hz, 3H), 4.16-4.20 (m, 1H) 4.96-5.00 (m, 3H), 5.07 (t, J=4.8 Hz, 1H), 7.23-7.52 (m, 3H).

PREPARATION EXAMPLE 65

(1S,2S)-1-(2,4-dichlorophenyl)-1-(methoxymethoxy)propan-2-yl carbamate

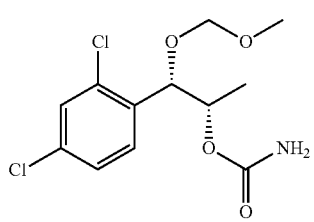 [SMILES: COCO[C@@H](c1ccc(Cl)cc1Cl)[C@H](C)OC(N)=O]

The substantially same method as described in preparation example 47 was conducted, except that (1S,2S)-1-(2,4-dichlorophenyl)-1-hydroxypropan-2-yl carbamate (Preparation example 64), was used instead of (1S,2S)-2-((tert-butyldimethylsilyl)oxy)-1-(2,6-dichlorophenyl)propan-1-ol (Preparation example 46), to obtain the title compound (5.84 g, yield 67%).

$^1$H NMR (400 MHz, CDCl$_3$) δ 1.37 (d, J=6.8 Hz, 3H), 3.30 (s, 3H), 4.71 (d, J=6.8 Hz, 2H), 4.82-4.88 (m, 2H), 5.45 (s, 2H), 7.24-7.30 (m, 2H), 7.73 (d, J=1.5 Hz, 1H).

PREPARATION EXAMPLE 66

(1S,2S)-1-(2,4-dichlorophenyl)-1-(methoxymethoxy)propan-2-ol

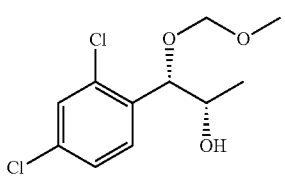 [SMILES: COCO[C@@H](c1ccc(Cl)cc1Cl)[C@H](C)O]

To a stirred solution of LiAlH$_4$ (0.71 g, 18.89 mmol) in THF (60 mL) was slowly added (1S,2S)-1-(2,4-dichlorophenyl)-1-(methoxymethoxy)propan-2-yl carbamate (Preparation example 65, 5.8 g, 18.89 mmol) in THF (5 mL) at 0° C. When the reaction was completed, the resulting mixture was filtered through Celite, diluted with EtOAc, washed with water dried over Na$_2$SO$_4$, filtered, and concentrated under reduced pressure. The crude product was purified by silica gel column chromatography to produce the title compound (2.99 g, yield 60%).

$^1$H NMR (400 MHz, CDCl$_3$) δ 1.15 (d, J=6.4 Hz, 3H), 3.30 (s, 3H), 3.91 (br s, 1H), 4.51-4.64 (m, 2H), 4.91 (d, J=6.8 Hz, 1H), 5.50-5.60 (m, 1H), 7.26-7.31 (m, 1H), 7.36-7.57 (m, 2H).

PREPARATION EXAMPLE 67

(1R,2R)-1-(2,4-dichlorophenyl)-1-hydroxypropan-2-yl carbamate

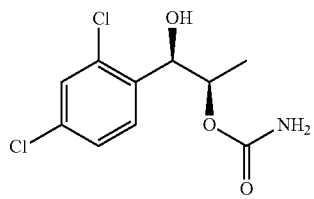 [SMILES: C[C@@H](OC(N)=O)[C@H](O)c1ccc(Cl)cc1Cl]

The substantially same method as described in preparation example 64 was conducted, except that 1-(2,4-dichlorophenyl)-(R,R)-1,2-propanediol (Preparation example 24), was used instead of 1-(2,4-dichlorophenyl)-(S,S)-1,2-propanediol (Preparation example 23), to obtain the title compound (0.62 g, 66%).

$^1$H NMR (400 MHz, CDCl$_3$) δ 1.22 (d, J=6.4 Hz, 3H), 4.16-4.20 (m, 1H) 4.96-5.00 (m, 3H), 5.07 (t, J=4.8 Hz, 1H), 7.23-7.52 (m, 3H).

PREPARATION EXAMPLE 68

(1R,2R)-1-(2,4-dichlorophenyl)-1-(methoxymethoxy)propan-2-yl carbamate

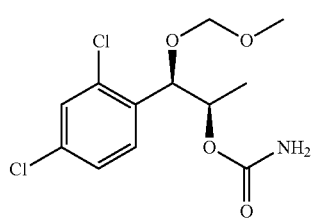 [SMILES: COCO[C@H](c1ccc(Cl)cc1Cl)[C@@H](C)OC(N)=O]

The substantially same method as described in preparation example 47 was conducted, except that (1R,2R)-1-(2,4-dichlorophenyl)-1-hydroxypropan-2-yl carbamate (Preparation example 67), was used instead of (1S,2S)-2-((tert-butyldimethylsilyl)oxy)-1-(2,6-dichlorophenyl)propan-1-ol (Preparation example 46), to obtain the title compound (0.85 g, yield 70%).

$^1$H NMR (400 MHz, CDCl$_3$) δ 1.37 (d, J=6.8 Hz, 3H), 3.30 (s, 3H), 4.71 (d, J=6.8 Hz, 2H), 4.82-4.88 (m, 2H), 5.45 (s, 2H), 7.24-7.30 (m, 2H), 7.73 (d, J=1.5 Hz, 1H).

PREPARATION EXAMPLE 69

(1R,2R)-1-(2,4-dichlorophenyl)-1-(methoxymethoxy)propan-2-ol

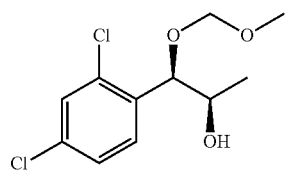 [SMILES: COCO[C@H](c1ccc(Cl)cc1Cl)[C@@H](C)O]

The substantially same method as described in preparation example 66 was conducted, except that (1R,2R)-1-(2,4-dichlorophenyl)-1-(methoxymethoxy)propan-2-yl carbamate (Preparation example 68), was used instead of (1S,2S)-1-(2,4-dichlorophenyl)-1-(methoxymethoxy)propan-2-yl carbamate (Preparation example 65), to obtain the title compound (0.32 g, yield 45%).

$^1$H NMR (400 MHz, CDCl$_3$) δ 1.15 (d, J=6.4 Hz, 3H), 3.30 (s, 3H), 3.91 (br s, 1H), 4.51-4.64 (m, 2H), 4.91 (d, J=6.8 Hz, 1H), 5.50-5.60 (m, 1H), 7.26-7.31 (m, 1H), 7.36-7.57 (m, 2H).

PREPARATION EXAMPLE 70

(1S,2S)-1-(3,4-dichlorophenyl)-1-hydroxypropan-2-yl carbamate

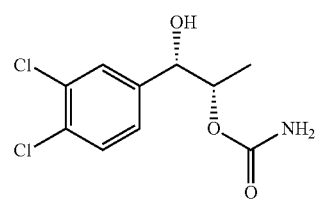 [SMILES: C[C@H](OC(N)=O)[C@@H](O)c1ccc(Cl)c(Cl)c1]

The substantially same method as described in preparation example 64 was conducted, except that (1S,2S)-1-(3,4-dichlorophenyl)propane-1,2-diol (Preparation example 25), was used instead of 1-(2,4-dichlorophenyl)-(S,S)-1,2-propanediol (Preparation example 23), to obtain the title compound (5.0 g, yield 49%).

$^1$H NMR (400 MHz, CDCl$_3$) δ 1.16 (d, J=6.4 Hz, 3H), 2.94 (d, J=4.0 Hz, 1H), 4.62-4.64 (m, 1H), 4.70 (br s, 2H), 4.92-4.98 (m, 1H), 7.23 (dd, J=8.4, 2.0 Hz, 1H), 7.45-7.51 (m, 2H).

PREPARATION EXAMPLE 71

(1S,2S)-1-(3,4-dichlorophenyl)-1-(methoxymethoxy)propan-2-yl carbamate

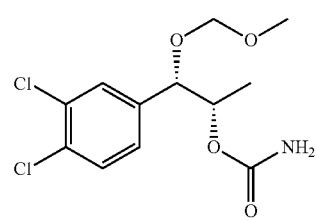 [SMILES: COCO[C@@H](c1ccc(Cl)c(Cl)c1)[C@H](C)OC(N)=O]

The substantially same method as described in preparation example 47 was conducted, except that (1S,2S)-1-(3,4-dichlorophenyl)-1-hydroxypropan-2-yl carbamate (Preparation example 70), was used instead of (1S,2S)-2-((tert-butyldimethylsilyl)oxy)-1-(2,6-dichlorophenyl)propan-1-ol (Preparation example 46), to obtain the title compound (4.65 g, yield 80%).

$^1$H NMR (400 MHz, CDCl$_3$) δ 1.30 (d, J=6.8 Hz, 3H), 3.32 (s, 3H), 4.55-4.63 (m, 2H), 4.71 (d, J=6.8 Hz, 1H), 4.82-4.88 (m, 1H), 5.45 (br s, 2H), 7.24-7.30 (m, 2H), 7.73 (d, J=1.5 Hz, 1H).

PREPARATION EXAMPLE 72

(1S,2S)-1-(3,4-dichlorophenyl)-1-(methoxymethoxy)propan-2-ol

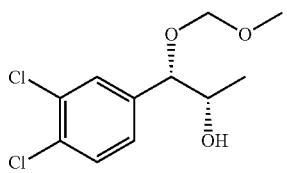 [SMILES: COCO[C@@H](c1ccc(Cl)c(Cl)c1)[C@H](C)O]

The substantially same method as described in preparation example 66 was conducted, except that (1S,2S)-1-(3,4-dichlorophenyl)-1-(methoxymethoxy)propan-2-yl carbamate (Preparation example 71), was used instead of (1S,2S)-1-(2,4-dichlorophenyl)-1-(methoxymethoxy)propan-2-yl carbamate (Preparation example 65), to obtain the title compound (2.47 g, yield 62%).

$^1$H NMR (400 MHz, CDCl$_3$) δ 1.05 (t, J=6.4 Hz, 3H), 2.84 (d, J=2.4 Hz, 1H), 3.87-3.89 (m, 1H), 4.29 (d, J=7.6 Hz, 1H), 4.56-4.63 (m, 2H), 7.16-7.18 (m, 1H), 7.43-7.46 (m, 2H).

PREPARATION EXAMPLE 73

(1R,2R)-1-(3,4-dichlorophenyl)-1-hydroxypropan-2-yl carbamate

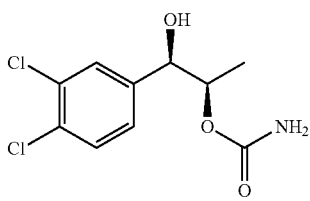 [SMILES: C[C@@H](OC(N)=O)[C@H](O)c1ccc(Cl)c(Cl)c1]

The substantially same method as described in preparation example 64 was conducted, except that (1R,2R)-1-(3,4-dichlorophenyl)propane-1,2-diol (Preparation example 26), was used instead of 1-(2,4-dichlorophenyl)-(S,S)-1,2-propanediol (Preparation example 23), to obtain the title compound (7.5 g, yield 90%).

$^1$H NMR (400 MHz, CDCl$_3$) δ 1.16 (d, J=6.4 Hz, 3H), 2.94 (d, J=4.0 Hz, 1H), 4.62-4.64 (m, 1H), 4.70 (br s, 2H), 4.92-4.98 (m, 1H), 7.23 (dd, J=8.4, 2.0 Hz, 1H), 7.45-7.51 (m, 2H).

PREPARATION EXAMPLE 74

(1R,2R)-1-(3,4-dichlorophenyl)-1-(methoxymethoxy)propan-2-yl carbamate

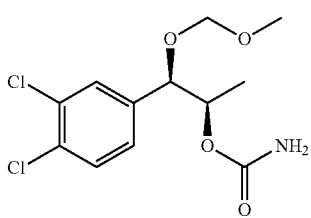 [SMILES: COCO[C@H](c1ccc(Cl)c(Cl)c1)[C@@H](C)OC(N)=O]

The substantially same method as described in preparation example 47 was conducted, except that (1R,2R)-1-(3,4-dichlorophenyl)-1-hydroxypropan-2-yl carbamate (Preparation example 73), was used instead of (1S,2S)-2-((tert-butyldimethylsilyl)oxy)-1-(2,6-dichlorophenyl)propan-1-ol (Preparation example 46), to obtain the title compound (8.9 g, yield 80%).

$^1$H NMR (400 MHz, CDCl$_3$) δ 1.30 (d, J=6.8 Hz, 3H), 3.32 (s, 3H), 4.55-4.63 (m, 2H), 4.71 (d, J=6.8 Hz, 1H), 4.82-4.88 (m, 1H), 5.45 (br s, 2H), 7.24-7.30 (m, 2H), 7.73 (d, J=1.5 Hz, 1H).

PREPARATION EXAMPLE 75

(1R,2R)-1-(3,4-dichlorophenyl)-1-(methoxymethoxy)propan-2-ol

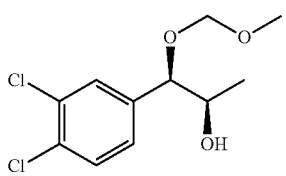 [SMILES: COCO[C@H](c1ccc(Cl)c(Cl)c1)[C@@H](C)O]

The substantially same method as described in preparation example 66 was conducted, except that (1R,2R)-1-(3,4-dichlorophenyl)-1-(methoxymethoxy)propan-2-yl carbamate (Preparation example 74), was used instead of (1S,2S)-1-(2,4-dichlorophenyl)-1-(methoxymethoxy)propan-2-yl carbamate (Preparation example 65), to obtain the title compound (3.9 g, yield 57%).

$^1$H NMR (400 MHz, CDCl$_3$) δ 1.05 (t, J=6.4 Hz, 3H), 2.84 (d, J=2.4 Hz, 1H), 3.87-3.89 (m, 1H), 4.29 (d, J=7.6 Hz, 1H), 4.56-4.63 (m, 2H), 7.16-7.18 (m, 1H), 7.43-7.46 (m, 2H).

PREPARATION EXAMPLE 76

1-(2,3-dichlorophenyl)-(S)-1-hydroxypropyl-(S)-2-carbamate

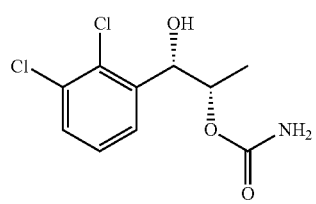 [SMILES: C[C@H](OC(N)=O)[C@@H](O)c1cccc(Cl)c1Cl]

The substantially same method as described in preparation example 64 was conducted, except that 1-(2,3-dichlorophenyl)-(S,S)-1,2-propanediol (Preparation example 29), was used instead of 1-(2,4-dichlorophenyl)-(S,S)-1,2-propanediol (Preparation example 23), to obtain the title compound (4.0 g, yield 73%).

$^1$H NMR (400 MHz, CDCl$_3$) δ 1.15 (d, J=6.4 Hz, 3H), 3.66 (d, J=9.2 Hz, 1H), 4.73 (br s, 2H), 5.43 (t, J=9.0 Hz, 1H), 5.62-5.69 (m, 1H), 7.18-7.22 (m, 3H).

PREPARATION EXAMPLE 77

(1S,2S)-1-(2,3-dichlorophenyl)-1-(methoxymethoxy)propan-2-yl carbamate

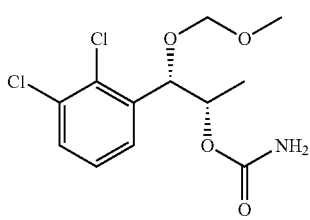 [SMILES: COCO[C@@H](c1cccc(Cl)c1Cl)[C@H](C)OC(N)=O]

The substantially same method as described in preparation example 47 was conducted, except that 1-(2,3-dichlorophenyl)-(S)-1-hydroxypropyl-(S)-2-carbamate (Preparation example 76), was used instead of (1S,2S)-2-((tert-butyldimethylsilyl)oxy)-1-(2,6-dichlorophenyl)propan-1-ol (Preparation example 46), to obtain the title compound (5.5 g, yield 60%).

$^1$H NMR (400 MHz, CDCl$_3$) δ 1.37 (d, J=6.8 Hz, 3H), 3.30 (s, 3H), 4.71 (d, J=6.8 Hz, 1H), 4.82-4.88 (m, 1H), 5.45 (s, 2H), 7.01-7.14 (m, 3H).

PREPARATION EXAMPLE 78

(1S,2S)-1-(2,3-dichlorophenyl)-1-(methoxymethoxy)propan-2-ol

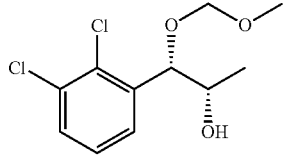 [SMILES: COCO[C@@H](c1cccc(Cl)c1Cl)[C@H](C)O]

The substantially same method as described in preparation example 66 was conducted, except that (1S,2S)-1-(2,3-dichlorophenyl)-1-(methoxymethoxy)propan-2-yl carbamate (Preparation example 77), was used instead of (1S,2S)-1-(2,4-dichlorophenyl)-1-(methoxymethoxy)propan-2-yl carbamate (Preparation example 65), to obtain the title compound (1.6 g, yield 38%).

$^1$H NMR (400 MHz, CDCl$_3$) δ 1.18 (d, J=6.4 Hz, 3H), 2.70 (d, J=4.0 Hz, 1H), 3.39 (s, 3H), 3.87-4.02 (m, 1H), 4.56 (d, J=6.8 Hz, 1H), 4.64 (d, J=6.4 Hz, 1H), 5.01 (d, J=6.4 Hz, 1H), 7.26 (t, J=8.0 Hz, 1H), 7.38 (dd, J=8.0, 1.6 Hz, 1H), 7.45 (dd, J=7.6, 1.6 Hz, 1H).

PREPARATION EXAMPLE 79

1-(2,3-dichlorophenyl)-(R)-1-hydroxypropyl-(R)-2-carbamate

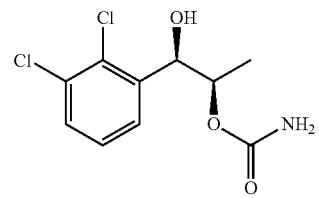 [SMILES: C[C@@H](OC(N)=O)[C@H](O)c1cccc(Cl)c1Cl]

The substantially same method as described in preparation example 64 was conducted, except that 1-(2,3-dichlorophenyl)-(R,R)-1,2-propanediol (Preparation example 30), was used instead of 1-(2,4-dichlorophenyl)-(S,S)-1,2-propanediol (Preparation example 23), to obtain the title compound (4.2 g, yield 78%).

$^1$H NMR (400 MHz, CDCl$_3$) δ 1.15 (d, J=6.4 Hz, 3H), 3.66 (d, J=9.2 Hz, 1H), 4.73 (br s, 2H), 5.43 (t, J=9.0 Hz, 1H), 5.62-5.69 (m, 1H), 7.18-7.22 (m, 3H).

PREPARATION EXAMPLE 80

(1R,2R)-1-(2,3-dichlorophenyl)-1-(methoxymethoxy)propan-2-yl carbamate

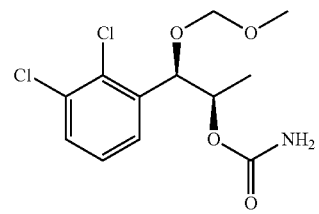 [SMILES: COCO[C@H](c1cccc(Cl)c1Cl)[C@@H](C)OC(N)=O]

The substantially same method as described in preparation example 47 was conducted, except that 1-(2,3-dichlorophenyl)-(R)-1-hydroxypropyl-(R)-2-carbamate (Preparation example 79), was used instead of (1S,2S)-2-((tert-butyldimethylsilyl)oxy)-1-(2,6-dichlorophenyl)propan-1-ol (Preparation example 46), to obtain the title compound (4.0 g, yield 61%).

$^1$H NMR (400 MHz, CDCl$_3$) δ 1.37 (d, J=6.8 Hz, 3H), 3.30 (s, 3H), 4.71 (d, J=6.8 Hz, 1H), 4.82-4.88 (m, 1H), 5.45 (s, 2H), 7.01-7.14 (m, 3H).

PREPARATION EXAMPLE 81

(1R,2R)-1-(2,3-dichlorophenyl)-1-(methoxymethoxy)propan-2-ol

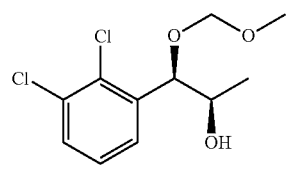 [SMILES: COCO[C@H](c1cccc(Cl)c1Cl)[C@@H](C)O]

The substantially same method as described in preparation example 66 was conducted, except that (1R,2R)-1-(2,3-dichlorophenyl)-1-(methoxymethoxy)propan-2-yl carbamate (Preparation example 80), was used instead of (1S,2S)-1-(2,4-dichlorophenyl)-1-(methoxymethoxy)propan-2-yl carbamate (Preparation example 65), to obtain the title compound (1.2 g, yield 35%).

$^1$H NMR (400 MHz, CDCl$_3$) δ 1.18 (d, J=6.4 Hz, 3H), 2.70 (d, J=4.0 Hz, 1H), 3.39 (s, 3H), 3.87-4.02 (m, 1H), 4.56 (d, J=6.8 Hz, 1H), 4.64 (d, J=6.4 Hz, 1H), 5.01 (d, J=6.4 Hz, 1H), 7.26 (t, J=8.0 Hz, 1H), 7.38 (dd, J=8.0, 1.6 Hz, 1H), 7.45 (dd, J=7.6, 1.6 Hz, 1H).

PREPARATION EXAMPLE 82

(1S,2S)-1-(2-fluorophenyl)-1-hydroxypropan-2-yl carbamate

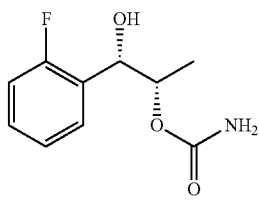

The substantially same method as described in preparation example 64 was conducted, except that 1-(2-fluorophenyl)-(S,S)-1,2-propanediol (Preparation example 37), was used instead of 1-(2,4-dichlorophenyl)-(S,S)-1,2-propanediol (Preparation example 23), to obtain the title compound (6.1 g, yield 40%).

$^1$H NMR (400 MHz, CDCl$_3$) δ 1.19 (d, J=5.2 Hz, 3H), 2.93 (d, J=4.4 Hz, 1H), 4.71 (br s, 2H), 4.99-5.06 (m, H), 7.04-7.48 (m, 4H).

PREPARATION EXAMPLE 83

(1S,2S)-1-(2-fluorophenyl)-1-(methoxymethoxy) propan-2-yl carbamate

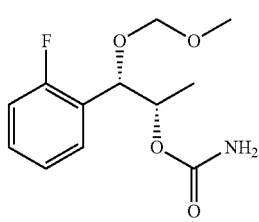

The substantially same method as described in preparation example 47 was conducted, except that (1S,2S)-1-(2-fluorophenyl)-1-hydroxypropan-2-yl carbamate (Preparation example 82), was used instead of (1S,2S)-2-((tert-butyldimethylsilyl)oxy)-1-(2,6-dichlorophenyl)propan-1-ol (Preparation example 46), to obtain the title compound (2.1 g, yield 63%).

$^1$H NMR (400 MHz, CDCl$_3$) δ 1.37 (d, J=6.8 Hz, 3H), 3.30 (s, 3H), 4.71 (d, J=6.8 Hz, 1H), 4.82-4.88 (m, 1H), 5.45 (s, 2H), 7.15-7.68 (m, 4H).

PREPARATION EXAMPLE 84

(1S,2S)-1-(2-fluorophenyl)-1-(methoxymethoxy) propan-2-ol

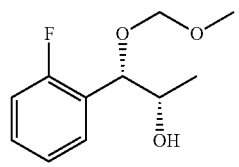

The substantially same method as described in preparation example 66 was conducted, except that (1S,2S)-1-(2-fluorophenyl)-1-(methoxymethoxy)propan-2-yl carbamate (Preparation example 83), was used instead of (1S,2S)-1-(2,4-dichlorophenyl)-1-(methoxymethoxy)propan-2-yl carbamate (Preparation example 65), to obtain the title compound (5.54 g, yield 80%).

$^1$H NMR (400 MHz, CDCl$_3$) δ 1.10 (t, J=6.4 Hz, 3H), 2.89 (br s, 1H), 3.39 (s, 3H), 3.98-4.03 (m, 1H), 4.62 (q, J=4.5 Hz, 2H), 4.74 (d, J=7.6 Hz, 1H), 7.05-7.10 (m, 1H), 7.16-7.20 (m, 1H), 7.30-7.34 (m, 1H), 7.38-7.49 (m, 1H).

PREPARATION EXAMPLE 85

(1R,2R)-1-(2-fluorophenyl)-1-hydroxypropan-2-yl carbamate

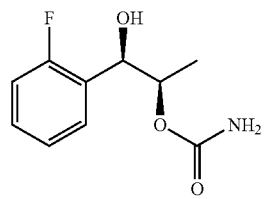

The substantially same method as described in preparation example 64 was conducted, except that 1-(2-fluorophenyl)-(R,R)-1,2-propanediol (Preparation example 38), was used instead of 1-(2,4-dichlorophenyl)-(S,S)-1,2-propanediol (Preparation example 23), to obtain the title compound (3.1 g, yield 40%).

$^1$H NMR (400 MHz, CDCl$_3$) δ 1.19 (d, J=5.2 Hz, 3H), 2.93 (d, J=4.4 Hz, 1H), 4.71 (br s, 2H), 4.99-5.06 (m, H), 7.04-7.48 (m, 4H).

PREPARATION EXAMPLE 86

(1R,2R)-1-(2-fluorophenyl)-1-(methoxymethoxy) propan-2-yl carbamate

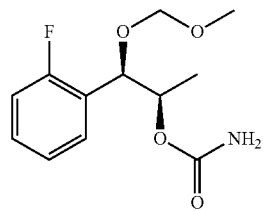

The substantially same method as described in preparation example 47 was conducted, except that (1R,2R)-1-(2-fluorophenyl)-1-hydroxypropan-2-yl carbamate (Preparation example 85), was used instead of (1S,2S)-2-((tert-butyldimethylsilyl)oxy)-1-(2,6-dichlorophenyl)propan-1-ol (Preparation example 46), to obtain the title compound (1.7 g, yield 65%).

$^1$H NMR (400 MHz, CDCl$_3$) δ 1.37 (d, J=6.8 Hz, 3H), 3.30 (s, 3H), 4.71 (d, J=6.8 Hz, 1H), 4.82-4.88 (m, 1H), 5.45 (s, 2H), 7.15-7.68 (m, 4H).

PREPARATION EXAMPLE 87

(1R,2R)-1-(2-fluorophenyl)-1-(methoxymethoxy)propan-2-ol

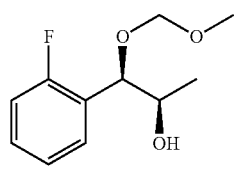

The substantially same method as described in preparation example 66 was conducted, except that (1S,2S)-1-(2-fluorophenyl)-1-(methoxymethoxy)propan-2-yl carbamate (Preparation example 86), was used instead of (1S,2S)-1-(2,4-dichlorophenyl)-1-(methoxymethoxy)propan-2-yl carbamate (Preparation example 65), to obtain the title compound (2.38 g, yield 78%).

$^1$H NMR (400 MHz, CDCl$_3$) δ 1.10 (t, J=6.4 Hz, 3H), 2.89 (br s, 1H), 3.39 (s, 3H), 3.98-4.03 (m, 1H), 4.62 (q, J=4.5 Hz, 2H), 4.74 (d, J=7.6 Hz, 1H), 7.05-7.10 (m, 1H), 7.16-7.20 (m, 1H), 7.30-7.34 (m, 1H), 7.38-7.49 (m, 1H).

PREPARATION EXAMPLE 88

(1S,2S)-1-hydroxy-1-(2-iodophenyl)propan-2-yl carbamate

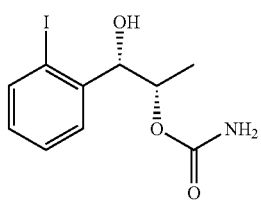

The substantially same method as described in preparation example 64 was conducted, except that 1-(2-iodophenyl)-(S,S)-1,2-propanediol (Preparation example 39), was used instead of 1-(2,4-dichlorophenyl)-(S,S)-1,2-propanediol (Preparation example 23), to obtain the title compound (2.2 g, yield 50%).

$^1$H NMR (400 MHz, CDCl$_3$) δ 1.27 (d, J=6.4 Hz, 3H), 3.09 (br s, 1H), 4.83 (br s, 2H), 5.00-5.10 (m, 2H), 7.00-7.76 (m, 4H).

PREPARATION EXAMPLE 89

(1S,2S)-1-(2-iodophenyl)-1-(methoxymethoxy)propan-2-yl carbamate

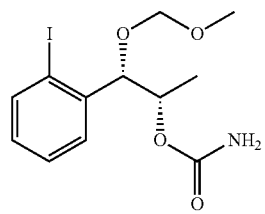 [SMILES: COCO[C@@H](c1ccccc1I)[C@H](C)OC(N)=O]

The substantially same method as described in preparation example 47 was conducted, except that (1S,2S)-1-hydroxy-1-(2-iodophenyl)propan-2-yl carbamate (Preparation example 88), was used instead of (1S,2S)-2-((tert-butyldimethylsilyl)oxy)-1-(2,6-dichlorophenyl)propan-1-ol (Preparation example 46), to obtain the title compound (2.7 g, yield 65%).

$^1$H NMR (400 MHz, CDCl$_3$) δ 1.37 (d, J=6.8 Hz, 3H), 3.30 (s, 3H), 4.71 (d, J=6.8 Hz, 1H), 4.82-4.88 (m, 1H), 5.45 (s, 2H), 7.13-7.88 (m, 4H).

PREPARATION EXAMPLE 90

(1S,2S)-1-(2-iodophenyl)-1-(methoxymethoxy)propan-2-ol

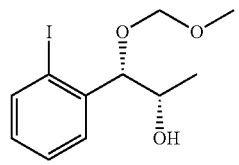

The substantially same method as described in preparation example 66 was conducted, except that (1S,2S)-1-(2-iodophenyl)-1-(methoxymethoxy)propan-2-yl carbamate (Preparation example 89), was used instead of (1S,2S)-1-(2,4-dichlorophenyl)-1-(methoxymethoxy)propan-2-yl carbamate (Preparation example 65), to obtain the title compound (3.16 g, yield 46%).

$^1$H NMR (400 MHz, CDCl$_3$) δ 1.19 (t, J=6.4 Hz, 3H), 3.40 (s, 3H), 3.95-4.00 (m, 1H), 4.56 (d, J=6.8 Hz, 1H), 4.63 (d, J=6.8 Hz, 1H), 4.79 (d, J=6.8 Hz, 1H), 7.01-7.05 (m, 1H), 7.31-7.41 (m, 2H), 7.86-7.88 (m, 1H).

PREPARATION EXAMPLE 91

(1R,2RS)-1-hydroxy-1-(2-iodophenyl)propan-2-yl carbamate

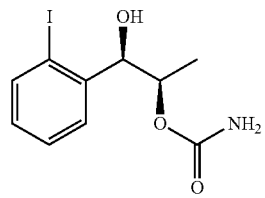

The substantially same method as described in preparation example 64 was conducted, except that 1-(2-iodophenyl)-(R,R)-1,2-propanediol (Preparation example 40), was used instead of 1-(2,4-dichlorophenyl)-(S,S)-1,2-propanediol (Preparation example 23), to obtain the title compound (2.8 g, yield 55%).

¹H NMR (400 MHz, CDCl₃) δ 1.27 (d, J=6.4 Hz, 3H), 3.09 (br s, 1H), 4.83 (br s, 2H), 5.00-5.10 (m, 2H), 7.00-7.76 (m, 4H).

PREPARATION EXAMPLE 92

(1R,2R)-1-(2-iodophenyl)-1-(methoxymethoxy)propan-2-yl carbamate

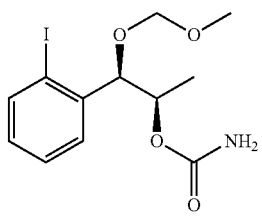 [SMILES: COCO[C@H](c1ccccc1I)[C@@H](C)OC(N)=O]

The substantially same method as described in preparation example 47 was conducted, except that (1R,2R)-1-hydroxy-1-(2-iodophenyl)propan-2-yl carbamate (Preparation example 91), was used instead of (1S,2S)-2-((tert-butyldimethylsilyl)oxy)-1-(2,6-dichlorophenyl)propan-1-ol (Preparation example 46), to obtain the title compound (2.5 g, yield 63%).

¹H NMR (400 MHz, CDCl₃) δ 1.37 (d, J=6.8 Hz, 3H), 3.30 (s, 3H), 4.71 (d, J=6.8 Hz, 1H), 4.82-4.88 (m, 1H), 5.45 (s, 2H), 7.13-7.88 (m, 4H).

PREPARATION EXAMPLE 93

(1R,2R)-1-(2-iodophenyl)-1-(methoxymethoxy)propan-2-ol

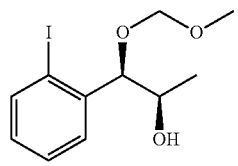

The substantially same method as described in preparation example 66 was conducted, except that (1R,2R)-1-(2-iodophenyl)-1-(methoxymethoxy)propan-2-yl carbamate (Preparation example 92), was used instead of (1S,2S)-1-(2,4-dichlorophenyl)-1-(methoxymethoxy)propan-2-yl carbamate (Preparation example 65), to obtain the title compound (2.08 g, yield 46%).

¹H NMR (400 MHz, CDCl₃) δ 1.19 (t, J=6.4 Hz, 3H), 3.40 (s, 3H), 3.95-4.00 (m, 1H), 4.56 (d, J=6.8 Hz, 1H), 4.63 (d, J=6.8 Hz, 1H), 4.79 (d, J=6.8 Hz, 1H), 7.01-7.05 (m, 1H), 7.31-7.41 (m, 2H), 7.86-7.88 (m, 1H).

PREPARATION EXAMPLE 94

(1S,2S)-1-(2,6-difluorophenyl)-1-hydroxypropan-2-yl carbamate

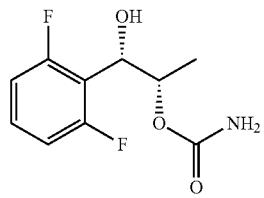 [SMILES: C[C@H](OC(N)=O)[C@@H](O)c1c(F)cccc1F]

The substantially same method as described in preparation example 64 was conducted, except that 1-(2,6-difluorophenyl)-(S,S)-1,2-propanediol (Preparation example 41), was used instead of 1-(2,4-dichlorophenyl)-(S,S)-1,2-propanediol (Preparation example 23), to obtain the title compound (2.4 g, yield 50%).

¹H NMR (400 MHz, CDCl₃) δ 1.15 (d, J=6.4 Hz, 3H), 3.66 (d, J=9.2 Hz, 1H), 4.73 (br s, 2H), 5.43 (t, J=9.0 Hz, 1H), 5.62-5.69 (m, 1H), 7.18-7.22 (m, 3H).

PREPARATION EXAMPLE 95

(1S,2S)-1-(2,6-difluorophenyl)-1-(methoxymethoxy)propan-2-yl carbamate

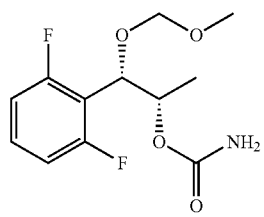 [SMILES: COCO[C@@H](c1c(F)cccc1F)[C@H](C)OC(N)=O]

The substantially same method as described in preparation example 47 was conducted, except that (1S,2S)-1-(2,6-difluorophenyl)-1-hydroxypropan-2-yl carbamate (Preparation example 94), was used instead of (1S,2S)-2-((tert-butyldimethylsilyl)oxy)-1-(2,6-dichlorophenyl)propan-1-ol (Preparation example 46), to obtain the title compound (2.3 g, yield 65%).

¹H NMR (400 MHz, CDCl₃) δ 1.37 (d, J=6.8 Hz, 3H), 3.30 (s, 3H), 4.71 (d, J=6.8 Hz, 1H), 4.82-4.88 (m, 1H), 5.45 (s, 2H), 6.67-7.15 (m, 3H).

PREPARATION EXAMPLE 96

(1S, 2S)-1-(2,6-difluorophenyl)-1-(methoxymethoxy)propan-2-ol

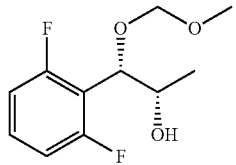 [SMILES: COCO[C@@H](c1c(F)cccc1F)[C@H](C)O]

The substantially same method as described in preparation example 66 was conducted, except that (1S,2S)-1-(2,6-difluorophenyl)-1-(methoxymethoxy)propan-2-yl carbamate (Preparation example 95), was used instead of (1S,2S)-1-(2,4-dichlorophenyl)-1-(methoxymethoxy)propan-2-yl carbamate (Preparation example 65), to obtain the title compound (1.8 g, yield 50%).

¹H NMR (400 MHz, CDCl₃) δ 1.06 (d, J=6.4 Hz, 3H), 3.07 (s, 1H), 3.35 (s, 3H), 4.29-4.41 (m, 1H), 4.66-4.84 (m, 3H), 6.91 (t, J=8.8 Hz, 2H), 7.25-7.42 (m, 1H).

PREPARATION EXAMPLE 97

(1S,2S)-1-(2,5-dichlorophenyl)-1-hydroxypropan-2-yl carbamate

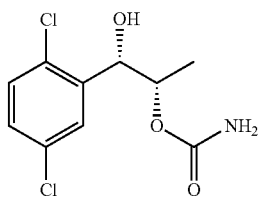 [SMILES: C[C@H](OC(N)=O)[C@@H](O)c1cc(Cl)ccc1Cl]

The substantially same method as described in preparation example 64 was conducted, except that 1-(2,5-dichlorophenyl)-(S,S)-1,2-propanediol (Preparation example 42), was used instead of 1-(2,4-dichlorophenyl)-(S,S)-1,2-propanediol (Preparation example 23), to obtain the title compound (2.29 g, yield 55%).

¹H NMR (400 MHz, CDCl₃) δ 1.15 (d, J=6.4 Hz, 3H), 3.66 (d, J=9.2 Hz, 1H), 4.73 (br s, 2H), 5.43 (t, J=9.0 Hz, 1H), 5.62-5.69 (m, 1H), 7.18-7.22 (m, 3H).

PREPARATION EXAMPLE 98

(1S,2S)-1-(2,5-dichlorophenyl)-1-(methoxymethoxy)propan-2-yl carbamate

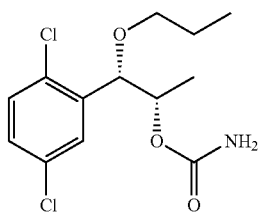 [SMILES: CCCO[C@@H](c1cc(Cl)ccc1Cl)[C@H](C)OC(N)=O]

The substantially same method as described in preparation example 47 was conducted, except that (1S,2S)-1-(2,5-dichlorophenyl)-1-hydroxypropan-2-yl carbamate (Preparation example 97), was used instead of (1S,2S)-2-((tert-butyldimethylsilyl)oxy)-1-(2,6-dichlorophenyl)propan-1-ol (Preparation example 46), to obtain the title compound (1.85 g, yield 63%).

¹H NMR (400 MHz, CDCl₃) δ 1.37 (d, J=6.8 Hz, 3H), 3.30 (s, 3H), 4.71 (d, J=6.8 Hz, 1H), 4.82-4.88 (m, 1H), 5.45 (s, 2H), 7.13-7.26 (m, 3H).

PREPARATION EXAMPLE 99

(1S,2S)-1-(2,5-dichlorophenyl)-1-(methoxymethoxy)propan-2-ol

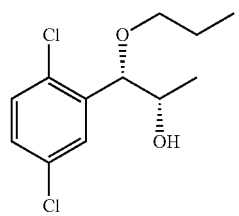 [SMILES: CCCO[C@@H](c1cc(Cl)ccc1Cl)[C@H](C)O]

The substantially same method as described in preparation example 66 was conducted, except that (1S,2S)-1-(2,5-dichlorophenyl)-1-(methoxymethoxy)propan-2-yl carbamate (Preparation example 98), was used instead of (1S,2S)-1-(2,4-dichlorophenyl)-1-(methoxymethoxy)propan-2-yl carbamate (Preparation example 65), to obtain the title compound (1.05 g, yield 45%).

¹H NMR (400 MHz, CDCl₃) δ 1.17 (d, J=6.4 Hz, 3H), 2.71 (s, 1H), 3.40 (s, 3H), 3.85-4.04 (m, 1H), 4.58 (d, J=6.4 Hz, 1H), 4.66 (d, J=6.4 Hz, 1H), 4.91 (d, J=6.4 Hz, 1H), 7.20-7.37 (m, 2H), 7.44 (s, 1H).

PREPARATION EXAMPLE 100

(1R,2R)-1-(2,5-dichlorophenyl)-1-hydroxypropan-2-yl carbamate

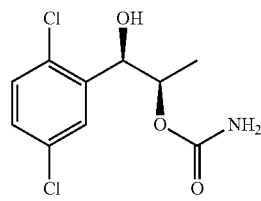 [SMILES: C[C@@H](OC(N)=O)[C@H](O)c1cc(Cl)ccc1Cl]

The substantially same method as described in preparation example 64 was conducted, except that 1-(2,5-dichlorophenyl)-(R,R)-1,2-propanediol (Preparation example 43), was used instead of 1-(2,4-dichlorophenyl)-(S,S)-1,2-propanediol (Preparation example 23), to obtain the title compound (2.41 g, yield 57%).

¹H NMR (400 MHz, CDCl₃) δ 1.15 (d, J=6.4 Hz, 3H), 3.66 (d, J=9.2 Hz, 1H), 4.73 (br s, 2H), 5.43 (t, J=9.0 Hz, 1H), 5.62-5.69 (m, 1H), 7.18-7.22 (m, 3H).

PREPARATION EXAMPLE 101

(1R,2R)-1-(2,5-dichlorophenyl)-1-(methoxymethoxy)propan-2-yl carbamate

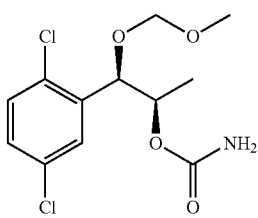 [SMILES: COCO[C@H](c1cc(Cl)ccc1Cl)[C@@H](C)OC(N)=O]

The substantially same method as described in preparation example 47 was conducted, except that (1R,2R)-1-(2,5-dichlorophenyl)-1-hydroxypropan-2-yl carbamate (Preparation example 100), was used instead of (1S,2S)-2-((tert-butyldimethylsilyl)oxy)-1-(2,6-dichlorophenyl)propan-1-ol (Preparation example 46), to obtain the title compound (1.76 g, yield 62%).

$^1$H NMR (400 MHz, CDCl$_3$) δ 1.37 (d, J=6.8 Hz, 3H), 3.30 (s, 3H), 4.71 (d, J=6.8 Hz, 1H), 4.82-4.88 (m, 1H), 5.45 (s, 2H), 7.13-7.26 (m, 3H).

PREPARATION EXAMPLE 102

(1R,2R)-1-(2,5-dichlorophenyl)-1-(methoxymethoxy)propan-2-ol

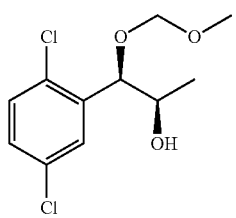 [SMILES: COCO[C@H](c1cc(Cl)ccc1Cl)[C@@H](C)O]

The substantially same method as described in preparation example 66 was conducted, except that (1R,2R)-1-(2,5-dichlorophenyl)-1-(methoxymethoxy)propan-2-yl carbamate (Preparation example 101), was used instead of (1S,2S)-1-(2,4-dichlorophenyl)-1-(methoxymethoxy)propan-2-yl carbamate (Preparation example 65), to obtain the title compound (0.85 g, yield 38%).

$^1$H NMR (400 MHz, CDCl$_3$) δ 1.17 (d, J=6.4 Hz, 3H), 2.71 (s, 1H), 3.40 (s, 3H), 3.85-4.04 (m, 1H), 4.58 (d, J=6.4 Hz, 1H), 4.66 (d, J=6.4 Hz, 1H), 4.91 (d, J=6.4 Hz, 1H), 7.20-7.37 (m, 2H), 7.44 (s, 1H).

PREPARATION EXAMPLE 103

(1S,2S)-1-(2-chloro-6-fluorophenyl)-1-hydroxypropan-2-yl carbamate

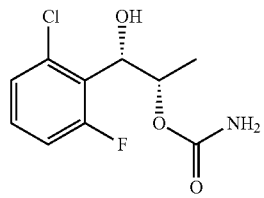

The substantially same method as described in preparation example 64 was conducted, except that (1S,2S)-1-(2-chloro-6-fluorophenyl)propane-1,2-diol (Preparation example 44), was used instead of 1-(2,4-dichlorophenyl)-(S,S)-1,2-propanediol (Preparation example 23), to obtain the title compound (1.2 g, yield 55%).

$^1$H NMR (400 MHz, CDCl$_3$) δ 1.15 (d, J=6.4 Hz, 3H), 3.66 (s, 1H), 4.73 (br s, 2H), 5.43 (t, J=9.0 Hz, 1H), 5.62-5.69 (m, 1H), 7.22-7.38 (m, 3H).

PREPARATION EXAMPLE 104

(1S,2S)-1-(2-chloro-6-fluorophenyl)-1-(methoxymethoxy)propan-2-yl-carbamate

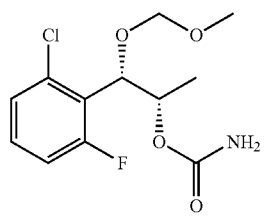 [SMILES: COCO[C@@H](c1c(F)cccc1Cl)[C@H](C)OC(N)=O]

The substantially same method as described in preparation example 47 was conducted, except that 1S,2S)-1-(2-chloro-6-fluorophenyl)-1-(methoxymethoxy)propan-2-yl-carbamate (Preparation example 104), was used instead of (1S,2S)-2-((tert-butyldimethylsilyl)oxy)-1-(2,6-dichlorophenyl)propan-1-ol (Preparation example 46), to obtain the title compound (0.9 g, yield 65%).

$^1$H NMR (400 MHz, CDCl$_3$) δ 1.37 (d, J=6.8 Hz, 3H), 3.30 (s, 3H), 4.71 (d, J=6.8 Hz, 1H), 4.82-4.88 (m, 1H), 5.45 (s, 2H), 7.21-7.35 (m, 3H).

PREPARATION EXAMPLE 105

(1S,2S)-1-(2-chloro-6-fluorophenyl)-1-(methoxymethoxy)propan-2-ol

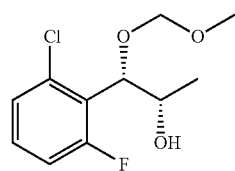 [SMILES: COCO[C@@H](c1c(F)cccc1Cl)[C@H](C)O]

The substantially same method as described in preparation example 66 was conducted, except that (1S,2S)-1-(2-chloro-6-fluorophenyl)-1-(methoxymethoxy)propan-2-yl-carbamate (Preparation example 104), was used instead of (1S,2S)-1-(2,4-dichlorophenyl)-1-(methoxymethoxy)propan-2-yl carbamate (Preparation example 65), to obtain the title compound (0.44 g, yield 45%).

$^1$H NMR (400 MHz, CDCl$_3$) δ 1.06 (d, J=6.4 Hz, 3H), 3.07 (s, 1H), 3.35 (s, 3H), 4.29-4.41 (m, 1H), 4.66-4.84 (m, 3H), 6.91-7.24 (m, 2H), 7.25-7.42 (m, 1H).

PREPARATION EXAMPLE 106

(1S,2S)-2-((tert-butyldimethylsilyl)oxy)-1-(2,6-dichlorophenyl)butan-1-ol

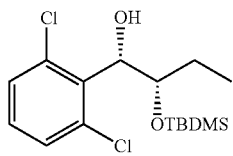 [SMILES: CC[C@H](O[Si](C)(C)C(C)(C)C)[C@@H](O)c1c(Cl)cccc1Cl]

The substantially same method as described in preparation example 46 was conducted, except that (1S,2S)-1-(2,6-dichlorophenyl)butane-1,2-diol (Preparation example 57), was used instead of (1S,2S)-1-(2,6-dichlorophenyl)propane-1,2-diol (Preparation example 27), to obtain the title compound (7.2 g, yield 70%).

$^1$H NMR (400 MHz, CDCl$_3$) δ 0.93 (s, 3H), 0.12 (s, 3H), 1.11 (s, 9H), 1.17 (d, J=7.6 Hz, 3H), 1.46-1.48 (m, 1H), 1.60-1.66 (m, 1H), 3.10 (s, 1H), 4.31-4.49 (m, 1H), 5.40 (d, J=8.8 Hz, 1H), 7.33-7.37 (m, 1H), 7.49-7.52 (m, 2H).

PREPARATION EXAMPLE 107 tert-butyl(((1S,2S)-1-(2,6-dichlorophenyl)-1-methoxybutan-2-yl)oxy)dimethylsilane

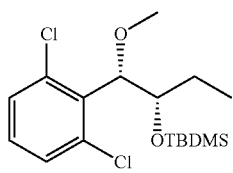

To a stirred solution of (1S,2S)-2-((tert-butyldimethylsilyl)oxy)-1-(2,6-dichlorophenyl)butan-1-ol (Preparation example 106, 3.6 g, 10.30 mmol) in THF (36 mL) was added potassium tert-butoxide (1.7 g, 15.46 mmol) at 0° C. then allowed to stir for 10 min. The mixture was added CH$_3$I (1.9 mL, 30.91 mmol) at 0° C. When the reaction was completed, the resulting mixture was diluted with EtOAc, washed with water, dried over Na$_2$SO$_4$, filtered, and concentrated under reduced pressure to produce the title compound (3.4 g, yield 90%).

$^1$H NMR (400 MHz, CDCl$_3$) δ 0.08-0.13 (m, 6H), 0.82-0.93 (m, 12H), 1.46-1.48 (m, 1H), 1.60-1.66 (m, 1H), 3.18 (s, 3H), 4.41-4.46 (m, 1H), 4.82 (d, J=8.0 Hz, 1H), 7.10-7.14 (m, 1H), 7.25-7.30 (m, 2H).

PREPARATION EXAMPLE 108

(5S,6S)-5-(2,6-dichlorophenyl)-6-ethyl-8,8,9,9-tetramethyl-2,4,7-trioxa-8-siladecane

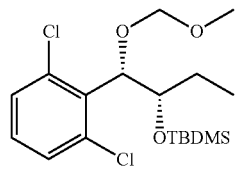

The substantially same method as described in preparation example 47 was conducted, except that (1S,2S)-2-((tert-butyldimethylsilyl)oxy)-1-(2,6-dichlorophenyl)butan-1-ol (Preparation example 106), was used instead of (1S,2S)-2-((tert-butyldimethylsilyl)oxy)-1-(2,6-dichlorophenyl)propan-1-ol (Preparation example 46), to obtain the title compound (3.9 g, yield 97%).

$^1$H NMR (400 MHz, CDCl$_3$) δ 0.93 (s, 3H), 0.12 (s, 3H), 0.83-0.93 (m, 12H), 1.13-1.18 (m, 1H), 1.32-1.37 (m, 1H), 3.44 (s, 3H), 4.29-4.35 (m, 1H), 4.72 (d, J=6.8 Hz, 1H), 5.16 (d, J=7.2 Hz, 1H), 5.31 (d, J=8.8 Hz, 1H), 7.08-7.12 (m, 1H), 7.25-7.30 (m, 2H).

PREPARATION EXAMPLE 109

(1S,2S)-1-(2,6-dichlorophenyl)-1-methoxybutan-2-ol

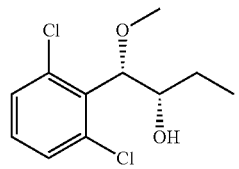

The substantially same method as described in preparation example 48 was conducted, except that tert-butyl(((1S,2S)-1-(2,6-dichlorophenyl)-1-methoxybutan-2-yl)oxy)dimethylsilane (Preparation example 107), was used instead of (5S,6S)-5-(2,6-dichlorophenyl)-6,8,8,9,9-pentamethyl-2,4,7-trioxa-8-siladecane (Preparation example 47), to obtain the title compound (1.7 g, yield 60%).

$^1$H NMR (400 MHz, CDCl$_3$) δ 0.92 (t, J=6.6 Hz, 3H), 1.18-1.27 (m, 1H), 1.38-1.45 (m, 1H), 2.94 (s, 1H), 3.27 (s, 3H), 4.26-4.31 (m, 1H), 4.88 (d, J=8.8 Hz, 1H), 7.14-7.18 (m, 1H), 7.28-7.32 (m, 2H).

PREPARATION EXAMPLE 110

(1S,2S)-1-(2,6-dichlorophenyl)-1-(methoxymethoxy)butan-2-ol

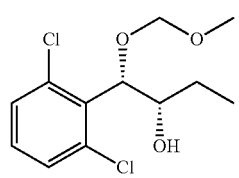 [SMILES: CC[C@H](O)[C@@H](OCOC)c1c(Cl)cccc1Cl]

The substantially same method as described in preparation example 48 was conducted, except that (5S,6S)-5-(2,6-dichlorophenyl)-6-ethyl-8,8,9,9-tetramethyl-2,4,7-trioxa-8-siladecane (Preparation example 108), was used instead of (5S,6S)-5-(2,6-dichlorophenyl)-6,8,8,9,9-pentamethyl-2,4,7-trioxa-8-siladecane (Preparation example 47), to obtain the title compound (2.4 g, yield 87%).

¹H NMR (400 MHz, CDCl₃) δ 0.90 (t, J=7.4 Hz, 3H), 1.22-1.32 (m, 1H), 1.41-1.48 (m, 1H), 3.45 (s, 3H), 3.95 (d, J=5.2 Hz, 1H), 4.08-4.21 (m, 1H), 4.76 (d, J=6.8 Hz, 1H), 4.82 (d, J=6.8 Hz, 1H), 5.33-5.36 (m, 1H), 7.10-7.14 (m, 1H), 7.25-7.29 (m, 2H).

PREPARATION EXAMPLE 111

(1R,2R)-2-((tert-butyldimethylsilyl)oxy)-1-(2,6-dichlorophenyl)butan-1-ol

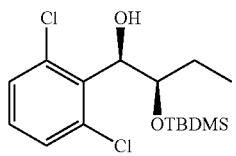

The substantially same method as described in preparation example 46 was conducted, except that (1R,2R)-1-(2,6-dichlorophenyl)butane-1,2-diol (Preparation example 58), was used instead of (1S,2S)-1-(2,6-dichlorophenyl)propane-1,2-diol (Preparation example 27), to obtain the title compound compound (3.6 g, yield 88%).

¹H NMR (400 MHz, CDCl₃) δ 0.93 (s, 3H), 0.12 (s, 3H), 1.11 (s, 9H), 1.17 (d, J=7.6 Hz, 3H), 1.46-1.48 (m, 1H), 1.60-1.66 (m, 1H), 3.10 (s, 1H), 4.31-4.49 (m, 1H), 5.40 (d, J=8.8 Hz, 1H), 7.33-7.37 (m, 1H), 7.49-7.52 (m, 2H).

PREPARATION EXAMPLE 112 tert-butyl(((1R,2R)-1-(2,6-dichlorophenyl)-1-methoxybutan-2-yl)oxy)dimethylsilane

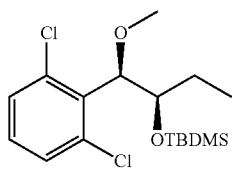

The substantially same method as described in preparation example 107 was conducted, except that (1R,2R)-2-((tert-butyldimethylsilyl)oxy)-1-(2,6-dichlorophenyl)butan-1-ol (Preparation example 111), was used instead of (1S,2S)-2-((tert-butyldimethylsilyl)oxy)-1-(2,6-dichlorophenyl)butan-1-ol (Preparation example 106), to obtain the title compound (2.1 g, yield 96%).

¹H NMR (400 MHz, CDCl₃) δ 0.08-0.13 (m, 6H), 0.82-0.93 (m, 12H), 1.46-1.48 (m, 1H), 1.60-1.66 (m, 1H), 3.18 (s, 3H), 4.41-4.46 (m, 1H), 4.82 (d, J=8.0 Hz, 1H), 7.10-7.14 (m, 1H), 7.25-7.30 (m, 2H).

PREPARATION EXAMPLE 113

(5R,6R)-5-(2,6-dichlorophenyl)-6-ethyl-8,8,9,9-tetramethyl-2,4,7-trioxa-8-siladecane

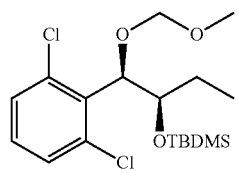

The substantially same method as described in preparation example 47 was conducted, except that (1R,2R)-2-((tert-butyldimethylsilyl)oxy)-1-(2,6-dichlorophenyl)butan-1-ol (Preparation example 111), was used instead of (1S,2S)-2-((tert-butyldimethylsilyl)oxy)-1-(2,6-dichlorophenyl)propan-1-ol (Preparation example 46), to obtain the title compound (2.2 g, yield 94%).

¹H NMR (400 MHz, CDCl₃) δ 0.93 (s, 3H), 0.12 (s, 3H), 0.83-0.93 (m, 12H), 1.13-1.18 (m, 1H), 1.32-1.37 (m, 1H), 3.44 (s, 3H), 4.29-4.35 (m, 1H), 4.72 (d, J=6.8 Hz, 1H), 5.16 (d, J=7.2 Hz, 1H), 5.31 (d, J=8.8 Hz, 1H), 7.08-7.12 (m, 1H), 7.25-7.30 (m, 2H).

PREPARATION EXAMPLE 114

(1R,2R)-1-(2,6-dichlorophenyl)-1-methoxybutan-2-ol

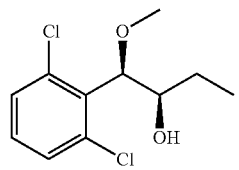

The substantially same method as described in preparation example 48 was conducted, except that tert-butyl(((1R,2R)-1-(2,6-dichlorophenyl)-1-methoxybutan-2-yl)oxy)dimethylsilane (Preparation example 112), was used instead of (5S,6S)-5-(2,6-dichlorophenyl)-6,8,8,9,9-pentamethyl-2,4,7-trioxa-8-siladecane (Preparation example 47), to obtain the title compound (1.2 g, yield 77%).

¹H NMR (400 MHz, CDCl₃) δ 0.92 (t, J=6.6 Hz, 3H), 1.18-1.27 (m, 1H), 1.38-1.45 (m, 1H), 2.94 (s, 1H), 3.27 (s, 3H), 4.26-4.31 (m, 1H), 4.88 (d, J=8.8 Hz, 1H), 7.14-7.18 (m, 1H), 7.28-7.32 (m, 2H).

PREPARATION EXAMPLE 115

(1R,2R)-1-(2,6-dichlorophenyl)-1-(methoxymethoxy)butan-2-ol

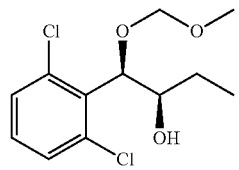 [SMILES: CC[C@@H](O)[C@H](OCOC)c1c(Cl)cccc1Cl]

The substantially same method as described in preparation example 48 was conducted, except that (5R,6R)-5-(2,6-dichlorophenyl)-6-ethyl-8,8,9,9-tetramethyl-2,4,7-trioxa-8-siladecane (Preparation example 113), was used instead of (5S,6S)-5-(2,6-dichlorophenyl)-6,8,8,9,9-pentamethyl-2,4,7-trioxa-8-siladecane (Preparation example 47), to obtain the title compound (1.3 g, yield 79%).

¹H NMR (400 MHz, CDCl₃) δ 0.90 (t, J=7.4 Hz, 3H), 1.22-1.32 (m, 1H), 1.41-1.48 (m, 1H), 3.45 (s, 3H), 3.95 (d, J=5.2 Hz, 1H), 4.08-4.21 (m, 1H), 4.76 (d, J=6.8 Hz, 1H), 4.82 (d, J=6.8 Hz, 1H), 5.33-5.36 (m, 1H), 7.10-7.14 (m, 1H), 7.25-7.29 (m, 2H).

PREPARATION EXAMPLE 116

(1S,2S)-2-((tert-butyldimethylsilyl)oxy)-1-(2,6-dichlorophenyl)-3-methylbutan-1-ol

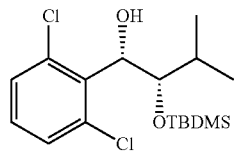

The substantially same method as described in preparation example 46 was conducted, except that (1S,2S)-1-(2,6-dichlorophenyl)-3-methylbutane-1,2-diol (Preparation example 59), was used instead of (1S,2S)-1-(2,6-dichlorophenyl)propane-1,2-diol (Preparation example 27), to obtain the title compound (5.37 g, yield 78%).

¹H NMR (400 MHz, CDCl₃) δ −0.22 (s, 3H), 0.10 (s, 3H), 0.89 (s, 9H), 0.94-0.99 (m, 6H), 1.42-1.49 (qd, J=6.8, 2.4 Hz, 1H), 2.83 (s, 1H), 4.15 (qt, J=8.8, 2.4 Hz, 1H), 5.27 (d, J=8.4 Hz, 1H), 7.13 (t, J=8.0 Hz, 1H), 7.27-7.30 (m, 2H).

PREPARATION EXAMPLE 117 tert-butyl(((1S,2S)-1-(2,6-dichlorophenyl)-1-methoxy-3-methylbutan-2-yl)oxy)dimethylsilane

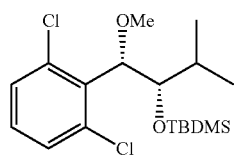

The substantially same method as described in preparation example 107 was conducted, except that (1S,2S)-2-((tert-butyldimethylsilyl)oxy)-1-(2,6-dichlorophenyl)-3-methylbutan-1-ol (Preparation example 116), was used instead of (1S,2S)-2-((tert-butyldimethylsilyl)oxy)-1-(2,6-dichlorophenyl)butan-1-ol (Preparation example 106), to obtain the title compound (1.20 g, yield 96%).

¹H NMR (400 MHz, CDCl₃) δ 0.13 (s, 3H), 0.15 (s, 3H), 0.83 (dd, J=28.4, 6.8 Hz, 6H), 0.94 (s, 9H), 1.23-1.30 (m, 1H), 3.16 (s, 3H), 4.54 (dd, J=8.0, 1.6 Hz, 1H), 4.84 (d, J=8.4 Hz, 1H), 7.14 (t, J=8.0 Hz, 1H), 7.29-7.32 (m, 2H).

PREPARATION EXAMPLE 118

(5S,6S)-5-(2,6-dichlorophenyl)-6-isopropyl-8,8,9,9-tetramethyl-2,4,7-trioxa-8-siladecane

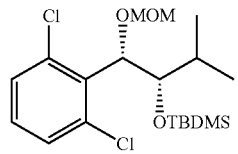

The substantially same method as described in preparation example 47 was conducted, except that (1S,2S)-2-((tert-butyldimethylsilyl)oxy)-1-(2,6-dichlorophenyl)-3-methylbutan-1-ol (Preparation example A), was used instead of (1S,2S)-2-((tert-butyldimethylsilyl)oxy)-1-(2,6-dichlorophenyl)propan-1-ol (Preparation example 46), to obtain the title compound (4.12 g, yield 90%).

¹H NMR (400 MHz, CDCl₃) δ −0.24 (s, 3H), 0.08 (s, 3H), 0.83 (s, 9H), 0.93 (dd, J=6.8, 2.4 Hz, 6H), 1.23-1.32 (m, 1H), 3.44 (s, 3H), 4.33 (dd, J=8.8, 1.2 Hz, 1H), 4.72 (d, J=6.8 Hz, 1H), 5.17 (d, J=6.8 Hz, 1H), 5.37 (d, J=9.2 Hz. 1H), 7.11 (t, J=8.0 Hz, 1H), 7.25-7.28 (m, 2H).

PREPARATION EXAMPLE 119

(1S,2S)-1-(2,6-dichlorophenyl)-1-methoxy-3-methylbutan-2-ol

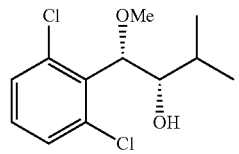 [SMILES: CO[C@@H](c1c(Cl)cccc1Cl)[C@@H](O)C(C)C]

The substantially same method as described in preparation example 48 was conducted, except that tert-butyl(((1S,2S)-1-(2,6-dichlorophenyl)-1-methoxy-3-methylbutan-2-yl)oxy)dimethylsilane (Preparation example 117), was used instead of (5S,6S)-5-(2,6-dichlorophenyl)-6,8,8,9,9-pentamethyl-2,4,7-trioxa-8-siladecane (Preparation example 47), to obtain the title compound (0.54 g, yield 65%).

¹H NMR (400 MHz, CDCl₃) δ 0.96 (d, J=6.8 Hz, 6H), 1.43-1.51 (m, 1H), 2.75 (d, J=2.4 Hz, 1H), 4.29 (td, J=8.4, 2.8 Hz, 1H), 4.96 (d, J=8.0 Hz, 1H), 7.18 (t, J=8.0 Hz, 1H), 7.32 (d, J=8.0 Hz, 2H).

PREPARATION EXAMPLE 120

(1S,2S)-1-(2,6-dichlorophenyl)-1-(methoxymethoxy)-3-methylbutan-2-ol

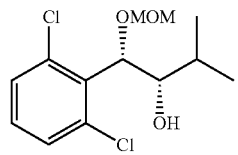

The substantially same method as described in preparation example 48 was conducted, except that (5S,6S)-5-(2,6-dichlorophenyl)-6-isopropyl-8,8,9,9-tetramethyl-2,4,7-trioxa-8-siladecane (Preparation example 118), was used instead of (5S,6S)-5-(2,6-dichlorophenyl)-6,8,8,9,9-pentamethyl-2,4,7-trioxa-8-siladecane (Preparation example 47), to obtain the title compound (3.72 g, 90%).

¹H NMR (400 MHz, CDCl₃) δ 0.92 (dd, J=15.2, 6.8 Hz, 6H), 1.53 (qd, J=6.8, 2.4 Hz, 1H), 3.48 (s, 3H), 4.02 (d, J=4.4 Hz, 1H), 4.22 (dd, J=8.0, 2.4 Hz, 1H), 4.76 (dd, J=31.6, 6.4 Hz, 2H), 5.39 (dd, J=8.0, 4.8 Hz, 1H), 7.13 (t, J=8.0 Hz, 1H), 7.29 (d, J=8.0 Hz, 2H).

PREPARATION EXAMPLE 121

(1R,2R)-2-((tert-butyldimethylsilyl)oxy)-1-(2,6-dichlorophenyl)-3-methylbutan-1-ol

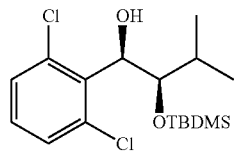

The substantially same method as described in preparation example 46 was conducted, except that (1R,2R)-1-(2,6-dichlorophenyl)-3-methylbutane-1,2-diol (Preparation example 60), was used instead of (1S,2S)-1-(2,6-dichlorophenyl)propane-1,2-diol (Preparation example 27), to obtain the title compound (5.12 g, yield 76%).

¹H NMR (400 MHz, CDCl₃) δ −0.20 (s, 3H), 0.12 (s, 3H), 0.91 (s, 9H), 1.00 (dd, J=13.6, 6.8 Hz, 6H), 1.44-1.52 (m, 1H), 2.85 (s, 1H), 4.17 (qd, J=12.8, 2.0 Hz, 1H), 5.29 (d, J=8.4 Hz, 1H), 7.16 (t, J=8.0 Hz, 1H), 7.30-7.33 (m, 2H).

PREPARATION EXAMPLE 122 tert-butyl(((1R,2R)-1-(2,6-dichlorophenyl)-1-methoxy-3-methylbutan-2-yl)oxy)dimethylsilane

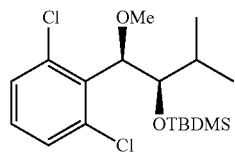

The substantially same method as described in preparation example 107 was conducted, except that (1R,2R)-2-((tert-butyldimethylsilyl)oxy)-1-(2,6-dichlorophenyl)-3-methylbutan-1-ol (Preparation example 121), was used instead of (1S,2S)-2-((tert-butyldimethylsilyl)oxy)-1-(2,6-dichlorophenyl)butan-1-ol (Preparation example 106), to obtain the title compound (1.28 g, yield 98%).

¹H NMR (400 MHz, CDCl₃) δ 0.12 (s, 3H), 0.15 (s, 3H), 0.85 (dd, J=28.4, 6.8 Hz, 6H), 0.95 (s, 9H), 1.23-1.30 (m, 1H), 3.16 (s, 3H), 4.54 (dd, J=8.4, 2.0 Hz, 1H), 4.83 (d, J=8.0 Hz, 1H), 7.14 (t, J=8.0 Hz, 1H), 7.29-7.32 (m, 2H).

PREPARATION EXAMPLE 123

(5R,6R)-5-(2,6-dichlorophenyl)-6-isopropyl-8,8,9,9-tetramethyl-2,4,7-trioxa-8-siladecane

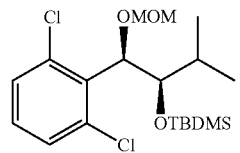

The substantially same method as described in preparation example 47 was conducted, except that (1R,2R)-2-((tert-butyldimethylsilyl)oxy)-1-(2,6-dichlorophenyl)-3-methylbutan-1-ol (Preparation example 121), was used instead of (1S,2S)-2-((tert-butyldimethylsilyl)oxy)-1-(2,6-dichlorophenyl)propan-1-ol (Preparation example 46), to obtain the title compound (4.04 g, yield 92%).

¹H NMR (400 MHz, CDCl₃) δ −0.24 (s, 3H), 0.08 (s, 3H), 0.83 (s, 9H), 0.94 (dd, J=5.2, 2.4 Hz, 6H), 1.24-1.33 (m, 1H), 3.44 (s, 3H), 4.34 (dd, J=8.8, 1.6 Hz, 1H), 4.72 (d, J=6.8 Hz, 1H), 5.17 (d, J=6.8 Hz, 1H), 5.37 (d, J=8.8 Hz. 1H), 7.12 (t, J=8.0 Hz, 1H), 7.26-7.29 (m, 2H).

PREPARATION EXAMPLE 124

(1R,2R)-1-(2,6-dichlorophenyl)-1-methoxy-3-methylbutan-2-ol

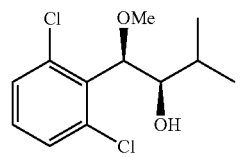 [SMILES: CO[C@H](c1c(Cl)cccc1Cl)[C@H](O)C(C)C]

The substantially same method as described in preparation example 48 was conducted, except that tert-butyl(((1R,2R)-1-(2,6-dichlorophenyl)-1-methoxy-3-methylbutan-2-yl)oxy)dimethylsilane (Preparation example 122), was used instead of (5S,6S)-5-(2,6-dichlorophenyl)-6,8,8,9,9-pentamethyl-2,4,7-trioxa-8-siladecane (Preparation example 47), to obtain the title compound (0.77 g, yield 79%).

¹H NMR (400 MHz, CDCl₃) δ 0.96 (d, J=6.8 Hz, 6H), 1.43-1.51 (m, 1H), 2.75 (d, J=2.4 Hz, 1H), 4.29 (td, J=8.4, 2.8 Hz, 1H), 4.96 (d, J=8.0 Hz, 1H), 7.18 (t, J=8.0 Hz, 1H), 7.32 (d, J=8.0 Hz, 2H).

PREPARATION EXAMPLE 125

(1R,2R)-1-(2,6-dichlorophenyl)-1-(methoxymethoxy)-3-methylbutan-2-ol

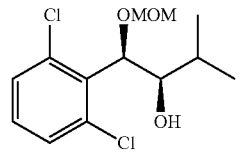

The substantially same method as described in preparation example 48 was conducted, except that (5R,6R)-5-(2,6-dichlorophenyl)-6-isopropyl-8,8,9,9-tetramethyl-2,4,7-trioxa-8-siladecane (Preparation example 123), was used instead of (5S,6S)-5-(2,6-dichlorophenyl)-6,8,8,9,9-pentamethyl-2,4,7-trioxa-8-siladecane (Preparation example 47), to obtain the title compound (2.73 g, yield 95%).

¹H NMR (400 MHz, CDCl₃) δ 0.90-0.96 (m, 6H), 1.50-1.57 (m, 1H), 3.49 (s, 3H), 4.02 (d, J=4.4 Hz, 1H), 4.22 (dd, J=7.6, 2.8 Hz, 1H), 4.77 (dd, J=30.8, 6.4 Hz, 2H), 5.40 (dd, J=7.6, 4.4 Hz, 1H), 7.14 (t, J=8.0 Hz, 1H), 7.30 (d, J=8.0 Hz, 2H).

PREPARATION EXAMPLE 126

(1S,2S)-2-((tert-butyldimethylsilyl)oxy)-1-(2,6-dichlorophenyl)hexan-1-ol

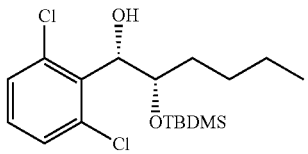 [SMILES: CCCC[C@H](O[Si](C)(C)C(C)(C)C)[C@@H](O)c1c(Cl)cccc1Cl]

The substantially same method as described in preparation example 46 was conducted, except that (1S,2S)-1-(2,6-dichlorophenyl)hexane-1,2-diol (Preparation example 61), was used instead of (1S,2S)-1-(2,6-dichlorophenyl)propane-1,2-diol (Preparation example 27), to obtain the title compound (7.1 g, yield 88%).

¹H NMR (400 MHz, CDCl₃) δ−0.20 (s, 3H), 0.10 (s, 3H), 0.83 (t, J=5.2 Hz, 3H), 0.91 (s, 9H), 1.05-1.50 (m, 6H), 2.80 (s, 1H), 4.27-4.33 (m, 1H), 5.20 (d, J=8.8 Hz, 1H), 7.13-7.17 (m, 1H), 7.28-7.32 (m, 2H).

PREPARATION EXAMPLE 127 tert-butyl(((1S,2S)-1-(2,6-dichlorophenyl)-1-methoxyhexan-2-yl)oxy)dimethylsilane

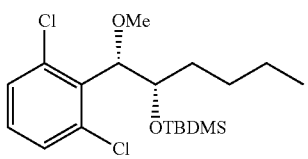 [SMILES: CCCC[C@H](O[Si](C)(C)C(C)(C)C)[C@@H](OC)c1c(Cl)cccc1Cl]

The substantially same method as described in preparation example 107 was conducted, except that (1S,2S)-2-((tert-butyldimethylsilyl)oxy)-1-(2,6-dichlorophenyl)hexan-1-ol (Preparation example 126), was used instead of (1S,2S)-2-((tert-butyldimethylsilyl)oxy)-1-(2,6-dichlorophenyl)butan-1-ol (Preparation example 106), to obtain the title compound (2.0 g, yield 95%).

¹H NMR (400 MHz, CDCl₃) δ 0.08 (d, J=2.4 Hz, 6H), 0.76 (s, 3H), 0.79 (s, 9H), 1.06-1.19 (m, 6H), 3.04 (s, 3H), 4.35-4.40 (m, 1H), 4.91 (d, J=8.0 Hz, 1H), 7.00 (t, J=8.0 Hz, 1H), 7.15-7.18 (m, 2H).

PREPARATION EXAMPLE 128

(5S,6S)-6-butyl-5-(2,6-dichlorophenyl)-8,8,9,9-tetramethyl-2,4,7-trioxa-8-siladecane

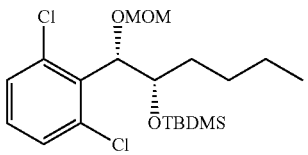

The substantially same method as described in preparation example 47 was conducted, except that (1S,2S)-2-((tert-butyldimethylsilyl)oxy)-1-(2,6-dichlorophenyl)hexan-1-ol (Preparation example 126), was used instead of (1S,2S)-2-((tert-butyldimethylsilyl)oxy)-1-(2,6-dichlorophenyl)propan-1-ol (Preparation example 46), to obtain the title compound (2.30 g, yield 98%).

¹H NMR (400 MHz, CDCl₃) δ−0.23 (s, 3H), 0.07 (s, 3H), 0.72 (t, J=6.2 Hz, 3H) 0.82 (s, 9H), 1.10-1.50 (m, 6H), 3.43 (s, 3H), 4.30-4.36 (m, 1H), 4.64 (d, J=6.8 Hz, 1H), 5.10 (d, J=7.2 Hz, 1H), 5.25 (d, J=8.8 Hz, 1H), 7.09-7.13 (m, 1H), 7.27-7.32 (m, 2H).

PREPARATION EXAMPLE 129

(1S,2S)-1-(2,6-dichlorophenyl)-1-methoxyhexan-2-ol

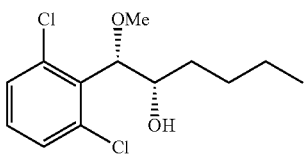 [SMILES: CCCC[C@H](O)[C@@H](OC)c1c(Cl)cccc1Cl]

The substantially same method as described in preparation example 48 was conducted, except that tert-butyl(((1S,2S)-1-(2,6-dichlorophenyl)-1-methoxyhexan-2-yl)oxy)dimethylsilane (Preparation example 127), was used instead of (5S,6S)-5-(2,6-dichlorophenyl)-6,8,8,9,9-pentamethyl-2,4,7-trioxa-8-siladecane (Preparation example 47), to obtain the title compound (1.04 g, yield 73%).

¹H NMR (400 MHz, CDCl₃) δ 0.84 (t, J=7.2 Hz, 1H), 1.12-1.52 (m, 6H), 2.92 (s, 1H), 3.26 (s, 3H), 4.35-4.40 (m, 1H), 4.89 (d, J=8.8 Hz, 1H) 7.17 (t, J=8.0 Hz, 1H), 7.31-7.33 (m, 2H).

PREPARATION EXAMPLE 130

(1S,2S)-1-(2,6-dichlorophenyl)-1-(methoxymethoxy)hexan-2-ol

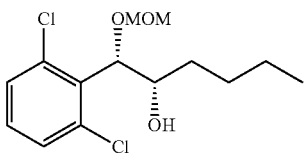

The substantially same method as described in preparation example 48 was conducted, except (5S,6S)-6-butyl-5-(2,6-dichlorophenyl)-8,8,9,9-tetramethyl-2,4,7-trioxa-8-siladecane (Preparation example 128), was used instead of (5S,6S)-5-(2,6-dichlorophenyl)-6,8,8,9,9-pentamethyl-2,4,7-trioxa-8-siladecane (Preparation example 47), to obtain the title compound (1.3 g, yield 80%).

$^1$H NMR (400 MHz, CDCl$_3$) δ 0.82 (t, J=7.2 Hz, 3H), 1.19-1.49 (m, 6H), 3.46 (s, 3H), 4.00 (d, J=5.2 Hz, 1H), 4.24-4.29 (m, 1H), 4.76 (d, J=6.8 Hz, 1H), 4.82 (d, J=6.8 Hz, 1H), 5.35 (dd, J=7.8, 5.0 Hz, 1H), 7.14 (t, J=8.0 Hz, 1H), 7.30 (d, J=8.4 Hz, 2H).

PREPARATION EXAMPLE 131

(1R,2R)-2-((tert-butyldimethylsilyl)oxy)-1-(2,6-dichlorophenyl)hexan-1-ol

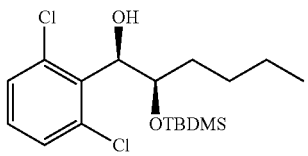 [SMILES: CCCC[C@@H](O[Si](C)(C)C(C)(C)C)[C@H](O)c1c(Cl)cccc1Cl]

The substantially same method as described in preparation example 46 was conducted, except that (1R,2R)-1-(2,6-dichlorophenyl)hexane-1,2-diol (Preparation example 62), was used instead of (1S,2S)-1-(2,6-dichlorophenyl)propane-1,2-diol (Preparation example 27), to obtain the title compound (8.6 g, yield 86%).

$^1$H NMR (400 MHz, CDCl$_3$) δ −0.20 (s, 3H), 0.10 (s, 3H), 0.83 (t, J=5.2 Hz, 3H) 0.91 (s, 9H), 1.05-1.5 (m, 6H), 2.8 (s, 1H), 4.27-4.33 (m, 1H), 5.20 (d, J=8.8 Hz, 1H), 7.13-7.17 (m, 1H), 7.28-7.32 (m, 2H).

PREPARATION EXAMPLE 132 tert-butyl(((1R,2R)-1-(2,6-dichlorophenyl)-1-methoxyhexan-2-yl)oxy)dimethylsilane

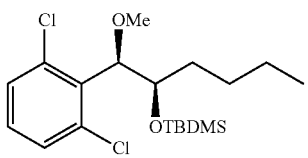 [SMILES: CCCC[C@@H](O[Si](C)(C)C(C)(C)C)[C@H](OC)c1c(Cl)cccc1Cl]

The substantially same method as described in preparation example 107 was conducted, except that (1R,2R)-2-((tert-butyldimethylsilyl)oxy)-1-(2,6-dichlorophenyl)hexan-1-ol (Preparation example 131), was used instead of (1S,2S)-2-((tert-butyldimethylsilyl)oxy)-1-(2,6-dichlorophenyl)butan-1-ol (Preparation example 106), to obtain the title compound (1.5 g, yield 99%).

$^1$H NMR (400 MHz, CDCl$_3$) δ 0.08 (d, J=2.4 Hz, 6H), 0.76 (s, 3H), 0.79 (s, 9H), 1.06-1.19 (m, 6H), 3.04 (s, 3H), 4.35-4.40 (m, 1H), 4.91 (d, J=8.0 Hz, 1H), 7.00 (t, J=8.0 Hz, 1H), 7.15-7.18 (m, 2H).

PREPARATION EXAMPLE 133

(5R,6R)-6-butyl-5-(2,6-dichlorophenyl)-8,8,9,9-tetramethyl-2,4,7-trioxa-8-siladecane

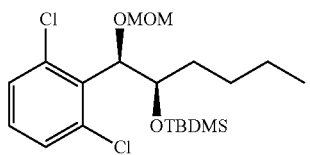

The substantially same method as described in preparation example 47 was conducted, except that (1R,2R)-2-((tert-butyldimethylsilyl)oxy)-1-(2,6-dichlorophenyl)hexan-1-ol (Preparation example 131), was used instead of (1S,2S)-2-((tert-butyldimethylsilyl)oxy)-1-(2,6-dichlorophenyl)propan-1-ol (Preparation example 46), to obtain the title compound (6.26 g, yield 93%).

$^1$H NMR (400 MHz, CDCl$_3$) δ −0.23 (s, 3H), 0.07 (s, 3H), 0.72 (t, J=6.2 Hz, 3H) 0.82 (s, 9H), 1.1-1.5 (m, 6H), 3.43 (s, 3H), 4.30-4.36 (m, 1H), 4.64 (d, J=6.8 Hz, 1H), 5.10 (d, J=7.2 Hz, 1H), 5.25 (d, J=8.8 Hz, 1H), 7.09-7.13 (m, 1H), 7.27-7.32 (m, 2H).

PREPARATION EXAMPLE 134

(1R,2R)-1-(2,6-dichlorophenyl)-1-methoxyhexan-2-ol

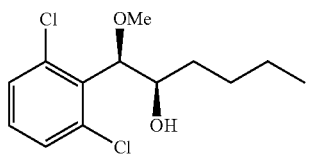

The substantially same method as described in preparation example 48 was conducted, except that tert-butyl(((1R,2R)-1-(2,6-dichlorophenyl)-1-methoxyhexan-2-yl)oxy)dimethylsilane (Preparation example 132), was used instead of (5S,6S)-5-(2,6-dichlorophenyl)-6,8,8,9,9-pentamethyl-2,4,7-trioxa-8-siladecane (Preparation example 47), to obtain the title compound (0.68 g, yield 64%).

$^1$H NMR (400 MHz, CDCl$_3$) δ 0.84 (t, J=7.2 Hz, 1H), 1.12-1.52 (m, 6H), 2.92 (s, 1H), 3.26 (s, 3H), 4.35-4.40 (m, 1H), 4.89 (d, J=8.8 Hz, 1H) 7.17 (t, J=8.0 Hz, 1H), 7.31-7.33 (m, 2H).

PREPARATION EXAMPLE 135

(1R,2R)-1-(2,6-dichlorophenyl)-1-(methoxymethoxy)hexan-2-ol

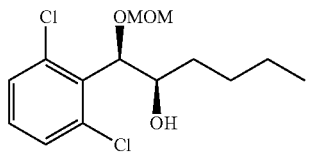

The substantially same method as described in preparation example 48 was conducted, except (5R,6R)-6-butyl-5-(2,6-dichlorophenyl)-8,8,9,9-tetramethyl-2,4,7-trioxa-8-siladecane (Preparation example 133), was used instead of (5S,6S)-5-(2,6-dichlorophenyl)-6,8,8,9,9-pentamethyl-2,4,7-trioxa-8-siladecane (Preparation example 47), to obtain the title compound (3.2 g, yield 71%).

$^1$H NMR (400 MHz, CDCl$_3$) δ 0.82 (t, J=7.2 Hz, 3H), 1.19-1.49 (m, 6H), 3.46 (s, 3H), 4.00 (d, J=5.2 Hz, 1H), 4.24-4.29 (m, 1H), 4.76 (d, J=6.8 Hz, 1H), 4.82 (d, J=6.8 Hz, 1H), 5.35 (dd, J=7.8, 5.0 Hz, 1H), 7.14 (t, J=8.0 Hz, 1H), 7.30 (d, J=8.4 Hz, 2H).

PREPARATION EXAMPLE 136

(1S,2S)-1-(2-chlorophenyl)-1-hydroxypropan-2-yl carbamate

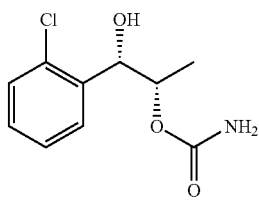

The substantially same method as described in preparation example 64 was conducted, except that (1S,2S)-1-(2-chlorophenyl)propane-1,2-diol (Preparation example 21), was used instead of 1-(2,4-dichlorophenyl)-(S,S)-1,2-propanediol (Preparation example 23), to obtain the title compound (1.40 g, yield 49%).

$^1$H NMR (400 MHz, CDCl$_3$) δ 1.24 (d, J=6.4 Hz, 3H), 2.91 (d, J=4.8 Hz, 1H), 4.68 (br s, 2H), 5.06-5.09 (m, 1H), 5.18-5.21 (m, 1H), 7.23-7.55 (m, 4H).

PREPARATION EXAMPLE 137

(1S,2S)-1-(2-chlorophenyl)-1-(methoxymethoxy)propan-2-yl carbamate

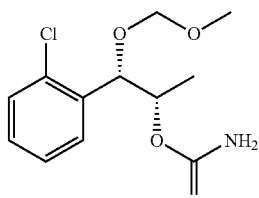

The substantially same method as described in preparation example 47 was conducted, except that (1S,2S)-1-(2-chlorophenyl)-1-hydroxypropan-2-yl carbamate (Preparation example 136), was used instead of (1S,2S)-2-((tert-butyldimethylsilyl)oxy)-1-(2,6-dichlorophenyl)propan-1-ol (Preparation example 46), to obtain the title compound (14.9 g, yield 84%).

$^1$H NMR (400 MHz, CDCl$_3$) δ 1.28 (d, J=5.6 Hz, 3H), 3.39 (s, 3H), 4.62 (d, J=6.8 Hz, 1H), 4.55 (br s, 2H), 4.64 (d, J=6.8 Hz, 1H), 5.16-5.20 (m, 2H), 7.24-7.34 (m, 2H), 7.39 (dd, J=7.8, 1.0 Hz, 1H), 7.49 (dd, J=7.6, 1.6 Hz, 1H).

PREPARATION EXAMPLE 138

(1S,2S)-1-(2-chlorophenyl)-1-(methoxymethoxy)propan-2-ol

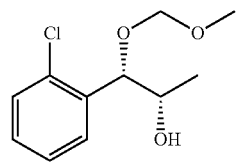

The substantially same method as described in preparation example 48 was conducted, except (1S,2S)-1-(2-chlorophenyl)-1-(methoxymethoxy)propan-2-yl carbamate (Preparation example 137), was used instead of (5S,6S)-5-(2,6-dichlorophenyl)-6,8,8,9,9-pentamethyl-2,4,7-trioxa-8-siladecane (Preparation example 47), to obtain the title compound (7.56 g, yield 30%).

$^1$H NMR (400 MHz, CDCl$_3$) δ 1.15 (d, J=6.4 Hz, 3H), 2.82 (d, J=2.8 Hz, 1H), 3.93 (s, 3H), 3.95-3.99 (m, 1H), 4.60 (dd, J=24.4, 6.4 Hz, 2H), 4.97 (d, J=6.8 Hz, 1H), 7.23-7.29 (m, 2H), 7.32 (dd, J=7.6, 1.2, 1H), 7.38 (dd, J=7.6, 1.2, 1H).

PREPARATION EXAMPLE 139

(1R,2R)-1-(2-chlorophenyl)-1-hydroxypropan-2-yl carbamate

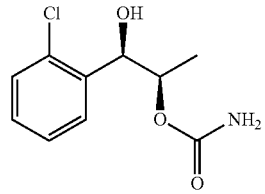

The substantially same method as described in preparation example 64 was conducted, except that (1R,2R)-1-(2-chlorophenyl)propane-1,2-diol (Preparation example 22), was used instead of 1-(2,4-dichlorophenyl)-(S,S)-1,2-propanediol (Preparation example 23), to obtain the title compound (9.5 g, yield 60%).

$^1$H NMR (400 MHz, CDCl$_3$) δ 1.24 (d, J=6.4 Hz, 3H), 3.00 (s, 1H), 4.76 (br s, 2H), 7.24-7.32 (m, 2H), 7.33 (dd, J=7.6, 1.2 Hz, 1H), 7.37 (dd, J=8.0, 1.6 Hz, 1H).

PREPARATION EXAMPLE 140

(1R,2R)-1-(2-chlorophenyl)-1-(methoxymethoxy)propan-2-yl carbamate

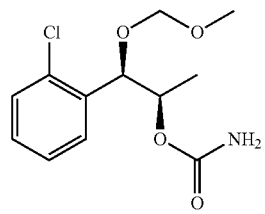 [SMILES: COCO[C@H](c1ccccc1Cl)[C@@H](C)OC(N)=O]

The substantially same method as described in preparation example 47 was conducted, except that (1R,2R)-1-(2-chlorophenyl)-1-hydroxypropan-2-yl carbamate (Preparation example 139), was used instead of (1S,2S)-2-((tert-butyldimethylsilyl)oxy)-1-(2,6-dichlorophenyl)propan-1-ol (Preparation example 46), to obtain the title compound (9.0 g, yield 84%).

$^1$H NMR (400 MHz, CDCl$_3$) δ 1.28 (d, J=5.6 Hz, 3H), 3.39 (s, 3H), 4.62 (d, J=6.8 Hz, 1H), 4.55 (br s, 2H), 4.64 (d, J=6.8 Hz, 1H), 5.16-5.20 (m, 2H), 7.24-7.34 (m, 2H), 7.39 (dd, J=7.8, 1.0 Hz, 1H), 7.49 (dd, J=7.6, 1.6 Hz, 1H).

PREPARATION EXAMPLE 141

(1R,2R)-1-(2-chlorophenyl)-1-(methoxymethoxy)propan-2-ol

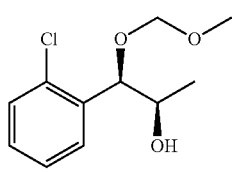

The substantially same method as described in preparation example 48 was conducted, except (1R,2R)-1-(2-chlorophenyl)-1-(methoxymethoxy)propan-2-yl carbamate (Preparation example 140), was used instead of (5S,6S)-5-(2,6-dichlorophenyl)-6,8,8,9,9-pentamethyl-2,4,7-trioxa-8-siladecane (Preparation example 47), to obtain the title compound (3.2 g, yield 42%).

$^1$H NMR (400 MHz, CDCl$_3$) δ 1.15 (d, J=6.4 Hz, 3H), 2.81 (d, J=2.4 Hz, 1H), 3.40 (s, 3H), 3.95-4.00 (m, 1H), 4.60 (dd, J=24.4, 6.4 Hz, 2H), 4.97 (d, J=7.2 Hz, 1H), 7.24-7.33 (m, 2H), 7.39 (dd, J=8.0, 2.0, 1H), 7.45 (dd, J=8.0, 2.0 Hz, 1H).

PREPARATION EXAMPLE 142 tert-butyl(((1S,2S)-1-(2,6-dichlorophenyl)-1-methoxypropan-2-yl)oxy)dimethylsilane

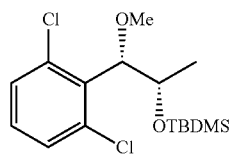 [SMILES: CO[C@@H](c1c(Cl)cccc1Cl)[C@H](C)O[Si](C)(C)C(C)(C)C]

The substantially same method as described in preparation example 107 was conducted, except that (1S,2S)-2-((tert-butyldimethylsilyl)oxy)-1-(2,6-dichlorophenyl)propan-1-ol (Preparation example 46), was used instead of (1S,2S)-2-((tert-butyldimethylsilyl)oxy)-1-(2,6-dichlorophenyl)butan-1-ol (Preparation example 106), to obtain the title compound (2.1 g, yield 90%).

$^1$H NMR (400 MHz, CDCl$_3$) δ 0.94-0.15 (m, 6H), 0.91-1.05 (m, 12H), 3.25 (s, 3H), 4.62-4.68 (m, 1H), 4.84 (d, J=8.0 Hz, 1H), 7.13-7.17 (m, 1H), 7.28-7.33 (m, 2H).

PREPARATION EXAMPLE 143

(1S,2S)-1-(2,6-dichlorophenyl)-1-methoxypropan-2-ol

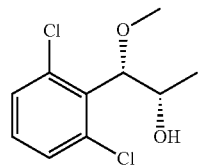

The substantially same method as described in preparation example 48 was conducted, except tert-butyl(((1S,2S)-1-(2,6-dichlorophenyl)-1-methoxypropan-2-yl)oxy)dimethylsilane (Preparation example 142), was used instead of (5S,6S)-5-(2,6-dichlorophenyl)-6,8,8,9,9-pentamethyl-2,4,7-trioxa-8-siladecane (Preparation example 47), to obtain the title compound (1.06 g, yield 81%).

$^1$H NMR (400 MHz, CDCl$_3$) δ 1.04 (d, J=6.4 Hz, 3H), 3.02 (s, 1H), 3.29 (s, 3H), 4.55-4.59 (m, 1H), 4.90 (d, J=8.8 Hz, 1H), 7.17-7.21 (m, 1H), 7.31-7.33 (m, 2H).

PREPARATION EXAMPLE 144 tert-butyl(((1R,2R)-1-(2,6-dichlorophenyl)-1-methoxypropan-2-yl)oxy)dimethylsilane

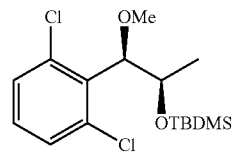 [SMILES: CO[C@H](c1c(Cl)cccc1Cl)[C@@H](C)O[Si](C)(C)C(C)(C)C]

The substantially same method as described in preparation example 107 was conducted, except that (1R,2R)-2-((tert-butyldimethylsilyl)oxy)-1-(2,6-dichlorophenyl)propan-1-ol (Preparation example 51), was used instead of (1S,2S)-2-((tert-butyldimethylsilyl)oxy)-1-(2,6-dichlorophenyl)butan-1-ol (Preparation example 106), to obtain the title compound (4.1 g, yield 98%).

$^1$H NMR (400 MHz, CDCl$_3$) δ 0.94-0.15 (m, 6H), 0.91-1.05 (m, 12H), 3.25 (s, 3H), 4.62-4.68 (m, 1H), 4.84 (d, J=8.0 Hz, 1H), 7.13-7.17 (m, 1H), 7.28-7.33 (m, 2H).

PREPARATION EXAMPLE 145

(1R,2R)-1-(2,6-dichlorophenyl)-1-methoxypropan-2-ol

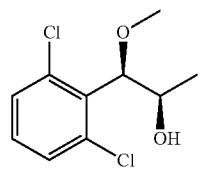

The substantially same method as described in preparation example 48 was conducted, except tert-butyl(((1R,2R)-

1-(2,6-dichlorophenyl)-1-methoxypropan-2-yl)oxy)dimethylsilane (Preparation example 144), was used instead of (5S,6S)-5-(2,6-dichlorophenyl)-6,8,8,9,9-pentamethyl-2,4,7-trioxa-8-siladecane (Preparation example 47), to obtain the title compound (2.2 g, yield 80%).

¹H NMR (400 MHz, CDCl₃) δ 1.04 (d, J=6.4 Hz, 3H), 3.02 (s, 1H), 3.29 (s, 3H), 4.55-4.59 (m, 1H), 4.90 (d, J=8.8 Hz, 1H), 7.17-7.21 (m, 1H), 7.31-7.33 (m, 2H).

PREPARATION EXAMPLE 146

(1S,2S)-2-((tert-butyldimethylsilyl)oxy)-1-(2-iodophenyl)propan-1-ol

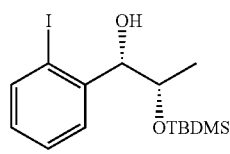 [SMILES: C[C@H](O[Si](C)(C)C(C)(C)C)[C@@H](O)c1ccccc1I]

The substantially same method as described in preparation example 46 was conducted, except that 1-(2-iodophenyl)-(S,S)-1,2-propanediol (Preparation example 39), was used instead of (1S,2S)-1-(2,6-dichlorophenyl)propane-1,2-diol (Preparation example 27), to obtain the title compound (2.8 g, yield 74%).

¹H NMR (400 MHz, CDCl₃) δ -0.32 (s, 3H), -0.07 (s, 3H), 0.87 (s, 9H), 1.35 (d, J=6.0 Hz, 3H), 3.24 (d, J=7.6 Hz, 1H), 4.02-4.11 (m, 1H), 4.66 (dd, J=7.2, 2.8 Hz, 1H), 6.95-7.01 (m, 1H), 7.33-7.41 (m, 2H), 7.78-7.73 (m, 1H).

PREPARATION EXAMPLE 147 tert-butyl(((1S,2S)-1-(2-iodophenyl)-1-methoxypropan-2-yl)oxy)dimethylsilane

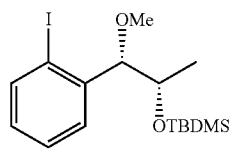 [SMILES: CO[C@@H](c1ccccc1I)[C@H](C)O[Si](C)(C)C(C)(C)C]

The substantially same method as described in preparation example 107 was conducted, except that (1S,2S)-2-((tert-butyldimethylsilyl)oxy)-1-(2-iodophenyl)propan-1-ol (Preparation example 146), was used instead of (1S,2S)-2-((tert-butyldimethylsilyl)oxy)-1-(2,6-dichlorophenyl)butan-1-ol (Preparation example 106), to obtain the title compound (2.6 g, yield 88%).

¹H NMR (400 MHz, CDCl₃) δ -0.32 (s, 3H), -0.07 (s, 3H), 0.87 (s, 9H), 1.35 (d, J=6.0 Hz, 3H), 3.12 (s, 3H), 4.02-4.11 (m, 1H), 4.66 (dd, J=7.2, 2.8 Hz, 1H), 6.95-7.01 (m, 1H), 7.33-7.41 (m, 2H), 7.78-7.73 (m, 1H).

PREPARATION EXAMPLE 148

(1S,2S)-1-(2-iodophenyl)-1-methoxypropan-2-ol

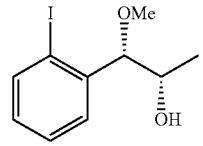

The substantially same method as described in preparation example 48 was conducted, except that tert-butyl(((1S,2S)-1-(2-iodophenyl)-1-methoxypropan-2-yl)oxy)dimethylsilane (Preparation example 147), was used instead of (5S,6S)-5-(2,6-dichlorophenyl)-6,8,8,9,9-pentamethyl-2,4,7-trioxa-8-siladecane (Preparation example 47), to obtain the title compound (1.4 g, yield 76%).

¹H NMR (400 MHz, CDCl₃) δ 1.24 (d, J=6.4 Hz, 3H), 3.20 (s, 3H), 4.12-4.18 (m, 1H), 5.06 (dd, J=7.2, 2.8 Hz, 1H), 6.91-7.01 (m, 1H), 7.38-7.42 (m, 2H), 7.64-7.73 (m, 1H).

PREPARATION EXAMPLE 149

(1S,2S)-2-((tert-butyldimethylsilyl)oxy)-1-(2-chlorophenyl)propan-1-ol

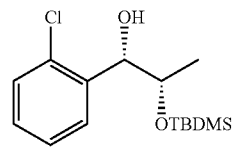 [SMILES: C[C@H](O[Si](C)(C)C(C)(C)C)[C@@H](O)c1ccccc1Cl]

The substantially same method as described in preparation example 46 was conducted, except that (1S,2S)-1-(2-chlorophenyl)propane-1,2-diol (Preparation example 21), was used instead of (1S,2S)-1-(2,6-dichlorophenyl)propane-1,2-diol (Preparation example 27), to obtain the title compound (2.26 g, yield 70%).

¹H NMR (400 MHz, CDCl₃) δ -0.29 (s, 3H), -0.04 (s, 3H), 0.87 (s, 9H), 1.30 (d, J=6.4 Hz, 3H), 3.19 (d, J=7.2 Hz, 1H), 4.06-4.11 (m, 1H), 4.89-4.96 (m, 1H), 7.18-7.24 (m, 1H), 7.27-7.31 (m, 1H), 7.35 (dd, J=7.8, 1.4 Hz, 1H), 7.48 (dd, J=7.6, 1.4 Hz, 1H).

PREPARATION EXAMPLE 150 tert-butyl(((1S,2S)-1-(2-chlorophenyl)-1-methoxypropan-2-yl)oxy)dimethylsilane

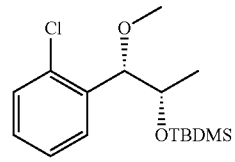 [SMILES: CO[C@@H](c1ccccc1Cl)[C@H](C)O[Si](C)(C)C(C)(C)C]

The substantially same method as described in preparation example 107 was conducted, except that (1S,2S)-2-((tert-butyldimethylsilyl)oxy)-1-(2-chlorophenyl)propan-1- ol (Preparation example 149), was used instead of (1S,2S)-2-((tert-butyldimethylsilyl)oxy)-1-(2,6-dichlorophenyl)butan-1-ol (Preparation example 106), to obtain the title compound (2.73 g, yield 97%).

$^1$H NMR (400 MHz, CDCl$_3$) δ −0.29 (s, 3H), −0.04 (s, 3H), 0.87 (s, 9H), 1.30 (d, J=6.4 Hz, 3H), 3.12 (s, 3H), 4.06-4.11 (m, 1H), 4.89-4.96 (m, 1H), 7.18-7.24 (m, 1H), 7.27-7.31 (m, 1H), 7.35 (dd, J=7.8, 1.4 Hz, 1H), 7.48 (dd, J=7.6, 1.4 Hz, 1H).

PREPARATION EXAMPLE 151

(1S,2S)-1-(2-chlorophenyl)-1-methoxypropan-2-ol

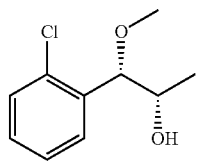

The substantially same method as described in preparation example 48 was conducted, except that tert-butyl(((1S,2S)-1-(2-chlorophenyl)-1-methoxypropan-2-yl)oxy)dimethylsilane (Preparation example 150), was used instead of (5S,6S)-5-(2,6-dichlorophenyl)-6,8,8,9,9-pentamethyl-2,4,7-trioxa-8-siladecane (Preparation example 47), to obtain the title compound (1.31 g, yield 72%).

$^1$H NMR (400 MHz, CDCl$_3$) δ 1.30 (d, J=6.4 Hz, 3H), 3.12 (s, 3H), 4.06-4.11 (m, 1H), 4.89-4.96 (m, 1H), 7.18-7.24 (m, 1H), 7.27-7.31 (m, 1H), 7.35 (dd, J=7.8, 1.4 Hz, 1H), 7.48 (dd, J=7.6, 1.4 Hz, 1H).

PREPARATION EXAMPLE 152

(E)-2-(prop-1-en-1-yl)pyridine

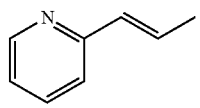

The substantially same method as described in preparation example 5 was conducted, except that 2-pyridinecarboxaldehyde was used instead of 2,6-dichlorobenzaldehyde, to obtain the title compound (8.1 g, yield 49%).

$^1$H NMR (400 MHz, DMSO-d$_6$) δ 1.88 (dd, J=6.8, 1.6 Hz, 3H), 6.45-6.52 (m, 1H), 6.67-6.82 (m, 1H), 7.14-7.21 (m, 1H), 7.36 (dd, J=6.8, 0.8 Hz, 1H), 7.66-7.73 (m, 1H), 8.44-8.51 (m, 1H).

PREPARATION EXAMPLE 153

(1R,2R)-1-(pyridin-2-yl)propane-1,2-diol

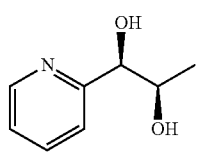

The substantially same method as described in preparation example 21 was conducted, except that (E)-2-(prop-1-en-1-yl)pyridine (Preparation example 152) and (DHQD)$_2$-PHAL were used instead of 1-(2-chlorophenyl)-trans-1-propene (Preparation example 1) and (DHQ)$_2$-PHAL, to obtain the title compound (1.8 g, yield 37%).

$^1$H NMR (400 MHz, DMSO-d$_6$) δ 0.97 (d, J=6.4 Hz, 3H), 3.77-3.88 (m, 1H), 4.37 (t, J=4.4 Hz, 1H), 4.53 (d, J=5.6 Hz, 1H), 5.28 (d, J=4.4 Hz, 1H) 7.21-7.28 (m, 1H), 7.44 (d, J=8.0 Hz, 1H), 7.72-7.79 (m, 1H), 8.44-8.50 (m, 1H).

PREPARATION EXAMPLE 154

(E)-3,5-dichloro-4-(prop-1-en-1-yl)pyridine

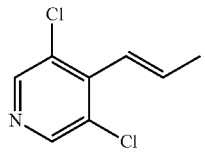

The substantially same method as described in preparation example 5 was conducted, except that 3,5-Dichloro-4-pyridinecarboxaldehyde was used instead of 2,6-dichlorobenzaldehyde, to obtain the title compound (5.71 g, yield 56%).

$^1$H NMR (400 MHz, CDCl$_3$) δ 2.00 (dd, J=6.8, 1.6 Hz, 3H), 6.39-6.44 (m, 1H), 6.56-6.68 (m, 1H), 8.44 (s, 2H).

PREPARATION EXAMPLE 155

(1R,2R)-1-(3,5-dichloropyridin-4-yl)propane-1,2-diol

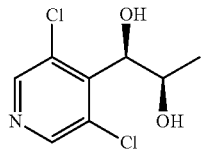

The substantially same method as described in preparation example 21 was conducted, except that (E)-3,5-dichloro-4-(prop-1-en-1-yl)pyridine (Preparation example 154) and (DHQD)$_2$-PHAL were used instead of 1-(2-chlorophenyl)-trans-1-propene (Preparation example 1) and (DHQ)$_2$-PHAL, to obtain the title compound (5.54 g, yield 82%).

$^1$H NMR (400 MHz, CDCl$_3$) δ 1.12 (d, J=6.4 Hz, 3H), 4.42 (q, J=6.4 Hz, 1H), 5.15 (d, J=8.0 Hz, 1H), 8.48 (s, 2H).

PREPARATION EXAMPLE 156

(1R,2R)-2-((tert-butyldimethylsilyl)oxy)-1-(3,5-dichloropyridin-4-yl)propan-1-ol

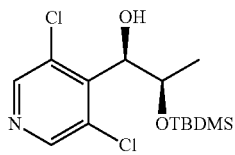 [SMILES: C[C@@H](O[Si](C)(C)C(C)(C)C)[C@H](O)c1c(Cl)cncc1Cl]

The substantially same method as described in preparation example 46 was conducted, except that (1R,2R)-1-(3,5-dichloropyridin-4-yl)propane-1,2-diol (Preparation example 155), was used instead of (1S,2S)-1-(2,6-dichlorophenyl)propane-1,2-diol (Preparation example 27), to obtain the title compound (0.16 g, yield 81%).

¹H NMR (400 MHz, CDCl₃) δ 0.05 (s, 3H), 0.07 (s, 3H), 0.91 (s, 9H), 1.16 (d, J=6.4 Hz, 3H), 3.13 (s, 1H), 4.34 (q, J=6.4 Hz, 1H), 5.09 (d, J=6.0 Hz, 1H), 8.45 (s, 2H).

PREPARATION EXAMPLE 157

4-((1R,2R)-2-((tert-butyldimethylsilyl)oxy)-1-methoxypropyl)-3,5-dichloropyridine

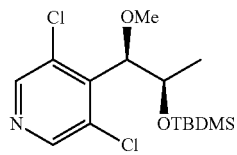 [SMILES: CO[C@H](c1c(Cl)cncc1Cl)[C@@H](C)O[Si](C)(C)C(C)(C)C]

The substantially same method as described in preparation example 107 was conducted, except that (1R,2R)-2-((tert-butyldimethylsilyl)oxy)-1-(3,5-dichloropyridin-4-yl)propan-1-ol (Preparation example 156), was used instead of (1S,2S)-2-((tert-butyldimethylsilyl)oxy)-1-(2,6-dichlorophenyl)butan-1-ol (Preparation example 106), to obtain the title compound (1.54 g, yield 58%).

¹H NMR (400 MHz, CDCl₃) δ 0.01 (d, J=4.8 Hz, 6H), 0.81 (s, 9H), 0.85 (d, J=6.4 Hz, 1H), 3.14 (s, 3H), 4.40-4.46 (m, 1H), 4.63 (d, J=6.8 Hz, 1H), 8.36 (s, 2H).

PREPARATION EXAMPLE 158

3,5-dichloro-4-((5R,6R)-6,8,8,9,9-pentamethyl-2,4,7-trioxa-8-siladecan-5-yl)pyridine

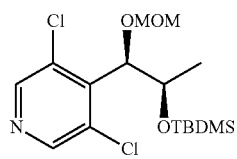

The substantially same method as described in preparation example 47 was conducted, except that (1R,2R)-2-((tert-butyldimethylsilyl)oxy)-1-(3,5-dichloropyridin-4-yl)propan-1-ol (Preparation example 156), was used instead of (1S,2S)-2-((tert-butyldimethylsilyl)oxy)-1-(2,6-dichlorophenyl)propan-1-ol (Preparation example 46), to obtain the title compound (6.68 g, yield 107%).

¹H NMR (400 MHz, CDCl₃) δ 0.02 (d, J=6.8 Hz, 6H), 0.81 (s, 9H), 0.85 (d, J=6.4 Hz, 1H), 3.01 (s, 3H), 4.44-4.52 (m, 2H), 4.63 (d, J=6.8 Hz, 1H), 4.90 (d, J=8.4 Hz, 1H), 8.34 (s, 2H).

PREPARATION EXAMPLE 159

(1R,2R)-1-(3,5-dichloropyridin-4-yl)-1-methoxypropan-2-ol

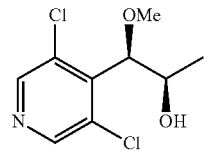

The substantially same method as described in preparation example 48 was conducted, except that 4-((1R,2R)-2-((tert-butyldimethylsilyl)oxy)-1-methoxypropyl)-3,5-dichloropyridine (Preparation example 157), was used instead of (5S,6S)-5-(2,6-dichlorophenyl)-6,8,8,9,9-pentamethyl-2,4,7-trioxa-8-siladecane (Preparation example 47), to obtain the title compound (0.82 g, yield 79%).

¹H NMR (400 MHz, CDCl₃) δ 1.04 (d, J=6.4 Hz, 3H), 3.97 (s, 1H), 3.29 (s, 3H), 4.42-4.49 (m, 1H), 4.79 (d, J=8.4 Hz, 1H), 8.50 (s, 2H).

PREPARATION EXAMPLE 160

(1R,2R)-1-(3,5-dichloropyridin-4-yl)-1-(methoxymethoxy)propan-2-ol

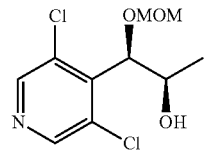

The substantially same method as described in preparation example 48 was conducted, except that 3,5-dichloro-4-((5R,6R)-6,8,8,9,9-pentamethyl-2,4,7-trioxa-8-siladecan-5-yl)pyridine (Preparation example 158), was used instead of (5S,6S)-5-(2,6-dichlorophenyl)-6,8,8,9,9-pentamethyl-2,4,7-trioxa-8-siladecane (Preparation example 47), to obtain the title compound (3.25 g, yield 70%).

¹H NMR (400 MHz, CDCl₃) δ 1.15 (d, J=6.4 Hz, 3H), 2.97 (s, 1H), 3.29 (s, 3H), 4.51-4.59 (m, 1H), 4.68 (dd, J=48.8, 6.8 Hz, 2H), 5.06 (d, J=8.4 Hz, 1H), 8.47 (s, 2H).

PREPARATION EXAMPLE 161

(E)-2,4-dichloro-5-(prop-1-en-1-yl)thiazole

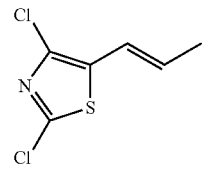

The substantially same method as described in preparation example 1 was conducted, except that 2,4-Dichlorothiazole-5-carboxaldehyde was used instead of 2-chlorobenzaldehyde, to obtain the title compound (3.4 g, yield 106%).

¹H NMR (400 MHz, CDCl₃) δ 2.05 (d, J=6.4 Hz, 3H), 6.09-6.14 (m, 1H), 6.41 (d, J=6.4 Hz, 1H).

PREPARATION EXAMPLE 162

(1R,2S)-1-(2,4-dichlorothiazol-5-yl)propane-1,2-diol

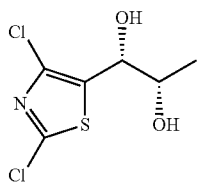

The substantially same method as described in preparation example 21 was conducted, except that (E)-2,4-dichloro-5-(prop-1-en-1-yl)thiazole (Preparation example 161) was used instead of 1-(2-chlorophenyl)-trans-1-propene (Preparation example 1), to obtain the title compound (2.0 g, yield 53%).

¹H NMR (400 MHz, CDCl₃) δ 1.11 (d, J=6.4 Hz, 3H), 3.66-3.70 (m, 1H), 4.63-4.65 (m, 1H), 5.03 (d, J=6.4 Hz, 1H), 6.03 (d, J=6.4 Hz, 1H).

PREPARATION EXAMPLE 163

(1R,2S)-1-(2,4-dichlorothiazol-5-yl)-1-hydroxypropan-2-yl carbamate

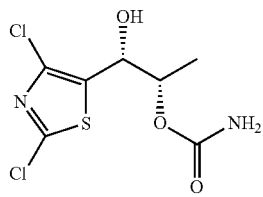

The substantially same method as described in preparation example 64 was conducted, except that (1R,2S)-1-(2,4-dichlorothiazol-5-yl)propane-1,2-diol (Preparation example 162), was used instead of 1-(2,4-dichlorophenyl)-(S,S)-1,2-propanediol (Preparation example 23), to obtain the title compound (0.68 g, yield 70%).

¹H NMR (400 MHz, DMSO-d₆) δ 1.23 (d, J=6.4 Hz, 3H), 4.49-4.83 (m, 1H), 4.91 (d, J=3.6 Hz, 1H), 6.46 (br s, 3H).

PREPARATION EXAMPLE 164

(1R,2S)-1-(2,4-dichlorothiazol-5-yl)-1-(methoxymethoxy)propan-2-yl carbamate

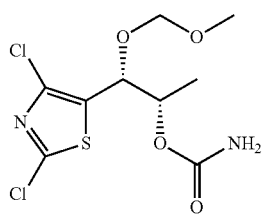 [SMILES: COCO[C@@H](c1sc(Cl)nc1Cl)[C@H](C)OC(N)=O]

The substantially same method as described in preparation example 47 was conducted, except that (1R,2S)-1-(2,4-dichlorothiazol-5-yl)-1-hydroxypropan-2-yl carbamate (Preparation example 163), was used instead of (1S,2S)-2-((tert-butyldimethylsilyl)oxy)-1-(2,6-dichlorophenyl)propan-1-ol (Preparation example 46), to obtain the title compound (2.3 g, yield 66%).

¹H NMR (400 MHz, DMSO-d₆) δ 1.24 (d, J=6.4 Hz, 3H), 3.28 (s, 3H), 3.39 (s, 3H), 4.55-4.68 (m, 2H), 4.80-4.87 (m, 1H), 4.95 (d, J=4.0 Hz, 1H), 6.68 (br s, 2H).

PREPARATION EXAMPLE 165

(1R,2S)-1-(2,4-dichlorothiazol-5-yl)-1-(methoxymethoxy)propan-2-ol

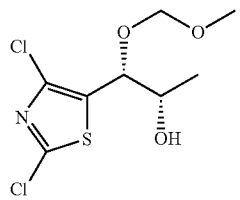

The substantially same method as described in preparation example 66 was conducted, except that (1R,2S)-1-(2,4-dichlorothiazol-5-yl)-1-(methoxymethoxy)propan-2-yl carbamate (Preparation example 164), was used instead of (1S,2S)-1-(2,4-dichlorophenyl)-1-(methoxymethoxy)propan-2-yl carbamate (Preparation example 65), to obtain the title compound (0.38 g, yield 38%).

¹H NMR (400 MHz, DMSO-d₆) δ 1.16 (s, 3H), 3.26 (s, 3H), 3.74-3.78 (m, 1H), 4.56 (dd, J=23.2, 6.8 Hz, 2H), 4.72 (d, J=4.0 Hz, 1H), 5.29 (d, J=6.4 Hz, 1H).

PREPARATION EXAMPLE 166

(E)-4-methyl-5-(prop-1-en-1-yl)thiazole

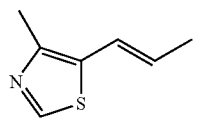

The substantially same method as described in preparation example 5 was conducted, except that 4-methylthiazole-5-carbaldehyde was used instead of 2,6-dichlorobenzaldehyde, to obtain the title compound (5.4 g, yield 99%).

¹H NMR (400 MHz, DMSO) δ 1.84 (d, J=6.8 Hz, 3H), 2.35 (s, 3H), 5.93-5.98 (m, 1H), 6.60-6.64 (m, 1H), 8.78 (s, 1H).

PREPARATION EXAMPLE 167

(1R,2S)-1-(4-methylthiazol-5-yl)propane-1,2-diol

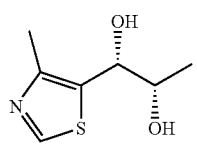

The substantially same method as described in preparation example 21 was conducted, except that (E)-4-methyl-5-(prop-1-en-1-yl)thiazole (Preparation example 166) was used instead of 1-(2-chlorophenyl)-trans-1-propene (Preparation example 1), to obtain the title compound (4.4 g, yield 65%).

¹H NMR (400 MHz, DMSO) δ 0.92 (d, J=6.4 Hz, 3H), 2.34 (s, 3H), 3.62-3.66 (m, 1H), 4.03 (d, J=7.2 Hz, 1H), 4.84 (d, J=4.8 Hz, 1H), 5.64 (s, 1H), 8.86 (s, 1H).

PREPARATION EXAMPLE 168

(1S,2R)-1-(2,4-dichlorothiazol-5-yl)propane-1,2-diol

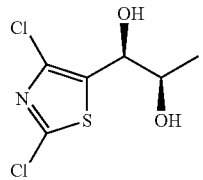

The substantially same method as described in preparation example 21 was conducted, except that (E)-2,4-dichloro-5-(prop-1-en-1-yl)thiazole (Preparation example 161) and (DHQD)₂-PHAL were used instead of 1-(2-chlorophenyl)-trans-1-propene (Preparation example 1) and (DHQ)₂-PHAL, to obtain the title compound (8.0 g, yield 68%).

¹H NMR (400 MHz, CDCl₃) δ 1.11 (d, J=6.4 Hz, 3H), 3.66-3.70 (m, 1H), 4.63-4.65 (m, 1H), 5.03 (d, J=6.4 Hz, 1H), 6.03 (d, J=6.4 Hz, 1H).

PREPARATION EXAMPLE 169

(E)-2-(prop-1-en-1-yl)thiophene

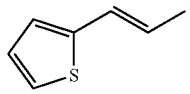

The substantially same method as described in preparation example 5 was conducted, except that 2-thiophenecarbaldehyde was used instead of 2,6-dichlorobenzaldehyde, to obtain the title compound (8.1 g, yield 49%).

¹H NMR (400 MHz, CDCl₃) δ 1.85 (dd, J=6.6, 1.8 Hz, 3H), 6.02-6.14 (m, 1H), 6.47-6.57 (m, 1H), 6.84 (d, J=3.6, 1H), 6.90-6.96 (m, 1H), 7.07 (d, J=5.2, 1H).

PREPARATION EXAMPLE 170

(1S,2R)-1-(thiophen-2-yl)propane-1,2-diol

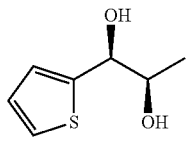

The substantially same method as described in preparation example 21 was conducted, except that (E)-2-(prop-1-en-1-yl)thiophene (Preparation example 169) and (DHQD)₂-PHAL were used instead of 1-(2-chlorophenyl)-trans-1-propene (Preparation example 1) and (DHQ)₂-PHAL, to obtain the title compound (1.8 g, yield 17%).

¹H NMR (400 MHz, CDCl₃) δ 1.15 (d, J=6.4 Hz, 3H), 2.51 (s, 1H), 2.75 (s, 1H), 3.90-4.00 (m, 1H), 4.66 (d, J=7.2 Hz, 1H), 6.97-7.01 (m, 1H), 7.02-7.06 (m, 2H), 7.27-7.31 (m, 1H).

PREPARATION EXAMPLE 171

(1S,2R)-2-((tert-butyldimethylsilyl)oxy)-1-(thiophen-2-yl)propan-1-ol

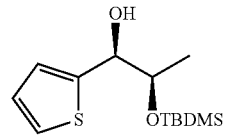

The substantially same method as described in preparation example 46 was conducted, except that (1S,2R)-1-(thiophen-2-yl)propane-1,2-diol (Preparation example 170), was used instead of (1S,2S)-1-(2,6-dichlorophenyl)propane-1,2-diol (Preparation example 27), to obtain the title compound (1.9 g, yield 78%).

¹H NMR (400 MHz, CDCl₃) δ 0.03 (s, 3H), 0.08 (s, 3H), 0.9 (s, 9H), 3.16 (d, J=4.0 Hz, 6H), 3.86-3.95 (m, 1H), 4.61-4.67 (m, 1H), 6.93-7.01 (m, 2H), 7.25-7.28 (m, 1H).

PREPARATION EXAMPLE 172 tert-butyl(((1S,2R)-1-methoxy-1-(thiophen-2-yl)propan-2-yl)oxy)dimethylsilane

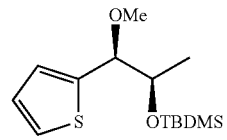 [SMILES: CO[C@H](c1cccs1)[C@@H](C)O[Si](C)(C)C(C)(C)C]

The substantially same method as described in preparation example 47 was conducted, except that (1S,2R)-2-((tert-butyldimethylsilyl)oxy)-1-(thiophen-2-yl)propan-1-ol (Preparation example 171), was used instead of (1S,2S)-2-((tert-butyldimethylsilyl)oxy)-1-(2,6-dichlorophenyl)propan-1-ol (Preparation example 46), to obtain the title compound (1.2 g, yield 52%).

¹H NMR (400 MHz, CDCl₃) δ 0.08 (d, J=6.8 Hz, 6H), 0.90 (s, 9H), 0.97 (d, J=6.0 Hz, 3H), 3.31 (s, 3H), 3.92-4.00 (m, 1H), 4.21 (d, J=6.4 Hz, 1H), 6.94-7.01 (m, 2H), 7.27 (d, J=1.2 Hz, 1H).

PREPARATION EXAMPLE 173: (1S,2R)-1-methoxy-1-(thiophen-2-yl)propan-2-ol

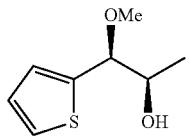

The substantially same method as described in preparation example 48 was conducted, except that tert-butyl(((1S,2R)-1-methoxy-1-(thiophen-2-yl)propan-2-yl)oxy)dimethylsilane (Preparation example 172), was used instead of (5S,6S)-5-(2,6-dichlorophenyl)-6,8,8,9,9-pentamethyl-2,4,7-trioxa-8-siladecane (Preparation example 47), to obtain the title compound (0.5 g, yield 66%).

$^1$H NMR (400 MHz, CDCl$_3$) δ 1.04 (d, J=6.4 Hz, 3H), 3.30 (s, 3H), 3.84-3.94 (m, 1H), 4.10 (d, J=8.4 Hz, 1H), 6.98-7.05 (m, 2H), 7.30-7.35 (m, 1H).

TABLE 1

| Example No. | Z | X(position) | A | B | R$^1$ | Chiral |
|---|---|---|---|---|---|---|
| 1 | Benzyl | Cl(2) | H | Aminosulfonyl | Methyl | SS |
| 2 | Benzyl | Cl(2) | H | Aminosulfonyl | Methyl | RR |
| 3 | Benzyl | Cl(2,4) | H | Aminosulfonyl | Methyl | SS |
| 4 | Benzyl | Cl(2,4) | H | Aminosulfonyl | Methyl | RR |
| 5 | Benzyl | Cl(3,4) | H | Aminosulfonyl | Methyl | SS |
| 6 | Benzyl | Cl(3,4) | H | Aminosulfonyl | Methyl | RR |
| 7 | Benzyl | Cl(2,6) | H | Aminosulfonyl | Methyl | SS |
| 8 | Benzyl | Cl(2,6) | H | Aminosulfonyl | Methyl | RR |
| 9 | Benzyl | Cl(2,3) | H | Aminosulfonyl | Methyl | SS |
| 10 | Benzyl | Cl(2,3) | H | Aminosulfonyl | Methyl | RR |
| 11 | Benzyl | Cl(2) | H | Aminosulfonyl | Ethyl | SS |
| 12 | Benzyl | Cl(2) | H | Aminosulfonyl | Ethyl | RR |
| 13 | Benzyl | Cl(2) | H | Aminosulfonyl | Iso-propyl | SS |
| 14 | Benzyl | Cl(2) | H | Aminosulfonyl | Iso-propyl | RR |
| 15 | Benzyl | Cl(2) | H | Aminosulfonyl | Propyl | SS |
| 16 | Benzyl | Cl(2) | H | Aminosulfonyl | Propyl | RR |
| 17 | Benzyl | F(2) | H | Aminosulfonyl | Methyl | SS |
| 18 | Benzyl | F(2) | H | Aminosulfonyl | Methyl | RR |
| 19 | Benzyl | I(2) | H | Aminosulfonyl | Methyl | SS |
| 20 | Benzyl | I(2) | H | Aminosulfonyl | Methyl | RR |
| 21 | Benzyl | F(2,6) | H | Aminosulfonyl | Methyl | SS |
| 22 | Benzyl | Cl(2,5) | H | Aminosulfonyl | Methyl | SS |
| 23 | Benzyl | Cl(2,5) | H | Aminosulfonyl | Methyl | RR |
| 24 | Benzyl | Cl(2),F(6) | H | Aminosulfonyl | Methyl | SS |
| 25 | Benzyl | OH(3) | H | Aminosulfonyl | Methyl | SS |
| 26 | Benzyl | Cl(2,6) | H | Aminosulfonyl | Methyl | SR |
| 27 | Benzyl | Cl(2,6) | H | Aminosulfonyl | Methyl | RS |
| 28 | Benzyl | I(2) | H | Aminosulfonyl | Ethyl | SS |
| 29 | Benzyl | Cl(2,6) | H | Aminosulfonyl | Ethyl | SS |
| 30 | Benzyl | Cl(2,6) | H | Aminosulfonyl | Ethyl | RR |
| 31 | Benzyl | Cl(2,6) | H | Aminosulfonyl | Iso-propyl | SS |
| 32 | Benzyl | Cl(2,6) | H | Aminosulfonyl | Iso-propyl | RR |
| 33 | Benzyl | Cl(2,6) | H | Aminosulfonyl | Butyl | SS |
| 34 | Benzyl | Cl(2,6) | H | Aminosulfonyl | Butyl | RR |
| 35 | Benzyl | Cl(2) | H | Methyl aminosulfonyl | Methyl | SS |
| 36 | Benzyl | Cl(2) | H | Methyl aminosulfonyl | Methyl | RR |
| 37 | Benzyl | Cl(2) | H | Iso-propyl aminosulfonyl | Methyl | SS |
| 38 | Benzyl | Cl(2) | H | Iso-propyl aminosulfonyl | Methyl | RR |
| 39 | Benzyl | Cl(2,6) | H | Iso-propyl aminosulfonyl | Methyl | SS |
| 40 | Benzyl | Cl(2) | H | Cyclopropyl aminosulfonyl | Methyl | SS |
| 41 | Benzyl | Cl(2) | H | Cyclopropyl aminosulfonyl | Methyl | RR |
| 42 | Benzyl | Cl(2,6) | Methyl | Aminosulfonyl | Methyl | SS |
| 43 | Benzyl | Cl(2,6) | Methyl | Aminosulfonyl | Methyl | RR |
| 44 | Benzyl | Cl(2,6) | Methyl | Aminosulfonyl | Ethyl | SS |
| 45 | Benzyl | Cl(2,6) | Methyl | Aminosulfonyl | Ethyl | RR |
| 46 | Benzyl | Cl(2,6) | Methyl | Aminosulfonyl | Iso-propyl | SS |
| 47 | Benzyl | Cl(2,6) | Methyl | Aminosulfonyl | Iso-propyl | RR |
| 48 | Benzyl | Cl(2,6) | Methyl | Aminosulfonyl | Butyl | SS |
| 49 | Benzyl | Cl(2,6) | Methyl | Aminosulfonyl | Butyl | RR |
| 50 | Benzyl | Cl(2,6) | Methyl | Iso-propyl aminosulfonyl | Methyl | SS |
| 51 | Benzyl | Cl(2,4) | Methoxymethyl | Aminosulfonyl | Methyl | SS |
| 52 | Benzyl | Cl(2,4) | Methoxymethyl | Aminosulfonyl | Methyl | RR |
| 53 | Benzyl | Cl(2,3) | Methoxymethyl | Aminosulfonyl | Methyl | SS |

TABLE 1-continued

| Example No. | Z | X(position) | A | B | R¹ | Chiral |
|---|---|---|---|---|---|---|
| 54 | Benzyl | Cl(2,3) | Methoxymethyl | Aminosulfonyl | Methyl | RR |
| 55 | Benzyl | Cl(3,4) | Methoxymethyl | Aminosulfonyl | Methyl | SS |
| 56 | Benzyl | Cl(3,4) | Methoxymethyl | Aminosulfonyl | Methyl | RR |
| 57 | Benzyl | Cl(2,6) | Methoxymethyl | Aminosulfonyl | Methyl | SS |
| 58 | Benzyl | Cl(2,6) | Methoxymethyl | Aminosulfonyl | Methyl | RR |
| 59 | Benzyl | Cl(2,5) | Methoxymethyl | aminosulfonyl | Methyl | SS |
| 60 | Benzyl | Cl(2,5) | Methoxymethyl | aminosulfonyl | Methyl | RR |
| 61 | Benzyl | Cl(2),F(6) | Methoxymethyl | Aminosulfonyl | Methyl | SS |
| 62 | Benzyl | F(2,6) | Methoxymethyl | Aminosulfonyl | Methyl | SS |
| 63 | Benzyl | Cl(2,6) | Methoxymethyl | Aminosulfonyl | Ethyl | SS |
| 64 | Benzyl | Cl(2,6) | Methoxymethyl | Aminosulfonyl | Ethyl | RR |
| 65 | Benzyl | Cl(2,6) | Methoxymethyl | Aminosulfonyl | Iso-propyl | SS |
| 66 | Benzyl | Cl(2,6) | Methoxymethyl | Aminosulfonyl | Iso-propyl | RR |
| 67 | Benzyl | Cl(2,6) | Methoxymethyl | Aminosulfonyl | Butyl | SS |
| 68 | Benzyl | Cl(2,6) | Methoxymethyl | Aminosulfonyl | Butyl | RR |
| 69 | Benzyl | Cl(2) | Methoxymethyl | Aminosulfonyl | Methyl | SS |
| 70 | Benzyl | Cl(2) | Methoxymethyl | Aminosulfonyl | Methyl | RR |
| 71 | Benzyl | Cl(2) | Methoxymethyl | Aminosulfonyl | Ethyl | RR |
| 72 | Benzyl | F(2) | Methoxymethyl | Aminosulfonyl | Methyl | SS |
| 73 | Benzyl | F(2) | Methoxymethyl | Aminosulfonyl | Methyl | RR |
| 74 | Benzyl | I(2) | Methoxymethyl | Aminosulfonyl | Methyl | SS |
| 75 | Benzyl | I(2) | Methoxymethyl | Aminosulfonyl | Methyl | RR |
| 76 | Benzyl | Cl(2) | Methoxymethyl | Methyl aminosulfonyl | Methyl | SS |
| 77 | Benzyl | Cl(2) | Methoxymethyl | Methyl aminosulfonyl | Methyl | RR |
| 78 | Benzyl | Cl(2) | Methoxymethyl | Cyclopropyl aminosulfonyl | Methyl | SS |
| 79 | Benzyl | Cl(2) | Methoxymethyl | Cyclopropyl aminosulfonyl | Methyl | RR |
| 80 | Benzyl | Cl(2,6) | Methoxymethyl | Iso-propyl aminosulfonyl | Methyl | SS |
| 81 | Benzyl | Cl(2) | Methoxymethyl | Iso-propyl aminosulfonyl | Methyl | SS |
| 82 | Benzyl | Cl(2) | Methoxymethyl | Iso-propyl aminosulfonyl | Methyl | RR |
| 83 | Benzyl | Cl(2,6) | Aminosulfonyl | H | Methyl | RR |
| 84 | Benzyl | Cl(2) | Aminosulfonyl | Aminosulfonyl | Methyl | SS |
| 85 | Benzyl | Cl(2) | Aminosulfonyl | Aminosulfonyl | Methyl | RR |
| 86 | Benzyl | Cl(2) | Aminosulfonyl | Aminosulfonyl | Ethyl | SS |
| 87 | Benzyl | Cl(2) | Aminosulfonyl | Aminosulfonyl | Ethyl | RR |
| 88 | Benzyl | Cl(2) | Aminosulfonyl | Aminosulfonyl | Iso-propyl | SS |
| 89 | Benzyl | Cl(2) | Aminosulfonyl | Aminosulfonyl | Iso-propyl | RR |
| 90 | Benzyl | Cl(2) | Aminosulfonyl | Aminosulfonyl | Propyl | SS |
| 91 | Benzyl | Cl(2) | Aminosulfonyl | Aminosulfonyl | Propyl | RR |
| 92 | Benzyl | I(2) | Methyl | Aminosulfonyl | Methyl | SS |
| 93 | Benzyl | Cl(2,6) | Aminosulfonyl | H | Methyl | SS |
| 94 | Benzyl | Cl(2,6) | Methyl | Cyclopropyl aminosulfonyl | Methyl | RR |
| 95 | Benzyl | Cl(2,6) | Methyl | Methyl aminosulfonyl | Methyl | RR |
| 96 | Benzyl | Cl(2,6) | H | Methyl aminosulfonyl | Methyl | RR |
| 97 | Benzyl | Cl(2) | Methyl | Aminosulfonyl | Methyl | SS |
| 98 | Pyridinyl | | H | Aminosulfonyl | Methyl | RR |
| 99 | Pyridinyl | | Methoxymethyl | Aminosulfonyl | Methyl | RR |
| 100 | Pyridinyl | | H | Aminosulfonyl | Methyl | RR |
| 101 | Pyridinyl | | Methyl | Aminosulfonyl | Methyl | RR |
| 102 | Thiazolyl | | H | Aminosulfonyl | Methyl | RS |
| 103 | Thiazolyl | | Methoxymethyl | Aminosulfonyl | Methyl | RS |
| 104 | Thiazolyl | | H | Aminosulfonyl | Methyl | RS |
| 105 | Thiazolyl | | H | Aminosulfonyl | Methyl | SR |
| 106 | Thiophenyl | | Methoxymethyl | Aminosulfonyl | Methyl | SR |

EXAMPLE 1

(1S, 2S)-1-(2-chlorophenyl)-1-hydroxypropan-2-yl sulfamate

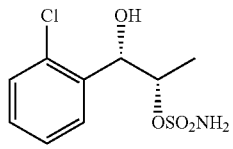

To a stirred solution of (1S,2S)-1-(2-chlorophenyl)propane-1,2-diol (Preparation example 21, 5.0 g, 22.79 mmol) in THF (50 mL) was added Et$_3$N (4.5 mL, 32.15 mmol) at 0° C. then allowed to stir for 30 min. The mixture was dropwise added tert-butyl chlorosulfonylcarbamate (Preparation example 63, 5.78 g, 26.79 mmol) in THF (25 mL) over a period of 30 min at 0° C. When the reaction was completed, the resulting mixture was diluted with EtOAc, washed with water and brine, dried over Na$_2$SO$_4$, filtered, and concentrated under reduced pressure.

To a stirred solution of an above crude product in EtOAc (50 mL) was slowly added concentrated HCl (5 mL) at room temperature and then heated to reflux. When the reaction was completed, the resulting mixture was diluted with EtOAc, washed with sat. NaHCO$_3$ and brine, dried over Na$_2$SO$_4$, filtered, and concentrated under reduced pressure. The crude product was purified by silica gel column chromatography to produce the title compound (3.76 g, yield 53%).

$^1$H NMR (400 MHz, CDCl$_3$) δ 1.37 (d, J=6.4, 3H), 2.93 (d, J=4.4, 1H), 4.89 (br s, 2H), 4.90-4.96 (m, 1H), 5.22-5.25 (m, 1H), 7.29-7.42 (m, 3H), 7.56 (dd, J=7.6, 1.6, 1H).

EXAMPLE 2

(1R, 2R)-1-(2-chlorophenyl)-1-hydroxypropan-2-yl sulfamate

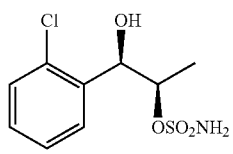

The substantially same method as described in example 1 was conducted, except that (1R,2R)-1-(2-chlorophenyl)propane-1,2-diol (Preparation example 22) was used instead of (1S,2S)-1-(2-chlorophenyl)propane-1,2-diol (Preparation example 21), to obtain the title compound (2.05 g, yield 46%).

$^1$H NMR (400 MHz, CDCl$_3$) δ 1.37 (d, J=6.4, 3H), 2.93 (d, J=4.4, 1H), 4.89 (br s, 2H), 4.90-4.96 (m, 1H), 5.22-5.25 (m, 1H), 7.29-7.42 (m, 3H), 7.56 (dd, J=7.6, 1.6, 1H).

EXAMPLE 3

(1S, 2S)-1-(2,4-dichlorophenyl)-1-hydroxypropan-2-yl sulfamate

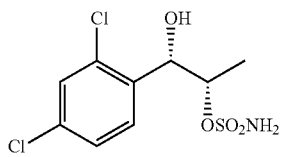

To a stirred solution of (1S, 2S)-1-(2,4-dichlorophenyl)-1-(methoxymethoxy)propan-2-yl sulfamate (example 51, 2.0 g, 5.88 mmol) in MeOH (20 mL) was dropwise added concentrated HCl (0.53 mL, 17.64 mmol) at room temperature. When the reaction was completed, the resulting mixture was removed the solvent, diluted with EtOAc, washed with sat. NaHCO$_3$ and brine, dried over Na$_2$SO$_4$, filtered, and concentrated under reduced pressure. The crude product was purified by silica gel column chromatography to produce the title compound (1.19 g, yield 68%).

$^1$H NMR (400 MHz, CDCl$_3$) δ 1.30 (d, J=6.4 Hz, 3H), 4.60-4.66 (m, 1H), 4.96 (d, J=4.0 Hz, 1H), 7.28 (br s, 2H), 7.44-7.47 (m, 1H), 7.55-7.57 (m, 2H).

EXAMPLE 4

(1R, 2R)-1-(2,4-dichlorophenyl)-1-hydroxypropan-2-yl sulfamate

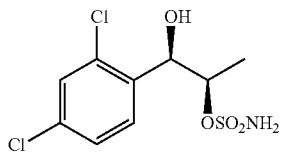

The substantially same method as described in example 3 was conducted, except that (1R, 2R)-1-(2,4-dichlorophenyl)-1-(methoxymethoxy)propan-2-yl sulfamate (example 52) was used instead of (1S, 2S)-1-(2,4-dichlorophenyl)-1-(methoxymethoxy)propan-2-yl sulfamate (example 51), to obtain the title compound (0.12 g, yield 76%).

$^1$H NMR (400 MHz, CDCl$_3$) δ 1.30 (d, J=6.4 Hz, 3H), 4.60-4.66 (m, 1H), 4.96 (d, J=4.0 Hz, 1H), 7.28 (br s, 2H), 7.44-7.47 (m, 1H), 7.55-7.57 (m, 2H).

EXAMPLE 5

(1S, 2S)-1-(3,4-dichlorophenyl)-1-hydroxypropan-2-yl sulfamate

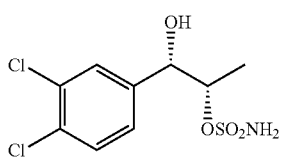

The substantially same method as described in example 3 was conducted, except that (1S, 2S)-1-(3,4-dichlorophenyl)-1-(methoxymethoxy)propan-2-yl sulfamate (example 55) was used instead of (1S, 2S)-1-(2,4-dichlorophenyl)-1-(methoxymethoxy)propan-2-yl sulfamate (example 51), to obtain the title compound (0.5 g, yield 52%).

¹H NMR (400 MHz, CDCl₃) δ 1.11 (t, J=6.4 Hz, 3H), 4.60-4.66 (m, 1H), 4.78 (d, J=4.4 Hz, 1H), 5.93 (br s, 1H), 7.34-7.37 (m, 1H), 7.46 (br s, 2H), 7.58-7.63 (m, 2H).

EXAMPLE 6

(1R, 2R)-1-(3,4-dichlorophenyl)-1-hydroxypropan-2-yl sulfamate

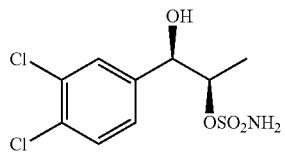

The substantially same method as described in example 3 was conducted, except that (1R, 2R)-1-(3,4-dichlorophenyl)-1-(methoxymethoxy)propan-2-yl sulfamate (example 56) was used instead of (1S, 2S)-1-(2,4-dichlorophenyl)-1-(methoxymethoxy)propan-2-yl sulfamate (example 51), to obtain the title compound (0.61 g, yield 40%).

¹H NMR (400 MHz, CDCl₃) δ 1.11 (t, J=6.4 Hz, 3H), 4.60-4.66 (m, 1H), 4.78 (d, J=4.4 Hz, 1H), 5.93 (br s, 1H), 7.34-7.37 (m, 1H), 7.46 (br s, 2H), 7.58-7.63 (m, 2H).

EXAMPLE 7

(1S, 2S)-1-(2, 6-dichlorophenyl)-1-hydroxypropan-2-yl sulfamate

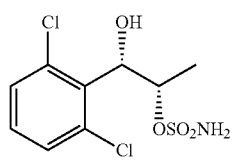

The substantially same method as described in example 1 was conducted, except that (1S,2S)-1-(2,6-dichlorophenyl)propane-1,2-diol (Preparation example 27) was used instead of (1S,2S)-1-(2-chlorophenyl)propane-1,2-diol (Preparation example 21), to obtain the title compound (3.82 g, yield 56%).

¹H NMR (400 MHz, CDCl₃) δ 1.26 (d, J=6.0 Hz, 3H), 3.62 (s, 1H), 5.26 (br s, 2H), 5.52-5.58 (m, 2H), 7.26 (t, J=8.0 Hz, 1H), 7.38 (d, J=8.0 Hz, 2H).

EXAMPLE 8

(1R, 2R)-1-(2, 6-dichlorophenyl)-1-hydroxypropan-2-yl sulfamate

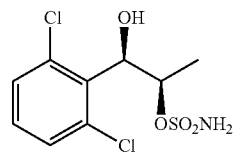

The substantially same method as described in example 1 was conducted, except that (1R,2R)-1-(2,6-dichlorophenyl)propane-1,2-diol (Preparation example 28) was used instead of (1S,2S)-1-(2-chlorophenyl)propane-1,2-diol (Preparation example 21), to obtain the title compound (25.7 g, yield 47%).

¹H NMR (400 MHz, CDCl₃) δ 1.26 (d, J=6.0 Hz, 3H), 3.76 (s, 1H), 5.28 (br s, 2H), 5.52-5.58 (m, 2H), 7.26 (t, J=8.0 Hz, 1H), 7.38 (d, J=8.0 Hz, 2H).

EXAMPLE 9

(1S, 2S)-1-(2,3-dichlorophenyl)-1-hydroxypropan-2-yl sulfamate

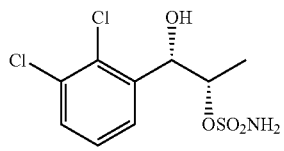

The substantially same method as described in example 3 was conducted, except that (1S, 2S)-1-(2,3-dichlorophenyl)-1-(methoxymethoxy)propan-2-yl sulfamate (example 53) was used instead of (1S, 2S)-1-(2,4-dichlorophenyl)-1-(methoxymethoxy)propan-2-yl sulfamate (example 51), to obtain the title compound (0.47 g, yield 62%).

¹H NMR (400 MHz, CDCl₃) δ 1.40 (d, J=6.4 Hz, 3H), 2.83 (d, J=4.8 Hz, 1H), 4.81 (s, 2H), 4.86-4.95 (m, 1H), 5.31 (dd, J=6.4, 4.8 Hz, 1H), 7.32 (t, J=7.8 Hz, 1H), 7.44-7.54 (m, 2H).

EXAMPLE 10

(1R, 2R)-1-(2,3-dichlorophenyl)-1-hydroxypropan-2-yl sulfamate

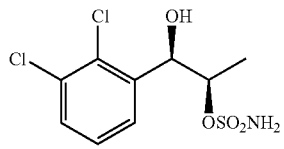

The substantially same method as described in example 3 was conducted, except that (1R, 2R)-1-(2,3-dichlorophenyl)-1-(methoxymethoxy)propan-2-yl sulfamate (example 54) was used instead of (1S, 2S)-1-(2,4-dichlorophenyl)-1-

(methoxymethoxy)propan-2-yl sulfamate (example 51), to obtain the title compound (0.47 g, yield 62%).

$^1$H NMR (400 MHz, CDCl$_3$) δ 1.40 (d, J=6.4 Hz, 3H), 2.83 (d, J=4.8 Hz, 1H), 4.81 (s, 2H), 4.86-4.95 (m, 1H), 5.31 (dd, J=6.4, 4.8 Hz, 1H), 7.32 (t, J=7.8 Hz, 1H), 7.44-7.54 (m, 2H).

EXAMPLE 11

(1S, 2S)-1-(2-chlorophenyl)-1-hydroxybutan-2-yl sulfamate

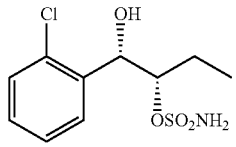

The substantially same method as described in example 1 was conducted, except that 1-(2-chlorophenyl)-(S,S)-1,2-butanediol (Preparation example 31) was used instead of (1S,2S)-1-(2-chlorophenyl)propane-1,2-diol (Preparation example 21), to obtain the title compound (1.51 g, yield 40%).

$^1$H NMR (400 MHz, CDCl$_3$) δ 1.01 (t, J=7.4 Hz, 3H), 1.54-1.60 (m, 1H), 1.69-1.77 (m, 1H), 2.72 (d, J=5.2 Hz, 1H), 4.77-4.82 (m, 3H), 5.29-5.32 (m, 1H), 7.27-7.41 (m, 3H), 7.54 (dd, J=7.6, 1.6 Hz, 1H).

EXAMPLE 12

(1R, 2R)-1-(2-chlorophenyl)-1-hydroxybutan-2-yl sulfamate

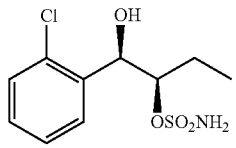

The substantially same method as described in example 1 was conducted, except that 1-(2-chlorophenyl)-(R,R)-1,2-butanediol (Preparation example 32) was used instead of (1S,2S)-1-(2-chlorophenyl)propane-1,2-diol (Preparation example 21), to obtain the title compound (1.70 g, yield 40%).

$^1$H NMR (400 MHz, CDCl$_3$) δ 1.01 (t, J=7.4 Hz, 3H), 1.54-1.60 (m, 1H), 1.69-1.77 (m, 1H), 2.72 (d, J=5.2 Hz, 1H), 4.77-4.82 (m, 3H), 5.29-5.32 (m, 1H), 7.27-7.41 (m, 3H), 7.54 (dd, J=7.6, 1.6 Hz, 1H).

EXAMPLE 13

(1S, 2S)-1-(2-chlorophenyl)-1-hydroxy-3-methylbutan-2-yl sulfamate

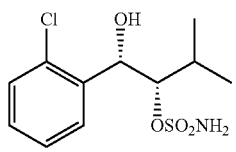

The substantially same method as described in example 1 was conducted, except that 1-(2-chlorophenyl)-3-methyl-(S, S)-1,2-butanediol (Preparation example 33) was used instead of (1S,2S)-1-(2-chlorophenyl)propane-1,2-diol (Preparation example 21), to obtain the title compound (1.99 g, yield 39%).

$^1$H NMR (400 MHz, DMSO-d$_6$) δ 0.87-0.98 (m, 6H), 1.91-1.98 (m, 1H), 4.42 (t, J=5.2 Hz, 1H), 5.14 (d, J=4.4 Hz, 1H), 7.22-7.27 (m, 1H), 7.31-7.41 (m, 2H), 7.60 (dd, J=7.6, 2.0 Hz, 1H).

EXAMPLE 14

(1R, 2R)-1-(2-chlorophenyl)-1-hydroxy-3-methylbutan-2-yl sulfamate

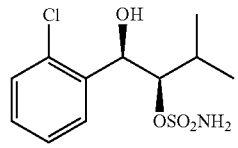

The substantially same method as described in example 1 was conducted, except that 1-(2-chlorophenyl)-3-methyl-(R, R)-1,2-butanediol (Preparation example 34) was used instead of (1S,2S)-1-(2-chlorophenyl)propane-1,2-diol (Preparation example 21), to obtain the title compound (2.81 g, yield 40%).

$^1$H NMR (400 MHz, DMSO-d$_6$) δ 0.87-0.98 (m, 6H), 1.91-1.98 (m, 1H), 4.42 (t, J=5.2 Hz, 1H), 5.14 (d, J=4.4 Hz, 1H), 7.22-7.27 (m, 1H), 7.31-7.41 (m, 2H), 7.60 (dd, J=7.6, 2.0 Hz, 1H).

EXAMPLE 15

(1S, 2S)-1-(2-chlorophenyl)-1-hydroxypentan-2-yl sulfamate

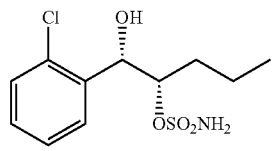

The substantially same method as described in example 1 was conducted, except that (1S,2S)-1-(2-chlorophenyl)pentane-1,2-diol (Preparation example 35) was used instead of (1S,2S)-1-(2-chlorophenyl)propane-1,2-diol (Preparation example 21), to obtain the title compound (0.6 g, yield 31%).

$^1$H NMR (400 MHz, DMSO-d$_6$) δ 0.89 (d, J=7.2 Hz, 3H), 1.35-1.46 (m, 2H), 1.46-1.58 (m, 1H), 1.71-1.82 (m, 1H), 4.50-4.57 (m, 1H), 5.13 (d, J=4.0 Hz, 1H), 6.80-7.55 (m, 5H), 7.58 (d, J=1.6 Hz, 1H).

EXAMPLE 16

(1R, 2R)-1-(2-chlorophenyl)-1-hydroxypentan-2-yl sulfamate

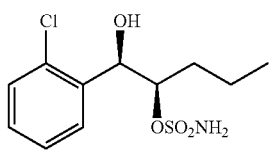

The substantially same method as described in example 1 was conducted, except that (1R,2R)-1-(2-chlorophenyl)pentane-1,2-diol (Preparation example 36) was used instead of (1S,2S)-1-(2-chlorophenyl)propane-1,2-diol (Preparation example 21), to obtain the title compound (0.7 g, yield 35%).

$^1$H NMR (400 MHz, DMSO-$d_6$) δ 0.89 (d, J=7.2 Hz, 3H), 1.35-1.46 (m, 2H), 1.46-1.58 (m, 1H), 1.71-1.82 (m, 1H), 4.50-4.57 (m, 1H), 5.13 (d, J=4.0 Hz, 1H), 6.80-7.55 (m, 5H), 7.58 (d, J=1.6 Hz, 1H).

EXAMPLE 17

(1S, 2S)-1-(2-fluorophenyl)-1-hydroxypropan-2-yl sulfamate

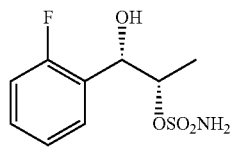

The substantially same method as described in example 3 was conducted, except that (1S, 2S)-1-(2-fluorophenyl)-1-(methoxymethoxy)propan-2-yl sulfamate (example 72) was used instead of (1S, 2S)-1-(2,4-dichlorophenyl)-1-(methoxymethoxy)propan-2-yl sulfamate (example 51), to obtain the title compound (2.16 g, yield 59%).

$^1$H NMR (400 MHz, CDCl$_3$) δ 1.22 (t, J=6.4 Hz, 3H), 4.78-4.85 (m, 1H), 4.96 (d, J=8.0 Hz, 1H), 5.60 (br s, 2H), 7.02-7.07 (m, 1H), 7.14-7.18 (m, 1H), 7.28-7.36 (m, 1H), 7.42-7.49 (m, 1H).

EXAMPLE 18

(1R, 2R)-1-(2-fluorophenyl)-1-hydroxypropan-2-yl sulfamate

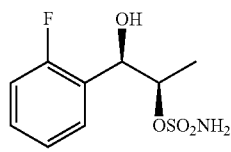

The substantially same method as described in example 3 was conducted, except that (1R, 2R)-1-(2-fluorophenyl)-1-(methoxymethoxy)propan-2-yl sulfamate (example 73) was used instead of (1S, 2S)-1-(2,4-dichlorophenyl)-1-(methoxymethoxy)propan-2-yl sulfamate (example 51), to obtain the title compound (1.86 g, yield 57%).

$^1$H NMR (400 MHz, CDCl$_3$) δ 1.22 (t, J=6.4 Hz, 3H), 4.78-4.85 (m, 1H), 4.96 (d, J=8.0 Hz, 1H), 5.60 (br s, 2H), 7.02-7.07 (m, 1H), 7.14-7.18 (m, 1H), 7.28-7.36 (m, 1H), 7.42-7.49 (m, 1H).

EXAMPLE 19

(1S, 2S)-1-(2-iodophenyl)-1-hydroxypropan-2-yl sulfamate

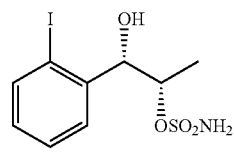

The substantially same method as described in example 3 was conducted, except that (1S, 2S)-1-(2-iodophenyl)-1-(methoxymethoxy)propan-2-yl sulfamate (example 74) was used instead of (1S, 2S)-1-(2,4-dichlorophenyl)-1-(methoxymethoxy)propan-2-yl sulfamate (example 51), to obtain the title compound (0.55 g, yield 82%).

$^1$H NMR (400 MHz, DMSO-$d_6$) δ 1.26 (d, J=6.4 Hz, 3H), 4.59-4.63 (m, 1H), 4.76 (d, J=4.8 Hz, 1H), 5.80 (br s, 1H), 7.01-7.05 (m, 1H), 7.25 (br s, 2H), 7.38-7.47 (m, 2H), 7.81 (d, J=7.8 Hz, 1H).

EXAMPLE 20

(1R, 2R)-1-(2-iodophenyl)-1-hydroxypropan-2-yl sulfamate

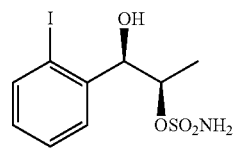

The substantially same method as described in example 3 was conducted, except that (1R, 2R)-1-(2-iodophenyl)-1-(methoxymethoxy)propan-2-yl sulfamate (example 75) was used instead of (1S, 2S)-1-(2,4-dichlorophenyl)-1-(methoxymethoxy)propan-2-yl sulfamate (example 51), to obtain the title compound (2.98 g, yield 82%).

$^1$H NMR (400 MHz, DMSO-$d_6$) δ 1.26 (d, J=6.4 Hz, 3H), 4.59-4.63 (m, 1H), 4.76 (d, J=4.8 Hz, 1H), 5.80 (br s, 1H), 7.01-7.05 (m, 1H), 7.25 (br s, 2H), 7.38-7.47 (m, 2H), 7.81 (d, J=7.8 Hz, 1H).

EXAMPLE 21

(1S, 2S)-1-(2,6-difluorophenyl)-1-hydroxypropan-2-yl sulfamate

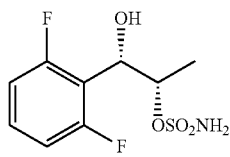

The substantially same method as described in example 3 was conducted, except that (1S, 2S)-1-(2,6-dichlorophenyl)-1-(methoxymethoxy)propan-2-yl sulfamate (example 62) was used instead of (1S, 2S)-1-(2,4-dichlorophenyl)-1-(methoxymethoxy)propan-2-yl sulfamate (example 51), to obtain the title compound (1.0 g, yield 75%).

$^1$H NMR (400 MHz, CDCl$_3$) δ 1.30 (d, J=6.4 Hz, 3H), 2.97 (d, J=8.0 Hz, 1H), 5.06 (s, 2H), 5.08-5.20 (m, 2H), 6.97 (t, J=8.4 Hz, 2H), 7.30-7.39 (m, 1H).

EXAMPLE 22

(1S, 2S)-1-(2,5-dichlorophenyl)-1-hydroxypropan-2-yl sulfamate

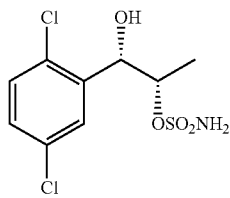

The substantially same method as described in example 3 was conducted, except that (1S, 2S)-1-(2,5-dichlorophenyl)-1-(methoxymethoxy)propan-2-yl sulfamate (example 59) was used instead of (1S, 2S)-1-(2,4-dichlorophenyl)-1-(methoxymethoxy)propan-2-yl sulfamate (example 51), to obtain the title compound (1.0 g, yield 87%).

$^1$H NMR (400 MHz, CDCl$_3$) δ 1.40 (d, J=6.4 Hz, 3H), 2.81 (d, J=4.4 Hz, 1H), 4.83 (s, 2H), 4.85-4.94 (m, 1H), 5.20-5.27 (m, 1H), 7.26-7.31 (m, 1H), 7.35 (d, J=8.4 Hz, 1H), 7.58 (d, J=2.4 Hz, 1H).

EXAMPLE 23

(1R, 2R)-1-(2,5-dichlorophenyl)-1-hydroxypropan-2-yl sulfamate

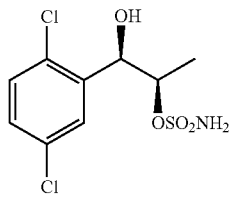

The substantially same method as described in example 3 was conducted, except that (1R, 2R)-1-(2,5-dichlorophenyl)-1-(methoxymethoxy)propan-2-yl sulfamate (example 60) was used instead of (1S, 2S)-1-(2,4-dichlorophenyl)-1-(methoxymethoxy)propan-2-yl sulfamate (example 51), to obtain the title compound (0.9 g, yield 85%).

$^1$H NMR (400 MHz, CDCl$_3$) δ 1.40 (d, J=6.4 Hz, 3H), 2.81 (d, J=4.4 Hz, 1H), 4.83 (s, 2H), 4.85-4.94 (m, 1H), 5.20-5.27 (m, 1H), 7.26-7.31 (m, 1H), 7.35 (d, J=8.4 Hz, 1H), 7.58 (d, J=2.4 Hz, 1H).

EXAMPLE 24

(1S, 2S)-1-(2-chloro-6-fluorophenyl)-1-hydroxypropan-2-yl sulfamate

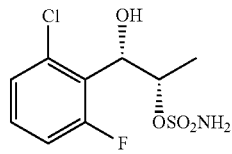

The substantially same method as described in example 3 was conducted, except that (1S, 2S)-1-(2-chloro-6-fluorophenyl)-1-(methoxymethoxy)propan-2-yl sulfamate (example 61) was used instead of (1S, 2S)-1-(2,4-dichlorophenyl)-1-(methoxymethoxy)propan-2-yl sulfamate (example 51), to obtain the title compound (0.7 g, yield 77%).

$^1$H NMR (400 MHz, DMSO-d$_6$) δ 1.11 (d, J=6.4 Hz, 3H), 4.91-5.15 (m, 2H), 5.88 (d, J=4.4 Hz, 1H), 7.18-7.27 (m, 1H), 7.33 (d, J=7.6, 1H) 7.36-7.49 (m, 3H).

EXAMPLE 25

(1S, 2S)-1-hydroxy-1-(3-hydroxyphenyl)propan-2-yl sulfamate

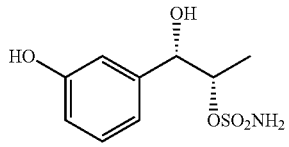

To a stirred solution of (1S,2S)-1-(3-(benzyloxy)phenyl)propane-1,2-diol (Preparation example 45, 8.0 g, 30.96 mmol) in THF (80 mL) was added Et$_3$N (3.76 mL, 37.15 mmol) at 0° C. then allowed to stir for 30 min. The mixture was dropwise added tert-butyl chlorosulfonyl carbamate (Preparation example 63, 7.34 g, 34.06 mmol) in THF (40 mL) over a period of 30 min at 0° C. When the reaction was completed, the resulting mixture was diluted with EtOAc, washed with water and brine, dried over Na$_2$SO$_4$, filtered, and concentrated to give 13.55 g as a crude product.

To a stirred solution of an above crude product in EtOAc (140 mL) was slowly added concentrated HCl (14 mL) at room temperature and then heated to reflux. When the reaction was completed, the resulting mixture was diluted with EtOAc, washed with sat. NaHCO$_3$ and brine, dried over Na$_2$SO$_4$, filtered, and concentrated under reduced pressure.

To a stirred solution of an above crude product in EtOAc (10 mL) was added Pd(OH)$_2$ (20 wt %, 0.26 g) then stirred for 3 h under H₂ gas balloon (1 atm). The resulting mixture was filtered through Celite, rinsed with EtOAc and then concentrated under reduced pressure. The crude product was purified by silica gel column chromatography to produce the title compound (2.67 g, yield 81%).

¹H NMR (400 MHz, DMSO-d₆) δ 1.03 (d, J=6.4 Hz, 3H), 4.53-4.65 (m, 2H), 5.57 (d, J=4.0 Hz, 1H), 6.50-6.68 (m, 1H), 6.73-6.79 (m, 2H), 7.12 (t, J=8.0 Hz, 1H), 7.40 (s, 2H), 9.33 (s, 1H).

EXAMPLE 26

(1S, 2R)-1-(2,6-dichlorophenyl)-1-hydroxypropan-2-yl sulfamate

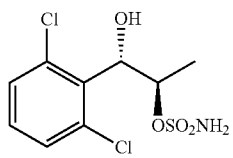

The substantially same method as described in example 1 was conducted, except that (1S,2R)-1-(2,6-dichlorophenyl)propane-1,2-diol (Preparation example 50) was used instead of (1S,2S)-1-(2-chlorophenyl)propane-1,2-diol (Preparation example 21), to obtain the title compound (0.41 g, yield 33%).

¹H NMR (400 MHz, DMSO-d₆) δ 1.49 (d, J=6.0 Hz, 3H), 5.05-5.12 (m, 1H), 5.15 (d, J=9.2 Hz, 1H), 6.01 (br s, 1H), 7.26-7.29 (m, 1H), 7.37-7.39 (m, 2H).

EXAMPLE 27

(1R, 2S)-1-(2,6-dichlorophenyl)-1-hydroxypropan-2-yl sulfamate

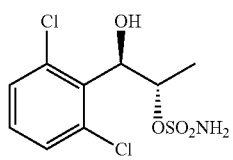

The substantially same method as described in example 1 was conducted, except that (1R,2S)-1-(2,6-dichlorophenyl)propane-1,2-diol (Preparation example 55) was used instead of (1S,2S)-1-(2-chlorophenyl)propane-1,2-diol (Preparation example 21), to obtain the title compound (0.55 g, yield 35%).

¹H NMR (400 MHz, DMSO-d₆) δ 1.49 (d, J=5.6 Hz, 3H), 5.05-5.12 (m, 1H), 5.15 (d, J=9.2 Hz, 1H), 6.00 (br s, 1H), 7.25-7.29 (m, 1H), 7.37-7.39 (m, 2H).

EXAMPLE 28

(1S, 2S)-1-(2-iodophenyl)-1-hydroxybutan-2-yl sulfamate

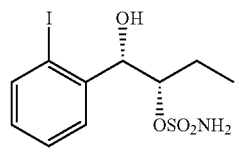

The substantially same method as described in example 1 was conducted, except that 1-(2-iodophenyl)-(S,S)-1,2-butanediol (Preparation example 56) was used instead of (1S,2S)-1-(2-chlorophenyl)propane-1,2-diol (Preparation example 21), to obtain the title compound (1.55 g, yield 45%).

¹H NMR (400 MHz, CDCl₃) δ 0.98 (t, J=7.2 Hz, 3H), 1.44-1.55 (m, 2H), 4.73-4.78 (m, 2H), 5.03 (s, 2H), 7.36-7.45 (m, 4H).

EXAMPLE 29

(1S, 2S)-1-(2,6-dichlorophenyl)-1-hydroxybutan-2-yl sulfamate

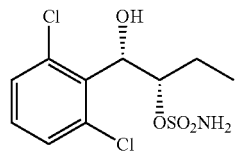

The substantially same method as described in example 1 was conducted, except that 1-(2-chlorophenyl)-(S,S)-1,2-butanediol (Preparation example 31) was used instead of (1S,2S)-1-(2-chlorophenyl)propane-1,2-diol (Preparation example 21), to obtain the title compound (0.9 g, yield 44%).

¹H NMR (400 MHz, CDCl₃) δ 0.98 (t, J=7.4 Hz, 3H), 1.24-1.33 (m, 1H), 1.54-1.64 (m, 1H), 3.57-3.59 (d, J=9.6 Hz, 1H), 5.18 (s, 2H), 5.36-5.40 (m, 1H), 5.57 (t, J=9.2 Hz, 1H), 7.19-7.26 (m, 1H), 7.35-7.37 (m, 2H).

EXAMPLE 30

(1R, 2R)-1-(2,6-dichlorophenyl)-1-hydroxybutan-2-yl sulfamate

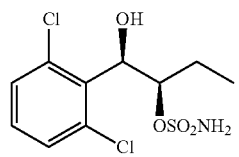

The substantially same method as described in example 1 was conducted, except that 1-(2-chlorophenyl)-(R,R)-1,2-butanediol (Preparation example 32) was used instead of (1S,2S)-1-(2-chlorophenyl)propane-1,2-diol (Preparation example 21), to obtain the title compound (1.7 g, yield 43%).

¹H NMR (400 MHz, CDCl₃) J=7.4 Hz, 3H), 1.24-1.33 (m, 1H), 1.54-1.64 (m, 1H), 3.57-3.59 (d, J=9.6 Hz, 1H), 5.18 (s, 2H), 5.36-5.40 (m, 1H), 5.57 (t, J=9.2 Hz, 1H), 7.19-7.26 (m, 1H), 7.35-7.37 (m, 2H).

EXAMPLE 31

(1S, 2S)-1-(2,6-dichlorophenyl)-1-hydroxy-3-methylbutan-2-yl sulfamate

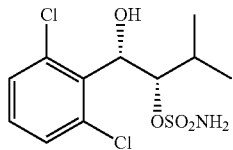

The substantially same method as described in example 3 was conducted, except that (1S, 2S)-1-(2,6-dichlorophenyl)-1-(methoxymethoxy)-3-methylbutan-2-yl sulfamate (example 65) was used instead of (1S, 2S)-1-(2,4-dichlorophenyl)-1-(methoxymethoxy)propan-2-yl sulfamate (example 51), to obtain the title compound (1.20 g, yield 70%).

¹H NMR (400 MHz, CDCl₃) δ 0.97 (dd, J=16.0, 7.2 Hz, 6H), 1.48 (qd, J=6.8, 2.4 Hz, 1H), 2.55 (br s, 1H), 4.62 (d, J=7.6 Hz, 1H), 5.00 (br s, 2H), 6.15 (d, J=8.4 Hz, 1H), 7.24 (t, J=8.0 Hz, 1H), 7.36 (td, J=7.6, 1.2 Hz, 2H).

EXAMPLE 32

(1R, 2R)-1-(2,6-dichlorophenyl)-1-hydroxy-3-methylbutan-2-yl sulfamate

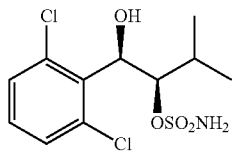

The substantially same method as described in example 3 was conducted, except that (1R, 2R)-1-(2,6-dichlorophenyl)-1-(methoxymethoxy)-3-methylbutan-2-yl sulfamate (example 66) was used instead of (1S, 2S)-1-(2,4-dichlorophenyl)-1-(methoxymethoxy)propan-2-yl sulfamate (example 51), to obtain the title compound (1.04 g, yield 79%).

¹H NMR (400 MHz, DMSO-d₆) δ 0.85 (dd, J=12.4, 6.8 Hz, 6H), 1.23-1.32 (m, 1H), 4.27 (dd, J=8.0, 2.8 Hz, 1H), 5.13 (br s, 1H), 5.83 (d, J=8.0 Hz, 1H), 7.33-7.37 (m, 2H), 7.35 (t, J=8.0 Hz, 1H), 7.44-7.49 (m, 2H).

EXAMPLE 33

(1S, 2S)-1-(2,6-dichlorophenyl)-1-hydroxyhexan-2-yl sulfamate

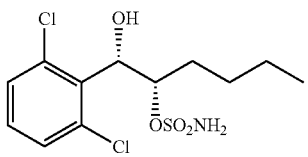

The substantially same method as described in example 3 was conducted, except that (1S, 2S)-1-(2,6-dichlorophenyl)-1-(methoxymethoxy)hexan-2-yl sulfamate (example 67) was used instead of (1S, 2S)-1-(2,4-dichlorophenyl)-1-(methoxymethoxy)propan-2-yl sulfamate (example 51), to obtain the title compound (0.93 g, yield 81%).

¹H NMR (400 MHz, CDCl₃) δ 0.81 (t, J=7.2 Hz, 3H), 1.14-1.47 (m, 5H), 1.57-1.63 (m, 1H), 3.55 (d, J=9.6 Hz, 1H), 5.21 (s, 2H), 5.40-5.47 (m, 1H), 5.56 (t, J=9.2 Hz, 1H), 7.22-7.24 (m, 1H), 7.35-7.37 (m, 2H).

EXAMPLE 34

(1R, 2R)-1-(2,6-dichlorophenyl)-1-hydroxyhexan-2-yl sulfamate

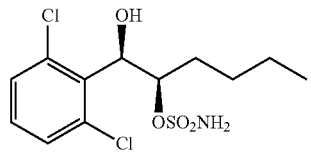

The substantially same method as described in example 3 was conducted, except that (1R, 2R)-1-(2,6-dichlorophenyl)-1-(methoxymethoxy)hexan-2-yl sulfamate (example 68) was used instead of (1S, 2S)-1-(2,4-dichlorophenyl)-1-(methoxymethoxy)propan-2-yl sulfamate (example 51), to obtain the title compound (0.91 g, yield 79%).

¹H NMR (400 MHz, CDCl₃) δ 0.81 (t, J=7.2 Hz, 3H), 1.14-1.47 (m, 5H), 1.57-1.63 (m, 1H), 3.55 (d, J=9.6 Hz, 1H), 5.21 (s, 2H), 5.40-5.47 (m, 1H), 5.56 (t, J=9.2 Hz, 1H), 7.22-7.24 (m, 1H), 7.35-7.37 (m, 2H).

EXAMPLE 35

(1S, 2S)-1-(2-chlorophenyl)-1-hydroxypropan-2-yl methylsulfamate

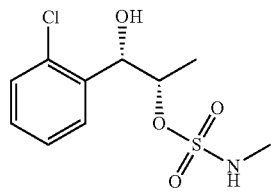 [SMILES: CNS(=O)(=O)O[C@@H](C)[C@@H](O)c1ccccc1Cl]

chlorophenyl)-1-(methoxymethoxy)propan-2-yl methylsulfamate (example 76) was used instead of (1S, 2S)-1-(2,4-dichlorophenyl)-1-(methoxymethoxy)propan-2-yl sulfamate (example 51), to obtain the title compound (2.0 g, yield 63%).

¹H NMR (400 MHz, CDCl₃) δ 1.40 (d, J=6.4, 3H), 2.71 (d, J=5.6 Hz, 3H), 2.73 (d, J=4.8 Hz, 1H), 4.39 (d, J=4.8 Hz, 1H), 4.82-4.90 (m, 1H), 5.23 (dd, J=6.6, 4.6 Hz, 1H), 7.31 (dd, J=7.6, 1.6 Hz, 1H), 7.36 (dt, J=7.6, 1.3 Hz, 1H), 7.41 (dd, J=7.8, 1.4 Hz, 1H), 7.58 (dd, J=6.6, 2.6 Hz, 1H).

EXAMPLE 36

(1R, 2R)-1-(2-chlorophenyl)-1-hydroxypropan-2-yl methylsulfamate

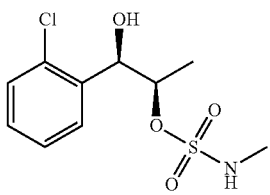 [SMILES: CNS(=O)(=O)O[C@H](C)[C@H](O)c1ccccc1Cl]

The substantially same method as described in example 3 was conducted, except that (1R, 2R)-1-(2-chlorophenyl)-1-(methoxymethoxy)propan-2-yl methylsulfamate (example 77) was used instead of (1S, 2S)-1-(2,4-dichlorophenyl)-1-(methoxymethoxy)propan-2-yl sulfamate (example 51), to obtain the title compound (0.4 g, yield 58%).

$^1$H NMR (400 MHz, CDCl$_3$) J=6.4 Hz, 3H), 2.71 (d, J=5.6 Hz, 3H), 2.74 (d, J=4.8 Hz, 1H), 4.39 (d, J=5.2 Hz, 1H), 4.82-4.90 (m, 1H), 5.23 (dd, J=6.4, 4.8 Hz, 1H), 7.31 (dd, J=7.6, 2.0 Hz, 1H), 7.33-7.39 (m, 1H), 7.41 (dd, J=7.2, 0.8 Hz, 1H), 7.58 (dd, J=7.8, 1.8 Hz, 1H).

EXAMPLE 37

(1S, 2S)-1-(2-chlorophenyl)-1-hydroxypropan-2-yl isopropylsulfamate

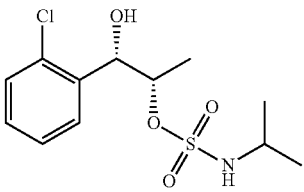 [SMILES: CC(C)NS(=O)(=O)O[C@@H](C)[C@@H](O)c1ccccc1Cl]

The substantially same method as described in example 3 was conducted, except that (1S,2S)-1-(2-chlorophenyl)-1-(methoxymethoxy)propan-2-yl isopropylsulfamate (example 81) was used instead of (1S, 2S)-1-(2,4-dichlorophenyl)-1-(methoxymethoxy)propan-2-yl sulfamate (example 51), to obtain the title compound (1.93 g, yield 79%).

$^1$H NMR (400 MHz, CDCl$_3$) δ 1.24 (dd, J=5.6, 4.2 Hz, 6H), 1.36 (d, J=5.6 Hz, 3H), 2.88 (d, J=4.0 Hz, 1H), 3.60 (q, J=6.8 Hz, 1H), 4.22 (d, J=7.2 Hz, 1H), 4.85 (q, J=6.8 Hz, 1H), 5.23 (dd, J=6.8, 4.4 Hz, 1H), 7.27-7.37 (m, 2H), 7.40 (dd, J=7.6, 2.0 Hz, 1H), 7.57 (dd, J=7.6, 2.0 Hz, 1H).

EXAMPLE 38

(1R, 2R)-1-(2-chlorophenyl)-1-hydroxypropan-2-yl isopropylsulfamate

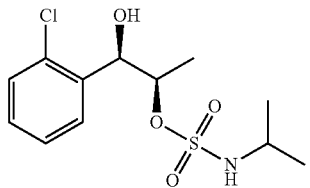 [SMILES: CC(C)NS(=O)(=O)O[C@H](C)[C@H](O)c1ccccc1Cl]

The substantially same method as described in example 3 was conducted, except that (1R,2R)-1-(2-chlorophenyl)-1-(methoxymethoxy)propan-2-yl isopropylsulfamate (example 82) was used instead of (1S, 2S)-1-(2,4-dichlorophenyl)-1-(methoxymethoxy)propan-2-yl sulfamate (example 51), to obtain the title compound (0.14 g, yield 80%).

$^1$H NMR (400 MHz, CDCl$_3$) δ 1.24 (dd, J=6.0, 5.6 Hz, 6H), 1.36 (d, J=5.6 Hz, 3H), 2.90 (d, J=4.0 Hz, 1H), 3.60 (q, J=6.4 Hz, 1H), 4.24 (d, J=7.2 Hz, 1H), 4.85 (q, J=6.8 Hz, 1H), 5.23 (dd, J=6.8, 4.4 Hz, 1H), 7.27-7.37 (m, 2H), 7.40 (d, J=8.0 Hz, 1H), 7.57 (d, J=7.6 Hz, 1H).

EXAMPLE 39

(1S, 2S)-1-(2,6-dichlorophenyl)-1-hydroxypropan-2-yl isopropylsulfamate

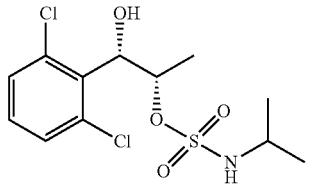 [SMILES: CC(C)NS(=O)(=O)O[C@@H](C)[C@@H](O)c1c(Cl)cccc1Cl]

The substantially same method as described in example 3 was conducted, except that (1S,2S)-1-(2,6-dichlorophenyl)-1-(methoxymethoxy)propan-2-yl isopropylsulfamate (example 80) was used instead of (1S, 2S)-1-(2,4-dichlorophenyl)-1-(methoxymethoxy)propan-2-yl sulfamate (example 51), to obtain the title compound (2.68 g, yield 66%).

$^1$H NMR (400 MHz, CDCl$_3$) δ 1.22 (d, J=6.4 Hz, 3H), 1.29 (t, J=6.2 Hz, 6H), 3.48 (d, J=8.0 Hz, 1H), 3.72-3.80 (m, 1H), 4.56 (d, J=7.2 Hz, 1H), 5.41-5.52 (m, 2H), 7.20 (t, J=8.0 Hz, 1H), 7.34 (d, J=8.0 Hz, 2H).

EXAMPLE 40

(1S, 2S)-1-(2-chlorophenyl)-1-hydroxypropan-2-yl cyclopropylsulfamate

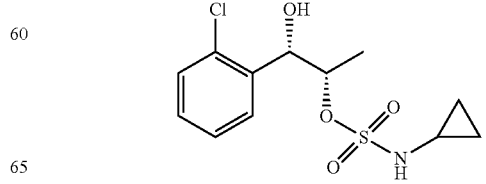

The substantially same method as described in example 3 was conducted, except that (1 S, 2S)-1-(2-chlorophenyl)-1-(methoxymethoxy)propan-2-yl cyclopropylsulfamate (example 78) was used instead of (1S, 2S)-1-(2,4-dichlorophenyl)-1-(methoxymethoxy)propan-2-yl sulfamate (example 51), to obtain the title compound (1.2 g, yield 76%).

¹H NMR (400 MHz, CDCl₃) δ 0.65-0.82 (m, 4H), 1.39 (d, J=6.4 Hz, 3H), 2.50-2.52 (m, 1H), 2.80 (d, J=4.0 Hz, 1H), 4.87-4.92 (m, 1H), 4.94 (s, 1H), 5.24-5.27 (m, 1H), 7.27-7.37 (m, 2H), 7.40 (d, J=7.6 Hz, 1H), 7.58 (d, J=7.6 Hz, 1H).

EXAMPLE 41

(1R, 2R)-1-(2-chlorophenyl)-1-hydroxypropan-2-yl cyclopropylsulfamate

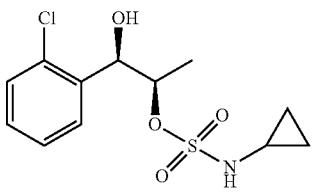 [SMILES: C[C@@H](OS(=O)(=O)NC1CC1)[C@H](O)c1ccccc1Cl]

The substantially same method as described in example 3 was conducted, except that (1R, 2R)-1-(2-chlorophenyl)-1-(methoxymethoxy)propan-2-yl cyclopropylsulfamate (example 79) was used instead of (1S, 2S)-1-(2,4-dichlorophenyl)-1-(methoxymethoxy)propan-2-yl sulfamate (example 51), to obtain the title compound (0.38 g, yield 72%).

¹H NMR (400 MHz, CDCl₃) δ 0.70-0.81 (m, 4H), 1.38 (d, J=6.4 Hz, 3H), 2.49-2.54 (m, 1H), 2.83 (d, J=4.4 Hz, 1H), 4.90 (q, J=7.2 Hz, 1H), 4.95 (s, 1H), 5.25 (dd, J=6.8, 4.4 Hz, 1H), 7.25-7.36 (m, 2H), 7.40 (d, J=7.6 Hz, 1H), 7.58 (d, J=7.6 Hz, 1H).

EXAMPLE 42

(1S, 2S)-1-(2,6-dichlorophenyl)-1-methoxypropan-2-yl sulfamate

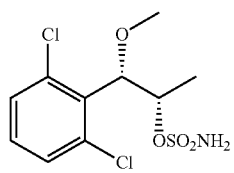

The substantially same method as described in example 51 was conducted, except that (1S,2S)-1-(2,6-dichlorophenyl)-1-methoxypropan-2-ol (Preparation example 143) was used instead of (1S,2S)-1-(2,4-dichlorophenyl)-1-(methoxymethoxy)propan-2-ol (Preparation example 66), to obtain the title compound (0.71 g, yield 53%).

¹H NMR (400 MHz, DMSO-d₆) δ 1.06 (d, J=6.8 Hz, 3H), 3.15 (s, 3H), 4.99 (d, J=8.0 Hz, 1H), 5.24-5.28 (m, 1H), 7.39-7.43 (m, 1H), 7.50-7.54 (m, 2H).

EXAMPLE 43

(1R, 2R)-1-(2,6-dichlorophenyl)-1-methoxypropan-2-yl sulfamate

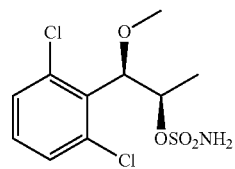

The substantially same method as described in example 51 was conducted, except that (1R,2R)-1-(2,6-dichlorophenyl)-1-methoxypropan-2-ol (Preparation example 145) was used instead of (1S,2S)-1-(2,4-dichlorophenyl)-1-(methoxymethoxy)propan-2-ol (Preparation example 66), to obtain the title compound (0.6 g, yield 50%).

¹H NMR (400 MHz, DMSO-d₆) δ 1.06 (d, J=6.8 Hz, 3H), 3.15 (s, 3H), 4.99 (d, J=8.0 Hz, 1H), 5.24-5.28 (m, 1H), 7.39-7.43 (m, 1H), 7.50-7.54 (m, 2H).

EXAMPLE 44

(1S, 2S)-1-(2,6-dichlorophenyl)-1-methoxybutan-2-yl sulfamate

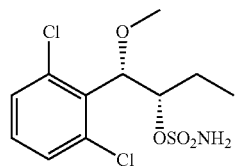

The substantially same method as described in example 51 was conducted, except that (1S,2S)-1-(2,6-dichlorophenyl)-1-methoxybutan-2-ol (Preparation example 109) was used instead of (1S,2S)-1-(2,4-dichlorophenyl)-1-(methoxymethoxy)propan-2-ol (Preparation example 66), to obtain the title compound (0.78 g, yield 46%).

¹H NMR (400 MHz, CDCl₃) δ 0.97 (t, J=7.4 Hz, 3H), 1.31-1.39 (m, 1H), 1.51-1.59 (m, 1H), 3.25 (s, 3H), 5.072 (br s, 2H), 5.26 (d, J=8.8 Hz, 1H), 5.40-5.45 (m, 1H), 7.24 (t, J=8.0 Hz, 1H), 7.34-7.38 (m, 2H).

EXAMPLE 45

(1R, 2R)-1-(2,6-dichlorophenyl)-1-methoxybutan-2-yl sulfamate

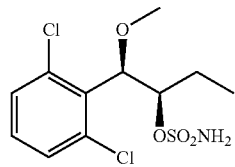

The substantially same method as described in example 51 was conducted, except that (1R,2R)-1-(2,6-dichlorophenyl)-1-methoxybutan-2-ol (Preparation example 114) was used instead of (1S,2S)-1-(2,4-dichlorophenyl)-1-(methoxymethoxy)propan-2-ol (Preparation example 66), to obtain the title compound (1.0 g, yield 65%).

$^1$H NMR (400 MHz, CDCl$_3$) δ 0.97 (t, J=7.4 Hz, 3H), 1.31-1.39 (m, 1H), 1.51-1.59 (m, 1H), 3.25 (s, 3H), 5.072 (br s, 2H), 5.26 (d, J=8.8 Hz, 1H), 5.40-5.45 (m, 1H), 7.24 (t, J=8.0 Hz, 1H), 7.34-7.38 (m, 2H).

EXAMPLE 46

(1S, 2S)-1-(2,6-dichlorophenyl)-1-methoxy-3-methylbutan-2-yl sulfamate

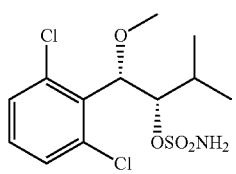

The substantially same method as described in example 51 was conducted, except that (1S,2S)-1-(2,6-dichlorophenyl)-1-methoxy-3-methylbutan-2-ol (Preparation example 119) was used instead of (1S,2S)-1-(2,4-dichlorophenyl)-1-(methoxymethoxy)propan-2-ol (Preparation example 66), to obtain the title compound (0.53 g, yield 76%).

$^1$H NMR (400 MHz, CDCl$_3$) δ 0.92 (d, J=6.8 Hz, 3H), 1.02 (d, J=6.8 Hz, 3H), 1.49-1.54 (m, 1H), 3.26 (s, 3H), 5.06 (br s, 2H), 5.29 (d, J=9.2 Hz, 1H), 5.59 (dd, J=9.2, 2.0 Hz, 1H), 7.25 (t, J=8.0 Hz, 1H), 7.36-7.40 (m, 2H).

EXAMPLE 47

(1R, 2R)-1-(2,6-dichlorophenyl)-1-methoxy-3-methylbutan-2-yl sulfamate

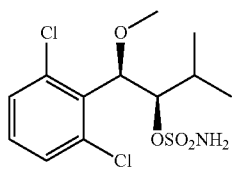

The substantially same method as described in example 51 was conducted, except that (1R,2R)-1-(2,6-dichlorophenyl)-1-methoxy-3-methylbutan-2-ol (Preparation example 124) was used instead of (1S,2S)-1-(2,4-dichlorophenyl)-1-(methoxymethoxy)propan-2-ol (Preparation example 66), to obtain the title compound (0.51 g, yield 51%).

$^1$H NMR (400 MHz, CDCl$_3$) δ 0.92 (d, J=6.8 Hz, 3H), 1.02 (d, J=6.8 Hz, 3H), 1.50-1.54 (m, 1H), 3.26 (s, 3H), 5.07 (br s, 2H), 5.29 (d, J=8.8 Hz, 1H), 5.59 (dd, J=9.6, 2.0 Hz, 1H), 7.25 (t, J=8.0 Hz, 1H), 7.36-7.40 (m, 2H).

EXAMPLE 48

(1S, 2S)-1-(2,6-dichlorophenyl)-1-methoxyhexan-2-yl sulfamate

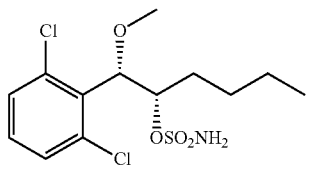

The substantially same method as described in example 51 was conducted, except that (1S,2S)-1-(2,6-dichlorophenyl)-1-methoxyhexan-2-ol (Preparation example 129) was used instead of (1S,2S)-1-(2,4-dichlorophenyl)-1-(methoxymethoxy)propan-2-ol (Preparation example 66), to obtain the title compound (0.6 g, yield 50%).

$^1$H NMR (400 MHz, CDCl$_3$) δ 0.80 (t, J=7.2 Hz, 3H), 1.20-1.53 (m, 6H), 3.24 (s, 3H), 5.06 (br s, 2H), 5.26 (d, J=9.2 Hz, 1H), 5.47-5.52 (m, 1H), 7.25 (t, J=8.0 Hz, 1H), 7.35-7.39 (m, 2H).

EXAMPLE 49

(1R, 2R)-1-(2,6-dichlorophenyl)-1-methoxyhexan-2-yl sulfamate

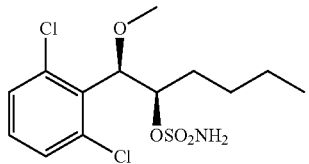

The substantially same method as described in example 51 was conducted, except that (1R,2R)-1-(2,6-dichlorophenyl)-1-methoxyhexan-2-ol (Preparation example 134) was used instead of (1S,2S)-1-(2,4-dichlorophenyl)-1-(methoxymethoxy)propan-2-ol (Preparation example 66), to obtain the title compound (0.5 g, yield 63%).

$^1$H NMR (400 MHz, CDCl$_3$) δ 0.80 (t, J=7.2 Hz, 3H), 1.20-1.53 (m, 6H), 3.24 (s, 3H), 5.06 (br s, 2H), 5.26 (d, J=9.2 Hz, 1H), 5.47-5.52 (m, 1H), 7.25 (t, J=8.0 Hz, 1H), 7.35-7.39 (m, 2H).

EXAMPLE 50

(1S, 2S)-1-(2,6-dichlorophenyl)-1-methoxypropan-2-yl isopropylsulfamate

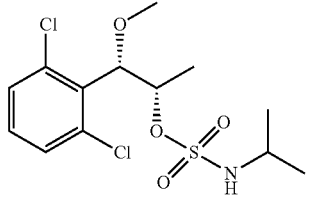 [SMILES: CO[C@@H](c1c(Cl)cccc1Cl)[C@H](C)OS(=O)(=O)NC(C)C]

The substantially same method as described in example 76 was conducted, except that (1S,2S)-1-(2,6-dichlorophenyl)-1-methoxypropan-2-ol (Preparation example 143) and isopropylamine were used instead of (1S,2S)-1-(2-chlorophenyl)-1-(methoxymethoxy)propan-2-ol (Preparation example 138) and methylamine, to obtain the title compound (1.4 g, yield 38%).

$^1$H NMR (400 MHz, CDCl$_3$) δ 1.19 (d, J=6.4 Hz, 3H), 1.30 (dd, J=6.4, 2.0 Hz, 6H), 3.23 (s, 3H), 3.72-3.80 (m, 1H), 4.45 (d, J=6.8 Hz, 1H), 5.17 (d, J=8.4 Hz, 1H), 5.42-5.49 (m, 1H), 7.22 (t, J=8.0 Hz, 1H), 7.33-7.37 (m, 2H).

EXAMPLE 51

(1S, 2S)-1-(2,4-dichlorophenyl)-1-(methoxymethoxy)propan-2-yl sulfamate

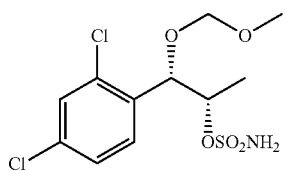

A 50 mL round-bottomed flask, equipped with a magnetic stirrer, was filled with acetonitrile (30 mL, 109.0 mmol) and cooled to 0° C. Chlorosulfonyl isocyanate (2.4 mL, 27.45 mmol) and formic acid (1.0 mL, 27.45 mmol) was added dropwise and stirred at room temperature for 15 h. (1S,2S)-1-(2,4-dichlorophenyl)-1-(methoxymethoxy)propan-2-ol (Preparation example 66, 2.9 g, 10.9 mmol) in N,N-dimethylacetamide (9.5 mL, 109.0 mmol) was slowly added at 0° C. and stirred at room temperature for 2 h. The reaction mixture was quenched with water, extracted with EtOAc, and washed with water and brine, dried over Na$_2$SO$_4$, filtered, and concentrated under reduced pressure. The crude product was purified by silica gel column chromatography to produce the title compound (2.73 g, yield 73%).

$^1$H NMR (400 MHz, CDCl$_3$) δ 1.43 (d, J=6.4 Hz, 3H), 3.40 (s, 3H), 4.52-4.66 (m, 4H), 4.88-4.91 (m, 1H), 5.17 (d, J=5.6 Hz, 1H), 7.35 (dd, J=8.0, 2.0 Hz, 1H), 7.44-7.48 (m, 2H).

EXAMPLE 52

(1R, 2R)-1-(2,4-dichlorophenyl)-1-(methoxymethoxy)propan-2-yl sulfamate

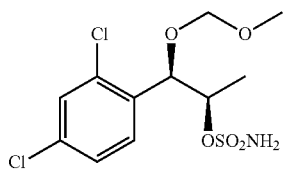

The substantially same method as described in example 51 was conducted, except that (1R,2R)-1-(2,4-dichlorophenyl)-1-(methoxymethoxy)propan-2-ol (Preparation example 69) was used instead of (1S,2S)-1-(2,4-dichlorophenyl)-1-(methoxymethoxy)propan-2-ol (Preparation example 66), to obtain the title compound (0.22 g, yield 54%).

$^1$H NMR (400 MHz, CDCl$_3$) δ 1.43 (d, J=6.4 Hz, 3H), 3.40 (s, 3H), 4.52-4.66 (m, 4H), 4.88-4.91 (m, 1H), 5.17 (d, J=5.6 Hz, 1H), 7.35 (dd, J=8.0, 2.0 Hz, 1H), 7.44-7.48 (m, 2H).

EXAMPLE 53

(1S, 2S)-1-(2,3-dichlorophenyl)-1-(methoxymethoxy)propan-2-yl sulfamate

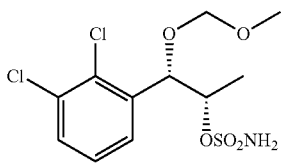

The substantially same method as described in example 51 was conducted, except that (1S,2S)-1-(2,3-dichlorophenyl)-1-(methoxymethoxy)propan-2-ol (Preparation example 78) was used instead of (1S,2S)-1-(2,4-dichlorophenyl)-1-(methoxymethoxy)propan-2-ol (Preparation example 66), to obtain the title compound (1.2 g, yield 59%).

$^1$H NMR (400 MHz, CDCl$_3$) δ 1.46 (d, J=6.4 Hz, 3H), 3.41 (s, 3H), 4.53 (d, J=6.4 Hz, 1H), 4.56 (s, 2H), 4.66 (d, J=6.4 Hz, 1H), 4.85-4.95 (m, 1H), 5.26 (d, J=5.9 Hz, 1H), 7.31 (t, J=8.0 Hz, 1H), 7.45-7.53 (m, 2H).

EXAMPLE 54

(1R, 2R)-1-(2,3-dichlorophenyl)-1-(methoxymethoxy)propan-2-yl sulfamate

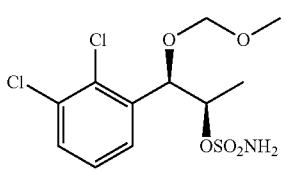

The substantially same method as described in example 51 was conducted, except that (1R,2R)-1-(2,3-dichlorophenyl)-1-(methoxymethoxy)propan-2-ol (Preparation example 81) was used instead of (1S,2S)-1-(2,4-dichlorophenyl)-1-(methoxymethoxy)propan-2-ol (Preparation example 66), to obtain the title compound (1.1 g, yield 71%).

$^1$H NMR (400 MHz, CDCl$_3$) δ 1.46 (d, J=6.4 Hz, 3H), 3.41 (s, 3H), 4.53 (d, J=6.4 Hz, 1H), 4.56 (s, 2H), 4.66 (d, J=6.4 Hz, 1H), 4.85-4.95 (m, 1H), 5.26 (d, J=5.9 Hz, 1H), 7.31 (t, J=8.0 Hz, 1H), 7.45-7.53 (m, 2H).

EXAMPLE 55

(1S, 2S)-1-(3,4-dichlorophenyl)-1-(methoxymethoxy)propan-2-yl sulfamate

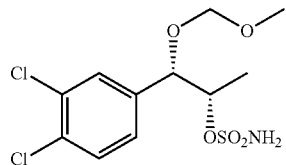

The substantially same method as described in example 51 was conducted, except that (1S,2S)-1-(3,4-dichlorophenyl)-1-(methoxymethoxy)propan-2-ol (Preparation example 72) was used instead of (1S,2S)-1-(2,4-dichlorophenyl)-1-(methoxymethoxy)propan-2-ol (Preparation example 66), to obtain the title compound (2.0 g, yield 60%).

$^1$H NMR (400 MHz, CDCl$_3$) δ 1.27 (t, J=6.4 Hz, 3H), 3.39 (s, 3H), 4.55 (d, J=6.8 Hz, 1H), 4.65 (t, J=6.4 Hz, 2H), 4.80-4.84 (m, 1H), 4.87 (br s, 2H), 7.22 (dd, J=8.0, 2.0 Hz, 1H), 7.48-7.50 (m, 2H).

EXAMPLE 56

(1R, 2R)-1-(3,4-dichlorophenyl)-1-(methoxymethoxy)propan-2-yl sulfamate

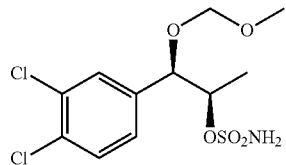

The substantially same method as described in example 51 was conducted, except that (1R,2R)-1-(3,4-dichlorophenyl)-1-(methoxymethoxy)propan-2-ol (Preparation example 75) was used instead of (1S,2S)-1-(2,4-dichlorophenyl)-1-(methoxymethoxy)propan-2-ol (Preparation example 66), to obtain the title compound (2.34 g, yield 60%).

$^1$H NMR (400 MHz, CDCl$_3$) δ 1.27 (t, J=6.4 Hz, 3H), 3.39 (s, 3H), 4.55 (d, J=6.8 Hz, 1H), 4.65 (t, J=6.4 Hz, 2H), 4.80-4.84 (m, 1H), 4.87 (br s, 2H), 7.22 (dd, J=8.0, 2.0 Hz, 1H), 7.48-7.50 (m, 2H).

EXAMPLE 57

(1S, 2S)-1-(2,6-dichlorophenyl)-1-(methoxymethoxy)propan-2-yl sulfamate

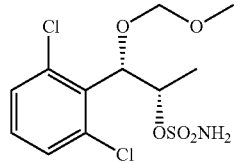

The substantially same method as described in example 51 was conducted, except that (1S,2S)-1-(2,6-dichlorophenyl)-1-(methoxymethoxy)propan-2-ol (Preparation example 48) was used instead of (1S,2S)-1-(2,4-dichlorophenyl)-1-(methoxymethoxy)propan-2-ol (Preparation example 66), to obtain the title compound (0.5 g, yield 65%).

$^1$H NMR (400 MHz, CDCl$_3$) δ 1.27 (d, J=6.4 Hz, 3H), 3.33 (s, 3H), 4.55 (d, J=6.4 Hz, 1H), 4.70 (d, J=6.4 Hz, 1H), 4.97 (s, 2H), 5.51-5.67 (m, 2H), 7.23-7.30 (m, 1H), 7.35-7.42 (m, 2H).

EXAMPLE 58

(1R, 2R)-1-(2,6-dichlorophenyl)-1-(methoxymethoxy)propan-2-yl sulfamate

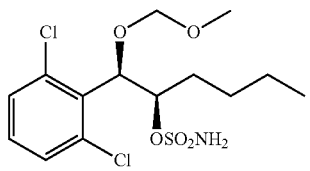

The substantially same method as described in example 51 was conducted, except that (1R,2R)-1-(2,6-dichlorophenyl)-1-(methoxymethoxy)propan-2-ol (Preparation example 53) was used instead of (1S,2S)-1-(2,4-dichlorophenyl)-1-(methoxymethoxy)propan-2-ol (Preparation example 66), to obtain the title compound (0.5 g, yield 65%).

$^1$H NMR (400 MHz, CDCl$_3$) δ 1.27 (d, J=6.4 Hz, 3H), 3.33 (s, 3H), 4.55 (d, J=6.4 Hz, 1H), 4.70 (d, J=6.4 Hz, 1H), 4.97 (s, 2H), 5.51-5.67 (m, 2H), 7.23-7.30 (m, 1H), 7.35-7.42 (m, 2H).

EXAMPLE 59

(1S, 2S)-1-(2,5-dichlorophenyl)-1-(methoxymethoxy)propan-2-yl sulfamate

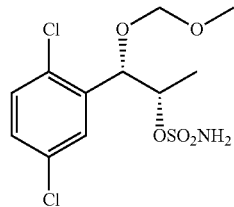

The substantially same method as described in example 51 was conducted, except that (1S,2S)-1-(2,5-dichlorophenyl)-1-(methoxymethoxy)propan-2-ol (Preparation example 99) was used instead of (1S,2S)-1-(2,4-dichlorophenyl)-1-(methoxymethoxy)propan-2-ol (Preparation example 66), to obtain the title compound (1.7 g, yield 73%).

$^1$H NMR (400 MHz, CDCl$_3$) δ 1.44 (d, J=6.4 Hz, 3H), 3.41 (s, 3H), 4.55 (d, J=6.8 Hz, 1H), 4.65 (s, 2H), 4.68 (d, J=6.8 Hz, 1H), 4.86-4.94 (m, 1H), 5.17 (d, J=6.0 Hz, 1H), 7.27-7.31 (m, 1H), 7.36 (d, J=8.4 Hz, 1H), 7.52 (d, J=2.4 Hz, 1H).

EXAMPLE 60

(1R, 2R)-1-(2,5-dichlorophenyl)-1-(methoxymethoxy)propan-2-yl sulfamate

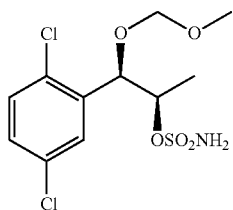

The substantially same method as described in example 51 was conducted, except that (1R,2R)-1-(2,5-dichlorophenyl)-1-(methoxymethoxy)propan-2-ol (Preparation example 102) was used instead of (1S,2S)-1-(2,4-dichlorophenyl)-1-(methoxymethoxy)propan-2-ol (Preparation example 66), to obtain the title compound (1.5 g, yield 66%).

$^1$H NMR (400 MHz, CDCl$_3$) δ 1.44 (d, J=6.4 Hz, 3H), 3.41 (s, 3H), 4.55 (d, J=6.8 Hz, 1H), 4.65 (s, 2H), 4.68 (d, J=6.8 Hz, 1H), 4.86-4.94 (m, 1H), 5.17 (d, J=6.0 Hz, 1H), 7.27-7.31 (m, 1H), 7.36 (d, J=8.4 Hz, 1H), 7.52 (d, J=2.4 Hz, 1H).

EXAMPLE 61

(1S, 2S)-1-(2-chloro-6-fluorophenyl)-1-(methoxymethoxy)propan-2-yl sulfamate

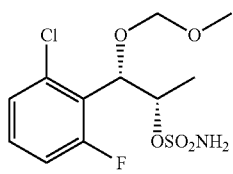

The substantially same method as described in example 51 was conducted, except that (1S,2S)-1-(2-chloro-6-fluorophenyl)-1-(methoxymethoxy)propan-2-ol (Preparation example 105) was used instead of (1S,2S)-1-(2,4-dichlorophenyl)-1-(methoxymethoxy)propan-2-ol (Preparation example 66), to obtain the title compound (1.0 g, yield 56%).

$^1$H NMR (400 MHz, DMSO-d$_6$) δ 1.11 (d, J=6.0 Hz, 3H), 3.16 (s, 3H), 4.47 (d, J=6.8 Hz, 1H), 4.61 (d, J=6.8 Hz, 1H), 5.09 (s, 2H), 7.24-7.32 (m, 1H), 7.38 (d, J=8.0 Hz, 1H) 7.41-7.49 (m, 1H), 7.54 (s, 2H).

EXAMPLE 62

(1S, 2S)-1-(2,6-dichlorophenyl)-1-(methoxymethoxy)propan-2-yl sulfamate

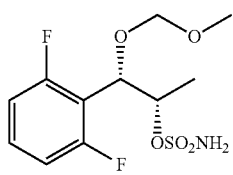

The substantially same method as described in example 51 was conducted, except that (1S, 2S)-1-(2,6-difluorophenyl)-1-(methoxymethoxy)propan-2-ol (Preparation example 96) was used instead of (1S,2S)-1-(2,4-dichlorophenyl)-1-(methoxymethoxy)propan-2-ol (Preparation example 66), to obtain the title compound (1.7 g, yield 71%).

$^1$H NMR (400 MHz, CDCl$_3$) δ 1.29 (d, J=7.2 Hz, 3H), 3.33 (s, 3H), 4.61 (d, J=6.4, 1H), 4.70 (d, J=6.4 Hz, 1H), 5.01 (s, 2H), 5.09 (d, J=8.8, 1H), 5.19-5.29 (m, 1H), 6.96 (t, J=8.6 Hz, 2H), 7.31-7.40 (m, 1H).

EXAMPLE 63

(1S, 2S)-1-(2,6-dichlorophenyl)-1-(methoxymethoxy)butan-2-yl sulfamate

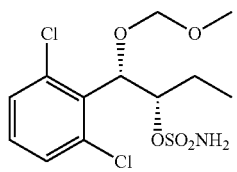

The substantially same method as described in example 51 was conducted, except that (1S,2S)-1-(2,6-dichlorophenyl)-1-(methoxymethoxy)butan-2-ol (Preparation example 110) was used instead of (1S,2S)-1-(2,4-dichlorophenyl)-1-(methoxymethoxy)propan-2-ol (Preparation example 66), to obtain the title compound (1.18 g, yield 46%).

$^1$H NMR (400 MHz, CDCl$_3$) δ 0.92 (t, J=7.4 Hz, 3H), 1.25-1.31 (m, 1H), 1.37-1.56 (m, 1H), 3.48 (s, 3H), 4.53-4.57 (m, 1H), 4.80 (d, J=6.4 Hz, 1H), 4.84 (br s, 2H), 4.95 (d, J=6.8 Hz, 1H), 6.16 (d, J=8.4 Hz, 1H), 7.21-7.26 (m, 1H), 7.33-7.37 (m, 2H).

EXAMPLE 64

(1R, 2R)-1-(2,6-dichlorophenyl)-1-(methoxymethoxy)butan-2-yl sulfamate

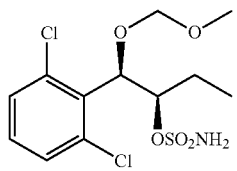

The substantially same method as described in example 51 was conducted, except that (1R,2R)-1-(2,6-dichlorophenyl)-1-(methoxymethoxy)butan-2-ol (Preparation example 114) was used instead of (1S,2S)-1-(2,4-dichlorophenyl)-1-(methoxymethoxy)propan-2-ol (Preparation example 66), to obtain the title compound (0.68 g, yield 41%).

$^1$H NMR (400 MHz, CDCl$_3$) δ 0.92 (t, J=7.4 Hz, 3H), 1.25-1.31 (m, 1H), 1.37-1.56 (m, 1H), 3.48 (s, 3H), 4.53-4.57 (m, 1H), 4.80 (d, J=6.4 Hz, 1H), 4.84 (br s, 2H), 4.95 (d, J=6.8 Hz, 1H), 6.16 (d, J=8.4 Hz, 1H), 7.21-7.26 (m, 1H), 7.33-7.37 (m, 2H).

EXAMPLE 65

(1S, 2S)-1-(2,6-dichlorophenyl)-1-(methoxymethoxy)-3-methylbutan-2-yl sulfamate

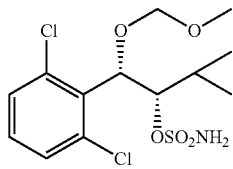

The substantially same method as described in example 51 was conducted, except that (1S,2S)-1-(2,6-dichlorophenyl)-1-(methoxymethoxy)-3-methylbutan-2-ol (Preparation example 120) was used instead of (1S,2S)-1-(2,4-dichlorophenyl)-1-(methoxymethoxy)propan-2-ol (Preparation example 66), to obtain the title compound (2.4 g, yield 64%).

$^1$H NMR (400 MHz, DMSO-d$_6$) δ 0.89 (dd, J=11.2, 6.8 Hz, 6H), 1.29 (qd, J=6.8, 1.6 Hz, 1H), 3.33 (s, 3H), 4.38 (dd, J=8.8, 2.0 Hz, 1H), 4.80 (dd, J=8.4, 6.8 Hz, 2H), 5.94 (d, J=8.8 Hz, 1H), 7.38 (t, J=8.0 Hz, 1H), 7.46-7.51 (m, 2H), 7.55 (br s, 2H).

EXAMPLE 66

(1R, 2R)-1-(2,6-dichlorophenyl)-1-(methoxymethoxy)-3-methylbutan-2-yl sulfamate

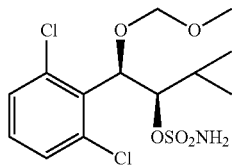

The substantially same method as described in example 51 was conducted, except that (1R,2R)-1-(2,6-dichlorophenyl)-1-(methoxymethoxy)-3-methylbutan-2-ol (Preparation example 125) was used instead of (1S,2S)-1-(2,4-dichlorophenyl)-1-(methoxymethoxy)propan-2-ol (Preparation example 66), to obtain the title compound (2.05 g, yield 60%).

$^1$H NMR (400 MHz, DMSO-d$_6$) δ 0.89 (dd, J=11.2, 6.8 Hz, 6H), 1.27-1.33 (m, 1H), 4.38 (dd, J=8.8, 1.6 Hz, 1H), 4.81 (dd, J=49.2, 6.8 Hz, 2H), 5.94 (d, J=8.4 Hz, 1H), 7.38 (t, J=8.0 Hz, 1H), 7.14-7.51 (m, 4H).

EXAMPLE 67

(1S, 2S)-1-(2,6-dichlorophenyl)-1-(methoxymethoxy)hexan-2-yl sulfamate

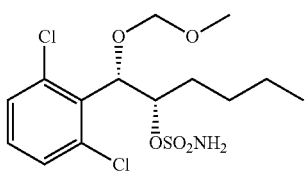

The substantially same method as described in example 51 was conducted, except that (1S,2S)-1-(2,6-dichlorophenyl)-1-(methoxymethoxy)hexan-2-ol (Preparation example 130) was used instead of (1S,2S)-1-(2,4-dichlorophenyl)-1-(methoxymethoxy)propan-2-ol (Preparation example 66), to obtain the title compound (0.59 g, yield 36%).

$^1$H NMR (400 MHz, CDCl$_3$) δ 0.80 (t, J=7.2 Hz, 3H), 1.15-1.55 (m, 6H), 3.49 (s, 3H), 4.57-4.62 (m, 1H), 4.79 (d, J=6.4 Hz, 1H), 4.84 (s, 2H), 4.95 (d, J=6.8 Hz, 1H), 6.16 (d, J=8.4 Hz, 1H), 7.23 (t, J=8.0 Hz, 1H), 7.33-7.37 (m, 2H).

EXAMPLE 68

(1R, 2R)-1-(2,6-dichlorophenyl)-1-(methoxymethoxy)hexan-2-yl sulfamate

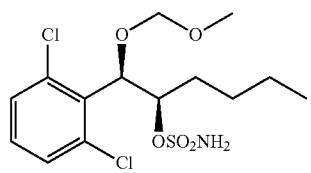

The substantially same method as described in example 51 was conducted, except that (1R,2R)-1-(2,6-dichlorophenyl)-1-(methoxymethoxy)hexan-2-ol (Preparation example 135) was used instead of (1S,2S)-1-(2,4-dichlorophenyl)-1-(methoxymethoxy)propan-2-ol (Preparation example 66), to obtain the title compound (1.52 g, yield 38%).

$^1$H NMR (400 MHz, CDCl$_3$) δ 0.80 (t, J=7.2 Hz, 3H), 1.15-1.55 (m, 6H), 3.49 (s, 3H), 4.57-4.62 (m, 1H), 4.79 (d, J=6.4 Hz, 1H), 4.84 (s, 2H), 4.95 (d, J=6.8 Hz, 1H), 6.16 (d, J=8.4 Hz, 1H), 7.23 (t, J=8.0 Hz, 1H), 7.33-7.37 (m, 2H).

EXAMPLE 69

(1S, 2S)-1-(2-chlorophenyl)-1-(methoxymethoxy)propan-2-yl sulfamate

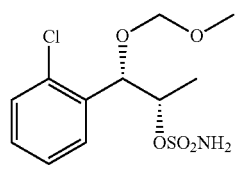

The substantially same method as described in example 51 was conducted, except that (1S,2S)-1-(2-chlorophenyl)-1-(methoxymethoxy)propan-2-ol (Preparation example 138) was used instead of (1S,2S)-1-(2,4-dichlorophenyl)-1-(methoxymethoxy)propan-2-ol (Preparation example 66), to obtain the title compound (5.17 g, yield 70%).

$^1$H NMR (400 MHz, CDCl$_3$) δ 1.42 (d, J=6.4 Hz, 3H), 3.39 (s, 3H), 4.54 (d, J=6.4 Hz, 1H), 4.65 (d, J=6.8 Hz, 1H), 4.69 (br s, 2H), 4.84-4.97 (m, 1H), 5.22 (d, J=6.0 Hz, 1H), 7.28-7.42 (m, 3H), 7.52-7.54 (m, 1H).

EXAMPLE 70

(1R, 2R)-1-(2-chlorophenyl)-1-(methoxymethoxy) propan-2-yl sulfamate

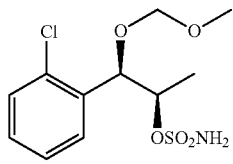

The substantially same method as described in example 51 was conducted, except that (1R,2R)-1-(2-chlorophenyl)-1-(methoxymethoxy)propan-2-ol (Preparation example 141) was used instead of (1S,2S)-1-(2,4-dichlorophenyl)-1-(methoxymethoxy)propan-2-ol (Preparation example 66), to obtain the title compound (4.52 g, yield 69%).

$^1$H NMR (400 MHz, CDCl$_3$) δ 1.42 (d, J=6.4 Hz, 3H), 3.39 (s, 3H), 4.54 (d, J=6.4 Hz, 1H), 4.65 (d, J=6.8 Hz, 1H), 4.69 (br s, 2H), 4.84-4.97 (m, 1H), 5.22 (d, J=6.0 Hz, 1H), 7.28-7.42 (m, 3H), 7.52-7.54 (m, 1H).

EXAMPLE 71

(1R, 2R)-1-(2-chlorophenyl)-1-(methoxymethoxy) butan-2-yl sulfamate

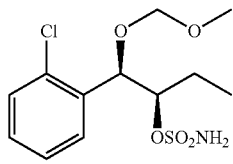

The substantially same method as described in example 51 was conducted, except that (1R,2R)-1-(2,6-dichlorophenyl)-1-(methoxymethoxy)butan-2-ol (Preparation example 115) was used instead of (1S,2S)-1-(2,4-dichlorophenyl)-1-(methoxymethoxy)propan-2-ol (Preparation example 66), to obtain the title compound (2.8 g, yield 73%).

$^1$H NMR (400 MHz, CDCl$_3$) δ 0.96 (t, J=7.4 Hz, 3H), 1.50-1.69 (m, 1H), 1.71-1.76 (m, 1H), 3.31 (s, 3H), 4.43-4.45 (m, 3H), 4.55 (d, J=6.4 Hz, 1H), 4.66-4.71 (m, 1H), 5.22 (d, J=5.6 Hz, 1H), 7.19-7.34 (m, 3H), 7.45 (dd, J=7.6, J=2.0 Hz, 1H).

EXAMPLE 72

(1S, 2S)-1-(2-fluorophenyl)-1-(methoxymethoxy) propan-2-yl sulfamate

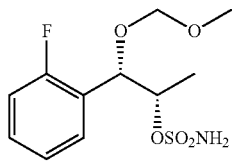

The substantially same method as described in example 51 was conducted, except that (1S,2S)-1-(2-fluorophenyl)-1-(methoxymethoxy)propan-2-ol (Preparation example 84) was used instead of (1S,2S)-1-(2,4-dichlorophenyl)-1-(methoxymethoxy)propan-2-ol (Preparation example 66), to obtain the title compound (5.37 g, yield 71%).

$^1$H NMR (400 MHz, CDCl$_3$) δ 1.40 (d, e the pain relief effect of the sulfamate compounds, a J=6.0 Hz, 3H), 3.39 (s, 3H), 4.58 (d, J=6.4 Hz, 1H), 4.65 (d, J=6.4 Hz, 1H), 4.77 (br s, 2H), 4.90-4.96 (m, 1H), 5.05 (d, J=6.8 Hz, 1H), 7.08-7.13 (m, 1H), 7.20-7.24 (m, 1H), 7.33-7.39 (m, 1H), 7.43-7.48 (m, 1H).

EXAMPLE 73

(1R, 2R)-1-(2-fluorophenyl)-1-(methoxymethoxy) propan-2-yl sulfamate

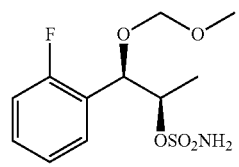

The substantially same method as described in example 51 was conducted, except that (1R,2R)-1-(2-fluorophenyl)-1-(methoxymethoxy)propan-2-ol (Preparation example 87) was used instead of (1S,2S)-1-(2,4-dichlorophenyl)-1-(methoxymethoxy)propan-2-ol (Preparation example 66), to obtain the title compound (4.02 g, yield 68%).

$^1$H NMR (400 MHz, CDCl$_3$) δ 1.36 (t, J=6.0 Hz, 3H), 3.39 (s, 3H), 4.58 (d, J=6.4 Hz, 1H), 4.65 (d, J=6.4 Hz, 1H), 4.77 (br s, 2H), 4.90-4.96 (m, 1H), 5.05 (d, J=6.8 Hz, 1H), 7.08-7.13 (m, 1H), 7.20-7.24 (m, 1H), 7.33-7.39 (m, 1H), 7.43-7.48 (m, 1H).

EXAMPLE 74

(1S, 2S)-1-(2-iodophenyl)-1-(methoxymethoxy) propan-2-yl sulfamate

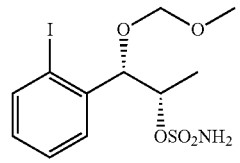

The substantially same method as described in example 51 was conducted, except that (1S,2S)-1-(2-iodophenyl)-1-(methoxymethoxy)propan-2-ol (Preparation example 90) was used instead of (1S,2S)-1-(2,4-dichlorophenyl)-1-(methoxymethoxy)propan-2-ol (Preparation example 66), to obtain the title compound (3.24 g, yield 75%).

$^1$H NMR (400 MHz, CDCl$_3$) δ 1.43 (d, J=6.4 Hz, 3H), 3.39 (s, 3H), 4.48 (br s, 2H), 4.50 (d, J=6.4 Hz, 1H), 4.62 (d, J=6.4 Hz, 1H), 4.85-4.93 (m, 1H), 5.03 (d, J=6.0 Hz, 1H), 7.03-7.07 (m, 1H), 7.38-7.45 (m, 2H), 7.86 (d, J=8.0 Hz, 1H).

EXAMPLE 75

(1R, 2R) 1-(2-iodophenyl)-1-(methoxymethoxy) propan-2-yl sulfamate

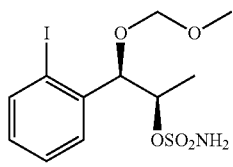

The substantially same method as described in example 51 was conducted, except that (1R,2R)-1-(2-iodophenyl)-1-(methoxymethoxy)propan-2-ol (Preparation example 93) was used instead of (1S,2S)-1-(2,4-dichlorophenyl)-1-(methoxymethoxy)propan-2-ol (Preparation example 66), to obtain the title compound (6.28 g, yield 78%).

$^1$H NMR (400 MHz, CDCl$_3$) δ 1.43 (d, J=6.4 Hz, 3H), 3.39 (s, 3H), 4.48 (br s, 2H), 4.50 (d, J=6.4 Hz, 1H), 4.62 (d, J=6.4 Hz, 1H), 4.85-4.93 (m, 1H), 5.03 (d, J=6.0 Hz, 1H), 7.03-7.07 (m, 1H), 7.38-7.45 (m, 2H), 7.86 (d, J=8.0 Hz, 1H).

EXAMPLE 76

(1S, 2S)-1-(2-chlorophenyl)-1-(methoxymethoxy) propan-2-yl methylsulfamate

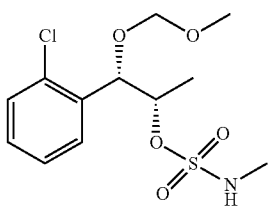 [SMILES: CNS(=O)(=O)O[C@@H](C)[C@@H](OCOC)c1ccccc1Cl]

To a stirred solution of (1S,2S)-1-(2-chlorophenyl)-1-(methoxymethoxy)propan-2-ol (Preparation example 138, 4.0 g, 17.34 mmol) in toluene (80 mL) was added pyridine (4.2 mL, 52.01 mmol) at room temperature under N$_2$. The mixture was added sulfuryl chloride (2.8 mL, 34.68 mmol) at −78° C. then allowed to stir for 2 h. The resulting mixture was quenched with 1M HCl, diluted with EtOAc, washed with water, dried over Na$_2$SO$_4$, filtered, and concentrated under reduced pressure.

To a stirred solution of an above crude product (6.2 g, 17.34 mmol) in THF (70 mL) was slowly added methylamine (33% in EtOH, 7 mL, 13.94 mmol) at 0° C. The mixture was stirred for 2 h. The resulting mixture was quenched with 1M HCl, diluted with EtOAc, washed with water, dried over Na$_2$SO$_4$, filtered, and concentrated under reduced pressure. The crude product was purified by silica gel column chromatography to produce the title compound (5.0 g, 89%).

$^1$H NMR (400 MHz, CDCl$_3$) δ 1.44 (d, J=6.4 Hz, 3H), 2.63 (d, J=5.2 Hz, 3H), 3.39 (s, 3H), 4.25-4.35 (m, 1H), 4.54 (d, J=6.8 Hz, 1H), 4.66 (d, J=6.8 Hz, 1H), 4.83-4.92 (m, 1H), 5.18 (d, J=5.6 Hz, 1H), 7.26-7.38 (m, 2H), 7.41 (dd, J=7.8, 1.4 Hz, 1H), 7.53 (dd, J=7.6, 2.0 Hz, 1H).

EXAMPLE 77

(1R, 2R)-1-(2-chlorophenyl)-1-(methoxymethoxy) propan-2-yl methylsulfamate

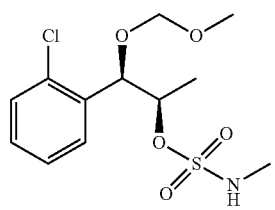 [SMILES: CNS(=O)(=O)O[C@H](C)[C@H](OCOC)c1ccccc1Cl]

The substantially same method as described in example 76 was conducted, except that (1R,2R)-1-(2-chlorophenyl)-1-(methoxymethoxy)propan-2-ol (Preparation example 141) was used instead of (1S,2S)-1-(2-chlorophenyl)-1-(methoxymethoxy)propan-2-ol (Preparation example 138), to obtain the title compound (1.1 g, yield 80%).

$^1$H NMR (400 MHz, CDCl$_3$) δ 1.45 (d, J=6.4 Hz, 3H), 2.63 (d, J=5.6 Hz, 3H), 3.39 (s, 3H), 4.26 (d, J=4.8 Hz, 1H), 4.55 (d, J=6.8 Hz, 1H), 4.66 (d, J=6.4 Hz, 1H), 4.83-4.92 (m, 1H), 5.19 (d, J=5.6 Hz, 1H), 7.26-7.37 (m, 2H), 7.41 (dd, J=7.6, 1.6 Hz, 1H), 7.53 (dd, J=7.6, 2.0 Hz, 1H).

EXAMPLE 78

(1S, 2S)-1-(2-chlorophenyl)-1-(methoxymethoxy) propan-2-yl cyclopropylsulfamate

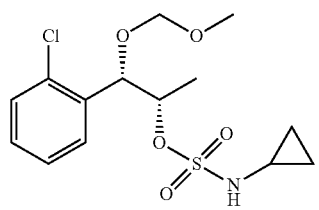 [SMILES: COCO[C@@H](c1ccccc1Cl)[C@H](C)OS(=O)(=O)NC1CC1]

The substantially same method as described in example 76 was conducted, except that cyclopropylamine was used instead of methylamine, to obtain the title compound (2.74 g, yield 52%).

$^1$H NMR (400 MHz, CDCl$_3$) δ 0.64-0.76 (m, 4H), 1.44 (d, J=6.4 Hz, 3H), 2.40-2.44 (m, 1H), 3.38 (s, 3H), 4.60 (dd, J=44.8, 6.8 Hz, 2H), 4.81 (s, 1H), 4.93 (q, J=6.4 Hz, 1H), 5.20 (d, J=6.0 Hz, 1H), 7.26-7.35 (m, 2H), 7.40 (dd, J=7.6, 2.0 Hz, 1H), 7.53 (dd, J=7.6, 2.0 Hz, 1H).

EXAMPLE 79

(1R, 2R)-1-(2-chlorophenyl)-1-(methoxymethoxy) propan-2-yl cyclopropylsulfamate

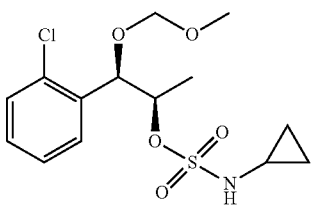 [SMILES: COCO[C@H](c1ccccc1Cl)[C@@H](C)OS(=O)(=O)NC1CC1]

The substantially same method as described in example 76 was conducted, except that (1R,2R)-1-(2-chlorophenyl)-1-(methoxymethoxy)propan-2-ol (Preparation example 141) and cyclopropylamine were used instead of (1S,2S)-1-(2-chlorophenyl)-1-(methoxymethoxy)propan-2-ol (Preparation example 138) and methylamine, to obtain the title compound (0.9 g, yield 68%).

$^1$H NMR (400 MHz, CDCl$_3$) δ 0.67-0.77 (m, 4H), 1.44 (d, J=6.4 Hz, 3H), 2.40-2.45 (m, 1H), 3.40 (s, 3H), 4.61 (dd, J=44.4, 6.4 Hz, 2H), 4.77 (s, 1H), 4.93 (q, J=6.4 Hz, 1H), 5.20 (d, J=6.0 Hz, 1H), 7.27-7.35 (m, 2H), 7.40 (dd, J=7.6, 1.2 Hz, 1H), 7.53 (dd, J=7.6, 1.2 Hz, 1H).

EXAMPLE 80

(1S,2S)-1-(2,6-dichlorophenyl)-1-(methoxymethoxy) propan-2-yl isopropylsulfamate

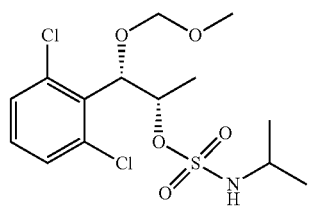 [SMILES: COCO[C@@H](c1c(Cl)cccc1Cl)[C@H](C)OS(=O)(=O)NC(C)C]

The substantially same method as described in example 76 was conducted, except that (1S,2S)-1-(2,6-dichlorophenyl)-1-(methoxymethoxy)propan-2-ol (Preparation example 48) and isopropylamine were used instead of (1S,2S)-1-(2-chlorophenyl)-1-(methoxymethoxy)propan-2-ol (Preparation example 138) and methylamine, to obtain the title compound (2.39 g, yield 32%).

$^1$H NMR (400 MHz, CDCl$_3$) δ 1.23 (d, J=6.4 Hz, 3H), 1.29 (d, J=6.4 Hz, 6H), 3.24 (s, 3H), 3.69-3.76 (m, 1H), 4.37 (d, J=7.2 Hz, 1H), 4.53 (d, J=6.4 Hz, 1H), 4.80 (d, J=6.4 Hz, 1H), 5.43-5.54 (m, 2H), 7.18-7.22 (m, 1H), 7.31-7.36 (m, 2H).

EXAMPLE 81

(1S,2S)-1-(2-chlorophenyl)-1-(methoxymethoxy) propan-2-yl isopropylsulfamate

The substantially same method as described in example 76 was conducted, except that isopropylamine was used instead of methylamine, to obtain the title compound (4.3 g, yield 67%).

$^1$H NMR (400 MHz, CDCl$_3$) δ 1.18 (dd, J=7.2, 6.4 Hz, 6H), 1.44 (d, J=6.4 Hz, 3H), 3.38 (s, 3H), 3.34-3.51 (m, 1H), 4.04 (d, J=7.2 Hz, 1H), 4.58 (dd, J=42.4, 6.8 Hz, 2H), 4.87 (q, J=6.8 Hz, 1H), 5.18 (d, J=5.6 Hz, 1H), 7.27-7.35 (m, 2H), 7.40 (dd, J=7.6, 2.0 Hz, 1H), 7.52 (dd, J=7.6, 2.0 Hz, 1H).

EXAMPLE 82

(1R, 2R)-1-(2-chlorophenyl)-1-(methoxymethoxy) propan-2-yl isopropylsulfamate

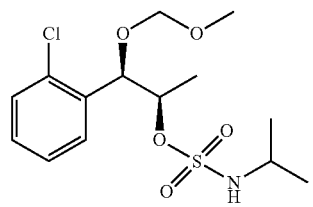 [SMILES: COCO[C@H](c1ccccc1Cl)[C@@H](C)OS(=O)(=O)NC(C)C]

The substantially same method as described in example 76 was conducted, except that (1R,2R)-1-(2-chlorophenyl)-1-(methoxymethoxy)propan-2-ol (Preparation example 141) and isopropylamine were used instead of (1S,2S)-1-(2-chlorophenyl)-1-(methoxymethoxy)propan-2-ol (Preparation example 138) and methylamine, to obtain the title compound (1.06 g, yield 69%).

$^1$H NMR (400 MHz, CDCl$_3$) δ 1.18 (dd, J=7.2, 6.8 Hz, 6H), 1.43 (d, J=6.4 Hz, 3H), 3.40 (s, 3H), 3.48 (q, J=6.4 Hz, 1H), 4.04 (s, 1H), 4.59 (dd, J=42.4, 6.8 Hz, 2H), 4.88 (q, J=6.4 Hz, 1H), 5.18 (d, J=5.6 Hz, 1H), 7.27-7.35 (m, 2H), 7.40 (dd, J=8.4, 2.0 Hz, 1H), 7.52 (dd, J=8.4, 2.0 Hz, 1H).

EXAMPLE 83

(1R, 2R)-1-(2,6-dichlorophenyl)-2-hydroxypropyl sulfamate

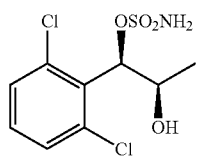

To a stirred solution of ((1R,2R)-2-((tert-butyldimethylsilyl)oxy)-1-(2,6-dichlorophenyl)propan-1-ol (Preparation example 51, 3.0 g, 8.95 mmol) in THF (20 mL) was added Et$_3$N (1.5 mL, 10.73 mmol) at 0° C. then allowed to stir for 30 min. The mixture was dropwise added sulfa-Boc reagent (2.1 g, 9.84 mmol) in THF (10 mL) at 0° C. When the reaction was completed, the resulting mixture was diluted with EtOAc, washed with water and brine, dried over Na$_2$SO$_4$, filtered, and concentrated to give 3.8 g as a crude product.

To a stirred solution of an above crude product (3.8 g, 7.38 mmol) in EtOAc (38 mL) was slowly added concentrated HCl (3.8 mL) at room temperature and then heated to reflux. When the reaction was completed, the resulting mixture was diluted with EtOAc, washed with sat. NaHCO$_3$ and brine, dried over Na$_2$SO$_4$, filtered, and concentrated under reduced pressure. The crude product was precipitated with EtOAc and hexane to produce the title compound (0.8 g, yield 36%).

¹H NMR (400 MHz, CDCl₃) δ 0.98 (t, J=7.4 Hz, 3H), 1.24-1.33 (m, 1H), 1.54-1.64 (m, 1H), 3.57-3.59 (d, J=9.6 Hz, 1H), 5.18 (s, 2H), 5.36-5.40 (m, 1H), 5.57 (t, J=9.2 Hz, 1H), 7.19-7.26 (m, 1H), 7.35-7.37 (m, 2H).

EXAMPLE 84

(1S, 2S)-1-(2-chlorophenyl)propane-1,2-diyl bis(sulfamate)

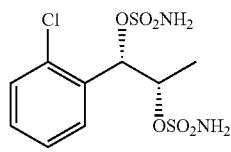

The substantially same method as described in example 1 was conducted, except that an excess amount of tert-butyl chlorosulfonylcarbamate (Preparation example 63) and base were used instead of a stoichiometric amount of (tert-butyl chlorosulfonylcarbamate (Preparation example 63) and base, to obtain the title compound (0.3 g, yield 40%).

¹H NMR (400 MHz, DMSO-d₆) δ 1.03 (d, J=6.8 Hz, 1H), 1.09 (d, J=6.8 Hz, 1H), 2.05-2.15 (m, 1H), 4.43 (dd, J=6.4, 3.2 Hz, 1H), 5.85 (d, J=3.2 Hz, 1H), 7.26 (br s, 2H), 7.30-7.40 (m, 2H), 7.56 (d, J=2.4 Hz, 1H), 7.43 (d, J=1.6 Hz, 1H), 7.73 (br s, 2H).

EXAMPLE 85

(1R, 2R)-1-2-chlorophenyl)propane-1,2-diyl bis(sulfamate)

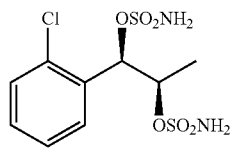

The substantially same method as described in example 1 was conducted, except that an excess amount of tert-butyl chlorosulfonylcarbamate (Preparation example 63), base, and (1R,2R)-1-(2-chlorophenyl)propane-1,2-diol (Preparation example 22) were used instead of a stoichiometric amount of (tert-butyl chlorosulfonylcarbamate (Preparation example 63), base and (1S,2S)-1-(2-chlorophenyl)propane-1,2-diol (Preparation example 21), to obtain the title compound (0.4 g, yield 40%).

¹H NMR (400 MHz, DMSO-d₆) δ 1.03 (d, J=6.8 Hz, 1H), 1.09 (d, J=6.8 Hz, 1H), 2.05-2.15 (m, 1H), 4.43 (dd, J=6.4, 3.2 Hz, 1H), 5.85 (d, J=3.2 Hz, 1H), 7.26 (br s, 2H), 7.30-7.40 (m, 2H), 7.56 (d, J=2.4 Hz, 1H), 7.43 (d, J=1.6 Hz, 1H), 7.73 (br s, 2H).

EXAMPLE 86

(1S, 2S)-1-(2-chlorophenyl)butane-1,2-diyl bis(sulfamate)

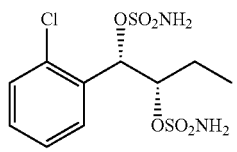

The substantially same method as described in example 1 was conducted, except that an excess amount of tert-butyl chlorosulfonylcarbamate (Preparation example 63), base, and 1-(2-chlorophenyl)-(S,S)-1,2-butanediol (Preparation example 31) were used instead of a stoichiometric amount of (tert-butyl chlorosulfonylcarbamate (Preparation example 63), base and (1S,2S)-1-(2-chlorophenyl)propane-1,2-diol (Preparation example 21), to obtain the title compound (0.28 g, yield 55%).

¹H NMR (400 MHz, DMSO-d₆) δ 0.92 (t, J=7.2 Hz, 3H), 1.39-1.58 (m, 2H), 4.55-4.67 (m, 1H), 5.80 (d, J=2.8 Hz, 1H), 7.30-7.95 (m, 8H).

EXAMPLE 87

(1R, 2R)-1-(2-chlorophenyl)butane-1,2-diyl bis(sulfamate)

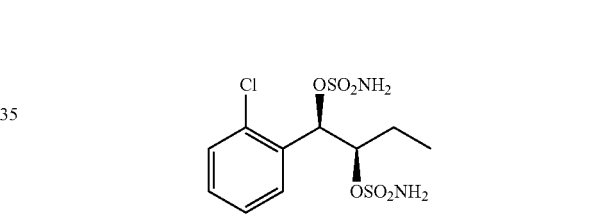

The substantially same method as described in example 1 was conducted, except that an excess amount of tert-butyl chlorosulfonylcarbamate (Preparation example 63), base, and 1-(2-chlorophenyl)-(R,R)-1,2-butanediol (Preparation example 32) were used instead of a stoichiometric amount of (tert-butyl chlorosulfonylcarbamate (Preparation example 63), base and (1S,2S)-1-(2-chlorophenyl)propane-1,2-diol (Preparation example 21), to obtain the title compound (0.34 g, yield 56%).

¹H NMR (400 MHz, DMSO-d₆) δ 0.92 (t, J=7.2 Hz, 3H), 1.39-1.58 (m, 2H), 4.55-4.67 (m, 1H), 5.80 (d, J=2.8 Hz, 1H), 7.30-7.95 (m, 8H).

EXAMPLE 88

(1S, 2S)-1-(2-chlorophenyl)-3-methylbutane-1,2-diyl bis(sulfamate)

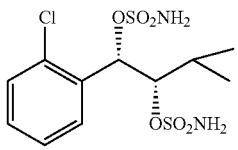

The substantially same method as described in example 1 was conducted, except that an excess amount of tert-butyl chlorosulfonylcarbamate (Preparation example 63), base, and 1-(2-chlorophenyl)-3-methyl-(S,S)-1,2-butanediol (Preparation example 33) were used instead of a stoichiometric amount of (tert-butyl chlorosulfonylcarbamate (Preparation example 63), base and (1S,2S)-1-(2-chlorophenyl)propane-1,2-diol (Preparation example 21), to obtain the title compound (0.41 g, yield 58%).

$^1$H NMR (400 MHz, DMSO-$d_6$) δ 0.92 (t, J=7.2 Hz, 3H), 1.20 (d, J=6.4 Hz, 3H), 1.39-1.58 (m, 1H), 4.55-4.67 (m, 1H), 5.80 (d, J=2.8 Hz, 1H), 7.30-7.95 (m, 8H).

EXAMPLE 89

(1R, 2R)-1-(2-chlorophenyl)-3-methylbutane-1,2-diyl bis(sulfamate)

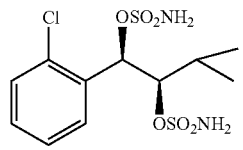

The substantially same method as described in example 1 was conducted, except that an excess amount of tert-butyl chlorosulfonylcarbamate (Preparation example 63), base, and 1-(2-chlorophenyl)-3-methyl-(R,R)-1,2-butanediol (Preparation example 34) were used instead of a stoichiometric amount of (tert-butyl chlorosulfonylcarbamate (Preparation example 63), base and (1S,2S)-1-(2-chlorophenyl)propane-1,2-diol (Preparation example 21), to obtain the title compound (0.53 g, yield 57%).

$^1$H NMR (400 MHz, DMSO-$d_6$) δ 0.92 (t, J=7.2 Hz, 3H), 1.20 (d, J=6.4 Hz, 3H), 1.39-1.58 (m, 1H), 4.55-4.67 (m, 1H), 5.80 (d, J=2.8 Hz, 1H), 7.30-7.95 (m, 8H).

EXAMPLE 90

(1S, 2S)-1-(2-chlorophenyl)pentane-1,2-diyl bis(sulfamate)

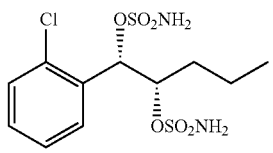

The substantially same method as described in example 1 was conducted, except that (1S,2S)-1-(2-chlorophenyl)pentane-1,2-diol (Preparation example 35) was used instead of (1S,2S)-1-(2-chlorophenyl)propane-1,2-diol (Preparation example 21), to obtain the title compound (0.5 g, yield 23%).

$^1$H NMR (400 MHz, DMSO-$d_6$) δ 0.92 (t, J=7.2 Hz, 3H), 1.39-1.58 (m, 2H), 1.68-1.80 (m, 1H), 1.80-1.94 (m, 1H), 4.55-4.67 (m, 1H), 5.80 (d, J=2.8 Hz, 1H), 7.30-7.95 (m, 8H).

EXAMPLE 91

(1R, 2R)-1-(2-chlorophenyl)pentane-1,2-diyl bis(sulfamate)

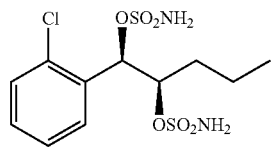

The substantially same method as described in example 1 was conducted, except that (1R,2R)-1-(2-chlorophenyl)pentane-1,2-diol (Preparation example 36) was used instead of (1S,2S)-1-(2-chlorophenyl)propane-1,2-diol (Preparation example 21), to obtain the title compound (0.6 g, yield 24%).

$^1$H NMR (400 MHz, DMSO-$d_6$) δ 0.92 (t, J=7.2 Hz, 3H), 1.39-1.58 (m, 2H), 1.68-1.80 (m, 1H), 1.80-1.94 (m, 1H), 4.55-4.67 (m, 1H), 5.80 (d, J=2.8 Hz, 1H), 7.30-7.95 (m, 8H).

EXAMPLE 92

(1S,2S)-1-(2-iodophenyl)-1-methoxypropan-2-yl sulfamate

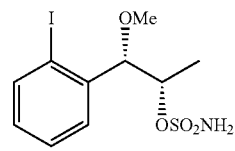

The substantially same method as described in example 51 was conducted, except that (1S,2S)-1-(2-iodophenyl)-1-methoxypropan-2-ol (Preparation example 148) was used instead of (1S,2S)-1-(2,4-dichlorophenyl)-1-(methoxymethoxy)propan-2-ol (Preparation example 66), to obtain the title compound (0.82 g, yield 55%).

$^1$H NMR (400 MHz, DMSO-$d_6$) δ 1.21 (d, J=6.4 Hz, 3H), 3.16 (s, 3H), 4.66-4.72 (m, 2H), 7.33-7.47 (m, 6H).

EXAMPLE 93

(1S, 2S)-1-(2,6-dichlorophenyl)-2-hydroxypropyl sulfamate

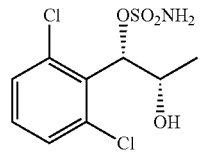

The substantially same method as described in example 83 was conducted, except that ((1S,2S)-2-((tert-butyldimethylsilyl)oxy)-1-(2,6-dichlorophenyl)propan-1-ol (Preparation example 46) was used instead of ((1R,2R)-2-((tert-butyldimethylsilyl)oxy)-1-(2,6-dichlorophenyl)propan-1-ol (Preparation example 51), to obtain the title compound (0.7 g, yield 40%).

¹H NMR (400 MHz, CDCl₃) δ 0.98 (t, J=7.4 Hz, 3H), 1.24-1.33 (m, 1H), 1.54-1.64 (m, 1H), 3.57-3.59 (d, J=9.6 Hz, 1H), 5.18 (s, 2H), 5.36-5.40 (m, 1H), 5.57 (t, J=9.2 Hz, 1H), 7.19-7.26 (m, 1H), 7.35-7.37 (m, 2H).

EXAMPLE 94

(1R,2R)-1-(2,6-dichlorophenyl)-1-methoxypropan-2-yl cyclopropylsulfamate

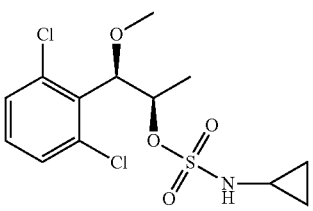 [SMILES: CO[C@H](c1c(Cl)cccc1Cl)[C@@H](C)OS(=O)(=O)NC1CC1]

The substantially same method as described in example 76 was conducted, except that (1R,2R)-1-(2,6-dichlorophenyl)-1-methoxypropan-2-ol (Preparation example 145) and cyclopropylamine were used instead of (1S,2S)-1-(2-chlorophenyl)-1-(methoxymethoxy)propan-2-ol (Preparation example 138) and methylamine, to obtain the title compound (1.32 g, yield 67%).

¹H NMR (400 MHz, CDCl₃) δ 0.67-0.89 (m, 4H), 1.20 (d, J=6.8 Hz, 3H), 2.73-2.78 (m, 1H), 3.25 (s, 3H), 5.18 (br s, 1H), 5.22 (d, J=8.8 Hz, 1H), 5.44-5.52 (m, 1H), 7.20-7.24 (m, 1H), 7.33-7.37 (m, 2H).

EXAMPLE 95

(1R,2R)-1-(2,6-dichlorophenyl)-1-methoxypropan-2-yl methylsulfamate

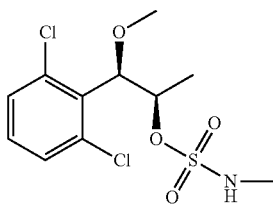 [SMILES: CNS(=O)(=O)O[C@H](C)[C@H](OC)c1c(Cl)cccc1Cl]

The substantially same method as described in example 76 was conducted, except that (1R,2R)-1-(2,6-dichlorophenyl)-1-methoxypropan-2-ol (Preparation example 145) was used instead of (1S,2S)-1-(2-chlorophenyl)-1-(methoxymethoxy)propan-2-ol (Preparation example 138), to obtain the title compound (1.07 g, yield 59%).

¹H NMR (400 MHz, CDCl₃) δ 1.19 (d, J=6.8 Hz, 3H), 2.89 (d, J=5.6 Hz, 3H), 3.25 (s, 3H), 4.25 (br s, 1H), 5.19 (d, J=8.4 Hz, 1H), 5.38-5.45 (m, 1H), 7.20-7.24 (m, 1H), 7.33-7.37 (m, 2H).

EXAMPLE 96

(1R,2R)-1-(2,6-dichlorophenyl)-1-hydroxypropan-2-yl methylsulfamate

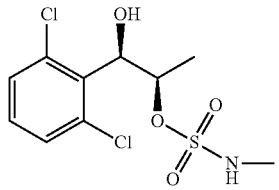 [SMILES: CNS(=O)(=O)O[C@H](C)[C@H](O)c1c(Cl)cccc1Cl]

To a stirred solution of (1R,2R)-1-(2,6-dichlorophenyl)-1-(methoxymethoxy)propan-2-ol (Preparation example 53, 4.6 g, 17.35 mmol) in toluene (46 mL) was added pyridine (4.4 mL, 52.05 mmol) at room temperature under N₂. The mixture was added sulfuryl chloride (2.8 mL, 34.70 mmol) at −78° C. then allowed to stir for 2 h. The resulting mixture was quenched with 1M HCl, diluted with EtOAc, washed with water, dried over Na₂SO₄, filtered, and concentrated under reduced pressure. The crude product (2.5 g, 6.87 mmol) was dissolved in THF (12.5 mL) then slowly added methylamine (33% in EtOH, 2.6 mL, 20.62 mmol) at 0° C. The mixture was stirred for 2 h. The resulting mixture was quenched with 1M HCl, diluted with EtOAc, washed with water, dried over Na₂SO₄, filtered, and concentrated under reduced pressure.

To a stirred solution of an above crude product in MeOH (6 mL) was dropwise added concentrated HCl (2.8 mL, 16.7 mmol) at room temperature. When the reaction was completed, the resulting mixture was removed the solvent, diluted with EtOAc, washed with sat. NaHCO₃ and brine, dried over Na₂SO₄, filtered, and concentrated under reduced pressure. The crude product was purified by silica gel column chromatography to produce the title compound (0.4 g, yield 77%).

¹H NMR (400 MHz, CDCl₃) δ 1.24 (d, J=6.4 Hz, 3H), 2.90 (d, J=5.2 Hz, 3H), 3.34 (d, J=8.0 Hz, 1H), 4.65 (br s, 1H), 5.39-5.53 (m, 2H), 7.19-7.23 (m, 1H), 7.34-7.36 (m, 2H).

EXAMPLE 97

(1S,2S)-1-(2-chlorophenyl)-1-methoxypropan-2-yl sulfamate

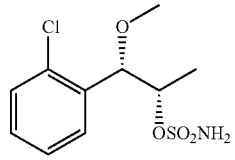

The substantially same method as described in example 51 was conducted, except that (1S,2S)-1-(2-chlorophenyl)-1-methoxypropan-2-ol (Preparation example 151) was used instead of (1S,2S)-1-(2,4-dichlorophenyl)-1-(methoxymethoxy)propan-2-ol (Preparation example 66), to obtain the title compound (1.8 g, yield 54%).

¹H NMR (400 MHz, CDCl₃) δ 1.30-1.31 (m, 3H), 3.26 (s, 3H), 4.81-4.88 (m, 2H), 4.92 (br s, 2H), 7.27-7.38 (m, 2H), 7.41 (dd, J=7.8, 1.4 Hz, 1H), 7.47 (dd, J=7.8, 1.8 Hz, 1H).

EXAMPLE 98

(1R,2R)-1-hydroxy-1-(pyridin-2-yl)propan-2-yl sulfamate

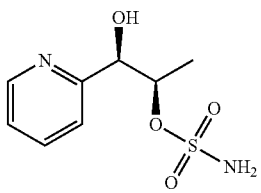

The substantially same method as described in example 1 was conducted, except that (1R,2R)-1-(pyridin-2-yl)propane-1,2-diol (Preparation example 153) was used instead of (1S,2S)-1-(2-chlorophenyl)propane-1,2-diol (Preparation example 21), to obtain the title compound (0.2 g, yield 66%).

¹H NMR (400 MHz, DMSO-d₆) δ 1.22 (d, J=6.4 Hz, 3H), 4.63 (d, J=4.8 Hz, 1H), 4.71-4.79 (m, 1H), 5.73 (br s, 1H), 6.88-7.43 (m, 3H), 7.46 (d, J=7.6 Hz, 1H), 7.75-7.84 (m, 1H), 8.47-8.53 (m, 1H).

EXAMPLE 99

(1R,2R)-1-(3,5-dichloropyridin-4-yl)-1-(methoxymethoxy)propan-2-yl sulfamate

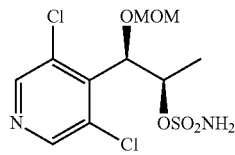

The substantially same method as described in example 51 was conducted, except that (1R,2R)-1-(3,5-dichloropyridin-4-yl)-1-(methoxymethoxy)propan-2-ol (Preparation example 160) was used instead of (1S,2S)-1-(2,4-dichlorophenyl)-1-(methoxymethoxy)propan-2-ol (Preparation example 66), to obtain the title compound (3.18 g, yield 75%).

¹H NMR (400 MHz, DMSO-d₆) δ 1.11 (s, 3H), 3.10 (s, 3H), 4.45 (d, J=7.2 Hz, 1H), 4.61 (d, J=7.2 Hz, 1H), 5.19 (s, 1H), 7.54 (br s, 2H), 8.62 (s, 2H).

EXAMPLE 100

(1R,2R)-1-(3,5-dichloropyridin-4-yl)-1-hydroxypropan-2-yl sulfamate

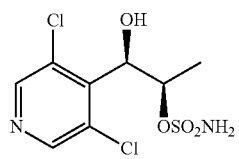

The substantially same method as described in example 3 was conducted, except that (1R,2R)-1-(3,5-dichloropyridin-4-yl)-1-(methoxymethoxy)propan-2-yl sulfamate (example 99) was used instead of (1S, 2S)-1-(2,4-dichlorophenyl)-1-(methoxymethoxy)propan-2-yl sulfamate (example 51), to obtain the title compound (1.07 g, yield 56%).

¹H NMR (400 MHz, DMSO-d₆) δ 1.13 (d, J=6.8 Hz, 3H), 5.06-5.12 (m, 1H), 5.21 (d, J=7.6 Hz, 1H), 7.41 (br s, 2H), 8.61 (m, 2H).

EXAMPLE 101

(1R,2R)-1-(3,5-dichloropyridin-4-yl)-1-methoxypropan-2-yl sulfamate

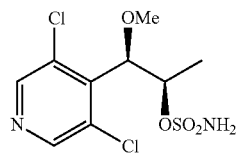

The substantially same method as described in example 51 was conducted, except that (1R,2R)-1-(3,5-dichloropyridin-4-yl)-1-methoxypropan-2-ol (Preparation example 159) was used instead of (1S,2S)-1-(2,4-dichlorophenyl)-1-(methoxymethoxy)propan-2-ol (Preparation example 66), to obtain the title compound (0.76 g, yield 69%).

¹H NMR (400 MHz, DMSO-d₆) δ 1.14 (d, J=6.8 Hz, 3H), 3.18 (s, 3H), 4.91 (d, J=7.2 Hz, 1H), 5.06-5.12 (m, 1H), 7.51 (br s, 2H), 8.63 (m, 2H).

EXAMPLE 102

(1R,2S)-1-(2,4-dichlorothiazol-5-yl)-1-hydroxypropan-2-yl sulfamate

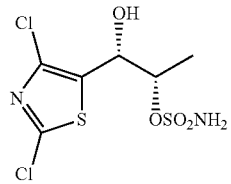

The substantially same method as described in example 3 was conducted, except that (1R,2S)-1-(2,4-dichlorothiazol-5-yl)-1-(methoxymethoxy)propan-2-yl sulfamate (example 103) was used instead of (1S, 2S)-1-(2,4-dichlorophenyl)-1-(methoxymethoxy)propan-2-yl sulfamate (example 51), to obtain the title compound (0.28 g, yield 74%).

¹H NMR (400 MHz, DMSO-d₆) δ 1.36 (d, J=6.4 Hz, 3H), 4.58-4.60 (m, 1H), 4.94 (s, 1H), 6.68 (s, 1H), 7.49 (br s, 2H).

EXAMPLE 103

(1R,2S)-1-(2,4-dichlorothiazol-5-yl)-1-(methoxymethoxy)propan-2-yl sulfamate

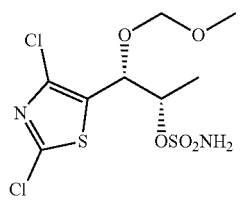

The substantially same method as described in example 51 was conducted, except that (1R,2S)-1-(2,4-dichlorothiazol-5-yl)-1-(methoxymethoxy)propan-2-ol (Preparation example 165) was used instead of (1S,2S)-1-(2,4-dichlorophenyl)-1-(methoxymethoxy)propan-2-ol (Preparation example 66), to obtain the title compound (0.26 g, yield 74%).

$^1$H NMR (400 MHz, DMSO-d$_6$) δ 1.36 (d, J=6.4 Hz, 3H), 3.30 (s, 3H), 4.26-4.33 (m, 1H), 5.39-5.45 (m, 2H), 5.67-5.70 (m, 1H).

EXAMPLE 104

(1R,2S)-1-hydroxy-1-(4-methylthiazol-5-yl)propan-2-yl sulfamate

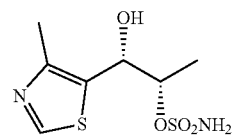

The substantially same method as described in example 1 was conducted, except that (1R,2S)-1-(4-methylthiazol-5-yl)propane-1,2-diol (Preparation example 167) was used instead of (1S,2S)-1-(2-chlorophenyl)propane-1,2-diol (Preparation example 21), to obtain the title compound (0.35 g, yield 24%).

$^1$H NMR (400 MHz, DMSO) δ 1.19 (d, J=6.4 Hz, 3H), 2.36 (s, 3H), 4.60-4.62 (m, 1H), 5.07 (t, J=4.6 Hz, 1H), 6.20 (d, J=4.0 Hz, 1H), 7.48 (s, 2H), 8.92 (s, 1H).

EXAMPLE 105

(1S,2R)-1-(2,4-dichlorothiazol-5-yl)-1-hydroxypropan-2-yl sulfamate

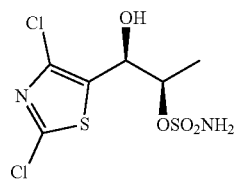

The substantially same method as described in example 1 was conducted, except that (1S,2R)-1-(2,4-dichlorothiazol-5-yl)propane-1,2-diol (Preparation example 168) was used instead of (1S,2S)-1-(2-chlorophenyl)propane-1,2-diol (Preparation example 21), to obtain the title compound (0.33 g, yield 49%).

$^1$H NMR (400 MHz, DMSO-d$_6$) δ 1.36 (d, J=6.4 Hz, 3H), 4.58-4.60 (m, 1H), 4.94 (s, 1H), 6.68 (s, 1H), 7.49 (br s, 2H).

EXAMPLE 106

(1S,2R)-1-methoxy-1-(thiophen-2-yl)propan-2-yl sulfamate

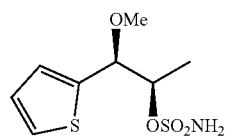

The substantially same method as described in example 51 was conducted, except that (1S,2R)-1-methoxy-1-(thiophen-2-yl)propan-2-ol (Preparation example 173) was used instead of (1S,2S)-1-(2,4-dichlorophenyl)-1-(methoxymethoxy)propan-2-ol (Preparation example 66), to obtain the title compound (0.3 g, yield 63%).

$^1$H NMR (400 MHz, CDCl$_3$) δ 1.23 (d, J=6.4 Hz, 3H), 3.30 (s, 3H), 4.48 (d, J=7.6 Hz, 1H), 4.76-4.86 (m, 2H), 4.96 (s, 2H), 7.00-7.05 (m, 1H), 7.05-7.08 (m, 1H), 7.35-7.40 (m, 1H).

BIOLOGICAL EXPERIMENTAL EXAMPLE 1

Writhing Test

To examine the pain relief effect of the sulfamate compounds, a writhing test was conducted, referring to Fischer, L. G. et al. (2008).

ICR mice (male, 24-28 g; Orient Bio, Korea) were habituated before test in test room for 1 hour. Animals were fasted 2 hr, before administration of compounds. Each of Compounds was orally administered at the three dose, 10 ul/g, by bodyweight (All compounds were dissolved in a vehicle of 30% (v/v) PEG 400 or 20% (v/v) Tween 80. The control group was treated with the vehicle without compounds.

0.25-2 hour after the administration of Compounds, 0.6% acetic acid at the dose of 10 ul/g, by bodyweight was injected into the mice. Animals were habituated in the cage for 5 min. 5 min after habituation, the number of writhes (abdominal constriction) was conted for 15 min, referring to Korzeniewska-Rybicka, I. et al. (1998) and compared with that of a control.

The relative values compared to the control (% control) were calculated and shown in Table 2.

TABLE 2

| Example | Writhing test(po) | |
|---|---|---|
| No. | ED50(mg/kg) | Peak Time(hr) |
| 7 | 69.6 | 0.5 |
| 8 | 50.6 | 0.25 |

BIOLOGICAL EXPERIMENTAL EXAMPLE 2

Evaluation of Antiallodynic Activity on Chung Model

Male Sprague-Dawley rats (100-130 g, Orient Bio, Korea) were habituated for 1 week before the experiment and allowed free access to food and water throughout the experimentation. Room temperature and humidity were maintained at 24±2 and 50±10%, respectively. The neuropathic surgery (SNL, Spinal nerve ligation) model was done as described in Kim and Chung (1992). Briefly, an animal was put under gaseous anesthesia with isoflurane. The left lumber spinal nerve L5 and L6 were isolated and tightly ligated with 6-0 silk thread. The wound muscle was closed with Catgut® chrom 3/0 thread and skin was closed with Dafilon 3/0 tread. Sham controls were prepared in the same manner with the spinal nerves exposed, but with no ligated L5 and L6 nerves. Preparation of the vehicle controls were identical to the group treated with compound, except for administration of vehicles without compound in the vehicle control group.

Tactile sensitivity (Mechanical allodynia) was evaluated using von Frey monofilaments before and after treatment, and animals were included in the study only if the withdrawal threshold value was less than 4 g. One week after surgery, SNL-operated animals, sham-operated animals and vehicle control animals were tested for tactile sensitivity with von Frey monofilaments 3 trials in each animal. All Animals were placed in a stainless steel mesh chamber and habituated for 30 min in the test cage. The tactile sensitivity for the ipsilateral hind paw was measured using the up-and-down method (Dixon, 1980) with seven von Frey monofilaments (0.4, 1, 2, 4, 6, 8, and 15 g) in 3 trials. The tactile sensitivity test was followed by Dixon's method (Dixon, 1980). The 50% paw withdrawal threshold for each paw was calculated using the following formula: [Xth] log=[vFr] log+ky where [vFr] is the force of the last von Frey used, k=0.2249 which is the average interval (in log units) between the von Frey monofilaments, and y is a value that depends upon the pattern of withdrawal responses (Dixon, 1980). If an animal did not respond to the highest von Frey hair (15 g), then the paw was assigned a value of 18.4 g.

All animals were fasted 18 h before the administration of the compounds. Antiallodynic effect of compounds were evaluated at the three dose, orally administrated in a volume of 5 ul/g, bw in a vehicle of 30% (v/v) PEG 400 or 20% (v/v) Tween 80. The test was performed at the peak time of efficacy after compound administration.

The relative values compared to the sham group (% control) were calculated and shown in Table 3, which show an antiallodynic effect of the test compounds on SNL model in rats.

TABLE 3

Antiallodynic effect of compound examples on SNL model

| Example No. | SNL ED50(mg/kg) | Peak Time(h) |
|---|---|---|
| 2 | 30(38.6%) | 1 |
| 7 | 4.4 | 0.5 |
| 8 | 35.3 | 1 |
| 17 | 46.9 | 1 |
| 18 | 30(48.2%) | 0.5 |
| 19 | 44.6 | 1 |
| 20 | 30(58.7%) | 1 |
| 57 | 30(26.3%) | 1 |
| 69 | 48.2 | 1 |
| 70 | 6.5 | 1 |
| 71 | 30(31.9%) | 0.5 |
| 73 | 30(31.3%) | 1 |
| 75 | 30(64.9%) | 1 |

*( ) is efficacy %

BIOLOGICAL EXPERIMENTAL EXAMPLE 3

Evaluation of Antiallodynic Activity on Complete Freund's Adjuvant (CFA)-Induced Inflammatory Pain Model Male, Sprague-Dawley rats (210-250 g, Nara Bio, Korea) were habituated for 1 week before CFA injection and allowed free access to food and water throughout the experimentation. Room temperature and humidity were maintained at 24±2 and 50±10%, respectively.

CFA-induced inflammatory pain was induced by the procedure of Nagakura et al. (2003) and Gregory P. et al. (2010) with minor modifications. CFA (sigma, USA) was injected in the right plantar with a 100 ul volume under gaseous anesthesia with isoflurane. Sham controls were injected with 100 ul of saline and preparation of the vehicles without compound in the vehicle control group. Tactile sensitivity (Mechanical allodynia) was evaluated using von Frey monofilaments before and after treatment, and the animals were included in the study only if the withdrawal threshold value was less than 4 g. One week after surgery, CFA-infused treatment animals (n=4-6), sham-operated animals (n=12), and vehicle control animals (n=17) were tested for tactile sensitivity with von Frey monofilaments 3 trials for each animal. All Animals were placed in a stainless steel mesh chamber and habituated for 30 min in the test box. The tactile sensitivity for ipsilateral hind paw was measured using the up-and-down method (Dixon, 1980) with seven von Frey monofilaments (0.4, 1, 2, 4, 6, 8, and 15 g) to 3 trials. Tactile sensitivity test was followed by Dixon's method (Dixon, 1980). The 50% paw withdrawal threshold for each paw was calculated using the following formula: [Xth] log=[vFr] log+ky where [vFr] is the force of the last von Frey used, k=0.2249 which is the average interval (in log units) between the von Frey monofilaments, and y is a value that depends upon the pattern of withdrawal responses (Dixon, 1980). If an animal did not respond to the highest von Frey hair (15 g), then the paw was assigned a value of 18.4 g.

Antiallodynic effect of compound was evaluated at the dose of 10-60 mg/kg (n=4-6), intraperitoneally administrated in a volume of 5 ul/g bw in a vehicle of 30% (v/v) PEG or 20% (v/v) Tween 80. The test was performed peak time of efficacy (0.5 or 1 hr) after compound administration.

The relative values compared to the sham (% control) were calculated and shown in Table 4, which show an antiallodynic effect of Compound 1 on CFA-induced pain model in rats.

TABLE 4

Antiallodynic effect of CFA-induced pain model

| Example No. | ED50(mg/kg) | Peak Time(h) |
| --- | --- | --- |
| 2 | 50(23.0%) | 1 |
| 7 | 31.9 | 1 |
| 8 | 52.7 | 0.5 |
| 12 | 50(21.9%) | 0.5 |
| 14 | 50(18.4%) | 1 |
| 17 | 48.7 | 0.5 |
| 18 | 50(46.6%) | 0.5 |
| 19 | 30(24.3%) | 1 |
| 20 | 50(28.7%) | 0.5 |
| 58 | 50(17.7%) | 0.5 |
| 69 | 29.5 | 0.5 |
| 70 | 50(23.7%) | 0.5 |
| 71 | 50(41.9%) | 0.5 |
| 72 | 50(25.9%) | 0.5 |
| 73 | 50(38.5%) | 0.5 |
| 74 | 50(19.9%) | 0.5 |
| 75 | 50(28.1%) | 0.5 |
| 92 | 50(31.8%) | 0.5 |

*( ) is efficacy %

BIOLOGICAL EXPERIMENTAL EXAMPLE 4

Evaluation of Antiallodynic Activity on Vincristine-Induced Pain Model

Male, Sprague-Dawley rats (160-180 g, Nara Bio, Korea) were habituated for 1 week before surgery and allowed free access to food and water throughout the experimentation. Room temperature and humidity were maintained at 24±2 and 50±10%, respectively.

The vincristine-induced pain model was established by the procedure of Natsuko et al. (2001) with minor modifications. Vincristine was intravenously infused continuously for 14 days using a mini-osmotic pump as follows: 30 ug/kg vincristine sulfate solution (Hospira, Australia) was diluted with 0.9% saline. The pumps (Alzet Model 2002, USA) were filled with the vincristine solution and primed by incubation at 37 for 4 hours before the infusion. Briefly, animal were put under gaseous anesthesia with isoflurane. A catheter made from PE-60 tube was inserted into an external jugular vein in rat. Sham controls were prepared in the same manner, with the external jugular vein exposed, but with the external jugular vein not cut down. Preparation of the vehicle controls were identical to the group threated with compound, except for administration of vehicles without compound in the vehicle control group.

Tactile sensitivity (Mechanical allodynia) was evaluated using von Frey monofilaments before and after treatment, and animals were used withdrawal threshold value was less than 4 g. One week after surgery, vincristine-infused animals, sham-operated animals and vehicle control animals were tested for tactile sensitivity with von Frey monofilaments 3 trials for each animal. All Animals were placed in a stainless steel mash chamber and habituated for 30 min in the test cage. The tactile sensitivity for ipsilateral hind paw was measured using the up-and-down method (Dixon, 1980) with seven von Frey monofilaments (0.4, 1, 2, 4, 6, 8, and 15 g) to 3 trials. Tactile sensitivity test was followed by Dixon's method. The 50% paw withdrawal threshold for each paw was calculated using the following formula: [Xth] log=[vFr] log+ky where [vFr] is the force of the last von Frey used, k=0.2249 which is the average interval (in log units) between the von Frey monofilaments, and y is a value that depends upon the pattern of withdrawal responses (Dixon, 1980). If an animal did not respond to the highest von Frey hair (15 g), then the paw was assigned a value of 18.4 g.

Antiallodynic effect of compound was evaluated at the three dose, intraperitoneally administered in a volume of 5 ul/g, bw in a vehicle of 30% (v/v) PEG or 20% (v/v) Tween 80. The test was performed at the peak time of efficacy (0.5 hr) after compound administration.

The relative values compared to the sham (% control) were calculated and shown in Table 5, which show an antiallodynic effect of Compound 2&7 on vincristine-induced pain model in rats.

TABLE 5

Antiallodynic effect of Compound 2&7 on Vincristine-induced pain model

| Example No. | ED50(mg/kg) | Peak Time(h) |
| --- | --- | --- |
| 2 | >20 | — |
| 7 | 10.3 | 0.5 |

BIOLOGICAL EXPERIMENTAL EXAMPLE 5

Tail-flick Test

To examine the pain relief effect of the sulfamate compounds, a tail-flick test was conducted, referring to Current Protocols in Neuroscience; Behavioral Neuroscience Unit 8.9.

ICR mice (male, 25-30 g; Orient Bio, Korea) were habituated before test (in test room) for 1 hour. Animals were fasted 2 hr before administration of compounds. Each of the tested compound were orally administered at the 1~3 dose, 10 ul/g, by bw (n=4-6/group). All compounds were dissolved in a vehicle of 30% (v/v) PEG 400 or 20% (v/v) Tween 80. The control group was treated the vehicle without compounds.

After the administration of compounds, the mice tail were put on a tail-flick analgesia meter. To avoid tissue damage, maximal exposure time to pain stimuli was restricted to 15 seconds. The withdrawal latency was measured to the time to the point when each mouse responded. The relative values compared to the control (% control) were calculated.

TABLE 6

Effect of the compound of examples in tail-flick test.

| Compound No. | Dose(mg/kg) | Peak Time(hr) |
| --- | --- | --- |
| 7 | 100 (19.0%) | 1~2 |
| 8 | >200 | — |

BIOLOGICAL EXPERIMENTAL EXAMPLE 6

Evaluation of Antiallodynic Activity on Post Operative-induced Pain Model

Male Sprague-Dawley rats (230-250 g, Orient Bio, Korea), were habituated at least 3 days before surgery and were allowed free access to food and water throughout the experimentation. Room temperature and humidity were maintained at 24±2 and 50±10%, respectively. The process of performing the post-operation model's surgery was adapted from Brennan et al (1996). At first, rats with allodynia (threshold valueless than 8 g) were excluded in Pre-von Frey Test. During the post-operation surgery, rats were anesthetized under gaseous anesthesia with 2% isoflurane. The rat was placed, lying face down on 37 degree warm plate to prevent against hypothermia. The ipsilateral plantar aspect (left side) of the hind paw was prepared in a sterile manner with a 10% povidone-iodine solution. A 1 cm longitudinal incision was made with a number 10 blade, through the skin and fascia of the ipsilateral plantar aspect of the foot, starting from 0.5 cm from the proximal edge of the heel and extending toward the toes. Rats' plantar muscles were elevated and incised longitudinally. After hemostasis with gentle pressure, the skin was opposed with 2 mattress sutures of 4-0 Dafilon.

After 24 hours of recovery, rats with a good response (threshold less than 4 g) in Pre-von Frey Test were selected. According to this response, we made three groups with each group having equal average responses: Group 1, post-operation and drug treated; Group 2, post-operation and vehicle treated; Group 3, no post-operation and vehicle treated. In this study, Group 3 was the sham control (positive) group. The group 2 was used to check for possible failures to generate post-operative pain.

For efficacy measure, the threshold value of group C was assigned 100% efficacy, and the percentage of the threshold values of group A compared to group C (for each different dose level) were calculated as the efficacies. Base on these efficacy values, ED50 was calculated using log fitting. If there was no clear ED50, then we marked the percent efficacy at the highest tested dose or larger than highest tested dose.

For pain threshold test, all animals were placed in a stainless steel meshed chamber and habituated for 30 min in the test cage. The tactile sensitivity of the ipsilateral hind paw was measured using the up-and-down method (Dixon, 1980) with seven von Frey monofilaments (0.4, 1, 2, 4, 6, 8, and 15 g) using 3 trials. The 50% paw withdrawal threshold for each paw was calculated using the following formula: [Xth] log=[vFr] log+ky, where [vFr] is the force of the last von Frey filament used, k=0.2249 which is the average interval (in log units) between the von Frey monofilaments, y which is a value that depends upon the pattern of withdrawal responses, and Xth which is the threshold value (Dixon, 1980). If an animal did not respond to the highest von Frey hair (15 g), then the threshold value was assigned as 18.4 g.

Drugs were dissolved 20% Tween 80. These vehicles were selected depending on the compound's solubility. Intraperitoneal injection (5 µl/g) was done for all drugs.

The relative values compared to the sham (% control) were calculated and shown in Table 7, which show an antiallodynic effect of the compound of examples on Post operation-induced pain model in rats.

TABLE 7

Antiallodynic effect of the compound of examples on Post operation-induced pain model

| Compound No. | Post Operation | |
|---|---|---|
| | ED50(mg/kg) | Peak Time(h) |
| 7 | 5.8 | 0.5 |
| 8 | 4.2 | 0.5 |

BIOLOGICAL EXPERIMENTAL EXAMPLE. 7

Measurement of Anti-epilepsy Activity (MES-test)

In the MES test (Ref., G. Villetti et al. Neuropharmacology 40 (2001) 866-878), an electrical stimulus (mice: 50 mA, 60 Hz, 0.2 sec, and rats: 150 mA, 60 Hz, 0.2 sec in the test animal) supplied by an 11A Shocker (IITC Life Science Company) was delivered through corneal electrodes. All mice or rats assigned to any electroshock at peak time were treated with each test compound sample which was dissolved in 30% PEG 400 or 20% tween 80 prepared by saline solvent applied orally before the test. If the test animal's stretching of its hind limb in a straight line wasn't observed in the MES test, these results indicated that the test samples had anti-epilepsy activity. Three doses of the test sample were administered orally to 9-18 animals (3-6 mice per dose) for evaluating the respective doses at which 50% of the animals were protected from seizure (ED50). The ED50 value (median effective dose) was calculated by Litchfield and Wicoxon log-probit method which is a dose-response relationship. Experimental animals, male ICR mice and male SD rats, were purchased from OrientBio, Samtako, or Nara Biotech, Korea, and housed in cages (4-5 mice or 3 rats per cage) for 4-5 days. The range of mice body weight was between 19 and 25 grams and range of rats body weight was between 100 and 130 grams. The obtained results are shown in following Table 8 and 9.

BIOLOGICAL EXPERIMENTAL EXAMPLE 8

Measurement of Anti-epilepsy Activity (scPTZ)

In this experiment, each test compound sample was formulated as described in Biological Experimental Example I, and administered intraperitoneally to the test animals (mice; ICR or Rat; SD); Experimental animals, male ICR mice and male SD rats, were purchased from OrientBio or Nara biotech, Korea, and housed 4-5 mice per a cage for 4-5 days. The range of mice body weight was used between 19 and 26 grams and range of rats body weight was used between 100 and 130 grams. After Peak time (0.5, 1, 2 and 4 hr) from the administration, PTZ (Pentylenetetrazol) was administered subcutaneously in the concentration capable of inducing 97% intermittent convulsions (mice: 76-110 mg/kg·bw, 10 µl/g, or rats: 79-110 mg/kg·bw, 2 µl/g). If clonic seizure was not observed for at least 30 minutes in the PTZ administered animal, it can be considered that the test compound has anti-epilepsy activity. The median effective dose (ED50) is determined using 6 animals per a concentration (total three different concen-trations), and calculated by Litchfield and Wicoxon log-probit method which is a dose-response relationship. The obtained results are shown in following Table 8 and 9.

BIOLOGICAL EXPERIMENTAL EXAMPLE 9

Lithium-pilocarpine Induced Epilepsy Test (LI-PILO Test)

Prevention Test

Male Sprague-Dawley rats (purchased from Orient Bio Inc. Korea) of body weight 175-200 grams were used for these studies and 3 rats per cage were housed for 4-5 days. On the day prior to SE, rats received 127 mg/kg lithium chloride (Sigma, St. Louis, Mo., U.S.A.) intraperitoneally (i.p.). Approximately 18-20 h following this treatment, rats were given an i.p. injection of CD97 dose (30-43 mg/kg) pilocarpine (Sigma). An i.p. injection of 2 mg/kg methyl-scopolamine (Sigma) was administered 30 min prior to pilocarpine to block the effects of the muscarinic agonist on peripheral cholinergic receptors. Test drugs were dissolved in 30% PEG 400 or 20% tween80 (Sigma).

The drugs were administered intraperitoneally (i.p.) in a volume of 2 ul/g body weight. Pharmacological effects of all of the test materials were evaluated to compare test groups (n=6) with a control group (n=6). Control group was administered vehicle only. The efficacy was measured 0.5, 1, 2, or 4 hours after the administration of the test material. The time point that the most animals were protected was defined as peak time and the ED50 was determined at peak time. The animals were then transferred to observation cages and observed continuously for 90 min. Seizure was elicited in approximately 95% of the control group. Protection was defined as complete absence of seizure grade 3-5 (Racine scale; Racine, 1972) over the 90-min observation period. The effective dose of the compound necessary to protect 50% of the animals against seizures compared to controls (i.e. ED50) was determined by a curve fitting program (Excel 2007, Microsoft). The obtained results are shown in following Table 9.

Intervention

Male Sprague-Dawley rats (purchased from Orient Bio Inc. Korea) of body weight 175 grams were used for these studies and 3 rats per cage were housed for 4-5 days. On the day prior to SE, rats received 127 mg/kg lithium chloride (Sigma, St. Louis, Mo., U.S.A.) intraperitoneally (i.p.). Approximately 18-20 h following this treatment, rats were given an i.p. injection of CD97 dose (30-43 mg/kg) pilocarpine (Sigma). An i.p. injection of 2 mg/kg methyl-scopolamine (Sigma) was administered 30 min prior to pilocarpine to block the effects of the muscarinic agonist on peripheral cholinergic receptors. Test drugs were dissolved in 20% tween80 (Sigma).

The drugs were administered intravenously (i.v.) in a volume of 2 ul/g body weight at SE onset. Pharmacological effects of all of the test materials were evaluated to compare test groups (n=3-6) with a control group (n=3-6). Control group was administered vehicle only. The animals were then transferred to observation cages and observed continuously for 90 min. Seizure was elicited in approximately 95% of the control group. Protection was defined as complete absence of seizure grade 3-5 (Racine scale; Racine, 1972) over the 90-min observation period. The effective dose of the compound necessary to protect 50% of the animals against seizures compared to controls (i.e. ED50) was determined by a curve fitting program (Excel 2007, Microsoft). The obtained results are shown in following Table 9.

TABLE 8

Pharmacological profile of compounds in mouse.

| No. | MES test (po) | | scPTZ test (ip) | |
|---|---|---|---|---|
| | ED50 (mg/kg) | Peak time (h) | ED50 (mg/kg) | Peak time (h) |
| 1 | 46.9 | 2 | 76.6 | 0.5 |
| 2 | 22.8 | 2 | 18.2 | 1 |
| 4 | — | — | 100(100%) | 2 |
| 7 | 40.7 | 1 | 8.6 | 0.5 |
| 8 | 27.9 | 2 | 13.5 | 1 |
| 9 | 61.8 | 4 | — | — |
| 10 | 100(83.3%) | 1 | — | — |
| 11 | 50(25.0%) | 2 | — | — |
| 13 | 50(25.0%) | 1 | — | — |
| 14 | 50(25.0%) | 1 | — | — |
| 18 | 62 | 1 | — | — |
| 19 | 30(66.6%) | 1 | — | — |
| 20 | 60(16.6%) | 1 | — | — |
| 38 | 50(50.0%) | 2 | — | — |
| 53 | 67.8 | 2 | — | — |
| 58 | 54.4 | 1 | — | — |
| 61 | 30(33.3%) | 2 | — | — |
| 70 | 50.5 | 2 | 50.2 | 2 |
| 73 | 60(33.3%) | 1 | — | — |
| 74 | 30(33.3%) | 0.5 | — | — |
| 75 | 60(33.3%) | 1 | — | — |
| 78 | 50(25.0%) | 4 | — | — |
| 79 | 50(25.0%) | 1 | — | — |
| 85 | 100(16.6%) | 2 | — | — |
| 102 | 42.7 | 2 | — | — |
| 103 | 52.7 | 2 | — | — |

*( ) is efficacy %

TABLE 9

Pharmacological profile of compounds in rats.

| | ED50 (mg/kg) | | | |
|---|---|---|---|---|
| No. | MES test (po) | scPTZ test (ip) | Lithium pi-locarpine model (pre) | Lithium pi-locarpine model(inter) |
| 2 | 5.0 (2 h) | 40 (33.3%, 1 h) | — | — |
| 3 | 20 (16.6%, 4 h) | — | — | — |
| 4 | 10 (33%, 4 h) | — | — | — |
| 7 | 23.5 (2 h) | 10 (0.5 h) | 23.3 (0.5 h) | 23.3 |
| 8 | 24 (1 h) | 15.3 (1 h) | 29.3 (2 h) | 44.8 |
| 10 | — | — | 100 (66.6%, 1 h) | — |
| 11 | 24 (33.3%, 2 h) | — | — | — |
| 12 | 100 (100%, 1 h) | — | — | — |
| 18 | 14.2 (2 h) | — | — | — |
| 20 | 20.1 (2 h) | — | — | — |
| 37 | 10 (16.6%, 2 h) | — | — | — |
| 69 | 20 (16.6%, 1 h) | — | 50 (33.3%, 1 h) | — |
| 70 | 46.6 (1 h) | 36 (1 h) | 100.5 (0.5 h) | — |

TABLE 9-continued

Pharmacological profile of compounds in rats.

| | ED50 (mg/kg) | | | |
|---|---|---|---|---|
| No. | MES test (po) | scPTZ test (ip) | Lithium pilocarpine model (pre) | Lithium pilocarpine model(inter) |
| 73 | 34.8 (4 h) | — | — | — |
| 75 | 4.2 (2 h) | — | — | — |

*The number in ( ) indicates the peak time and efficacy %.

BIOLOGICAL EXPERIMENTAL EXAMPLE 10

The Neuroprotection SE Model

In the neuroprotection model, the seizure induction method was the same as in Lithium-pilocarpine induced epilepsy test (LI-PILO test) except that compound was administered by ip route at 30 min after seizure onset (Racine scale 4-5). For 14 days, the bodyweight and mortality were monitored.

On the 14th day, the rats were deeply anesthetized using Ketamine with Rumpun, 7:3 (v/v) i.p., and perfused transcardially with 150 ml of ice-cold 0.01 M phosphate buffer followed by 250 ml of freshly prepared ice-cold 4% paraformaldehyde (PFA) in 0.1 M phosphate buffer, pH 7.4. The brains were removed and postfixed in the same fixative for an additional 22-24 h at 4° C., and then transferred to 30% sucrose for cry-oprotection until the samples were precipitated. Brains were frozen in methyl butane with dry ice and stored at −80° C. Serial coronal 25-mm slices were cut in a cryostat (Microtome HM 1850, Leica, Germany) and the sections were put onto slides, and air-dried before thionine staining. Every fifth section was selected for morphometric analysis. The stained hippocampus was imaged under a microscopic and enlarged 200- or 400-fold. The number of cells in the region of interest (dorsal hippocampus—CA1, CA3, DG) was counted by observers blinded to the animals' treatment. The mean number was recorded. As a normal group, four naive rats were used. The test result was shown in FIG. 1.

BIOLOGICAL EXPERIMENTAL EXAMPLE 11

The Chemical Induced Seizure Model (PIC)

Picrotoxin (PIC) were used to induce the behavioral seizures in the experiments. Male ICR mice (purchased from Orient Bio Inc. Korea) of body weight 19-26 g (mice) were used for these studies. The test materials were administered intraperitoneal (ip) route in a volume of 10 ul/g (mice) weight in mice, respectively. Pharmacological effects of the test materials were evaluated to compared test groups (n=6) with a control group (n=6). Control group was administrated vehicle, only. The peak time was determined by administration of test material's random dose for 0.5, 1, 2, 4 hour. The time that the most protect was defined as a peak time and ED50 was determined by other dose administration at the peak time. Chemical (PIC) was dissolved in 0.9% saline and administered subcutaneously (s.c.) at its CD97 (convulsive dose 97%), the dose of Chemical (PIC) that produced clonic seizures in 97% into a loose fold of skin in the midline of the neck in a volume of 10 ul/g (mice) body weight. The animals were then transferred to observation cages and observed continuously for 45 min (PIC). Clonic seizure was elicited in approximately 97% of control group. Protection was defined as a complete absence of clonic seizure over the 45-min observation period. The effective dose of compound necessary to protect against generalized convulsive seizures to 50% of controls (i.e. ED50) was determined by log probit analysis using SPSS software program (SPSS Inc.). The obtained results are shown in following Table 10. (Reference; White H. S., J. H. Woodhead, K. S. Wilcox, J. P. Stables, H. J. Kupferberg, and H. H. Wolf. General Principles; Discovery and Preclinical De-velopment of Antiepileptic Drugs. In: R. H. Levy, R. H. Mattson, B. S. Meldrum, and E. Perucca, eds. Antiepileptic Drugs, 5$^{th}$ Ed. Lippincott Williams & Wilkins, Philadelphia 2002: pp. 36-48.) The obtained results are shown in following Table 10.

TABLE 10

Pharmacological profile of compounds in the test animals (Mice)

| | PIC(ip) | |
|---|---|---|
| Compound No. | ED50(mg/kg) | Peak Time(h) |
| 2 | 24.1 | 1 |
| 7 | 28.5 | 0.5 |
| 8 | 73.9 | 1 |
| 85 | 30(33.3%) | 4 |

*( ) is efficacy %

EXPERIMENTAL EXAMPLE 12

The Chemical Induced Seizure Model (Strychnine)

Male ICR mice (purchased from Orient Bio Inc. Korea) of body weight 19-27 g were used for these studies. The test materials were administered intraperitoneal route in a volume of 10 ul/g weight. Pharmacological effects of all the test materials were evaluated to compared test groups (n=6) with a control group (n=6). Control group was administrated vehicle, only. The peak time was determined by administration test material's random dose for 0.5, 1, 2 hour. The time that the most protect was defined peak time and ED50 was determined by other dose administration at peak time. Strychnine was dissolved in 0.9% saline and administered intraperitoneally (i.p.) at its CD97 (convulsive dose 97%) the dose of strychnine that produced clonic seizures in 97% in a volume of 10 ul/g body weight. The animals were then transferred to observation cages and observed continuously for 30 min. Clonic seizure was elicited in approximately 95% of control group. Protection was defined as complete absence of a clonic seizure over the 30-min observation period. The time that the most protect was defined peak time and ED50 was determined by other dose administration at peak time. The effective dose of compound necessary to protect against seizures to 50% of controls (i.e. ED50) was determined by log probit analysis using Excel 2007 (Microsoft). The obtained results are shown in following Table 11.

TABLE 11

Effect of compound in Strychnine test

| Example No. | ED50(mg/kg) | Peak Time(h) |
|---|---|---|
| 7 | 75.8 | 0.5 |

EXPERIMENTAL EXAMPLE 13

The Chemical Induced Seizure Model (BIC)

Male ICR mice (purchased from Orient Bio Inc. Korea) of body weight 19-26 g were used for these studies. The test materials were administered intraperitoneal route in a volume of 10 ul/g weight. Pharmacological effects of all the test materials were evaluated to compared test groups (n=6) with a control group (n=6). Control group was administrated vehicle, only. The peak time was determined by administration test material's random dose for 0.5-4 hour. The time that the most protect was defined peak time and ED50 was determined by other dose administration at peak time. BIC was dissolved in 0.9% saline and administered subcutaneously (s.c.) at its CD97 (convulsive dose 97%) the dose of BIC that produced clonic seizures in 97% into a loose fold of skin in the midline of the neck in a volume of 10 ul/g body weight. The animals were then transferred to observation cages and observed continuously for 30 min. Clonic seizure was elicited in approximately 95% of control group. Protection was defined as complete absence of a clonic seizure over the 30-min observation period. The time that the most protect was defined peak time and ED50 was determined by other dose administration at peak time. The effective dose of compound necessary to protect against seizures to 50% of controls (i.e. ED50) was determined by log probit analysis using Excel 2007 (Microsoft). The obtained results are shown in following Table 12.

TABLE 12

Effect of compound in BIC test

| | BIC(ip) | |
| Compound No. | ED50(mg/kg) | Peak Time(h) |
|---|---|---|
| 7 | 30.8 | 1 |
| 8 | 73.9 | 1 |

EXPERIMENTAL EXAMPLE 14

Multiple-Hit Rat Model of IS (Infantile Spasms)

This study was used male offspring of timed pregnant Sprague-Dawley rats (Nara biotech, Seoul, Korea). Animal preparation and surgical procedures were as described before (Scantlebury et al., 2010). At postnatal day 3 (PN3), doxorubicin (right intracerebroventricular) and lipopolysaccharide (right intraparietal) were infused stereo-tactically, under isoflurane anesthesia. At PN4, rats were separated for video monitoring as described (Scantlebury et al., 2010). The monitoring session consisted of 1 hour before injection and 5 hour after injection. The test materials were administered subcutaneously in a volume of 10 ul/g weight. Behavioral spasms were considered the sudden and synchronous high-amplitude movements of all limbs and body to a flexion or extension posture. Flexion or extension events that had asynchronous limb movements or appeared as an attempt of the pup to reposition were excluded to minimize false-positive events (Reference; Scantlebury M. H., Galanopoulou A. G., Chudomelova L., Raffo E., Betancourth D. and Moshe S. L. (2010). A model of symptomatic infantile spasm syndrome. Neurobiol. Dis. 37: 604-612/Ono T., Moshe S. L. and Galanopoulou A. G. (2011). Carisbamate acutely suppresses spasm in a rat model of symptomatic infantile spasms. Epilepsia 52: 1678-1684.) The test result was shown in FIG. 2.

Provided are non-human mammals treated with doxorubicin, lipopolysaccharide (LPS), and p-chlorophenylalanine (PCPA), where the mammal exhibits a symptom characteristic of infantile spasms. Also provided are methods of making a non-human mammal exhibit a symptom of infantile spasms. Additionally, methods are provided for screening a compound for the potential to attenuate a symptom of infantile spasms. The obtained results are shown in following FIG. 2.

The invention claimed is:
1. A compound having the formula 1 or a pharmaceutically acceptable salt thereof:
[Chemical formula I]

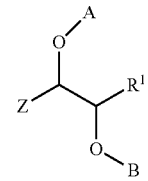

wherein,
Z is selected from

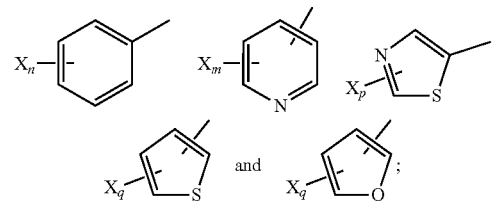

X is selected from the group consisting of halogen, hydroxyl, $C_1$-$C_5$ alkoxy, $C_1$-$C_5$ alkyl, $C_2$-$C_5$ alkenyl, $C_2$-$C_5$ alkynyl, $C_6$-$C_{10}$ aryl, $C_1$-$C_5$alkoxycarbonyl, carboxyl, $C_2$-$C_5$ acyl, $C_1$-$C_5$ alkylthio, cyano, nitro, amine and $C_1$-$C_5$ alkylamine;
n is an integer from 1 to 5;
m is an integer from 1 to 4;
p is an integer from 1 to 2;
q is an integer from 1 to 3;
$R^1$ is selected from the group consisting of hydrogen, $C_1$-$C_5$ alkoxy, $C_1$-$C_5$ alkyl, $C_2$-$C_5$ alkenyl, $C_2$-$C_5$ alkynyl and $C_6$-$C_{10}$ aryl;
A and B are each independently selected from the group consisting of hydrogen, $C_1$-$C_{10}$alkyl, $C_1$-$C_5$alkoxy$C_1$-$C_5$alkyl, $C_6$-$C_{10}$arylalkyloxy$C_1$-$C_5$alkyl, $C_1$-$C_5$alkoxy ($C_1$-$C_5$alkoxy)$C_1$-$C_5$alkyl, $C_3$-$C_5$ heterocyclyl, $C_1$-$C_5$alkylthio$C_1$-$C_5$alkyl and

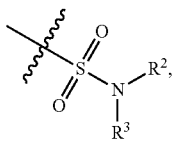

wherein at least one of A and B is

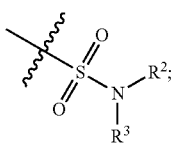

and $R^2$ and $R^3$ are each independently selected from the group consisting of hydrogen, $C_1$-$C_5$ alkyl, $C_3$-$C_8$ cycloalkyl, $C_6$-$C_{10}$ aryl and $C_1$-$C_5$ alkoxycarbonyl.

2. The compound or the pharmaceutically acceptable salt thereof according to claim 1, wherein Z is

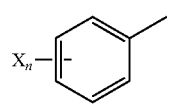

and n is an integer from 1 to 5.

3. The compound or the pharmaceutically acceptable salt thereof according to claim 1, wherein X is F, Br, Cl or I.

4. The compound or the pharmaceutically acceptable salt thereof according to claim 1, wherein A and B are each independently selected from the group consisting of hydrogen, $C_1$-$C_{10}$ alkyl, methoxymethyl (MOM), 2-methoxyethoxymethyl (MEM), ethoxyethyl (EE), tetrahydropyranyl (THP) methylthiomethyl (MTM) and benzyloxymethyl (BOM) and

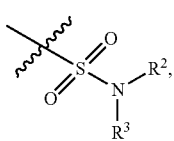

wherein at least one of A and B is

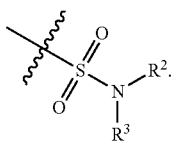

5. The compound or the pharmaceutically acceptable salt thereof according to claim 1, wherein,
Z is

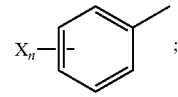

X is F, Br, Cl or I;
n is an integer from 1 to 5;
$R^1$ is selected from the group consisting of hydrogen, methoxy, ethoxy, propoxy, butoxy, methyl, ethyl, propyl, isopropyl, sec-butyl and t-butyl;
A and B are each independently selected from the group consisting of hydrogen, methyl, ethyl, propyl, isopropyl, sec-butyl or t-butyl, methoxymethyl (MOM), 2-methoxyethoxymethyl (MEM), ethoxyethyl (EE), tetrahydropyranyl (THP) methylthiomethyl (MTM), benzyloxymethyl (BOM) and

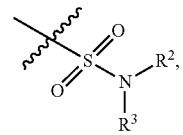

wherein at least one of A and B is

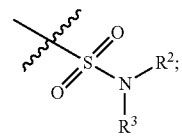

and
$R^2$ and $R^3$ are each independently selected from the group consisting of hydrogen, methyl, ethyl, propyl, isopropyl, sec-butyl or t-butyl, cyclopropyl, cyclohexyl, bicyclo[2.2.1]heptyl, phenyl and benzyl.

6. The compound or the pharmaceutically acceptable salt thereof according to claim 1, wherein the compound is selected from the group consisting of:

(1) (1S, 2S)-1-(2-chlorophenyl)-1-hydroxypropan-2-yl sulfamate
(2) (1R, 2R)-1-(2-chlorophenyl)-1-hydroxypropan-2-yl sulfamate
(3) (1S, 2S)-1-(2,4-dichlorophenyl)-1-hydroxypropan-2-yl sulfamate
(4) (1R, 2R)-1-(2,4-dichlorophenyl)-1-hydroxypropan-2-yl sulfamate
(5) (1S, 2S)-1-(3,4-dichlorophenyl)-1-hydroxypropan-2-yl sulfamate
(6) (1R, 2R)-1-(3,4-dichlorophenyl)-1-hydroxypropan-2-yl sulfamate
(7) (1S, 2S)-1-(2,6-dichlorophenyl)-1-hydroxypropan-2-yl sulfamate
(8) (1R, 2R)-1-(2,6-dichlorophenyl)-1-hydroxypropan-2-yl sulfamate
(9) (1S, 2S)-1-(2,3-dichlorophenyl)-1-hydroxypropan-2-yl sulfamate
(10) (1R, 2R)-1-(2,3-dichlorophenyl)-1-hydroxypropan-2-yl sulfamate

(11) (1S, 2S)-1-(2-chlorophenyl)-1-hydroxybutan-2-yl sulfamate
(12) (1R, 2R)-1-(2-chlorophenyl)-1-hydroxybutan-2-yl sulfamate
(13) (1S, 2S)-1-(2-chlorophenyl)-1-hydroxy-3-methylbutan-2-yl sulfamate
(14) (1R, 2R)-1-(2-chlorophenyl)-1-hydroxy-3-methylbutan-2-yl sulfamate
(15) (1S, 2S)-1-(2-chlorophenyl)-1-hydroxypentan-2-yl sulfamate
(16) (1R, 2R)-1-(2-chlorophenyl)-1-hydroxypentan-2-yl sulfamate
(17) (1S, 2S)-1-(2-fluorophenyl)-1-hydroxypropan-2-yl sulfamate
(18) (1R, 2R)-1-(2-fluorophenyl)-1-hydroxypropan-2-yl sulfamate
(19) (1S, 2S)-1-(2-iodophenyl)-1-hydroxypropan-2-yl sulfamate
(20) (1R, 2R)-1-(2-iodophenyl)-1-hydroxypropan-2-yl sulfamate
(21) (1S, 2S)-1-(2,6-difluorophenyl)-1-hydroxypropan-2-yl sulfamate
(22) (1S, 2S)-1-(2,5-dichlorophenyl)-1-hydroxypropan-2-yl sulfamate
(23) (1R, 2R)-1-(2,5-dichlorophenyl)-1-hydroxypropan-2-yl sulfamate
(24) (1S, 2S)-1-(2-chloro-6-fluorophenyl)-1-hydroxypropan-2-yl sulfamate
(25) (1S, 2S)-1-hydrpxy-1-(3-hydroxyphenyl)propan-2-yl sulfamate
(26) (1S, 2R)-1-(2,6-dichlorophenyl)-1-hydroxypropan-2-yl sulfamate
(27) (1R, 2S)-1-(2,6-dichlorophenyl)-1-hydroxypropan-2-yl sulfamate
(28) (1S, 2S)-1-(2-iodophenyl)-1-hydroxybutan-2-yl sulfamate
(29) (1S, 2S)-1-(2,6-dichlorophenyl)-1-hydroxybutan-2-yl sulfamate
(30) (1R, 2R)-1-(2,6-dichlorophenyl)-1-hydroxybutan-2-yl sulfamate
(31) (1S, 2S)-1-(2,6-dichlorophenyl)-1-hydroxy-3-methylbutan-2-yl sulfamate
(32) (1R, 2R)-1-(2,6-dichlorophenyl)-1-hydroxy-3-methylbutan-2-yl sulfamate
(33) (1S, 2S)-1-(2,6-dichlorophenyl)-1-hydroxyhexan-2-yl sulfamate
(34) (1R, 2R)-1-(2,6-dichlorophenyl)-1-hydroxyhexan-2-yl sulfamate
(35) (1S, 2S)-1-(2-chlorophenyl)-1-hydroxypropan-2-yl methyl sulfamate
(36) (1R, 2R)-1-(2-chlorophenyl)-1-hydroxypropan-2-yl methylsulfamate
(37) (1S, 2S)-1-(2-chlorophenyl)-1-hydroxypropan-2-yl isopropyl sulfamate
(38) (1R, 2R)-1-(2-chlorophenyl)-1-hydroxypropan-2-yl isopropyl sulfamate
(39) (1S, 2S)-1-(2,6-dichlorophenyl)-1-hydroxypropan-2-yl i sopropyl sulfamate
(40) (1S, 2S)-1-(2-chlorophenyl)-1-hydroxypropan-2-yl cyclopropylsulfamate
(41) (1R, 2R)-1-(2-chlorophenyl)-1-hydroxypropan-2-yl cyclopropylsulfamate
(42) (1S, 2S)-1-(2,6-dichlorophenyl)-1-methoxypropan-2-yl sulfamate
(43) (1R, 2R)-1-(2,6-dichlorophenyl)-1-methoxypropan-2-yl sulfamate
(44) (1S, 2S)-1-(2,6-dichlorophenyl)-1-methoxybutan-2-yl sulfamate
(45) (1R, 2R)-1-(2,6-dichlorophenyl)-1-methoxybutan-2-yl sulfamate
(46) (1S, 2S)-1-(2,6-dichlorophenyl)-1-methoxy-3-methylbutan-2-yl sulfamate
(47) (1R, 2R)-1-(2,6-dichlorophenyl)-1-methoxy-3-methylbutan-2-yl sulfamate
(48) (1S, 2S)-1-(2,6-dichlorophenyl)-1-methoxyhexan-2-yl sulfamate
(49) (1R, 2R)-1-(2,6-dichlorophenyl)-1-methoxyhexan-2-yl sulfamate
(50) (1S, 2S)-1-(2,6-dichlorophenyl)-1-methoxypropan-2-yl i sopropyl sulfamate
(51) (1S, 2S)-1-(2,4-dichlorophenyl)-1-(methoxymethoxy)propan-2-yl sulfamate
(52) (1R, 2R)-1-(2,4-dichlorophenyl)-1-(methoxymethoxy)propan-2-yl sulfamate
(53) (1S, 2S)-1-(2,3-dichlorophenyl)-1-(methoxymethoxy)propan-2-yl sulfamate
(54) (1R, 2R)-1-(2,3-dichlorophenyl)-1-(methoxymethoxy)propan-2-yl sulfamate
(55) (1S, 2S)-1-(3,4-dichlorophenyl)-1-(methoxymethoxy)propan-2-yl sulfamate
(56) (1R, 2R)-1-(3,4-dichlorophenyl)-1-(methoxymethoxy)propan-2-yl sulfamate
(57) (1S, 2S)-1-(2,6-dichlorophenyl)-1-(methoxymethoxy)propan-2-yl sulfamate
(58) (1R, 2R)-1-(2,6-dichlorophenyl)-1-(methoxymethoxy)propan-2-yl sulfamate
(59) (1S, 2S)-1-(2,5-dichlorophenyl)-1-(methoxymethoxy)propan-2-yl sulfamate
(60) (1R, 2R)-1-(2,5-dichlorophenyl)-1-(methoxymethoxy)propan-2-yl sulfamate
(61) (1S, 2S)-1-(2-chloro-6-fluorophenyl)-1-(methoxymethoxy)propan-2-yl sulfamate
(62) (1S, 2S)-1-(2,6-dichlorophenyl)-1-(methoxymethoxy)propan-2-yl sulfamate
(63) (1S, 2S)-1-(2,6-dichlorophenyl)-1-(methoxymethoxy)butan-2-yl sulfamate
(64) (1R, 2R)-1-(2,6-dichlorophenyl)-1-(methoxymethoxy)butan-2-yl sulfamate
(65) (1S, 2S)-1-(2,6-dichlorophenyl)-1-(methoxymethoxy)-3-methylbutan-2-yl sulfamate
(66) (1R, 2R)-1-(2,6-dichlorophenyl)-1-(methoxymethoxy)-3-methylbutan-2-yl sulfamate
(67) (1S, 2S)-1-(2,6-dichlorophenyl)-1-(methoxymethoxy)hexan-2-yl sulfamate
(68) (1R, 2R)-1-(2,6-dichlorophenyl)-1-(methoxymethoxy)hexan-2-yl sulfamate
(69) (1S, 2S)-1-(2-chlorophenyl)-1-(methoxymethoxy)propan-2-yl sulfamate
(70) (1R, 2R)-1-(2-chlorophenyl)-1-(methoxymethoxy)propan-2-yl sulfamate
(71) (1R, 2R)-1-(2-chlorophenyl)-1-(methoxymethoxy)butan-2-yl sulfamate
(72) (1S, 2S)-1-(2-fluorophenyl)-1-(methoxymethoxy)propan-2-yl sulfamate
(73) (1R, 2R)-1-(2-fluorophenyl)-1-(methoxymethoxy)propan-2-yl sulfamate
(74) (1S, 2S)-1-(2-iodophenyl)-1-(methoxymethoxy)propan-2-yl sulfamate
(75) (1R, 2R)-1-(2-iodophenyl)-1-(methoxymethoxy)propan-2-yl sulfamate
(76) (1S, 2S)-1-(2-chlorophenyl)-1-(methoxymethoxy)propan-2-yl methyl sulfamate

(77) (1R, 2R)-1-(2-chlorophenyl)-1-(methoxymethoxy)propan-2-yl methyl sulfamate
(78) (1S, 2S)-1-(2-chlorophenyl)-1-(methoxymethoxy)propan-2-yl cyclopropylsulfamate
(79) (1R, 2R)-1-(2-chlorophenyl)-1-(methoxymethoxy)propan-2-yl cyclopropylsulfamate
(80) (1S,2S)-1-(2,6-dichlorophenyl)-1-(methoxymethoxy)propan-2-yl isopropylsulfamate
(81) (1S,2S)-1-(2-chlorophenyl)-1-(methoxymethoxy)propan-2-yl isopropylsulfamate
(82) (1R, 2R)-1-(2-chlorophenyl)-1-(methoxymethoxy)propan-2-yl isopropylsulfamate
(83) (1R, 2R)-1-(2,6-dichlorophenyl)-2-hydroxypropyl sulfamate
(84) (1S, 2S)-1-(2-chlorophenyl)propane-1,2-diyl bis(sulfamate)
(85) (1R, 2R)-1-(2-chlorophenyl)propane-1,2-diyl bis(sulfamate)
(86) (1S, 2S)-1-(2-chlorophenyl)butane-1,2-diyl bis(sulfamate)
(87) (1R, 2R)-1-(2-chlorophenyl)butane-1,2-diyl bis(sulfamate)
(88) (1S, 2S)-1-(2-chlorophenyl)-3-methylbutane-1,2-diyl bis(sulfamate)
(89) (1R, 2R)-1-(2-chlorophenyl)-3-methylbutane-1,2-diyl bis(sulfamate)
(90) (1S, 2S)-1-(2-chlorophenyl)pentane-1,2-diyl bis(sulfamate)
(91) (1R, 2R)-1-(2-chlorophenyl)pentane-1,2-diyl bis(sulfamate)
(92) (1S,2S)-1-(2-iodophenyl)-1-methoxypropan-2-yl sulfamate
(93) (1S, 2S)-1-(2,6-dichlorophenyl)-2-hydroxypropyl sulfamate
(94) (1R,2R)-1-(2,6-dichlorophenyl)-1-methoxypropan-2-yl cyclopropyl sulfamate
(95) (1R,2R)-1-(2,6-dichlorophenyl)-1-methoxypropan-2-yl methyl sulfamate
(96) (1R,2R)-1-(2,6-dichlorophenyl)-1-hydroxypropan-2-yl methyl sulfamate
(97) (1S,2S)-1-(2-chlorophenyl)-1-methoxypropan-2-yl sulfamate
(98) (1R,2R)-1-hydroxy-1-(pyridin-2-yl)propan-2-yl sulfamate
(99) (1R,2R)-1-(3,5-dichloropyridin-4-yl)-1-(methoxymethoxy)propan-2-yl sulfamate
(100) (1R,2R)-1-(3,5-dichloropyridin-4-yl)-1-hydroxypropan-2-yl sulfamate
(101) (1R,2R)-1-(3,5-dichloropyridin-4-yl)-1-methoxypropan-2-yl sulfamate
(102) (1R,2S)-1-(2,4-dichlorothiazol-5-yl)-1-hydroxypropan-2-yl sulfamate
(103) (1R,2S)-1-(2,4-dichlorothiazol-5-yl)-1-(methoxymethoxy)propan-2-yl sulfamate
(104) (1R,2S)-1-hydroxy-1-(4-methylthiazol-5-yl)propan-2-yl sulfamate
(105) (1S,2R)-1-(2,4-dichlorothiazol-5-yl)-1-hydroxypropan-2-yl sulfamate
(106) (1S,2R)-1-methoxy-1-(thiophen-2-yl)propan-2-yl sulfamate.

7. The pharmaceutical composition comprising a therapeutically effective amount of the compound having the formula 1 according to claim 1, or a pharmaceutically acceptable salt thereof as an active ingredient.

8. The pharmaceutical composition according to claim 7 for preventing or treating pain and/or for treating a CNS disorder, wherein the CNS disorder is selected from the group consisting of epilepsy, memory loss related disease, neurodegenerative disease, and Autism spectrum disease.

9. The pharmaceutical composition according to claim 8, wherein the epilepsy is selected from the group consisting of epilepsy-related syndrome, pediatric epilepsy and pediatric epilepsy related syndrome.

10. The pharmaceutical composition according to claim 8, wherein the neurodegenerative disease is prion disease.

11. A method of preventing or treating pain and/or for treating a CNS disorder, comprising administering a therapeutically effective amount of the compound having the formula 1 according to claim 1, or a pharmaceutically acceptable salt thereof as an active ingredient, to a subject in need of treatment;
wherein the CNS disorder is selected from the group consisting of epilepsy, memory loss related disease, neurodegenerative disease, and Autism spectrum disease.

12. The method according to claim 11, wherein the pain is one or more selected from nociceptive pain, psychogenic pain, inflammatory pain, pathological pain, neuropathic pain, cancer pain, postoperative pain, trigeminal neuralgia pain, idiopathic pain, diabetic neuropathic pain, and migraine.

13. The method according to claim 11, wherein the epilepsy is an intractable epilepsy, localization-related epilepsy, cortical epilepsy, frontal lobe epilepsy, parietal lobe epilepsy, occipital lobe epilepsy, temporal lobe epilepsy, generalized epilepsy or syndromes thereof.

14. The method according to claim 11, wherein the epilepsy-related syndrome is an epileptic seizure, an intractable localization-related epilepsy, an intractable secondary generalized seizure, an intractable complex partial seizure or an intractable status epilepticus.

15. The method according to claim 11, wherein the pediatric epilepsy or pediatric epilepsy-related syndrome is selected from the group consisting of Benign Myoclonic Epilepsy (BME), Severe Myoclonic Epilepsy of Infancy Borderland (SMEB), Severe Infantile Multifocal Epilepsy (SIMFE), Intractable Childhood Epilepsy with Generalized Tonic Clonic Seizures (ICE-GTC), Dravet syndrome (Ds), Severe Myoclonic Epilepsy of Infancy (SMEI), Benign neonatal convulsions, Benign neonatal familial convulsions, Miscellaneous neonatal seizures, Febrile seizures, Early infantile epileptic encephalopathy, Early myoclonic encephalopathy, Infantile spasm, West syndromes, Severe myoclonic epilepsy of infancy, Benign myoclonic epilepsy of infancy, Benign partial epilepsy of infancy, Benign infantile familial convulsion, Symptomatic/cryptogenic partial epilepsies, Epilepsy with myoclonic absences, Lennox-Gastaut syndrome, Doose syndrome, Landaw-Kleffner syndrome, Epilepsy with continuous spike-wave during low-wave sleep, Epilepsy with gastric seizures and hypothalamic hamartoma, Symptomatic/cryptogenic partial epilepsies and Childhood absence epilepsy.

16. The method according to claim 11, wherein the compound is in the form of racemate, enantiomer, diastereomer, a mixture of enantiomer, or a mixture of diastereomer.

* * * * *